(12) United States Patent
Nakae

(10) Patent No.: US 11,922,277 B2
(45) Date of Patent: Mar. 5, 2024

(54) PAIN DETERMINATION USING TREND ANALYSIS, MEDICAL DEVICE INCORPORATING MACHINE LEARNING, ECONOMIC DISCRIMINANT MODEL, AND IoT, TAILORMADE MACHINE LEARNING, AND NOVEL BRAINWAVE FEATURE QUANTITY FOR PAIN DETERMINATION

(71) Applicant: Osaka University, Osaka (JP)

(72) Inventor: Aya Nakae, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 628 days.

(21) Appl. No.: 16/628,989

(22) PCT Filed: Jul. 6, 2018

(86) PCT No.: PCT/JP2018/025769
§ 371 (c)(1),
(2) Date: Jan. 6, 2020

(87) PCT Pub. No.: WO2019/009420
PCT Pub. Date: Jan. 10, 2019

(65) Prior Publication Data
US 2022/0004913 A1 Jan. 6, 2022

(30) Foreign Application Priority Data
Jul. 7, 2017 (JP) .................................. 2017-133422
Oct. 13, 2017 (JP) .................................. 2017-199374
(Continued)

(51) Int. Cl.
*G06N 3/04* (2023.01)
*G06N 3/004* (2023.01)
(Continued)

(52) U.S. Cl.
CPC ............. *G06N 20/00* (2019.01); *G06N 3/004* (2013.01); *G06N 3/045* (2023.01)

(58) Field of Classification Search
CPC ............................ G06N 20/20; G06N 3/045
See application file for complete search history.

(56) References Cited

U.S. PATENT DOCUMENTS

| 2005/0102246 A1 | 5/2005 | Movellan et al. |
| 2010/0280979 A1 | 11/2010 | Raaijmakers |

(Continued)

FOREIGN PATENT DOCUMENTS

| EP | 3263026 A1 | 5/2005 |
| EP | 3263026 D2 | 5/2005 |

(Continued)

OTHER PUBLICATIONS

Duarte, Edson, and Jacques Wainer. "Empirical comparison of cross-validation and internal metrics for tuning SVM hyperparameters." Pattern Recognition Letters 88 (2017): 6-11. (Year: 2017).*

(Continued)

*Primary Examiner* — Hal Schnee
(74) *Attorney, Agent, or Firm* — MUNCY, GEISSLER, OLDS & LOWE, P.C.

(57) ABSTRACT

A high accuracy information extracting device construction system includes: a feature quantity extraction expression list generating unit for generating a feature quantity extraction expression list; a feature quantity calculating unit for calculating feature quantities of teacher data by means of respective feature quantity extracting expressions; a teacher data supply unit for supplying teacher data; an evaluation value calculating unit for generating information extracting expressions by means of machine learning on the basis of the calculated feature quantities of teacher data and the teacher data, and calculating evaluation values for the respective (Continued)

feature quantity extracting expressions; and a synthesis unit for constructing a high accuracy information extracting device using T weak information extracting parts F(X)t output from the evaluation value calculating unit 15 and confidence levels Ct corresponding thereto.

5 Claims, 104 Drawing Sheets

(30) Foreign Application Priority Data

Dec. 28, 2017 (JP) .................................. 2017-254560
Dec. 28, 2017 (JP) .................................. 2017-254565
Jan. 11, 2018 (JP) .................................. 2018-002777

(51) Int. Cl.
*G06N 3/045* (2023.01)
*G06N 20/00* (2019.01)

(56) References Cited

U.S. PATENT DOCUMENTS

| 2018/0228447 | A1 | 1/2018 | Junichiro et al. | |
| 2019/0034797 | A1* | 1/2019 | Sakai | A61B 5/165 |
| 2020/0184382 | A1* | 6/2020 | Fishkov | G06N 20/20 |
| 2020/0349416 | A1* | 11/2020 | Yang | G06N 20/20 |
| 2022/0230310 | A1* | 7/2022 | Xie | G06V 10/758 |

FOREIGN PATENT DOCUMENTS

| JP | 2013-164863 D3 | 11/2013 |
| JP | 2013-164863 B2 | 5/2014 |
| WO | 2008/124566 A2 | 10/2008 |
| WO | 2011/017778 A1 | 2/2011 |

OTHER PUBLICATIONS

Varoquaux, Gaël, et al. "Assessing and tuning brain decoders: cross-validation, caveats, and guidelines." NeuroImage 145 (2017): 166-179. (Year: 2017).*

Bai, Y., Huang, G., Tu, Y., Tan, A., Hung, Y. S., & Zhang, Z. (2016). Normalization of pain-evoked neural responses using spontaneous EEG improves the performance of EEG-based cross-individual pain prediction. Frontiers in computational neuroscience, 10, 31. (Year: 2016).*

Krstajic, Damjan, et al. "Cross-validation pitfalls when selecting and assessing regression and classification models." Journal of cheminformatics 6 (2014): 1-15. (Year: 2014).*

PCT Search Report and Written Opinion issued in connection with corresponding PCT Application No. PCT/ JP2018/025769 dated Oct. 1, 2019.

Communication pursuant to Rule 164(1) EPC, and the partial supplementary European Search Report Issued in connection with corresponding European counterpart 18828566.2 dated Mar. 11, 2021.

Marquand et al., "Quantitative prediction of subjective pain intensity from whole-brain fiVIRI data using Gaussian processes", Neuroimage 49 (2010) 2178-2189, www.elsevier.com/locate/ynimg, Oct. 29, 2009, 12 pgs.

Wandekokem Estefhand., "Support Vector Machine Ensemble Based on Feature and Hyperparameter Variation", Epartamento De Informatica, Centro Tecnologico, Universidade Federal Do Espirito Santo, Feb. 23, 2011, 74 pgs.

* cited by examiner

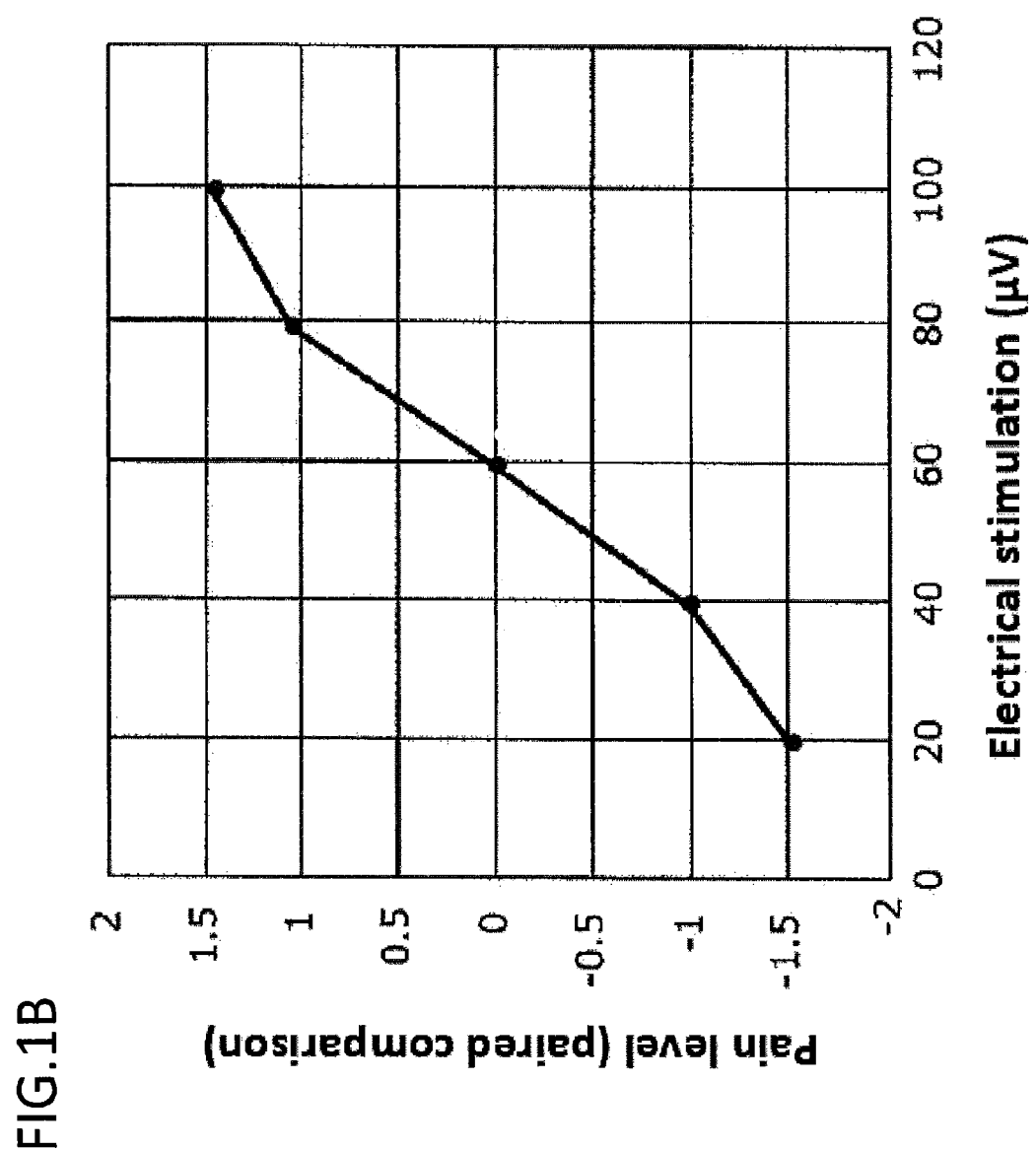

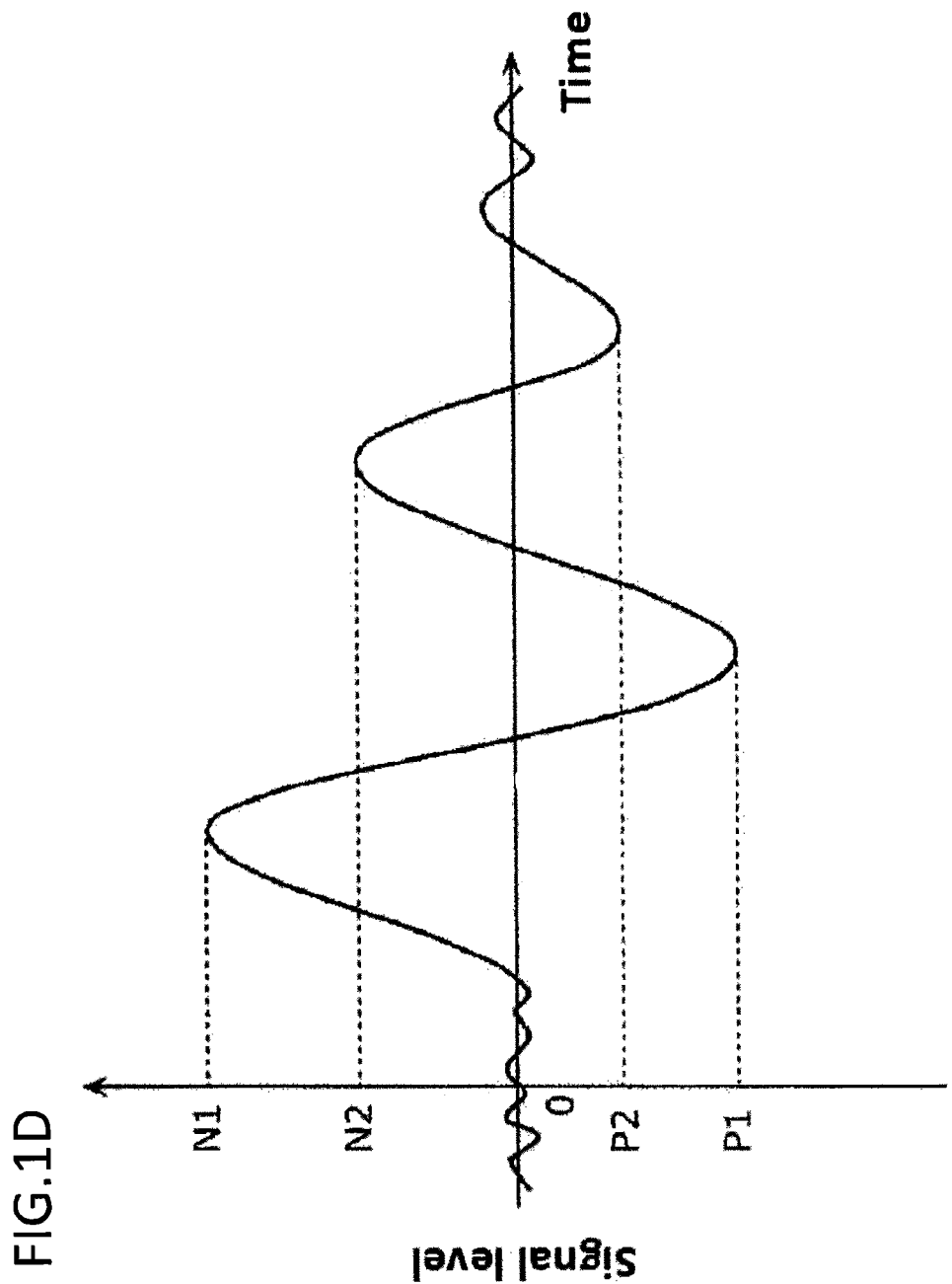

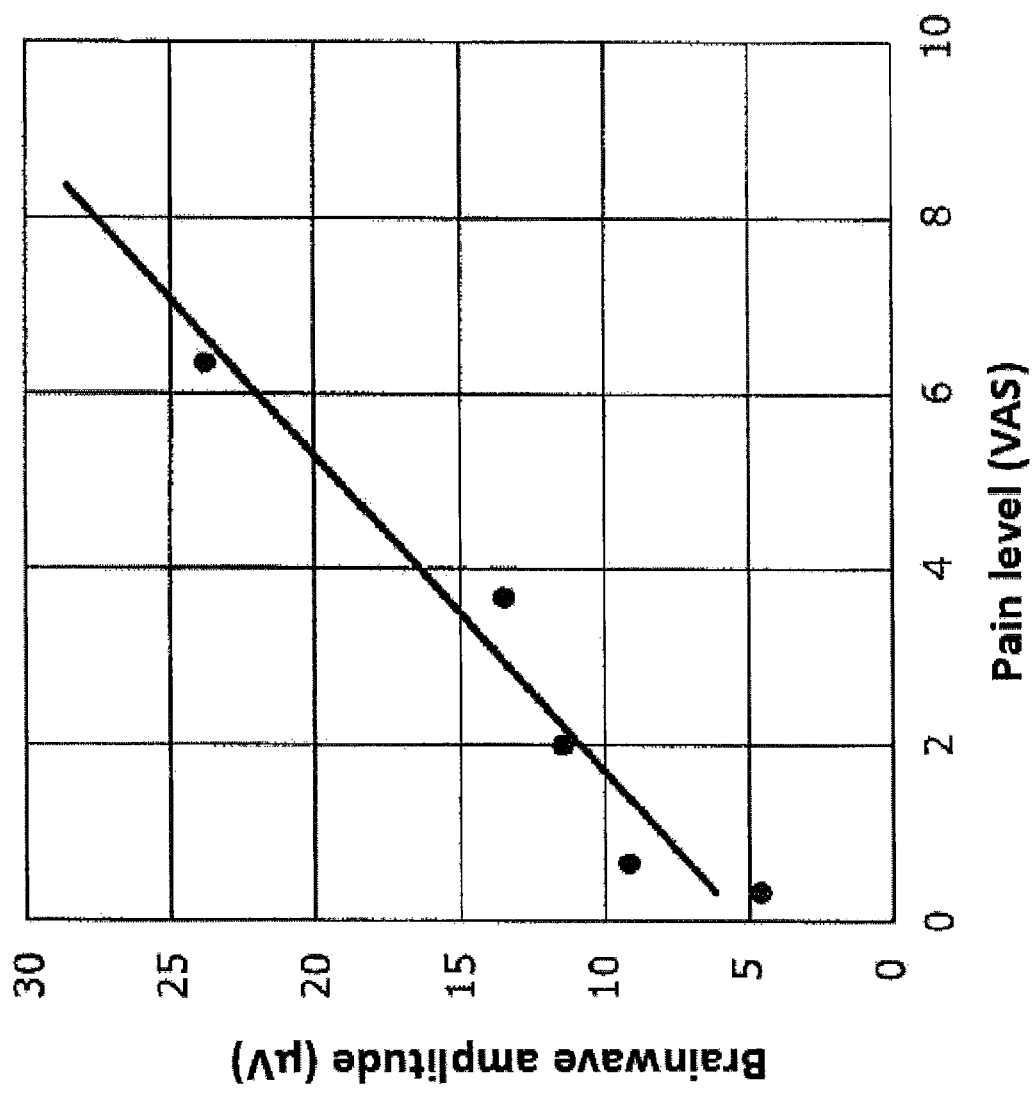

FIG.1I
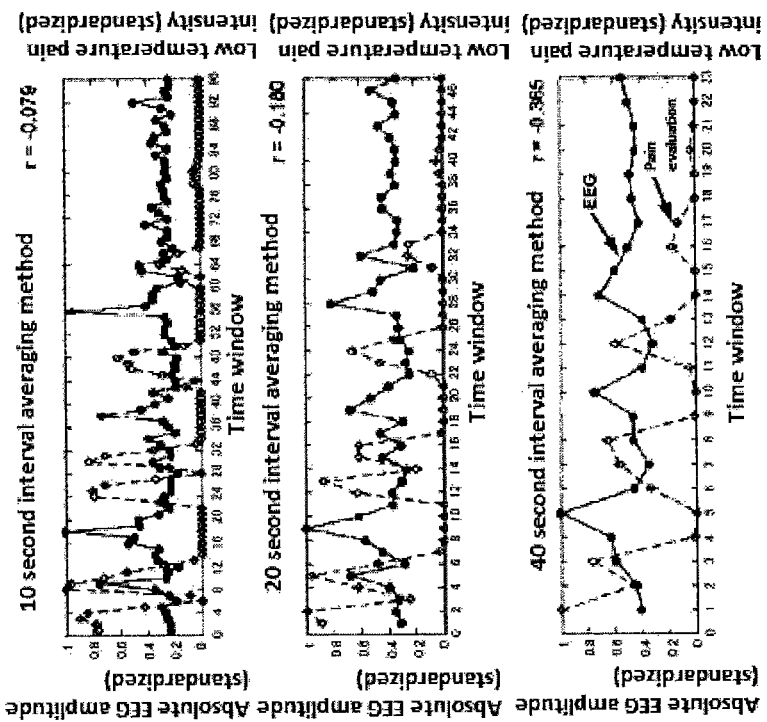
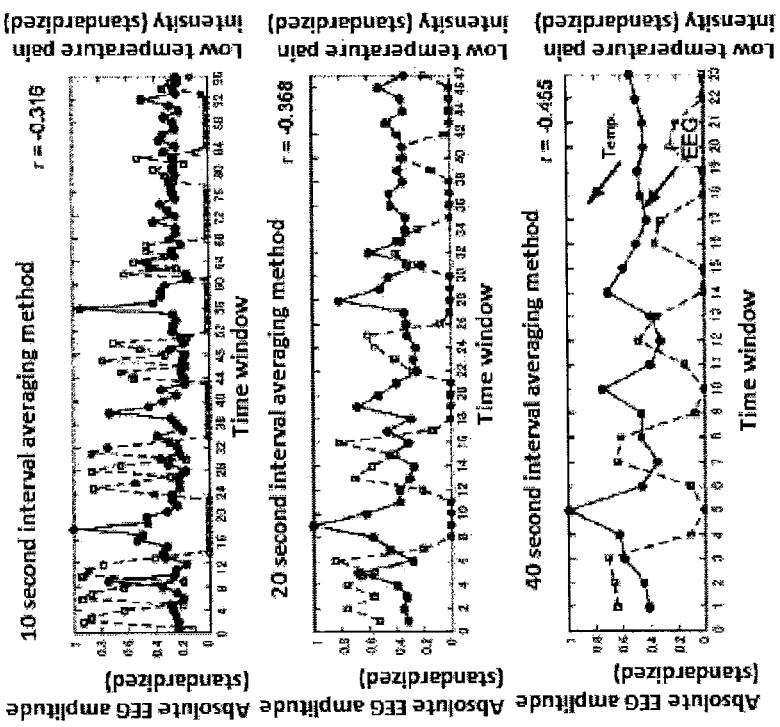

FIG.6
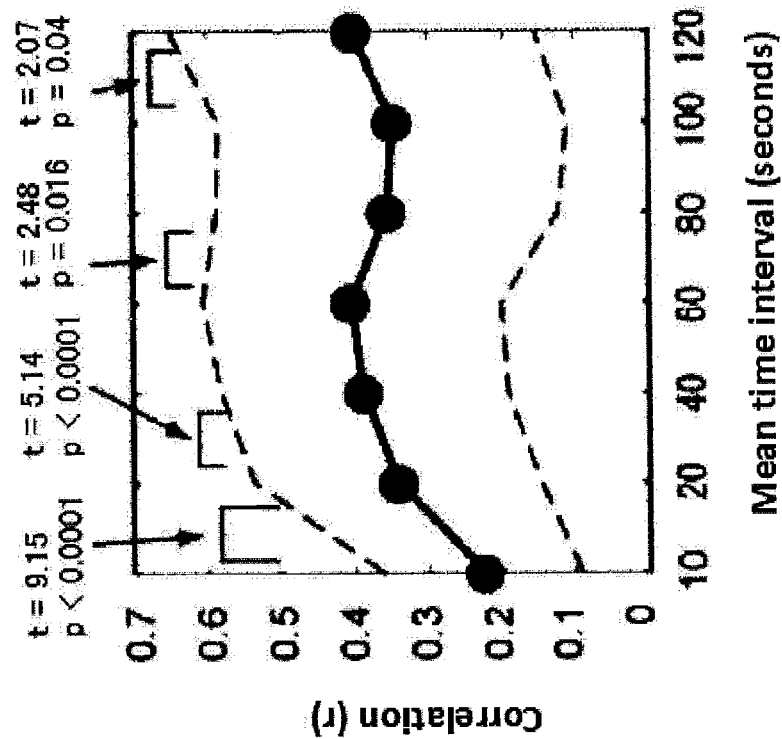
A Correlation between mean potential amplitude (absolute value) and subjective pain evaluation of low temperature stimulation
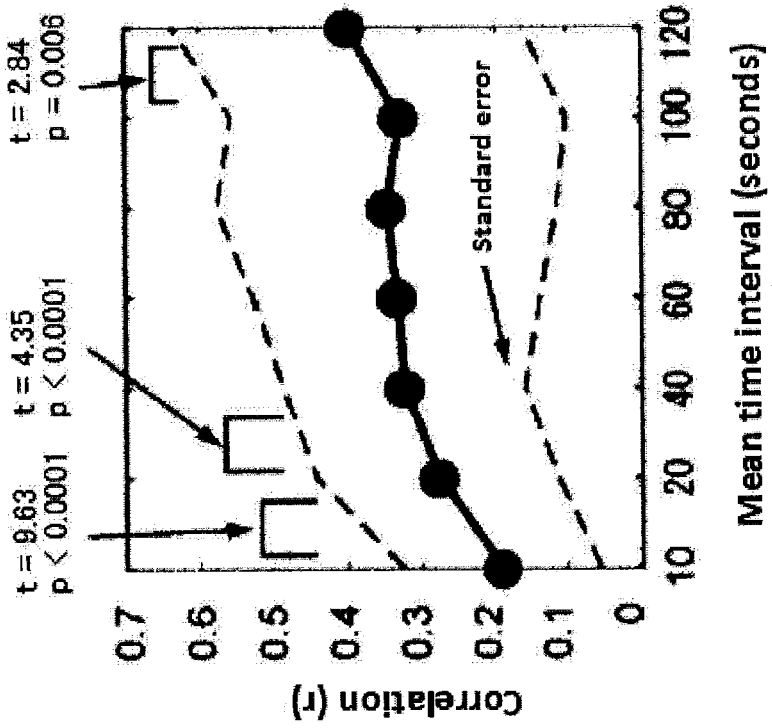
B Correlation between mean potential amplitude (absolute value) and low temperature stimulation intensity FIG.8
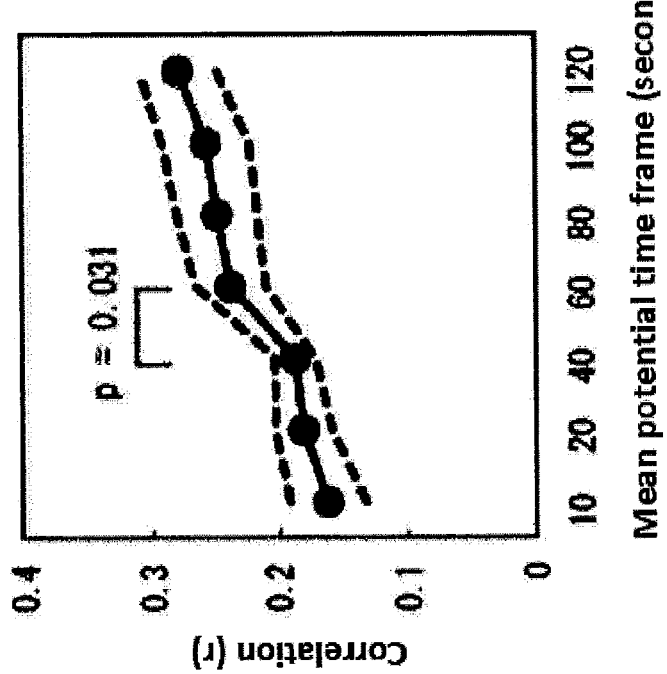
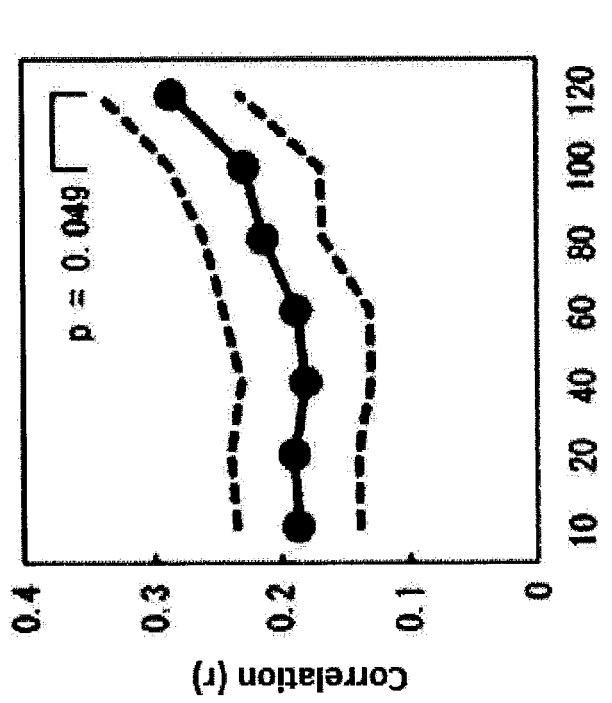

FIG.9
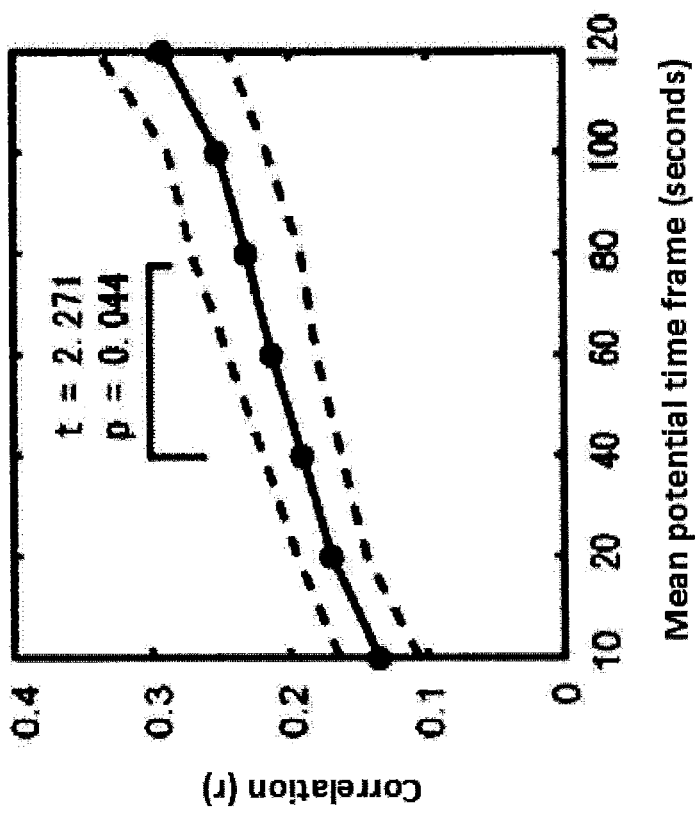
B Correlation between geometric mean potential amplitude (absolute value) and high temperature stimulation intensity
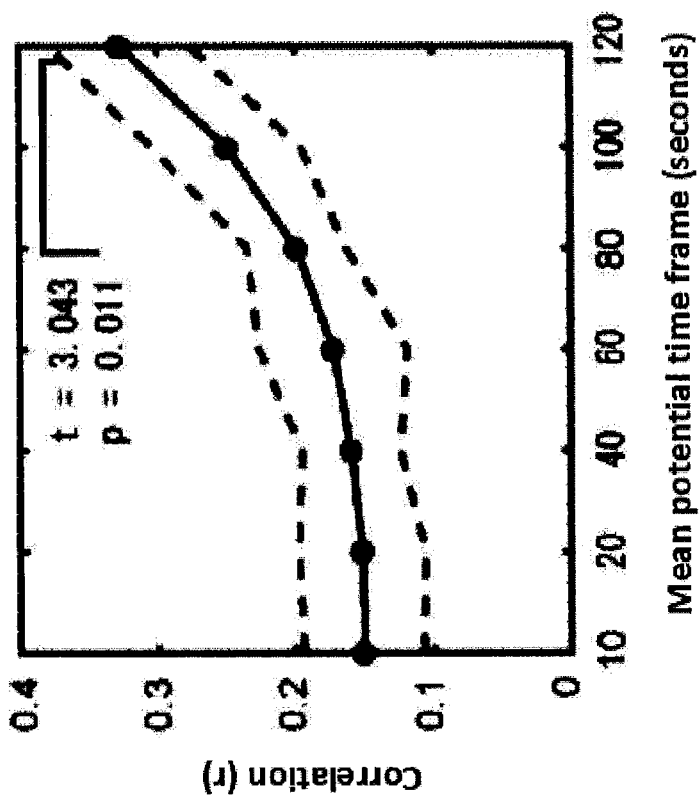
A Correlation between geometric mean potential amplitude (absolute value) and subjective pain evaluation

FIG.14

Outline of experiment

1. Pain data collection

*Subject: hot stimulation data (158 subjects), cold stimulation data (151 subjects)

*Experimental design:
  6 hot levels (increased by 2°C from 40°C to 50°C, base temperature of 36°C, 3 runs at each level)
  6 cold levels (decreased by 5°C from 15°C to -10°C, base temperature of 36°C, 3 stimulations at each level)

*Stimulation application interval: basic setting is sustained for 5 seconds, 15 seconds including increase and decrease time

*Brainwave recording electrode: 7 electrodes (Fp1, Fp2, F3, F4, C3, C4, Pz)

II. Brainwave feature extraction

*Extracted feature: absolute mean amplitude from the time of applying stimulation to 15 seconds after applying, 7 features of 7 electrodes

*Extraction process: EOG removal → EMG removal → sampling of 15 second segment → conversion of amplitude to absolute value → calculation of segment mean value → conversion to z value iii. Differentiation model creation by machine learning

*Differentiation level: 2 classifications of no pain (level 1) and having pain (level 6)

*Differentiation model: linear multiplication regression model including 7 features

*Parameter estimation: L1 regularization

*Machine learning process: estimate parameter using hot and cold samples for 308 subjects, which exclude 1 subject (6 samples × 309 subjects =1854) and differentiate/estimate 6 samples of the remaining one subject

*Model refinement: repeat model creation until there is no subjects with less than chance level iv. Pain trend using created model (temporal change analysis)

*Analysis data: brainwave data in different experiments that randomly apply 40°C, 44°C, 48°C was used.

*Test model: multiple regression model using feature coefficient (7 coefficients) of refined model

FIG.25

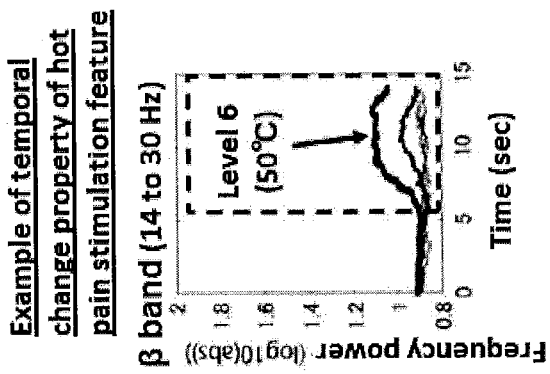

Example of temporal change property of hot pain stimulation feature

Outline of analysis method

*Data used*
1. Electrode used: 4 electrodes at the frontal portions (Fp1, Fp2, F3, F4)
2. Experimental designs: 6 levels of hot stimulation (15 second interval between stimulations, 3 runs each, increased by 2°C from 40°C to 50°C)
3. Number of samples and subjects: 170

*Feature extraction unit (5 features × 5 electrodes)*
1. EOG removal: "main component analysis" → "filter" → "regression filter"
2. EMG removal: 0.022 (stimulation segment × 3) × 30 Hz (before γ region)
3. Addition of EOG feature: added EOG main component as "reverse utilization of noise"
4. Extraction of amplitude and frequency (δ, θ, α, β) features (5 features × 4 electrodes)
   *use segment from 5 to 15 sec after applying stimulation ("delayed pain feature")

*Differentiation estimation unit (Lasso, multiple regression)*
1. Differentiation levels: 2 levels; level 1 (30 samples) and level 6 (30 samples) (10,200 samples)
2. Standardization: frequency power (5 sec × 6 sections) and amplitude (30 sec overall) which is 30 sec before starting application of stimulation
3. Refinement: exclude subject with differentiation accuracy of 70% or less
4. Determine feature coefficient of differentiation model (same number of means as number of subjects)
5. Calculate judgment indicator "pain estimation value"
6. Calculate judgment support indicator "pain occupancy": certainty of having pain

FIG.26

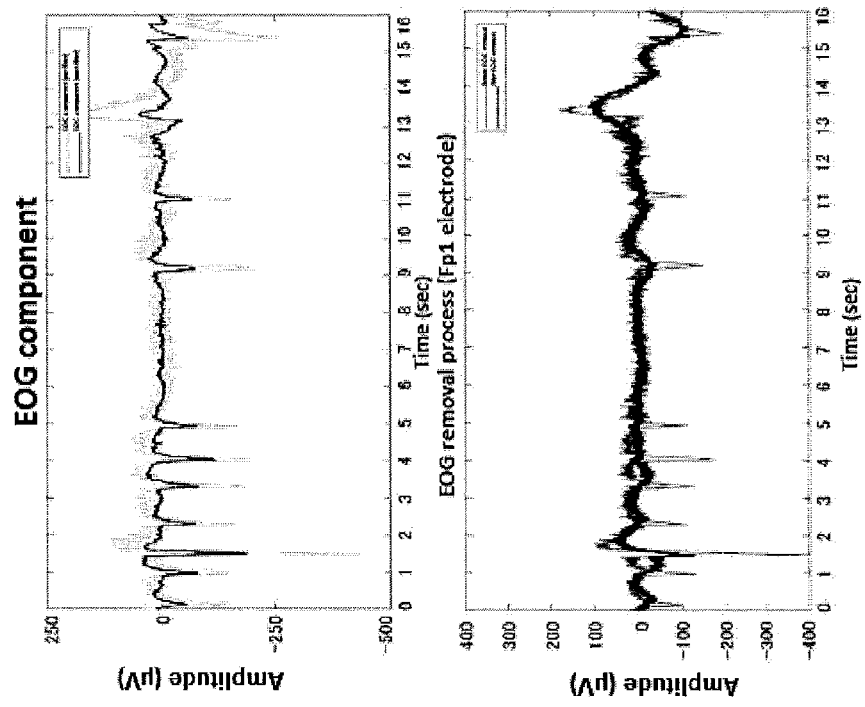

Feature extraction process (1): EOG removal process

Process 1:
*Perform main component analysis on data for 4 electrodes and retrieve EOG component (first component: blue)
*Apply 1 to 30 Hz band pass filter, and reduce slow and fast changes to generate smooth EOG waveform (red).

Process 2:
*Regress original data of each electrode with EOG data to obtain β coefficient for each electrode.
*Remove component obtained by multiplying EOG by β coefficient from original recorded data.
Blue: original Fp1 data
Red: data after EOG removal Feature extraction process (2): EMG removal process Process:

*Remove noise component from waveform after EOG removal by setting the length of 3 × stimulation segment to low pass frequency (0.022 Hz) and 30 Hz high pass, frequency for the waveform.

FIG.28

Feature extraction process (3): Addition of EOG feature

Process:

* Added primary component data 1 ch for removal of EOG to the feature by "reverse utilization of noise"

* Applied band pass filter at 1 to 3 Hz as the processing.

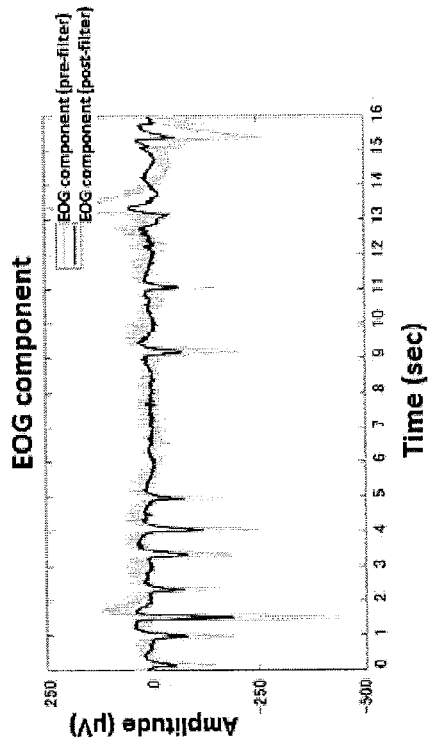

Gray: original EOG component
Black: EOG component after filter (model input)

After processes (1) to (3), a section from 5 to 15 seconds after applying stimulation was divided at each second, and features of frequency ($\delta, \theta, \alpha, \beta$) and amplitude were created at each electrode

FIG.30

Outline of differentiation model

*Model was created at L1 and L6 (30 samples each). Total of "10200" samples were used.
*Criteria for refinement was set so that only subjects with differentiation accuracy of 70% would remain after 4 runs, resulting in 81 subjects.
*Differentiation accuracy at L1 and L6 (feature of 5 to 10 seconds after applying stimulation, 6 samples) for all 170 subjects was "79.4 ± 26.4%" using a refined model.
*There were "93" subjects, i.e., "54.7%", with 70% or greater differentiation accuracy, and "147" subjects, i.e., "86.5%", with a chance level of 50% or greater.

FIG.31

Pain occupancy

*Certainly of when a pain estimation value is differentiated as "having pain".

*Calculation method:

i. Calculate an estimate for no pain (30 samples × 81 subjects) and having pain (30 samples × 81 subjects) by a differentiation model for 81 subjects (differentiation accuracy > 70%) after refinement.

ii. The minimum value (-1) and maximum value (2) of all pain estimation values are divided into, for example, 0.1 widths, and the occupancy of estimation value for having pain for each estimation value is calculated:

"Occupancy (%) for having pain = number of estimation value for having pain/(number of estimation values for having pain + number of estimation values for no pain)".

iii. This is fitted to a sigmoid function to obtain a "pain occupancy function" to create an occupancy model.

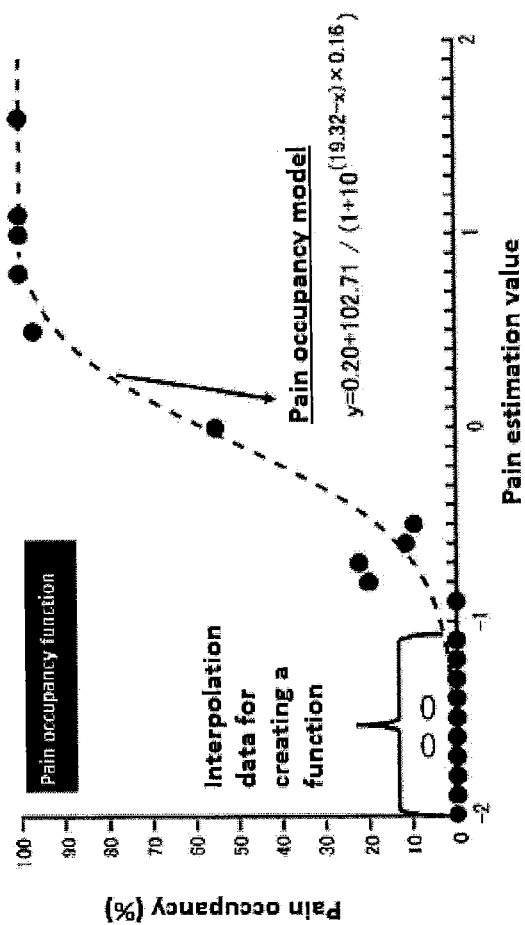

Pain occupancy model
$y = 0.20 + 102.71 / (1 + 10^{(19.32-x) \times 0.16})$

FIG.32

Pain trend analysis (one subject)

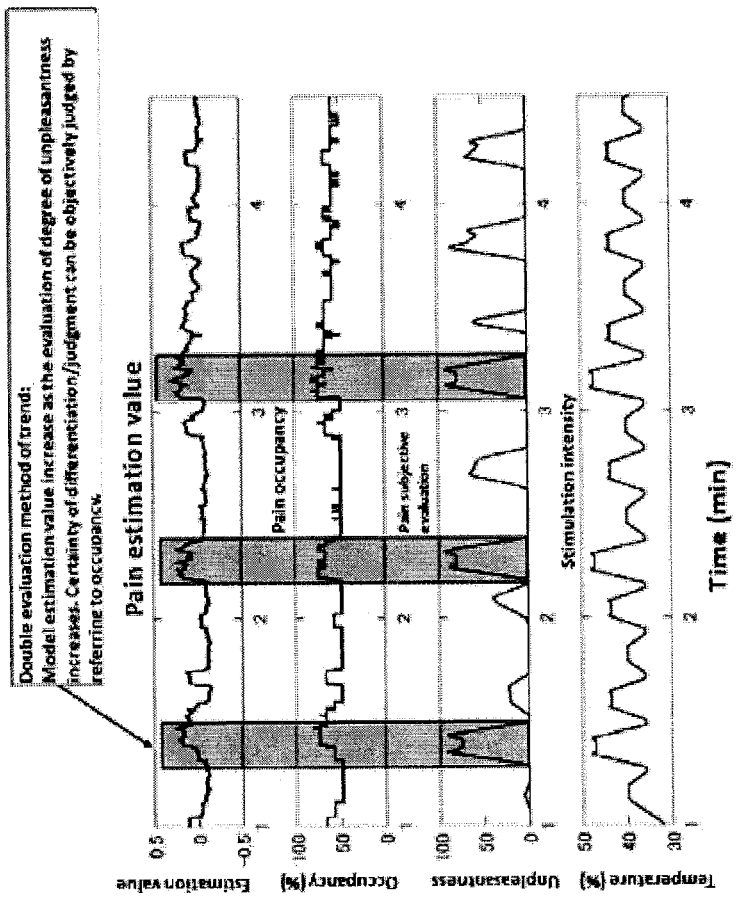

Feature of another experimental data was inputted into a pain model. Pain scores were "displayed as a pain trend" by a temporal change.

EEG data processing:
In the rest segment at 30 seconds from the start of recording, subsequent EEG features were standardized, and then inputted into a refined differentiation model.

Estimation values increased with an increase in subjective evaluation and stimulation intensity. The occurrence rate (certainty) also increased.

The correlation between estimation value and COVAS: r = 0.45, and p ≈ 0.

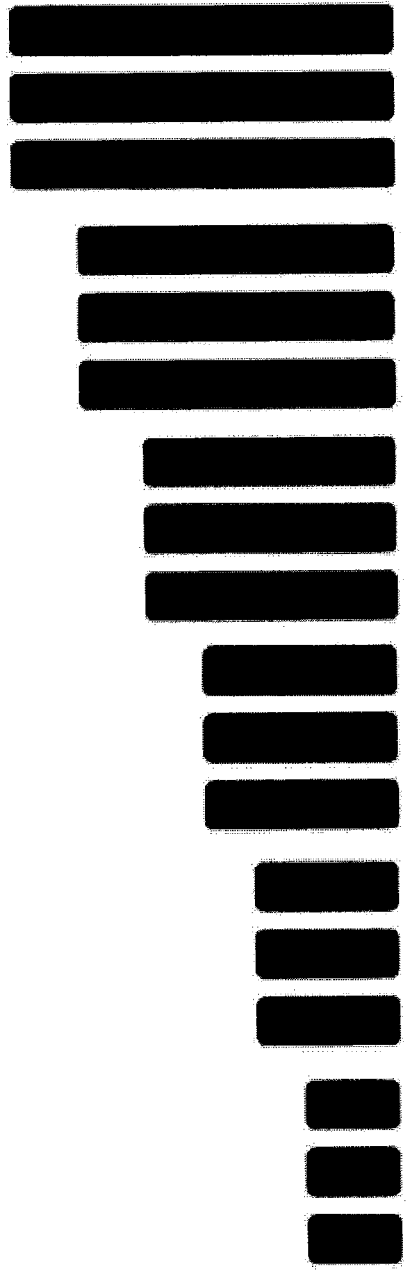

FIG.33

High temperature stimulation paradigm

*6 levels of high temperature stimulation
*3 stimulations at each level
*15 seconds of stimulation application time
*100 second interval between level blocks
*Features:
 mean frequency power ($\delta$, $\theta$, $\alpha$, $\beta$, and $\gamma$)
 mean amplitude of 3 stimulations at each level (15 seconds)
*Differentiation levels: weak pain (levels 1 to 3) and strong pain (levels 4 to 6).
*Number of samples: strong/weak × 3 levels × 40 subjects = 240.

Results of differentiation analysis with condensing of features (present invention)

Feature ranking and differentiation accuracy

FIG.36

Result of differentiation analysis with condensing of features (existing SVM-RFE)

Feature ranking and differentiation accuracy

| Ranking | Feature | | Differentiation accuracy |
|---------|---------|-----|--------------------------|
| 1 | θ | Fz | 0.713 |
| 2 | γ | C4 | 0.696 |
| 3 | β | C3 | 0.708 |
| 4 | Mean amplitude | C4 | 0.708 |
| 5 | Mean amplitude | C3 | 0.679 |
| 6 | Mean amplitude | Cz | 0.667 |
| 7 | θ | Cz | 0.679 |
| 8 | α | Cz | 0.650 |
| 9 | α | C4 | 0.625 |
| 10 | δ | C3 | 0.650 |
| 11 | α | Fz | 0.713 |
| 12 | γ | Cz | 0.696 |
| 13 | δ | Fz | 0.700 |
| 14 | β | C4 | 0.713 |
| 15 | θ | C4 | 0.704 |
| 16 | α | C3 | 0.704 |
| 17 | γ | Fz | 0.717 |
| 18 | γ | C3 | 0.717 |
| 19 | β | Fz | 0.696 |
| 20 | θ | C3 | 0.679 |
| 21 | δ | C4 | 0.692 |
| 22 | δ | Cz | 0.679 |
| 23 | β | Cz | 0.679 |
| 24 | Mean amplitude | Fz | 0.675 |

Economic differentiation/estimation model

1. Top 4 types of features of existing SVM with condensing of features include the same types as the case using sigmoid condensing.

2. While the same differentiation accuracy of "71.3%" is materialized with a single feature, this is only a difference of one feature.

3. Calculation cost is high because leave-one-out cross validation is performed 240 times for SVM model construction, and this process is performed 24 times for ranking 24 features.

FIG.37

Difference in calculation cost between sigmoid condensing and condensing in SVM-RFE

A. SVM-RFE

Training data
  Sample = $[x_1, x_2, \cdots, x_k, \cdots, x]$
Classification label
  Class = $[1, 0, 1, 0, \cdots, y_k, \cdots, y]$
Set of features remaining after RFE
  Sfeature = $[1, 2, \cdots, n]$
Ranking of features
  Rank = [ ]

1. Limit training data to remaining features
   X = Sample(:, Sfeature)
2. Train differentiator (SVM)
   Classifier = SVM (X, Class)
3. Calculate weighting coefficient of features
   Weight = $\Sigma \alpha_k y_k x_k$
4. Calculate ranking criteria for all features
   Criterion$_i$ = (Weight$_i$)$^2$ for all $i$
5. Find feature with smallest ranking criteria
   F = argmin (Criterion)
6. Update ranking list of remaining features
   Rank = [Sfeature (F), Rank]
7. Exclude feature with smallest ranking criteria
   Sfeature = Sfeature (1: f − 1, f + 1: length (Sfeature))
8. Output feature ranking list
   Feature ranked list r.

B. Sigmoid condensing

1. Create a differentiation function
2. Fit function to each feature to calculate weighting coefficient
3. Rank features based on coefficient Repeat the same number of times as number of features

FIG.38

Validation of economical differentiation model 240 samples were divided into 10 (10 data sets of 4 subjects × 6 data). 90% were used as data for creating a machine learning (SVM) model to differentiate/estimate the pain level of the remaining 10%. Only the top two features were used.

| Cross validation | Test sample | | | | | | | | | | | | | | | | | | | | | | | | Differentiation accuracy (%) |
|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | |
| Test 1 | 0 | 0 | 0 | 1 | 1 | 0 | 0 | 0 | 0 | 1 | 1 | 0 | 0 | 0 | 0 | 0 | 0 | 0 | 1 | 1 | 1 | 1 | 0 | 0 | 75.0 |
| Test 2 | 0 | 0 | 0 | 1 | 1 | 0 | 0 | 0 | 0 | 1 | 0 | 0 | 1 | 1 | 1 | 0 | 0 | 0 | 0 | 0 | 0 | 1 | 0 | 0 | 70.8 |
| Test 3 | 1 | 1 | 0 | 1 | 0 | 0 | 1 | 1 | 1 | 0 | 0 | 0 | 0 | 0 | 0 | 0 | 1 | 0 | 1 | 0 | 1 | 0 | 0 | 0 | 58.3 |
| Test 4 | 0 | 0 | 0 | 0 | 1 | 1 | 0 | 0 | 0 | 1 | 1 | 0 | 0 | 0 | 0 | 1 | 0 | 0 | 0 | 0 | 0 | 1 | 1 | 0 | 70.8 |
| Test 5 | 1 | 1 | 0 | 1 | 0 | 0 | 0 | 0 | 0 | 0 | 0 | 0 | 0 | 0 | 1 | 0 | 0 | 0 | 1 | 0 | 1 | 0 | 1 | 1 | 70.8 |
| Test 6 | 0 | 0 | 0 | 1 | 1 | 0 | 0 | 0 | 0 | 1 | 0 | 0 | 0 | 1 | 1 | 1 | 0 | 0 | 0 | 0 | 0 | 1 | 1 | 0 | 62.5 |
| Test 7 | 0 | 0 | 1 | 1 | 0 | 0 | 0 | 0 | 1 | 0 | 0 | 0 | 1 | 1 | 1 | 0 | 0 | 0 | 0 | 0 | 0 | 0 | 0 | 0 | 75.0 |
| Test 8 | 0 | 0 | 0 | 1 | 0 | 0 | 0 | 1 | 1 | 0 | 0 | 0 | 0 | 1 | 1 | 1 | 0 | 0 | 0 | 0 | 0 | 0 | 1 | 0 | 66.7 |
| Test 9 | 0 | 0 | 0 | 1 | 0 | 0 | 0 | 0 | 0 | 0 | 1 | 0 | 0 | 0 | 0 | 1 | 0 | 0 | 0 | 0 | 0 | 0 | 0 | 0 | 83.3 |
| Test 10 | 1 | 1 | 0 | 0 | 0 | 0 | 0 | 0 | 0 | 0 | 0 | 0 | 0 | 0 | 0 | 0 | 1 | 0 | 0 | 0 | 0 | 0 | 1 | 0 | 79.2 |

0 = no differentiation error; 1 = differentiation error

Mean differentiation accuracy is "71.5%". Differentiation/estimation of independent samples is materialized at a 70% level even with 2 features.

Patterns of change in differentiation accuracy and gain

FIG.43

List of 23 features of model with highest gain in differentiation accuracy

| Inputted number of features | Electrode position | Feature | Cross validation differentiation accuracy Mean | SD | Test data differentiation accuracy |
|---|---|---|---|---|---|
| 1 | Pz | γ2 | 60.69 | 0.90 | 60.59 |
| 2 | C4 | γ2 | 61.28 | 0.67 | 60.79 |
| 3 | Fp2 | γ1 | 61.52 | 0.74 | 60.96 |
| 4 | Fp1 | γ1 | 61.48 | 0.80 | 60.99 |
| 5 | Fp1 | γ2 | 61.50 | 0.83 | 60.88 |
| 6 | F4 | α | 61.67 | 0.71 | 60.71 |
| 7 | F3 | α | 61.80 | 0.82 | 61.18 |
| 8 | Pz | γ1 | 61.78 | 0.79 | 61.07 |
| 9 | F3 | β | 61.70 | 0.82 | 60.96 |
| 10 | Fp2 | β | 61.83 | 0.64 | 60.91 |
| 11 | C4 | δ | 61.91 | 0.70 | 60.99 |
| 12 | Fp2 | α | 62.05 | 1.11 | 61.04 |
| 13 | Pz | β | 62.65 | 1.07 | 61.52 |
| 14 | C3 | γ2 | 62.60 | 1.13 | 61.72 |
| 15 | Fp2 | Mean absolute amplitude | 63.99 | 0.70 | 63.25 |
| 16 | C3 | θ | 63.97 | 0.71 | 63.22 |
| 17 | C3 | δ | 63.93 | 0.70 | 63.23 |
| 18 | Fp1 | β | 63.94 | 0.68 | 63.39 |
| 19 | Fp1 | Mean absolute amplitude | 64.18 | 0.66 | 63.62 |
| 20 | C4 | γ1 | 64.22 | 0.78 | 63.37 |
| 21 | F4 | θ | 64.21 | 0.78 | 63.46 |
| 22 | F3 | δ | 64.17 | 0.91 | 63.65 |
| 23 | Fp2 | θ | 64.18 | 0.82 | 63.82 |

Maximum gain model: 23 features

FIG.44

Differentiation model determination process 2 using a double condensing process

S10050 Quantification of differentiation property of features

For example, brainwave features (e.g., 49 features) are fitted using a 2 value function with 2 value change pattern "0, 1" and $R^2$ value is calculated for each individual.

↓

S10060 Ranking of features

For example, mean value of $R^2$ values of each feature is calculated and features (e.g., 49 features) are ranked.

↓

S10070 Hierarchical differentiation analysis 1 including features in order from top ranking features For example, features are inputted into a logistic regression model in order from top ranking features. For example, differentiation accuracy of 32160 samples are calculated by 5 × 4 fold leave-one-out cross validation.

↓

S10070-1 Re-ranking of features by Diff value

For example, the following is performed:
1. single main feature: number 1 ranking feature
2. supporter feature: others
Find difference in adjacent features by diff and rearrange in descending order.

↓

S10070-2 Hierarchical differentiation analysis 2 including features in order from top ranking features For example, "economical differentiation model" is determined by performing sigmoid approximation of differentiation accuracy change patterns of all 49 models and identifying inflection point with the highest gain in accuracy improvement with the fewest features.

↓

S10080 Determination of differentiation model

FIG.45

Determination of differentiation model by re-ranking features

Re-ranking of features using a value of difference (Diff) in differentiation accuracy of adjacent models has the effect of efficiently aggregating supporter features to the top of ranking. Features that have the potential to contribute the most to increase in differentiation accuracy are added in order from the top.

2. Repeated re-ranking tends to result in aggregation of features with high contribution to the top of ranking. For example, differentiation accuracy nearly reached the ceiling with the second re-ranking as the earliest stage, with the few features (10 to 15 features).

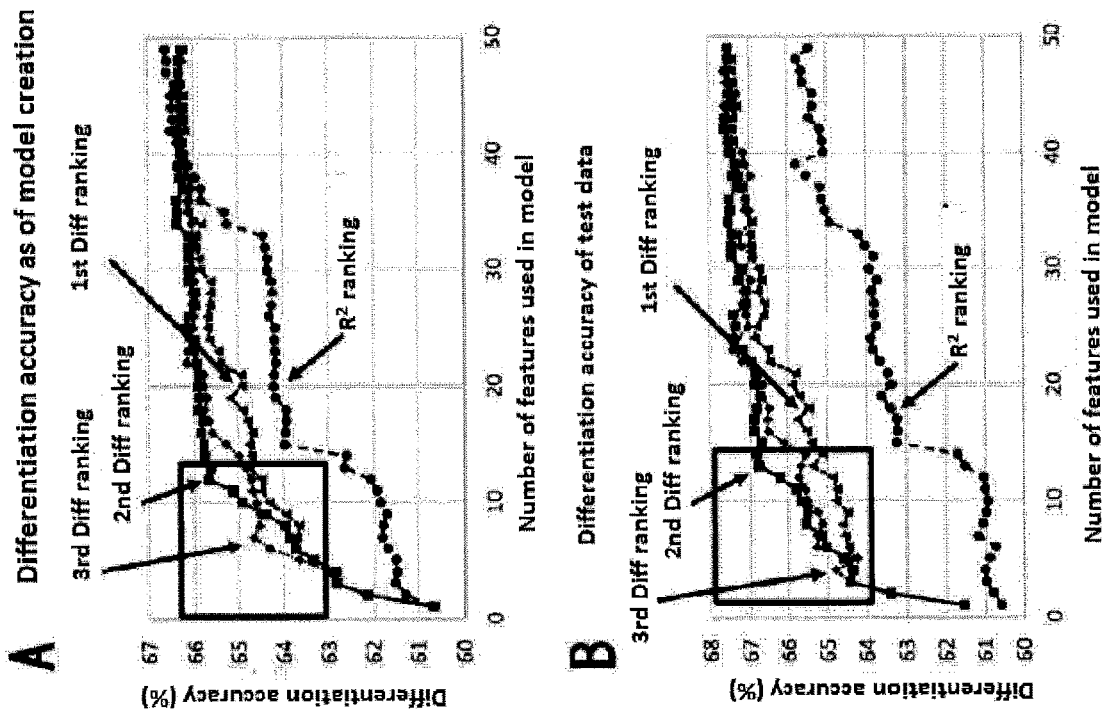

EEG feature extraction process (49 features)

FIG.56

Outline of "tailor-made pain differentiation estimation method 1"

Procedure 1:
Hyperparameter (C and γ for support vector machine (SVM)) is determined in all samples by cross validation (CV)

Procedure 2:
Model is created from all samples using the hyperparameter of procedure 1 to calculate differentiation accuracy at the individual level

Procedure 3:
Group of subjects with close differentiation accuracy is created from the ranking of differentiation accuracy at an individual level

Procedure 4:
Hyperparameter of each group is determined by CV

Procedure 5:
Model is created from a sample of each group using the hyperparameter found in procedure 4, differentiation accuracy at an individual level is calculated, and a "differentiation MAX model" is identified.

Procedure 2:
Model is created from all samples using the hyperparameter of procedure 1 (C and γ) to calculate differentiation accuracy at the individual level C = 2, and γ = 0.125 was used in this example.

FIG.62

Differentiation MAX model in demographic group

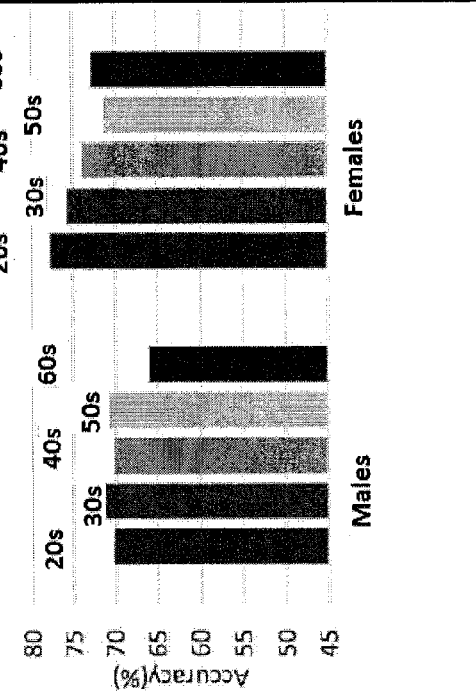

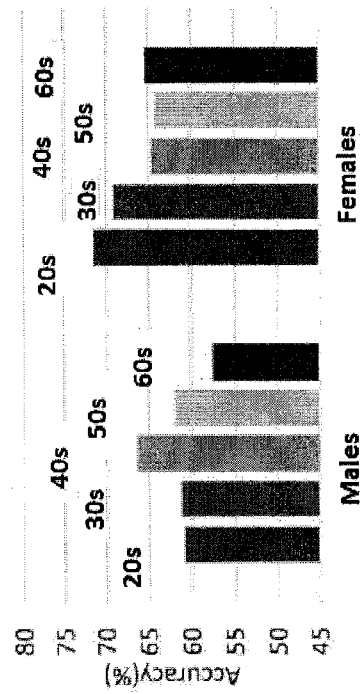

*In all sample model,
- differentiation accuracy was higher in males than females
- differentiation accuracy was highest for 40s in males and 20s for females
- differentiation was the lowest in males older than 60.

*In MAX model
- differentiation accuracy was higher in males than females just as in the all sample model.
- difference in differentiation accuracy was small in males in their 20s to 50s, which was around 70%.

FIG.63

Outline of "tailor-made pain differentiation estimation method 2"

Procedure 1:
Hyperparameter (C and γ for SVM) is determined in all samples by cross validation (CV)

Procedure 2:
Model is created from all samples using the hyperparameter of procedure 1 to calculate differentiation accuracy at the individual level Procedure 3:
Group of subjects with close differentiation accuracy is created from the ranking of differentiation accuracy at an individual level Procedure 4:
Hyperparameter of each group is determined by CV Procedure 5:
Model is created from a sample of each group using the hyperparameter found in procedure 4, differentiation accuracy at an individual level is calculated, and a "differentiation maximum (MAX) model" is identified.

---

Improvement in differentiation accuracy by differentiation model combination technology (ensemble method)

Procedure 6:
Models are rearranged in descending order by differentiation accuracy using 62 models one at a time Procedure 7:
Differential model is increased one at a time, differentiation accuracy is calculated by "ensemble method", and the number of differentiation models with the highest differentiation accuracy is employed ("ensemble pruning")

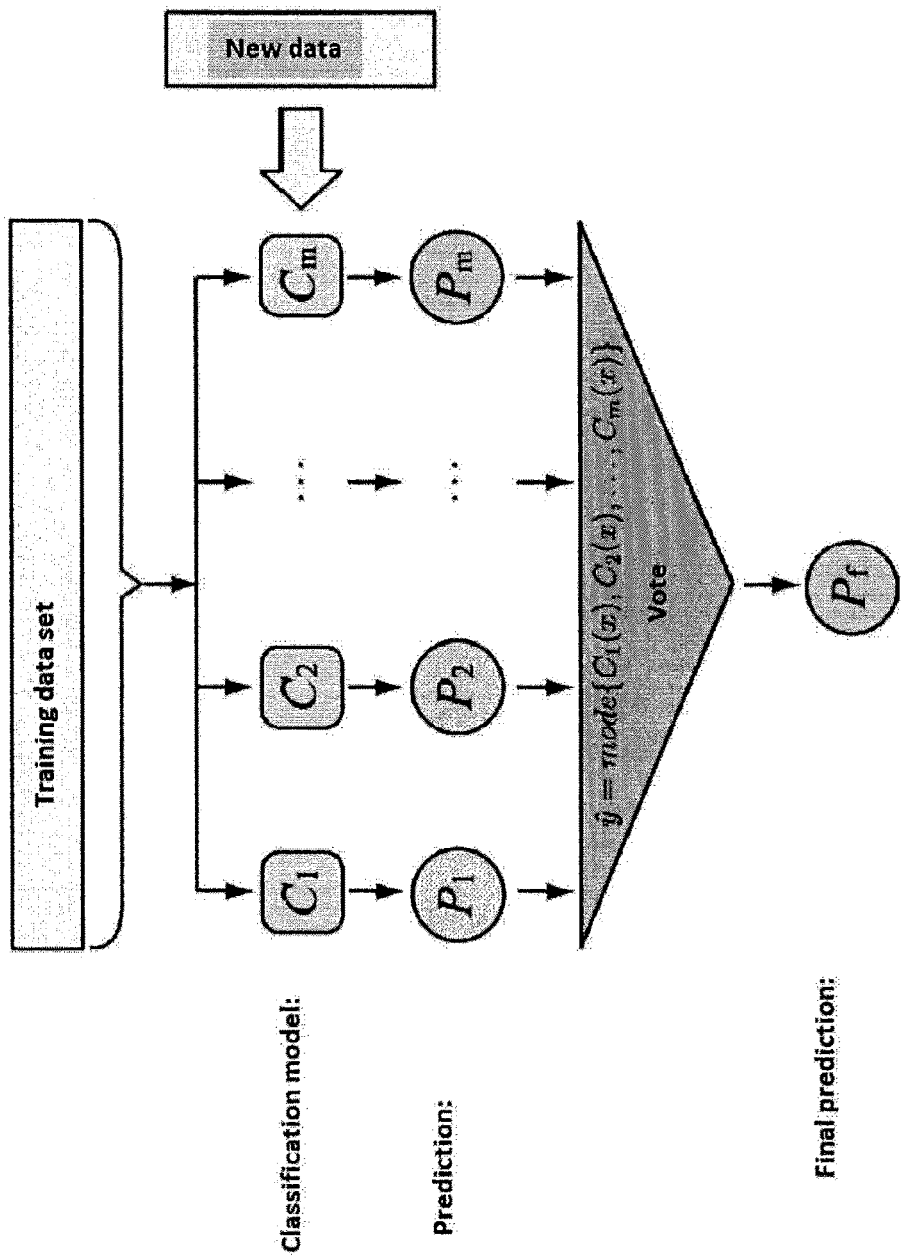
FIG.64 Conceptual diagram 1 of ensemble method

Example for improved differentiation accuracy by ensemble pruning: object 1

Differentiation accuracy from the ensemble method improved about 7% compared to the differentiation maximum (MAX) method in Example 16

Example for improved differentiation accuracy by ensemble pruning: object 2

Differentiation accuracy from the ensemble method improved about 7% compared to the differentiation maximum (MAX) method in Example 16

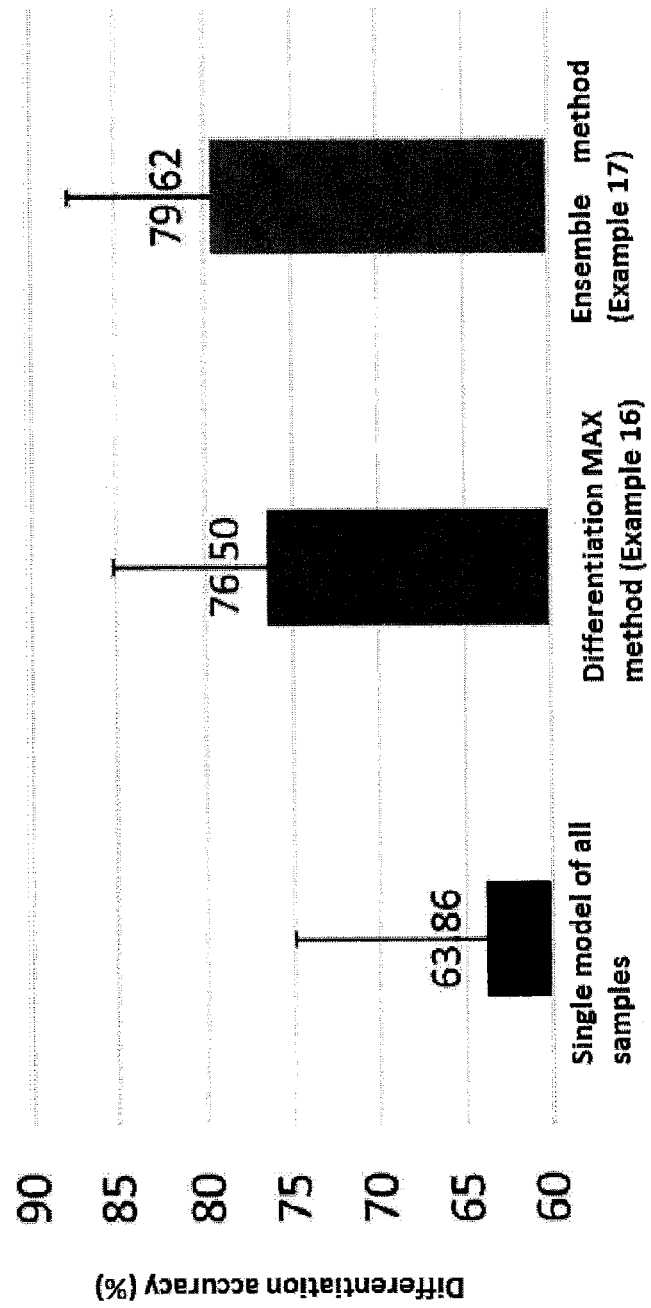
FIG. 68 Summary of improvement in differentiation accuracy by ensemble method 1

FIG.69

Outline of "tailor-made pain differentiation estimation method 3"

Procedure 1:
Hyperparameter (C and γ for SVM) is determined in all samples by cross validation (CV)

Procedure 2:
Model is created from all samples using the hyperparameter of procedure 1 to calculate differentiation accuracy at the individual level Procedure 3:
Group of subjects with close differentiation accuracy is created from the ranking of differentiation accuracy at an individual level Procedure 4:
Hyperparameter of each group is determined by CV Procedure 5:
Model is created from a sample of each group using the hyperparameter found in procedure 4, differentiation accuracy at an individual level is calculated, and a "differentiation MAX model" is identified.

Improvement in differentiation accuracy by differentiation model combination technology (ensemble method)

Procedure 6A:
Models are rearranged in descending order by differentiation accuracy using 62 models one at a time Procedure 7A:
Differentiation MAX model is selected as the "main model", and the remaining "supporter models" are comprehensively added one by one for all combinations to improve differentiation accuracy stepwise.

FIG.70

Detailed description of new ensemble method

1. Differentiation maximum (MAX) model is selected from all models (N models) as the "main model"

2. N-1 models obtained from excluding the main model from all models are selected as "supporter models"

3. Two model sets that improve differentiation accuracy the most by the ensemble method when one model is selected from N - 1 supporter models and added to the main model are selected as the "updated main models". All supporter models are inputted one at a time to cover all combinations.

4. N - 2 models obtained from excluding the updated main models from all models are selected as "updated supporter models"

5. Procedures 3 to 4 are similarly repeated for the model set that improves differentiation accuracy the most by the ensemble method to update the updated main models and updated supporter models, and these procedures are repeated until there is no more updated supporter models.

Example of improved differentiation accuracy by improved ensemble pruning method

*Differentiation accuracy improved 5 to 10% for all objects.

FIG.73 Outline of "tailor-made pain differentiation estimation method 4 with calibration"

Comparison of differentiation accuracy of ensemble method using calibration (one object)

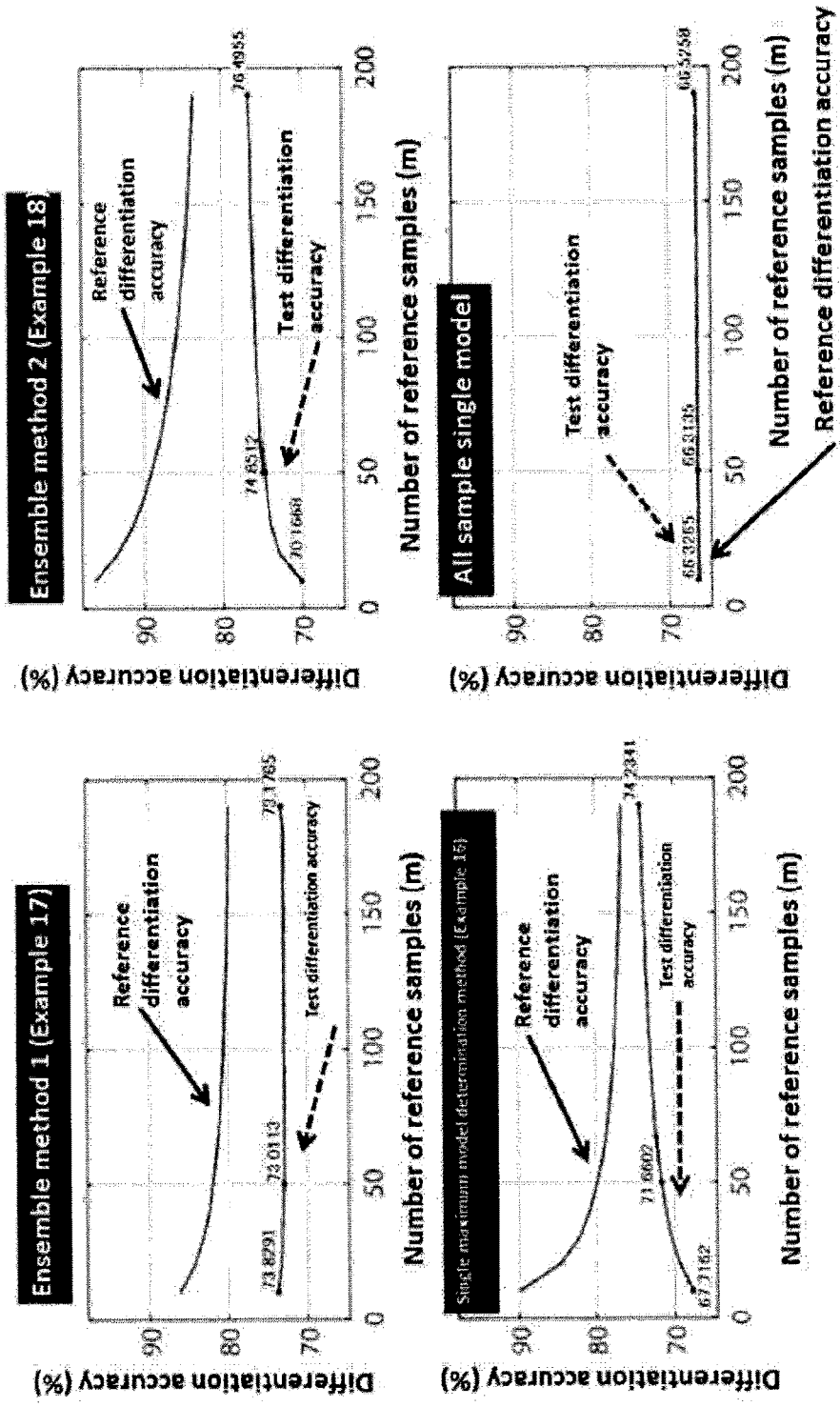

FIG.76

Comparison of differentiation accuracy of ensemble method with calibration 2

Test differentiation accuracy was similar even if number of reference samples increases for single model of all samples and ensemble method 1 (Example 17)

All sample single model:
63.9 ⇔ 63.9%

Ensemble method 1 (Example 17)
73.8 ⇔ 73.0%

Ensemble method 2 (Example 18)
Accuracy improved about 5%
70.2 ⇒ 74.9%

Single maximum model determination method (Example 16)
Accuracy improved about 4%
67.7 ⇒ 71.7%

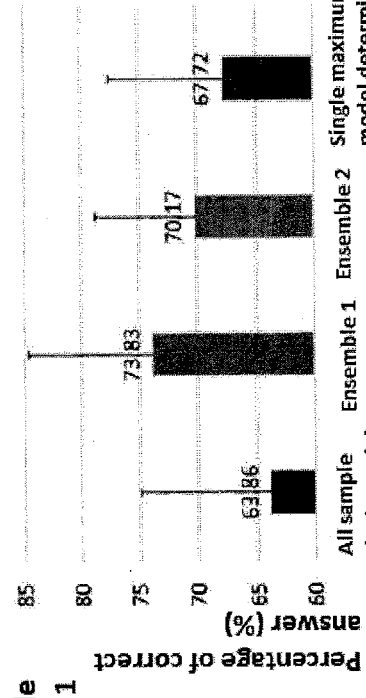
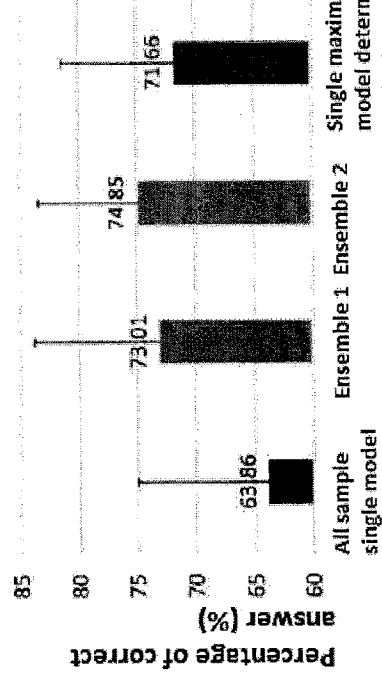

Electrode arrangement example (10-20 system)

FIG.82

Extraction of dominant features by a process of condensing features

Feature ranking and differentiation accuracy

| Ranking | Feature | | R² value | Differentiation accuracy |
|---|---|---|---|---|
| 1 | Mean amplitude | C4 | 0.197 | 0.654 |
| 2 | θ | Fz | 0.196 | 0.713 |
| 3 | β | C3 | 0.194 | 0.700 |
| 4 | γ | C4 | 0.194 | 0.708 |
| 5 | Mean amplitude | C3 | 0.186 | 0.679 |
| 6 | Mean amplitude | Cz | 0.180 | 0.667 |
| 7 | α | Cz | 0.179 | 0.667 |
| 8 | Mean amplitude | Fz | 0.176 | 0.663 |
| 9 | β | Cz | 0.086 | 0.675 |
| 10 | γ | C3 | 0.081 | 0.658 |
| 11 | δ | C4 | 0.070 | 0.671 |
| 12 | α | Fz | 0.062 | 0.663 |
| 13 | β | Fz | 0.041 | 0.650 |
| 14 | γ | Cz | 0.039 | 0.650 |
| 15 | β | C4 | 0.039 | 0.642 |
| 16 | δ | C3 | 0.037 | 0.642 |
| 17 | δ | Fz | 0.034 | 0.638 |
| 18 | θ | C4 | 0.031 | 0.679 |
| 19 | α | C3 | 0.031 | 0.679 |
| 20 | θ | Cz | 0.028 | 0.692 |
| 21 | γ | Fz | 0.026 | 0.667 |
| 22 | α | C4 | 0.023 | 0.654 |
| 23 | δ | Cz | 0.021 | 0.675 |
| 24 | θ | C3 | 0.019 | |

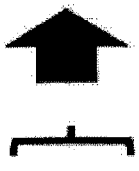

Economical pain differentiation/estimation model
Dominant features were found, which exhibit "71.3%" of two level pain differentiation accuracy by using only two top ranking features with high sigmoid function approximation Feature extraction process

FIG.85

Determination of differentiation model by re-ranking of features

1. Repeated re-ranking of features by value of difference (Diff) of adjacent differentiation accuracy tends to result in aggregation of features with high contribution to the top of ranking.

2. Differentiation accuracy nearly reached the ceiling with the second re-ranking as the earliest stage, with the fewest features (12 features).

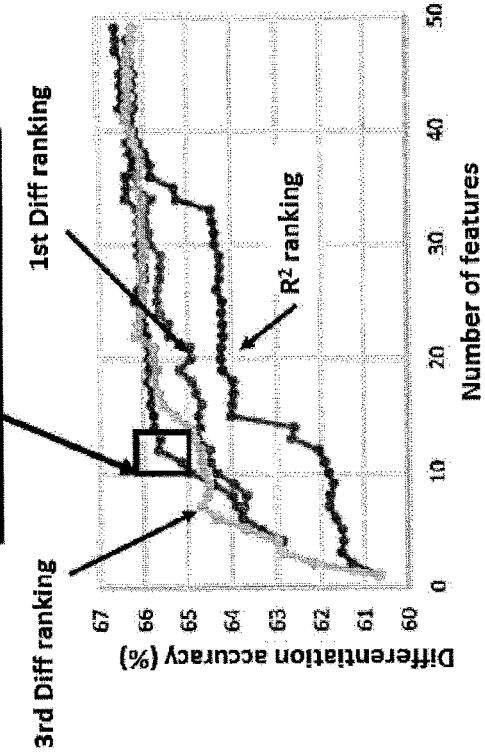

FIG.86 objects (n = 158)

| Age group | Number | Male | Female |
|---|---|---|---|
| 20s | 38 | 29 | 9 |
| 30s | 29 | 12 | 17 |
| 40s | 38 | 12 | 26 |
| 50s | 35 | 14 | 21 |
| 60s | 17 | 11 | 6 |
| 70s | 1 | 0 | 1 |
| All generations | 158 | 78 | 80 |

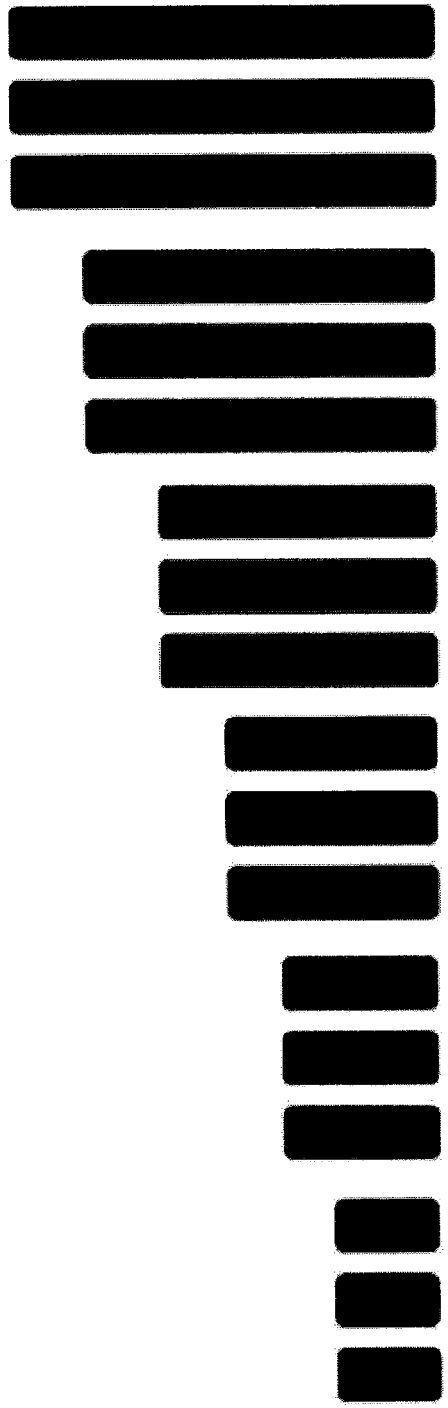
FIG.87 High temperature stimulation paradigm
*6 levels of high temperature stimulation
*3 stimulations at each level
*15 seconds of stimulation application time
*100 second interval between level blocks
*Differentiation levels: weak pain and strong pain
*Number of samples: strong/weak × 3 levels × 158 subjects =948 samples

FIG.88

EEG feature extraction (53 features)

1. Mean amplitude (7 mean amplitudes):
Mean value of absolute values of amplitudes during 15 seconds after applying stimulation, standardized among individuals.
2. Frontal-parietal potential correlation (4 correlations)
Potential correlation of four frontal electrodes (Fp1, Fp2, F3, and F4) and parietal Pz
3. Frequency power (35 frequency powers)
5 bands of "δ, θ, α, β, and γ" at 7 electrodes
4. Complexity index (multiscale entropy: 7 indices)
MSE at seven electrodes 1. Scale factor: 20~50ms
2. Comparison: Between 2 points
3. Threshold: 15% of SD or greater

FIG.89

Multiscale entropy (MSE)

MSE calculates sample entropy ($S_E$) of each time scale ($\tau$).

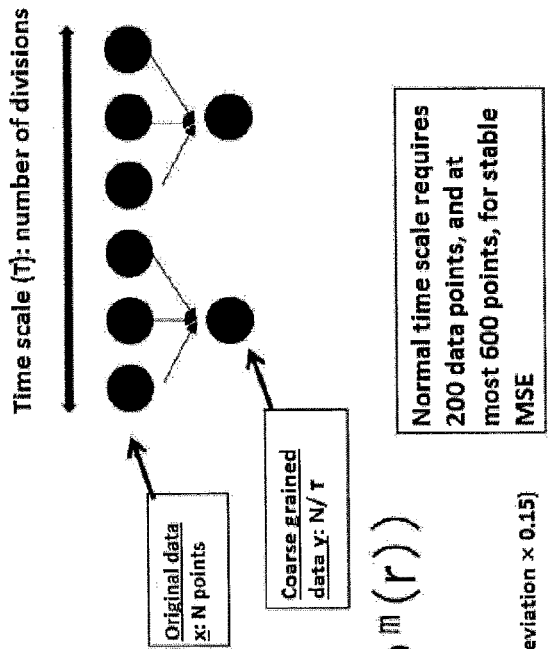

Time scale ($\tau$): number of divisions

Original data
$\underline{x}$: N points

Coarse grained
data $\underline{y}$: N/$\tau$

Normal time scale requires 200 data points, and at most 600 points, for stable MSE $$y = \sum x_i / \tau \; ; \; 1 \leq y \leq N/\tau$$

$x$ = Original data
$y$ = Coarse grained data
$\tau$ = Time scale (number of divisions of original data)
$N$ = Number of original data $$S_E(m, r, N) = -\ln(\phi^{m+1}(r)/\phi^m(r))$$

$S_E$ = Sample entropy
$m$ = Distance of compared time points
$r$ = Similarity threshold value, range (<original data standard deviation × 0.15)
$N$ = Number of data points
$\ln$ = Natural logarithm
$\phi$ = Percentage of points with distance between m points within similarity threshold value r $$Complexity\ index© = \sum S_E(i) \quad (1 < I < N)$$

$S_E$ = Sample entropy
$I$ = Time scale number
$N$ = Number of time scales

Busa & Emmerik, 2016

Discrete feature

FIG.92

Extraction of dominant features (binomial classification)

| | EEG feature | | | Ranking by feature coefficient (standardized β) | | | | Ratio of coefficient with no effect (zero) | | |
|---|---|---|---|---|---|---|---|---|---|---|
| | Electrode | Feature type | | L4 vs. 5 | L5 vs. 6 | L1 vs. L6 | Mean ranking | L4 vs 5 | L5 vs 6 | L1 vs L6 |
| ① | Pz | freq | γ | 1 | 1 | 1 | 1.0 | 0 | 0 | 0 |
| ② | F4_Pz | corr | | 8 | 4 | 4 | 5.3 | 0 | 0 | 0 |
| ③ | Fp1 | MSE | | 13 | 6 | 2 | 7.0 | 11 | 1 | 0 |
| ④ | Fp2 | freq | β | 9 | 8 | 7 | 8.0 | 19 | 4 | 0 |
| ⑤ | Fp2 | amp | | 12 | 12 | 6 | 10.0 | 16 | 8 | 40 |
| | Fp1 | freq | α | 5 | 10 | 22 | 12.3 | 6 | 4 | 0 |
| ⑥ | Fp2_Pz | corr | | 15 | 14 | 11 | 13.3 | 22 | 9 | 2 |
| | Pz | freq | θ | 7 | 31 | 5 | 14.3 | 9 | 59 | 0 |
| | F3 | freq | δ | 2 | 26 | 20 | 16.0 | 0 | 46 | 31 |
| | F4 | freq | β | 18 | 19 | 16 | 17.7 | 30 | 29 | 17 |
| | C4 | freq | β | 16 | 22 | 17 | 18.3 | 24 | 38 | 19 |
| | Fp1 | freq | β | 19 | 2 | 36 | 19.0 | 31 | 0 | 89 |
| | C3 | freq | γ | 3 | 18 | 37 | 19.3 | 1 | 29 | 89 |
| | Fp1 | amp | | 10 | 39 | 13 | 20.7 | 15 | 79 | 7 |
| | Pz | freq | δ | 28 | 13 | 21 | 20.7 | 56 | 9 | 33 |
| | F3 | freq | α | 33 | 20 | 10 | 21.0 | 71 | 32 | 1 |
| | C3 | freq | δ | 23 | 28 | 14 | 21.7 | 50 | 52 | 7 |
| | F3_Pz | corr | | 6 | 27 | 33 | 22.0 | 9 | 46 | 86 |
| | C4 | freq | γ | 42 | 21 | 3 | 22.0 | 89 | 37 | 0 |
| | C4 | freq | θ | 17 | 42 | 8 | 22.3 | 27 | 82 | 0 |
| | Pz | freq | α | 24 | 5 | 38 | 22.3 | 50 | 0 | 89 |
| | F4 | freq | α | 26 | 35 | 9 | 23.3 | 56 | 70 | 1 |
| | C4 | freq | δ | 22 | 23 | 29 | 24.7 | 49 | 42 | 77 |
| | F4 | freq | θ | 41 | 17 | 18 | 25.3 | 89 | 27 | 23 |
| | C3 | MSE | | 31 | 30 | 15 | 25.3 | 69 | 58 | 9 |
| | F3 | freq | θ | 34 | 15 | 31 | 26.7 | 71 | 17 | 84 |

1. Features are rearranged by the magnitude of standardizing coefficient in descending order 2. Features containing 30% or more zero coefficients in 100 differentiations and estimations are eliminated.
↓
6 features are extracted

FIG.94

Differentiation accuracy of a generalized model for high/low temperature pain stimulation 1. Number of samples: 2 levels × 3 runs × 309 subjects
2. 7 electrodes: Fp1, Fp2, F3, F4, C3, C4, Pz
3. Features
   a. absolute mean amplitude
   b. frontal-parietal potential correlation
   c. frequency power
      δ, θ, α, β, and γ
   d. multiscale entropy
   e. phase synchronization between electrodes
      δ, θ, α, β, and γ

4. Differentiation model
   Multiple regression model

5. Differentiation method
   Feature coefficient of differentiation model was determined by leave-one-out cross validation using learning data (n-1): pain level of remaining one subject was differentiated and estimated (total of 309 times).

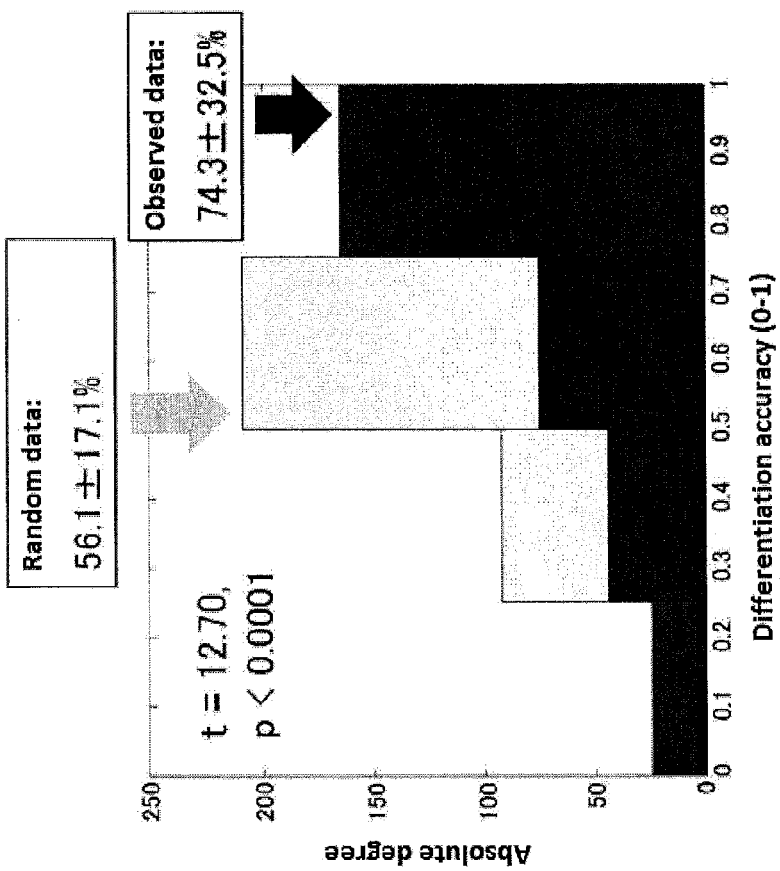

us 11,922,277 B2

PAIN DETERMINATION USING TREND ANALYSIS, MEDICAL DEVICE INCORPORATING MACHINE LEARNING, ECONOMIC DISCRIMINANT MODEL, AND IoT, TAILORMADE MACHINE LEARNING, AND NOVEL BRAINWAVE FEATURE QUANTITY FOR PAIN DETERMINATION

CROSS-REFERENCE TO RELATED APPLICATION

This application is a national stage application filed under 35 U.S.C. § 371, of International Patent Application No. PCT/JP2018/025769 filed Jul. 6, 2018, which claims the benefit of and priority to Japanese Application No. 2017-133422 filed Jul. 7, 2017; Japanese Application No. 2017-199374 filed Oct. 13, 2017; Japanese Application No. 2017-254565 filed Dec. 28, 2017; Japanese Application No. 2017-254560 filed Dec. 28, 2017; and Japanese Application No. 2018-002777 filed on Jan. 11, 2018, the contents of each of which are hereby incorporated by reference in their entirety.

TECHNICAL FIELD

The present invention relates to differentiation of the quality and quantity of pain by utilizing trend analysis of biological signals such as a brainwave obtained from an object. More specifically, the present invention relates to grouping biological signal values (especially brainwave signals) by time frames (blocks) and averaging measurements, and analyzing changes in the mean value thereof to conduct analysis that better corresponds to subjective pain. The present invention also relates to an economical differentiation model of a technology for differentiating pain using brainwaves. The present invention also relates to technologies for materializing individualized (tailor-made) machine learning. The present invention also relates to a novel feature of brainwaves for differentiating pain.

BACKGROUND ART

Pain is intrinsically subjective, but objective evaluation thereof is desirable for therapy. Patients often suffer from an undesirable experience due to underestimation of pain. In this regard, a method for objectively estimating pain using brainwaves has been proposed (see, for example, Patent Literature 1).

However, the intensity of pain is subjective, so that objective evaluation is challenging. Brainwave signals also vary widely such that the signals do not necessarily correspond to subjective evaluation. Further, a methodology for effectively monitoring temporal changes in pain has not been established. Pain differentiation is still at a nascent stage, such that efficient model generation and differentiation methods have not been provided.

Machine learning is widely used as a method for materializing artificial intelligence. A methodology referred to as ensemble learning is known as a method for constructing an algorithm that is capable of extracting information indicating characteristics of input data with high precision from the input data (e.g., Patent Literatures 2 to 3).

Ensemble learning is a methodology for obtaining a highly accurate information extraction apparatus by generating a plurality of information extraction apparatuses with relatively low accuracy (hereinafter, referred to as weak learners) using a plurality of supervisory data and combining outputs of the plurality of generated weak learners.

CITATION LIST

Patent Literature

[PTL 1] Japanese National Phase PCT Laid-open Publication No. 2010-523226
[PTL 2] Japanese Laid-Open Publication No. 2005-44330
[PTL 3] Japanese Laid-Open Publication No. 2013-164863

SUMMARY OF INVENTION

Solution to Problem

In one aspect, the present invention relates to differentiating the quality and quantity of pain by utilizing trend analysis (chronological analysis) of biological signals such as brainwaves obtained from an object. More specifically, the present invention is an invention based on discovering that grouping biological signal values (especially brainwave signals) by time frames (blocks) and averaging measurements, and analyzing changes in the mean value thereof leads to results that better corresponds to changes in subjective pain.

In this aspect, the present invention provides, for example, the following.
(Item 1)
A method of monitoring pain of an object being estimated based on a brainwave of the object being estimated, comprising:
  a) obtaining from the object being estimated brainwave data or analysis data thereof by measuring a brainwave in response to stimulation;
  b) obtaining a temporal change of a mean value of the brainwave data and analysis data thereof in a specific time frame; and
  c) evaluating or monitoring a level of pain of the object being estimated from the brainwave data or analysis data thereof based on the temporal change of the mean value.
(Item 2)
The method of item 1, wherein the specific time frame is at least 20 seconds or greater.
(Item 3)
The method of item 1 or 2, wherein the specific time frame is at least 30 seconds or greater.
(Item 4)
The method of any one of items 1 to 3, wherein the specific time frame is at least 40 seconds or greater.
(Item 5)
The method of any one of items 1 to 4, wherein the pain is judged to be strong if the temporal change of the mean value is a monotonic increase, and the pain is judged to be weak if the temporal change is a monotonic decrease.
(Item 6)
The method of any one of items 1 to 5, wherein a mean value in the specific time frame is calculated by a non-overlapping block averaging method.
(Item 7)
The method of any one of items 1 to 6, wherein a mean value of two or more time frames is used as the mean value.
(Item 8)
The method of item 7, wherein the two or more time frames have time frames of at least 10 to 120 seconds and 30 to 300 seconds, and optionally comprise a time frame of 120 seconds or greater.

(Item 9)
The method of any one of items 1 to 8, wherein a pain index is used when monitoring the level of pain.

(Item 10)
The method of item 9, wherein the pain index comprises a numerical value that facilitates reading of a temporal change in pain.

(Item 11)
The method of item 10, wherein the numerical value is a value that is expressed continuously, sequentially, or nominally by using a brain feature of a strong pain level as a baseline.

(Item 12)
The method of any one of items 1 to 11, further comprising generating a pain index from the brainwave data or analysis data thereof.

(Item 13)
The method of any one of items 1 to 12, further comprising calculating a baseline from the pain index and further comprising determining or estimating pain based on the baseline for the monitoring.

(Item 14)
The method of item 13, further comprising correcting the baseline in addition to calculating the baseline.

(Item 14A)
The method of item 13, further comprising referencing pain occupancy in step (c), wherein the pain occupancy indicates certainty when a pain estimation value is differentiated as having pain.

(Item 14B)
The method of item 13, wherein the pain occupancy is calculated by:
  (a) calculating an estimation value for differentiating having pain and no pain by a differentiation model;
  (b) dividing a pain estimation value into sectional ranges and calculating occupancy of an estimation value for having pain of each estimation value in the sectional range; and
  (c) generating a pain occupancy function by functionalizing the occupancy and calculating the pain occupancy with the pain occupancy function.

(Item 15)
An apparatus for monitoring pain of an object being estimated based on a brainwave of the object being estimated, comprising:
  A) a brainwave data measurement unit for obtaining brainwave data or analysis data thereof of the object being estimated;
  B) a value feature extraction unit for plotting a temporal change of a mean value of the brainwave data and analysis data thereof in a specific time frame; and
  C) a pain level monitoring unit for monitoring a level of pain of the object being estimated from the brainwave data or analysis data thereof based on the plot.

(Item 16)
The apparatus of item 15, comprising one or more features of items 2 to 14.

(Item 17)
A program for implementing a method of monitoring pain of an object being estimated based on a brainwave of the object being estimated on a computer, the method comprising:
  a) making the computer obtain from the object being estimated brainwave data by measuring a brainwave in response to stimulation;
  b) extracting a feature for plotting a temporal change of a mean value of the brainwave data or analysis data thereof in a specific time frame to the computer; and
  c) making the computer monitor a level of pain of the object being estimated from the brainwave data or analysis data thereof based on the plotting.

(Item 18)
The program of item 17, comprising one or more features of items 2 to 14.

(Item 19)
A recording medium storing a program for implementing a method of monitoring pain of an object being estimated based on a brainwave of the object being estimated on a computer, the method comprising:
  a) making the computer measure from the object being estimated brainwave data or analysis data thereof by measuring a brainwave in response to stimulation;
  b) extracting a feature for plotting a temporal change of a mean value of the brainwave data or analysis data thereof in a specific time frame to the computer; and
  c) making the computer monitor a level of pain of the object being estimated from the brainwave data or analysis data thereof based on the plotting.

(Item 20)
The recording medium of item 19, comprising one or more features of items 2 to 14.

In another aspect, the inventors discovered a technology that can efficiently provide a differentiation model with high accuracy for various sensations as a result of diligent study.

In this aspect, the invention provides, for example, the following.

(Item X1)
A method of generating a model for differentiating pain of an object, comprising:
  a) obtaining brainwave data or analysis data thereof from the object;
  b) contracting features in the brainwave data or analysis data thereof with respect to the pain;
  c) differentiating and analyzing by machine learning and cross validation from top of ranking of the features that have been weighted after the contracting or a combination thereof; and
  d) determining a model that attains a given accuracy.

(Item X2)
The method of item X1, comprising selecting a model with fewer types of features in the model that attains a given accuracy.

(Item X3)
The method of item X1, further comprising, after step c), calculating a value of difference (Diff) of adjacent models in differentiation accuracy obtained by differentiating and analyzing, wherein the adjacent models are models comprising n−1 features and n features, wherein n is 2 or greater, and wherein judgment of a differentiation model in step d) takes into consideration the value of difference.

(Item X4)
The method of item X3, wherein taking into consideration the value of difference comprises a process of re-ranking features from values with a greater value of difference and recalculating differentiation accuracy to generate a model with higher differentiation accuracy.

(Item X5)
The method of item X3 or X4, wherein the judgement based on the value of difference comprises classifying the features into a main feature and supporter features and re-ranking the supporter features.

(Item X6)

The method of item X5, comprising, after the re-ranking, changing the features and repeating step c).

(Item X7)

The method of item X5 or X6, comprising, after the re-ranking, changing the features and performing machine learning and cross validation to calculate differentiation accuracy of each model.

(Item X8)

The method of any one of items X3 to X7, wherein at least one step of items X3 to X7 is repeated at least once.

(Item X9)

The method of any one of items X1 to X8, wherein the given accuracy comprises the highest accuracy.

(Item X10)

The method of any one of items X1 to X9, wherein the contracting performs fitting using a differentiation function model corresponding to a differentiation stage, calculates a model approximation index, and selects any number from top of ranking thereof.

(Item X11)

The method of any one of items X1 to X10, wherein the contracting extracts an effective feature in accordance with a differentiation stage.

(Item X12)

The method of any one of items X1 to X11, wherein the weighting coefficient is selected from the group consisting of an $R^2$ value, a correlation coefficient, a regression coefficient, and a residual sum of squares.

(Item X13)

The method of item X12, wherein the differentiation function model is selected from the group consisting of a sigmoid function and a step function.

(Item X14)

The method of item X10 or X12, wherein the model approximation index is a subset of weighting coefficients.

(Item X15)

The method of item X11, wherein the effective feature, for binomial classification, is presence or absence corresponding to having pain or no pain, i.e., a 2 value feature, or a feature with higher approximation to a differentiation function.

(Item X16)

A method of differentiating pain of an object, comprising;
  a) obtaining brainwave data or analysis data thereof from a reference object;
  b) contracting features in the brainwave data or analysis data thereof with respect to the pain;
  c) differentiating and analyzing by machine learning and cross validation from top of ranking of weighting coefficients of each feature;
  d) determining a model that attains a given accuracy;
  e) obtaining brainwave data or analysis data thereof from a test object; and
  f) differentiating pain by fitting the model to the test object.

(Item X17)

A method of differentiating pain of an object, comprising:
  e) obtaining brainwave data or analysis data thereof from a test object; and
  f) differentiating pain by fitting a model for differentiating pain to the test object, wherein the model is generated by
  a) obtaining brainwave data or analysis data thereof from a reference object;
  b) contracting features of the brainwave data or analysis data thereof with respect to the pain;
  c) differentiating and analyzing by machine learning and cross validation from top of ranking of weighting coefficients of each feature; and
  d) determining a model that attains a given accuracy.

(Item X18)

A method of differentiating pain of an object, comprising differentiating pain of an object using a model for differentiating pain of an object, comprising a feature in at least two electrodes at Fz, Fpz, or a vicinity thereof.

(Item X19)

The method of item X18, wherein the vicinity comprises at least one of F3, F4, Fp1, and Fp2.

(Item X20)

A program for implementing a method of generating a model for differentiating pain of an object on a computer, the method comprising:
  a) obtaining brainwave data or analysis data thereof from the object;
  b) contracting features in the brainwave data or analysis data thereof with respect to the pain;
  c) differentiating and analyzing by machine learning and cross validation from top of ranking of the features that have been weighted after the contracting or a combination thereof; and
  d) determining a model that attains a given accuracy.

(Item X20A)

The program of item X20, further comprising one or more features of items X1 to X19.

(Item X21)

A recording medium for storing a program for implementing a method of generating a model for differentiating pain of an object on a computer, the method comprising:
  a) obtaining brainwave data or analysis data thereof from the object;
  b) contracting features in the brainwave data or analysis data thereof with respect to the pain;
  c) differentiating and analyzing by machine learning and cross validation from top of ranking of the features that have been weighted after the contracting or a combination thereof; and
  d) determining a model that attains a given accuracy.

(Item X21A)

The recording medium of item X21, further comprising one or more features of items X1 to X19.

(Item X22)

A system or apparatus for generating a model for differentiating pain of an object, the system or apparatus comprising:
  A) a brainwave data obtaining unit for obtaining brainwave data or analysis data thereof from the object;
  B) a feature contracting unit for contracting features in the brainwave data or analysis data thereof with respect to the pain; and
  C) a pain differentiation/estimation model generation unit for differentiating and analyzing by machine learning and cross validation from top of ranking of the features that have been weighted after the contracting or a combination thereof to determine a model that attains a given accuracy.

(Item X22A)

The system or apparatus of item X22, further comprising one or more features of items X1 to X19.

(Item X23)

A program for implementing a method of differentiating pain of an object on a computer, the method comprising:
  a) obtaining brainwave data or analysis data thereof from a reference object;

b) contracting features in the brainwave data or analysis data thereof with respect to the pain;
c) differentiating and analyzing by machine learning and cross validation from top of ranking of weighting coefficients of each feature;
d) determining a model that attains a given accuracy;
e) obtaining brainwave data or analysis data thereof from a test object; and
f) differentiating pain by fitting the model to the test object.

(Item X23A)
The program of item X23, further comprising one or more features of items X1 to X19.

(Item X24)
A recording medium storing a program for implementing a method of differentiating pain of an object on a computer, the method comprising:
a) obtaining brainwave data or analysis data thereof from a reference object;
b) contracting features in the brainwave data or analysis data thereof with respect to the pain;
c) differentiating and analyzing by machine learning and cross validation from top of ranking of weighting coefficients of each feature;
d) determining a model that attains a given accuracy;
e) obtaining brainwave data or analysis data thereof from a test object; and
f) differentiating pain by fitting the model to the test object.

(Item X24A)
The recording medium of item X24, further comprising one or more features of items X1 to X19.

(Item X25)
A system or apparatus for differentiating pain of an object, the system or apparatus comprising:
A) a brainwave obtaining unit for obtaining brainwave data or analysis data thereof from a reference object;
B) a feature contracting unit for contracting features in the brainwave data or analysis data thereof with respect to the pain;
C) a pain differentiation/estimation model for differentiating and analyzing by machine learning and cross validation from top of ranking of weighting coefficients of each feature to determine a model that attains a given accuracy;
D) a brainwave data measurement unit for obtaining brainwave data or analysis data thereof from a test object; and
E) a pain differentiation/estimation unit for differentiating pain by fitting the model to the test object.

(Item X25A)
The system or apparatus of item X25, further comprising one or more features of items X1 to X19.

(Item X26)
A program for implementing a method of differentiating pain of an object on a computer, the method comprising:
e) obtaining brainwave data or analysis data thereof from a test object; and
f) differentiating pain by fitting a model for differentiating pain to the test object, wherein the model is generated by
a) obtaining brainwave data or analysis data thereof from a reference object;
b) contracting features of the brainwave data or analysis data thereof with respect to the pain;
c) differentiating and analyzing by machine learning and cross validation from top of ranking of weighting coefficients of each feature; and
d) determining a model that attains a given accuracy.

(Item X26A)
The program of item X26, further comprising one or more features of items X1 to X19.

(Item X27)
A recording medium storing a program for implementing a method of differentiating pain of an object on a computer, the method comprising:
e) obtaining brainwave data or analysis data thereof from a test object; and
f) differentiating pain by fitting a model for differentiating pain to the test object, wherein the model is generated by
a) obtaining brainwave data or analysis data thereof from a reference object;
b) contracting features of the brainwave data or analysis data thereof with respect to the pain;
c) differentiating and analyzing by machine learning and cross validation from top of ranking of weighting coefficients of each feature; and
d) determining a model that attains a given accuracy.

(Item X27A)
The recording medium of item X27, further comprising one or more features of items X1 to X19.

(Item X28)
The system or apparatus for differentiating pain of an object, the system or apparatus comprising:
D) a brainwave data measurement unit for obtaining brainwave data or analysis data thereof from a test object; and
E) a pain differentiation/estimation unit for differentiating pain by fitting a model for differentiating pain to the test object, wherein the model is generated by
a) obtaining brainwave data or analysis data thereof from a reference object;
b) contracting features of the brainwave data or analysis data thereof with respect to the pain;
c) differentiating and analyzing by machine learning and cross validation from top of ranking of weighting coefficients of each feature; and
d) determining a model that attains a given accuracy.

(Item X28A)
The system or apparatus of item X28, further comprising one or more features of items X1 to X19.

In another aspect, the present invention also provides the following.

(Item A1)
A method of generating a model for differentiating pain of an object, comprising:
a) obtaining brainwave data or analysis data thereof from the object;
b) contracting features based on the brainwave data or analysis data thereof with respect to the pain after determining feature coefficients associated with the pain;
c) creating a differentiation and analysis model by machine learning and validation based on the features that have been weighted after the contracting or a combination thereof; and
d) determining a differentiation and analysis model that attains a given accuracy.

(Item A2)
The method of item A1, wherein the contracting is performed in step b), after determining the feature coefficients, by repeating differentiation and estimation, calculating a mean of and ranking the feature coefficients for the differentiation and estimation, and selecting a feature based on a given threshold value.

(Item A3)

The method of item A1 or A2, wherein the feature coefficients are determined by machine learning.

(Item A4)

The method of any one of items A1 to A3, comprising, upon determining the feature coefficients in step b), determining a hyperparameter resulting in the highest differentiation accuracy, and determining the feature coefficients based on the hyperparameter, and excluding a feature which has no effect or a low ratio of contribution for differentiation.

(Item A5)

The method of item A4, wherein the feature coefficients and the hyperparameter are determined by machine learning.

(Item A6)

The method of any one of items A1 to A5, wherein (b) to (d) comprise:
 (C1) dividing the features and data corresponding to the pain corresponding to the features into data for learning and data for testing;
 (C2) performing machine learning using the learning data to create a differentiation model;
 (C3) calculating differentiation accuracy of the differentiation model by using the data for testing;
 (C4) if there is a target sample with the differentiation accuracy at or below a chance level in the objects, repeating steps C1 to C3 after excluding the sample, and if there is no sample at or below a chance level, ending the steps to determine a differentiation model, wherein the chance level is a numerical value obtained by dividing 100% by the number of classifications.

(Item A7)

The method of any one of items A1 to A6, comprising selecting a model with fewer types of features in the model that attains a given accuracy.

(Item A8)

The method of any one of items A1 to A7, further comprising, after step c), calculating a value of difference (Diff) of adjacent models in differentiation accuracy obtained by differentiating and analyzing, wherein the adjacent models are models comprising n−1 features and n features, wherein n is 2 or greater, and wherein judgment of a differentiation model in step d) takes into consideration the value of difference.

(Item A9)

The method of item A8, wherein taking into consideration the value of difference comprises a process of re-ranking features from values with greater value of difference and recalculating differentiation accuracy to generate a model with higher differentiation accuracy.

(Item A10)

The method of item A8 or A9, wherein the judgment based on the value of difference comprises classifying the features into a main feature and supporter features and re-ranking the supporter features.

(Item A11)

The method of item A10, comprising, after the re-ranking, changing the features and repeating step c).

(Item A12)

The method of item A10 or A11, comprising, after the re-ranking, changing the features and performing machine learning and cross validation to calculate differentiation accuracy of each model.

(Item A13)

The method of any one of items A8 to A12, wherein at least step of items A8 to A12 is repeated at least once.

(Item A14)

The method of any one of items A1 to A13, wherein the given accuracy comprises the highest accuracy.

(Item A15)

The method of any one of items A1 to A14, wherein the contracting performs fitting using a differentiation function model corresponding to a differentiation stage, calculates a model approximation index, and selects any number from top of ranking thereof.

(Item A16)

The method of any one of items A1 to A15, wherein the contracting extracts an effective feature in accordance with a differentiation stage.

(Item A17)

The method of any one of items A1 to A16, wherein the weighting coefficient is selected from the group consisting of an $R^2$ value, a correlation coefficient, a regression coefficient, and a residual sum of squares.

(Item A18)

The method of item A17, wherein the differentiation function model is selected from the group consisting of a sigmoid function and a step function.

(Item A19)

The method of any one of items A15 to A18, wherein the model approximation index is a subset of weighting coefficients.

(Item A20)

The method of any one of items A16 to A19, wherein the effective feature, for binomial classification, is presence or absence corresponding to having pain or no pain, i.e., a 2 value feature, or a feature with higher approximation to a differentiation function.

(Item A21)

A method of differentiating pain of an object, comprising:
 a) obtaining brainwave data or analysis data thereof from a reference object;
 b) contracting features based on the brainwave data or analysis data thereof with respect to the pain after determining a feature coefficient associated with the pain;
 c) creating a differentiation and analysis model by machine learning and validation based on the features that have been weighted after the contracting or a combination thereof;
 d) determining a differentiation and analysis model that attains a given accuracy;
 e) obtaining brainwave data or analysis data thereof from a test object; and
 f) differentiating pain by fitting the brainwave data or analysis data thereof of the test object to the model.

(Item A22)

A method of differentiating pain of an object, comprising:
 e) obtaining brainwave data or analysis data thereof from a test object; and
 f) differentiating pain by fitting the brainwave data or analysis data of the test object to a model for differentiating pain, wherein the model is generated by
 a) obtaining brainwave data or analysis data thereof from a reference object;
 b) contracting features based on the brainwave data or analysis data thereof with respect to the pain after determining a feature coefficient associated with the pain;

c) creating a differentiation and analysis model by machine learning and validation based on the features that have been weighted after the contracting or a combination thereof; and d) determining a differentiation and analysis model that attains a given accuracy.

(Item A23)

A method of differentiating pain of an object, comprising differentiating pain of an object using a model for differentiating pain of an object, comprising a feature in at least two electrodes at Fz, Fpz, or a vicinity thereof.

(Item A24)

The method of item A23, wherein the vicinity comprises at least one of F3, F4, Fp1, and Fp2.

(Item A25)

A program for implementing a method of generating a model for differentiating pain of an object on a computer, the method comprising:

a) obtaining brainwave data or analysis data thereof from the object;

b) contracting features based on the brainwave data or analysis data thereof with respect to the pain after determining a feature coefficient associated with the pain;

c) creating a differentiation and analysis model by machine learning and validation based on the features that have been weighted after the contracting or a combination thereof; and d) determining a differentiation and analysis model that attains a given accuracy.

(Item A25A)

The program of item A25, further comprising one or more features of items A1 to A24 and A34 to A36.

(Item A26)

A recording medium for storing a program for implementing a method of generating a model for differentiating pain of an object on a computer, the method comprising:

a) obtaining brainwave data or analysis data thereof from the object;

b) contracting features based on the brainwave data or analysis data thereof with respect to the pain after determining a feature coefficient associated with the pain;

c) creating a differentiation and analysis model by machine learning and validation based on the features that have been weighted after the contracting or a combination thereof; and d) determining a differentiation and analysis model that attains a given accuracy.

(Item A26A)

The recording medium of item A26, further comprising one or more features of items A1 to A24 and A34 to A36.

(Item A27)

A system for generating a model for differentiating pain of an object, the system comprising:

A) a brainwave data obtaining unit for obtaining brainwave data or analysis data thereof from the object;

B) a feature contracting unit for contracting features based on the brainwave data or analysis data thereof with respect to the pain after determining a feature coefficient associated with the pain; and C) a pain differentiation/estimation model generation unit for creating a differentiation and analysis model by machine learning and validation based on the features that have been weighted after the contracting or a combination thereof.

(Item A27A)

The system of item A27, further comprising one or more features of items A1 to A24 and A34 to A36.

(Item A28)

A program for implementing a method of differentiating pain of an object on a computer, the method comprising:

a) obtaining brainwave data or analysis data thereof from a reference object;

b) contracting features based on the brainwave data or analysis data thereof with respect to the pain after determining a feature coefficient associated with the pain;

c) creating a differentiation and analysis model by machine learning and validation based on the features that have been weighted after the contracting or a combination thereof;

d) determining a differentiation and analysis model that attains a given accuracy;

e) obtaining brainwave data or analysis data thereof from a test object; and f) differentiating pain by fitting the brainwave data or analysis data thereof of the test object to the model.

(Item A28A)

The program of item A28, further comprising one or more features of items A1 to A24 and A34 to A36.

(Item A29)

A recording medium storing a program for implementing a method of differentiating pain of an object on a computer, the method comprising:

a) obtaining brainwave data or analysis data thereof from a reference object;

b) contracting features based on the brainwave data or analysis data thereof with respect to the pain after determining a feature coefficient associated with the pain;

c) creating a differentiation and analysis model by machine learning and validation based on the features that have been weighted after the contracting or a combination thereof;

d) determining a differentiation and analysis model that attains a given accuracy;

e) obtaining brainwave data or analysis data thereof from a test object; and f) differentiating pain by fitting the brainwave data or analysis data thereof of the test object to the model.

(Item A29A)

The recording medium of item A29, further comprising one or more features of items A1 to A24 and A34 to A36.

(Item A30)

A system for differentiating pain of an object, the system comprising:

A) a brainwave data obtaining unit for obtaining brainwave data or analysis data thereof from a reference object;

B) a feature contracting unit for contracting features based on the brainwave data or analysis data thereof with respect to the pain after determining a feature coefficient associated with the pain;

C) a pain differentiation/estimation model generation unit for creating a differentiation and analysis model by machine learning and validation based on the features that have been weighted after the contracting or a combination thereof;

D) a brainwave data measurement unit for obtaining brainwave data or analysis data thereof from a test object; and E) a pain differentiation/estimation unit for differentiating pain by fitting the brainwave data or analysis data thereof of the test object to the differentiation and analysis model.

(Item A30A)

The system of item A30, further comprising one or more features of items A1 to A24 and A34 to A36.

(Item A31)

A program for implementing a method of differentiating pain of an object on a computer, the method comprising:
  e) obtaining brainwave data or analysis data thereof from a test object; and
  f) differentiating pain by fitting the brainwave data or analysis data thereof of the test object to a model for differentiating pain, wherein the model is generated by
  a) obtaining brainwave data or analysis data thereof from a reference object;
  b) contracting features based on the brainwave data or analysis data thereof with respect to the pain after determining a feature coefficient associated with the pain;
  c) creating a differentiation and analysis model by machine learning and validation based on the features that have been weighted after the contracting or a combination thereof; and
  d) determining a differentiation and analysis model that attains a given accuracy.

(Item A31A)

The program of item A31, further comprising one or more features of items A1 to A24 and A34 to A36.

(Item A32)

A recording medium storing a program for implementing a method of differentiating pain of an object on a computer, the method comprising:
  e) obtaining brainwave data or analysis data thereof from a test object; and
  f) differentiating pain by fitting the brainwave data or analysis data thereof of the test object to a model for differentiating pain, wherein the model is generated by
  a) obtaining brainwave data or analysis data thereof from a reference object;
  b) contracting features based on the brainwave data or analysis data thereof with respect to the pain after determining a feature coefficient associated with the pain;
  c) creating a differentiation and analysis model by machine learning and validation based on the features that have been weighted after the contracting or a combination thereof; and
  d) determining a differentiation and analysis model that attains a given accuracy.

(Item A32A)

The recording medium of item A32, further comprising one or more features of items A1 to A24 and A34 to A36.

(Item A33)

A system for differentiating pain of an object, the system comprising:
  D) a brainwave data measurement unit for obtaining brainwave data or analysis data thereof from a test object; and
  E) a pain differentiation/estimation unit for differentiating pain by fitting the brainwave data or analysis data thereof of the test object to a model for differentiating pain, wherein the model is generated by
  a) obtaining brainwave data or analysis data thereof from a reference object;
  b) contracting features based on the brainwave data or analysis data thereof with respect to the pain after determining a feature coefficient associated with the pain;
  c) creating a differentiation and analysis model by machine learning and validation based on the features that have been weighted after the contracting or a combination thereof; and
  d) determining a differentiation and analysis model that attains a given accuracy.

(Item A33A)

The system of item A33, further comprising one or more features of items A1 to A24 and A34 to A36.

(Item A34)

The method of items A1 to A24, further comprising filtering the brainwave data or analysis data thereof.

(Item A35)

The method, program, recording medium, or system of item A34, wherein the filtering comprises filtering for at least one selected from the group consisting of eye movement elimination and attenuation of myogenic potential.

(Item A36)

The method of items A1 to A24, A34 or A35, wherein the brainwave data or analysis data thereof comprises at least one selected from the group consisting of a mean amplitude, a frontal-parietal potential correlation, frequency power, and a complexity index (multiscale entropy).

(Item A37)

A program for implementing a method of differentiating pain of an object on a computer, the method comprising:
  a) obtaining brainwave data or analysis data thereof from the object;
  b) generating a differentiation model based on the brainwave data or analysis data thereof; and
  c) differentiating pain by fitting the brainwave data or analysis data thereof from the object to the differentiation model.

(Item A37A)

The program of item A37, comprising one or more features of the preceding items.

(Item A37B)

The recording medium storing the program of item A37 or item A37A.

(Item A38)

A system for differentiating pain of an object, the system comprising:
  X) a brainwave data obtaining unit for obtaining brainwave data or analysis data thereof from an object;
  Y) a pain differentiation/estimation model generating unit for generating a differentiation model based on the brainwave data or analysis data thereof; and
  Z) a pain differentiation/estimation unit for differentiating pain by fitting the brainwave data or analysis data thereof from the object to the model.

(Item A38A)

The system of item 38A, comprising one or more features of the preceding items.

(Item A39)

A system for differentiating pain of an object, the system comprising X) a pain differentiation terminal and Y) a pain differentiation/estimation server,
  wherein the pain differentiation terminal comprises:
    X-1) a brainwave data obtaining terminal for obtaining brainwave data or analysis data thereof from an object; and X-2) a module for transmitting and receiving the brainwave data or analysis data thereof and a differentiation result to a pain differentiation/estimation server, wherein the pain differentiation/estimation server comprises:

Y-1) a pain differentiation/estimation model generation module for generating a differentiation model based on the brainwave data or analysis data thereof;

Y-2) a pain differentiation/estimation module for generating a differentiation result from differentiating pain by fitting the brainwave data or analysis data thereof from the object to the model; and Y-3) a differentiation result transceiver module for transmitting and receiving the brainwave data or analysis data thereof and the differentiation result.

(Item A39A)

The system of item A39, comprising one or more features of the preceding items.

(Item A40)

A system for differentiating pain of an object, the system comprising X) a pain differentiation terminal and Y) a pain differentiation/estimation server, wherein the pain differentiation terminal comprises:

X-1) a brainwave data obtaining terminal for obtaining brainwave data from an object; and X-2) a module for transmitting and receiving the brainwave data and a differentiation result to the pain differentiation/estimation server, wherein the pain differentiation/estimation server comprises:

Y-1) a pain differentiation/estimation model generation module for generating a differentiation model based on the brainwave data or analysis data thereof;

Y-1') a brainwave feature extraction module for extracting analysis data from the brainwave data;

Y-2) a pain differentiation/estimation module for generating a differentiation result from differentiating pain by fitting the brainwave data or analysis data thereof from the object to the model; and Y-3) a differentiation result transceiver module for transmitting and receiving the brainwave data or analysis data thereof and the differentiation result.

(Item A40A)

The system of item A40, comprising one or more features of the preceding items.

(Item A41)

A system for differentiating pain of an object, the system comprising X) a pain differentiation terminal and Y) a pain differentiation/estimation server, wherein the pain differentiation terminal comprises:

X-1) a brainwave data obtaining terminal for obtaining brainwave data or analysis data thereof from an object;

X-2) a module for transmitting and receiving the brainwave data or analysis data thereof and a differentiation model to the pain differentiation/estimation server; and X-3) a differentiation model module for storing a differentiation model, wherein pain is differentiated by fitting the brainwave data or analysis data thereof from the object to the differentiation model, wherein the pain differentiation/estimation server comprises:

Y-1) a pain differentiation/estimation model generation module for generating a differentiation model based on the brainwave data or analysis data thereof;

Y-2) a model transmission module for transmitting the differentiation model to the pain differentiation terminal; and optionally a brainwave feature extraction module for extracting analysis data from the brainwave data.

(Item A41A)

The system of item A41, comprising one or more features of the preceding items.

In another aspect, machine learning is a technology that attempts to impart the ability to learn to a computer without explicit programming, which repeats prediction, searching, testing, and the like. A label for differentiation may be provided (supervised learning) or may not be provided (unsupervised learning). It is important in this disclosure that this is materialized as tailor-made machine learning.

Thus, in this aspect, the present invention provides, for example, the following.

(Item B1)

A method of improving machine learning, comprising:

A) generating a differentiation model by machine learning;

B) determining a hyperparameter in all samples by cross validation;

C) generating a differentiation model by using the hyperparameter to calculate differentiation accuracy for each sample;

D) grouping each sample based on the differentiation accuracy;

E) determining an individual hyperparameter for each of the groups; and

F) generating an individual differentiation model for each group using the individual hyperparameter and calculating differentiation accuracy of each sample to generate a differentiation maximum (MAX) model from thereamong.

(Item B2)

The method of item B1, wherein the generating the differentiation maximum (MAX) model comprises an ensemble method and pruning thereof.

(Item B3)

The method of item B1 or B2, wherein the differentiation maximum (MAX) model is selected as a main model and the rest are selected as supporter models, and the supporter models are added one at a time to improve differentiation accuracy.

(Item B4)

The method of any one of items B1 to B3, wherein the differentiation maximum (MAX) model is selected as a main model and the rest are selected as supporter models, and the supporter models are comprehensively added one at a time to the main model to improve differentiation accuracy stepwise.

(Item B5)

The method of item B4, wherein a stepwise improvement of the differentiation accuracy comprises:

A) selecting two model sets that improve differentiation accuracy the most by an ensemble method when selecting and adding one of N−1 supporter models to the main model as updated main models;

B) selecting N−2 models resulting from taking out the updated main models from all N models as updated supporter models; and C) repeating steps A) to B) in the same manner for a model set that improves differentiation accuracy the most by an ensemble method to update updated main models and updated supporter models until there is no more updated supporter model.

(Item B6)

The method of any one of items B1 to B5, further comprising dividing all the samples into a reference sample and a test sample, determining the differentiation maximum (MAX) model or an optimal differentiation model from a plurality of differentiation model sets including the maximum model as a reference differentiation model by using the reference sample, differentiating and estimating with the test sample using the reference differentiation model to test the reference differentiation model, and determining a final preferred differentiation model based on a result of the differentiating and estimating.

(Item B7)

The method of any one of items B1 to B6, wherein step A comprises providing a reference sample and generating the differentiation model based on the reference sample.

(Item B8)

The method of any one of items B1 to B7, wherein an objective of the machine learning is differentiation of pain.

(Item B9)

The method of any one of items B1 to B5, wherein an objective of the machine learning is differentiation of pain, wherein the sample is brainwave data of a subject in response to experimental stimulation, and wherein the differentiation model is calculated based on the brainwave data.

(Item B10)

The method of any one of items B1 to B9, wherein an objective of the machine learning is differentiation of pain, wherein the sample is brainwave data of a subject in response to experimental stimulation, wherein the differentiation model is calculated based on the brainwave data, and wherein the method further comprises dividing all the samples into a reference sample and a test sample, determining the differentiation maximum (MAX) model or an optimal differentiation model from a plurality of differentiation model sets including the maximum model as a reference differentiation model by using the reference sample, differentiating and estimating with the test sample using the reference differentiation model to test the reference differentiation model, and determining a final preferred differentiation model based on a result of the differentiating and estimating.

(Item B11)

The method of item B10, wherein the earliest segment of brainwave data of the sample is selected as the reference sample, and others are selected as the test sample.

(Item B12)

The method of any one of items B1 to B11, wherein step A) comprises providing a reference sample of a brainwave obtained by applying reference stimulation to a body part of an object, and generating the differentiation model based on the reference sample.

(Item B13)

A program for implementing a method of improving machine learning on a computer, the method comprising:
  A) generating a differentiation model by machine learning;
  B) determining a hyperparameter in all samples by cross validation;
  C) generating a differentiation model by using the hyperparameter to calculate differentiation accuracy for each sample;
  D) grouping each sample based on the differentiation accuracy;
  E) determining an individual hyperparameter for each of the groups; and
  F) generating an individual differentiation model for each group using the individual hyperparameter and calculating differentiation accuracy of each sample to generate a differentiation maximum (MAX) model from thereamong.

(Item B14)

A recording medium storing a program for implementing a method of improving machine learning on a computer, the method comprising:
  A) generating a differentiation model by machine learning;
  B) determining a hyperparameter in all samples by cross validation;
  C) generating a differentiation model by using the hyperparameter to calculate differentiation accuracy for each sample;
  D) grouping each sample based on the differentiation accuracy;
  E) determining an individual hyperparameter for each of the groups; and
  F) generating an individual differentiation model for each group using the individual hyperparameter and calculating differentiation accuracy of each sample to generate a differentiation maximum (MAX) model from thereamong.

(Item B15)

A system implementing a method of improving machine learning, the system comprising:
  A) a differentiation model generation module for generating a differentiation model by machine learning;
  B) a hyperparameter determination module for determining a hyperparameter in all samples by cross validation;
  C) a differentiation accuracy calculation module for generating a differentiation model by using the hyperparameter to calculate differentiation accuracy for each sample;
  D) a grouping module for grouping each sample based on the differentiation accuracy;
  E) an individual hyperparameter module for determining an individual hyperparameter for each of the groups; and
  F) a differentiation maximum model generation module for generating an individual differentiation model for each group using the individual hyperparameter and calculating differentiation accuracy of each sample to generate a differentiation maximum (MAX) model from thereamong.

(Item B16)

A system for executing a method of improving machine learning, the system comprising a machine learning execution module, wherein the machine learning execution module is configured to execute a method comprising:
  A) generating a differentiation model by machine learning;
  B) determining a hyperparameter in all samples by cross validation;
  C) generating a differentiation model by using the hyperparameter to calculate differentiation accuracy for each sample;
  D) grouping each sample based on the differentiation accuracy;
  E) determining an individual hyperparameter for each of the groups; and
  F) generating an individual differentiation model for each group using the individual hyperparameter and calculating differentiation accuracy of each sample to generate a differentiation maximum (MAX) model from thereamong.

(Item B17)

A method of differentiating pain, comprising:
- A) generating a pain differentiation model by machine learning;
- B) determining a hyperparameter in all samples by cross validation;
- C) generating a pain differentiation model by using the hyperparameter to calculate pain differentiation accuracy for each sample;
- D) grouping each sample based on the differentiation accuracy;
- E) determining an individual hyperparameter for each of the groups; and
- F) generating an individual pain differentiation model for each group using the individual hyperparameter and calculating pain differentiation accuracy of each sample to generate a pain differentiation maximum (MAX) model from thereamong.

(Item B18)

The method of item B17, wherein the differentiation model is generated by a processing method selected from supervised machine learning models consisting of LASSO (Least Absolute Shrinkage and Selection Operator), linear and logistic regression, support vector machine, neural network, random forest, Bayes, clustering, and decision tree, or unsupervised machine learning models including deep learning.

(Item B19)

A program for implementing a method of differentiating pain on a computer, the method comprising:
- A) generating a pain differentiation model by machine learning;
- B) determining a hyperparameter in all samples by cross validation;
- C) generating a pain differentiation model by using the hyperparameter to calculate differentiation accuracy for each sample;
- D) grouping each sample based on the differentiation accuracy;
- E) determining an individual hyperparameter for each of the groups; and
- F) generating an individual pain differentiation model for each group using the individual hyperparameter and calculating pain differentiation accuracy of each sample to generate a pain differentiation maximum (MAX) model from thereamong.

(Item B20)

A recording medium storing a program for implementing a method of differentiating pain on a computer, the method comprising:
- A) generating a pain differentiation model by machine learning;
- B) determining a hyperparameter in all samples by cross validation;
- C) generating a pain differentiation model by using the hyperparameter to calculate differentiation accuracy for each sample;
- D) grouping each sample based on the differentiation accuracy;
- E) determining an individual hyperparameter for each of the groups; and
- F) generating an individual pain differentiation model for each group using the individual hyperparameter and calculating pain differentiation accuracy of each sample to generate a pain differentiation maximum (MAX) model from thereamong.

(Item B21)

A pain differentiation system, comprising:
- A) a differentiation model generation module for generating a pain differentiation model by machine learning;
- B) a hyperparameter determination module for determining a hyperparameter in all samples by cross validation;
- C) a differentiation accuracy calculation module for generating a pain differentiation model by using the hyperparameter to calculate differentiation accuracy for each sample;
- D) a grouping module for grouping each sample based on the differentiation accuracy;
- E) an individual hyperparameter module for determining an individual hyperparameter for each of the groups; and
- F) a differentiation maximum (MAX) model generation module for generating an individual pain differentiation model for each group using the individual hyperparameter and calculating pain differentiation accuracy of each sample to generate a pain differentiation maximum (MAX) model from thereamong.

(Item B22)

A pain differentiation system, the system comprising a machine learning execution module, wherein the machine learning execution module is configured to execute a method comprising:
- A) generating a pain differentiation model by machine learning;
- B) determining a hyperparameter in all samples by cross validation;
- C) generating a pain differentiation model by using the hyperparameter to calculate pain differentiation accuracy for each sample;
- D) grouping each sample based on the differentiation accuracy;
- E) determining an individual hyperparameter for each of the groups; and
- F) generating an individual pain differentiation model for each group using the individual hyperparameter and calculating pain differentiation accuracy of each sample to generate a pain differentiation maximum (MAX) model from thereamong.

In another aspect, the inventors have discovered novel parameters that can be used as a brainwave feature for differentiating pain as a result of diligent study. The inventors discovered a technology, wherein a complexity index such as entropy and interrelation of brainwave features (e.g., mean amplitude (potential), frequency power, complexity indicator, or the like) (interrelation of brainwave features such as synchronicity or correlation) in particular can efficiently provide pain differentiation with high accuracy.

In this aspect, the present invention provides, for example, the following.

(Item C1A)

A method of determining pain using one or more features of a brainwave.

(Item C1B)

The method of item C1A, wherein the features comprise at least one selected from an amplitude, interrelation of brainwave features, frequency power, and a complexity index.

(Item C1C)

The method of any one of the preceding items, wherein the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

(Item C1D)

The method of any one of the preceding items, comprising creating a differentiation model using the features.

(Item C1)

A method of determining pain using a complexity index of a brainwave.

(Item C2)

The method of items C1A to C1D or item C1, wherein the complexity index comprises entropy.

(Item C3)

The method of any one of the preceding items, wherein the complexity index comprises at least one selected from the group consisting of multiscale entropy (MSE), sample entropy, self entropy, mean entropy, joint entropy, relative entropy, and conditional entropy.

(Item C4)

The method of any one of the preceding items, wherein the complexity index is from at least one selected from the group consisting of electrode Fp1, electrode Fp2, electrode F3, electrode F4, electrode C3, electrode C4, and electrode Pz.

(Item C5)

The method of any one of the preceding items, comprising generating a determination model by machine learning using the complexity index.

(Item C6A)

A method of generating a model for differentiating pain of an object, comprising:
  a) obtaining a feature of a brainwave from the object;
  b) contracting the feature with respect to the pain after determining a feature coefficient associated with the pain;
  c) creating a differentiation and analysis model by machine learning and validation based on each feature after the contracting or a combination thereof; and
  d) determining a differentiation and analysis model that attains a given accuracy.

(Item C6B)

The method of item C6A, wherein the feature comprises at least one selected from an amplitude, interrelation of brainwave features, frequency power, and a complexity index.

(Item C6C)

The method of any one of the preceding items, wherein the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

(Item C6)

A method of generating a model for differentiating pain of an object, comprising:
  a) obtaining a complexity index of a brainwave from the object;
  b) contracting the complexity index with respect to the pain after determining a feature coefficient associated with the pain;
  c) creating a differentiation and analysis model by machine learning and validation based on each feature after the contracting or a combination thereof; and
  d) determining a differentiation and analysis model that attains a given accuracy.

(Item C7A)

A method of differentiating pain of an object, comprising:
  a) obtaining a feature of a brainwave from a reference object;
  b) contracting the feature with respect to the pain after determining a feature coefficient associated with the pain;
  c) creating a differentiation and analysis model by machine learning and validation based on each feature after the contracting or a combination thereof;
  d) determining a differentiation and analysis model that attains a given accuracy;
  e) obtaining a complexity index from a test object; and
  f) differentiating pain by fitting the complexity index of the test object to the model.

(Item C7B)

The method of item C7A, wherein the feature comprises at least one selected from an amplitude, interrelation of brainwave features, frequency power, and a complexity index.

(Item C7C)

The method of any one of the preceding items, wherein the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

(Item C7)
A method of differentiating pain of an object, comprising:
a) obtaining a complexity index from a reference object;
b) contracting the complexity index with respect to the pain after determining a feature coefficient associated with the pain;
c) creating a differentiation and analysis model by machine learning and validation based on each feature after the contracting or a combination thereof;
d) determining a differentiation and analysis model that attains a given accuracy;
e) obtaining a complexity index from a test object; and
f) differentiating pain by fitting the complexity index of the test object to the model.

(Item C8A)
A method of differentiating pain of an object, comprising:
e) obtaining a feature of a brainwave from a test object; and
f) differentiating pain by fitting the feature of the test object to a model for differentiating pain, wherein the model is generated by:
a) obtaining the feature of a brainwave from a reference object;
b) contracting the feature with respect to the pain after determining a feature coefficient associated with the pain;
c) creating a differentiation and analysis model by machine learning and validation based on each feature after the contracting or a combination thereof;
d) determining a differentiation and analysis model that attains a given accuracy.

(Item C8B)
The method of item C8A, wherein the feature comprises at least one selected from an amplitude, interrelation of brainwave features, frequency power, and a complexity index.

(Item C8C)
The method of any one of the preceding items, wherein the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

(Item C8)
A method of differentiating pain of an object, comprising:
e) obtaining a complexity index from a test object; and
f) differentiating pain by fitting the complexity index of the test object to a model for differentiating pain, wherein the model is generated by:
a) obtaining a complexity index from a reference object;
b) contracting the complexity index with respect to the pain after determining a feature coefficient associated with the pain;
c) creating a differentiation and analysis model by machine learning and validation based on each feature after the contracting or a combination thereof;
d) determining a differentiation and analysis model that attains a given accuracy.

(Item C9)
The method of any one of the preceding items, wherein the each feature after the contracting or combination thereof comprises an alternative integrated brainwave feature (this feature set is referred to as such because it is extracted by various signal processing methods from limited electrodes (Fp1, Fp2, or the like) and adaptively alternated depending on the monitoring environment or individual difference by the contracting process and "integrally" contributes to a pain differentiation model via, for example, a linear regression model.)

(Item C10)
A program for implementing the method of any one of the preceding items on a computer.

(Item C11)
A recording medium for storing a program for implementing the method of any one of the preceding items on a computer.

(Item C12)
A method of differentiating pain using interrelation between brainwave features.

(Item C13)
The method of any one of the preceding items, wherein the interrelation between brainwave features is interrelation between brainwave features in the same or different electrodes.

(Item C14)
The method of any one of the preceding items, wherein the interrelation is selected from the group consisting of temporal correlation, spatial correlation, spatiotemporal synchronicity, spatial relationship or connectivity, unrelatedness or uncorrelatedness, delay or breakdown in temporal correlation, positive/negative or correlated property, similarity or level of a correlation coefficient, and a match or complete correlation.

(Item C15)
The method of item C14, wherein the synchronicity comprises phase synchronization (phase locking value) or coherence.

(Item C16)
The method of any one of the preceding items, wherein the correlation of brainwave features is correlation of brainwave features between different electrodes.

(Item C17)
The method of item C16, wherein the different electrodes have a relationship of being positioned relatively in front and back of a head.

(Item C18)
The method of item C16 or C17, wherein at least one of the different electrodes is at a front portion of a head.

(Item C19)
The method of any one of items C16 to C18, wherein at least one of the different electrodes is at a back portion of a head.

(Item C20)
The method of any one of items C16 to C19, wherein at least one of the different electrodes is at a front portion of a head, and another electrode is at a back portion of the head.

(Item C21)
The method of any one of the preceding items, wherein the correlation comprises correlation between an electrode at a front portion of a head and an electrode at a back portion of the head.

(Item C22)
The method of any one of the preceding items, wherein the correlation comprises correlation between an electrode at a frontal portion and an electrode at a parietal portion.

(Item C23)
The method of any one of the preceding items, wherein the frontal portion comprises at least one selected from the group consisting of frontal pole Fp1, frontal pole Fp2, frontal portion F3, frontal portion F4, anterior-temporal portion F7, anterior-temporal portion F8, and midline frontal portion Fz and adjacent sites, and the parietal portion comprises midline parietal portion Pz, parietal portion P3, and parietal portion P4.

(Item C24)
The method of any one of the preceding items, wherein the brainwave feature comprises at least one selected from the group consisting of a mean amplitude, frequency power, and a complexity index.

(Item C25)
The method of any one of the preceding items, wherein the mean amplitude is dependent on a stimulation application time and is a mean value of an absolute value of amplitude during 15 seconds after applying stimulation.

(Item C26)
The method of any one of the preceding items, wherein the frequency power comprises at least one of 5 bandwidths $\delta$, $\theta$, $\alpha$, $\beta$, and $\gamma$ in frontal pole Fp1, frontal pole Fp2, frontal portion F3, frontal portion F4, central portion C3, central portion C4, and midline parietal portion Pz.

(Item C27)
The method of any one of the preceding items, comprising generating a differentiation model by machine learning using the brainwave feature.

(Item C28)
A method of differentiating pain of an object, comprising differentiating pain of an object using a model for differentiating pain of an object, comprising a feature in at least two electrodes comprising at least one electrode at a front portion of a head.

(Item C29)
A method for differentiating pain of an object comprising differentiating pain of an object using a model for differentiating pain of an object, comprising a feature in at least two electrodes at Fz or Fpz or the vicinity thereof.

(Item C30)
The method of any of the preceding items, wherein the vicinity comprises at least one of F3, F4, Fp1, and Fp2.

(Item C31)
A method of generating a model for differentiating pain of an object, comprising:
a) obtaining correlation of brainwave features from an object;
b) contracting the correlation of brainwave features with respect to the pain after determining a feature coefficient associated with the pain;
c) creating a differentiation and analysis model by machine learning and validation based on each feature after the contracting or a combination thereof; and
d) determining a differentiation and analysis model that attains a given accuracy.

(Item C32)
A method of differentiating pain of an object, comprising:
a) obtaining correlation of brainwave features from a reference object;
b) contracting the correlation of brainwave features with respect to the pain after determining a feature coefficient associated with the pain;
c) creating a differentiation and analysis model by machine learning and validation based on each feature after the contracting or a combination thereof;
d) determining a differentiation and analysis model that attains a given accuracy;
e) obtaining correlation of brainwave features from a test object; and
f) differentiating pain by fitting the correlation of brainwave features of the test object to the model.

(Item C33)
A method of differentiating pain of an object, comprising:
e) obtaining correlation of brainwave features from a test object; and
f) differentiating pain by fitting the correlation of brainwave features of the test object to a model for differentiating pain, wherein the model is generated by:
a) obtaining correlation of brainwave features from a reference object;
b) contracting the correlation of brainwave features with respect to the pain after determining a feature coefficient associated with the pain;
c) creating a differentiation and analysis model by machine learning and validation based on each feature after the contracting or a combination thereof; and
d) determining a differentiation and analysis model that attains a given accuracy.

(Item C34)
The method of any one of items 31 to 33, wherein the each feature after the contracting or combination thereof comprises an alternative integrated brainwave feature (this feature set is referred to as such because it is extracted by various signal processing methods from limited electrodes (Fp1, Fp2, or the like) and adaptively alternated depending on the monitoring environment or individual difference by the contracting process and integrally contributes to a pain differentiation model via, for example, a linear regression model.)

(Item C35)
A program for implementing the method of any one of the preceding items on a computer.

(Item C36)
A recording medium for storing a program for implementing the method of any one of the preceding items on a computer.

(Item C37A)
An apparatus for evaluating or determining pain experienced by an object, the apparatus comprising:
A) a headset comprising at least one electrode for obtaining a brainwave signal; and
B) a base unit;
wherein the base unit calculates a parameter of at least one feature of a brainwave,
wherein a differentiation model correlating the parameter with a pain level of the object is generated, and
wherein the pain level of the object is calculated and displayed by applying the parameter of the object to the differentiation model.

(Item C37B)
The apparatus of item C37A, wherein the feature comprises at least one selected from an amplitude, interrelation of brainwave features, frequency power, and a complexity index.

(Item C37C)

The apparatus of any one of the preceding items, wherein the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

(Item C37)

An apparatus for evaluating or differentiating pain experienced by an object, the apparatus comprising:
- A) a headset comprising at least one electrode for obtaining a brainwave signal; and
- B) a base unit;
- wherein the base unit calculates at least one parameter selected from the group consisting of interrelation of brainwave features and a complexity index of a brainwave,
- wherein a differentiation model correlating the parameter with a pain level of the object is generated, and
- wherein the pain level of the object is calculated and displayed by applying the parameter of the object to the differentiation model.

(Item C38)

The apparatus of item C37, wherein the interrelation of brainwave features and the complexity index of a brainwave further comprise one or more features of any one of the preceding items.

(Item C39A)

A computer program for making an apparatus implement a process for evaluating or determining pain experienced by an object, the process:
- calculating a parameter comprising at least one feature of a brainwave;
- generating a differentiation model for correlating the parameter with a pain level of the object; and
- calculating and displaying the pain level of the object by applying the parameter of the object to the differentiation model.

(Item C39B)

The apparatus of item C39A, wherein the feature comprises at least one selected from an amplitude, interrelation of brainwave features, frequency power, and a complexity index.

(Item C39C)

The apparatus of any one of the preceding items, wherein the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

(Item C39)

A computer program for making an apparatus implement a process for evaluating or determining pain experienced by an object, the process:
- calculating a parameter comprising at least one selected from the group consisting of interrelation of brainwave features and a complexity index of brainwave;
- generating a differentiation model for correlating the parameter with a pain level of the object; and
- calculating and displaying the pain level of the object by applying the parameter of the object to the differentiation model.

(Item C40)

The program of item C39, wherein the interrelation of brainwave features and the complexity index of a brainwave further comprise one or more features of any one of the preceding items.

(Item C41A)

A recording medium storing a computer program for making an apparatus implement a process for evaluating or determining pain experienced by an object, the process:
- calculating a parameter comprising at least one feature of a brainwave;
- generating a differentiation model for correlating the parameter with a pain level of the object; and
- calculating and displaying the pain level of the object by applying the parameter of the object to the differentiation model.

(Item C41B)

The recording medium of item C37A, wherein the feature comprises at least one selected from an amplitude, interrelation of brainwave features, frequency power, and a complexity index.

(Item C41C)

The apparatus of any one of the preceding items, wherein the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

(Item C41)

A recording medium storing a computer program for making an apparatus implement a process for evaluating or determining pain experienced by an object, the process:

calculating a parameter comprising at least one selected from the group consisting of interrelation of brainwave features and a complexity index of a brainwave;

generating a differentiation model for correlating the parameter with a pain level of the object; and calculating and displaying the pain level of the object by applying the parameter of the object to the differentiation model.

(Item C42)

The recording medium of item C41, wherein the interrelation of brainwave features and the complexity index of a brainwave further comprise one or more features of any one of the preceding items.

(Item C43A)

A method of evaluating or determining pain experienced by an object, the method comprising:

calculating a parameter comprising at least one feature of a brainwave;

generating a differentiation model for correlating the parameter with a pain level of the object; and calculating and displaying the pain level of the object by applying the parameter of the object to the differentiation model.

(Item C43B)

The method of item C43A, wherein the feature comprises at least one selected from an amplitude, interrelation of brainwave features, frequency power, and a complexity index.

(Item C43C)

The method of any one of the preceding items, wherein the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

(Item C43)

A method of evaluating or determining pain experienced by an object, the method comprising:

calculating a parameter comprising at least one selected from the group consisting of interrelation of brainwave features and a complexity index of brainwave;

generating a differentiation model for correlating the parameter with a pain level of the object; and calculating and displaying the pain level of the object by applying the parameter of the object to the differentiation model.

(Item C44)

The method of item C43, wherein the interrelation of brainwave features and the complexity index of a brainwave further comprise one or more features of any one of the preceding items.

The present invention is intended so that one or more of the aforementioned characteristics can be provided not only as the explicitly disclosed combinations, but also as other combinations thereof. Additional embodiments and advantages of the invention are recognized by those skilled in the art by reading and understanding the following detailed description as needed.

Advantageous Effects of Invention

The present invention can accurately monitor the change in subjective pain. The present invention enables therapy or surgery that is more detailed and in alignment with subjectivity based on the change in accurately recorded pain, and is useful in the medicine related industries.

The present invention can also efficiently differentiate pain. The present invention is capable of differentiating pain at a significantly higher level of accuracy, enables therapy or surgery that is more detailed and in alignment with subjectivity, and is useful in the medicine related industries.

The present invention materializes a methodology that enables tailor-made machine learning. This is important in any field that requires tailor-made machine learning. Applications thereof in various fields such as communication, electronics, acoustics, machinery, chemistry, and biology are envisioned. This is especially useful in fields where tailor-made machine learning is important such as individualized medicine (Precision Medicine). In this example, the present invention can efficiency differentiate pain. Pain can be differentiated at a significantly higher level of accuracy. The present invention enables the administration of more detailed and precise diagnosis, therapy, or surgery for pain that was difficult to understand from subjective expression, and is useful in the medicine related industries.

Pain can be efficiently differentiated by using the present invention. Pain can be differentiated at a significantly higher level of accuracy. The present invention enables the administration of therapy or surgery that is more detailed, in alignment with subjectivity, and objectively appropriate, and is useful in the medicine related industries.

The present invention also attains an effect of being able to simultaneously cover not only the pattern of "increase in pain→increase in EEG feature", but also the pattern of "increase in pain→decrease in EEG feature" by efficiently applying interrelation of brainwave features (phase synchronization, coherence, connectivity, or causality) for differentiating pain. The ability to cover phenomena where pain cannot be comprehensively differentiated with a single feature is a worthy discovery. The feature known as the "integrated EEG feature" of the invention attains such an effect. Those skilled in the art can adaptively implement the feature as appropriate depending on the situation in the contracting process by referring to the descriptions herein.

BRIEF DESCRIPTION OF DRAWINGS

FIG. 1B is a graph showing the relationship between electrical stimulation and pain levels (paired comparison).

FIG. 1D is a graph showing an example of a waveform of a brainwave.

FIG. 1G is a graph showing the relationship between pain level due to hot stimulation (VAS) and brainwave amplitude.

FIG. 1I shows a comparison between EEG amplitude in a mean time interval of 10 seconds (top row), 20 seconds (middle row), and 40 seconds (bottom row) (converted to absolute value and standardized) and change in pain at a low temperature (A), and comparison between EEG amplitude and change in subjective pain intensity (B). The correlation coefficients of both improve for longer mean time intervals. The horizontal axis indicates the time window, and the vertical axis indicates the absolute EEG amplitude (standardized) or pain intensity at a low temperature (standardized).

FIG. 6 shows how the correlation between mean change in potential and pain index changes due to a change in mean time interval. FIG. 6A shows the change in the correlation coefficient of subjective evaluation of pain (correlation between mean potential amplitude (absolute value) and subjective evaluation of pain for low temperature stimulation), and FIG. 6B shows the change in the correlation coefficient of cold stimulation intensity (correlation between mean potential amplitude (absolute value) and low temperature stimulation intensity). The vertical axis indicates the correlation coefficient, and the horizontal axis indicates the mean time interval (seconds).

FIG. 8 shows the change in the correlation coefficient when changing the arithmetic mean time interval from 10 seconds to 120 seconds using high temperature stimulation test data (six levels of pain). A tendency for a correlation coefficient to increase with longer mean time interval is observed. A shows the correlation between arithmetic mean potential amplitude (absolute value) and subjective pain evaluation, and B shows correlation between arithmetic mean potential amplitude (absolute value) and high temperature stimulation intensity. The vertical axis indicates the correlation coefficient, and the horizontal axis indicates the arithmetic mean time interval (seconds).

FIG. 9 shows the change in the correlation coefficient when changing the geometric mean time interval from 10 seconds to 120 seconds using high temperature stimulation test data (six levels of pain). A tendency for a correlation coefficient to increase with longer mean time interval is observed. A shows the correlation between geometric mean potential amplitude (absolute value) and subjective pain evaluation, and B shows correlation between geometric mean potential amplitude (absolute value) and high temperature stimulation intensity. The vertical axis indicates the correlation coefficient, and the horizontal axis indicates the geometric mean time interval (seconds).

FIG. 14 shows results of analyzing brainwave data during application of pain stimulation using a differentiation model using a mean amplitude (multiple regression model). A differentiation model was created by an experimental protocol that is different from brainwave data to be tested. Different pain stimulation protocols of high temperature and low temperature stimulation were used for modeling. The time frame was set to 15 seconds to make a pain trend visible. A trend similar to subjective evaluation of pain was exhibited. Observation used a sample size of 51. Data for the top 10 subjects are illustrated.

FIG. 25 shows an outline of the analysis method of Example 2 in Example 7. The property of temporal change in the frequency feature ($\beta$ band) exhibiting the property of delayed pain sensation of C fiber is illustrated (displayed by time frequency analysis). In particular, the frequency power is increased compared to other levels with a delay of 5 seconds after applying stimulation of level 6.

FIG. 26 shows feature extraction process (1): process for removal of EOG. Process 1: Primary component analysis is conducted on four electrode data to retrieve an EOG component (first component: gray). A 1 to 30 Hz band pass filter is then applied to reduce slow and fast changes, resulting in a smooth EOG waveform (black). Process 2: The original data for each electrode is regressed with EOG data to obtain a $\beta$ coefficient for each electrode. A component obtained from multiplying EOG by the $\beta$ coefficient is removed from the original recorded data. Gray (data with deviations): original Fp1 data. Black (data moving near the middle): data after removal of EOG.

FIG. 28 shows feature extraction process (3): addition of EOG feature. Process: Primary component data 1 ch for removal of EOG was added to the feature by "reverse utilization of noise". *A band pass filter is applied as the processing. After processes (1) to (3), a section from 5 to 15 seconds after applying stimulation is divided at each second, and features of frequency ($\delta$, $\theta$, $\alpha$, $\beta$) and amplitude were created at each electrode. Specifically, total of 25 features×6 levels×3 runs×10 sections.

FIG. 30 shows an outline of a differentiation model. A model was created at L1 and L6 (30 samples each). The number of sample of "total of 10200" was used. The criteria for refinement was set so that only subjects with differentiation accuracy of 70% would remain after 4 runs, resulting in 81 subjects. The differentiation accuracy of differentiation of L1 and L6 (feature of 5 to 10 seconds after applying stimulation, 6 samples) for all 170 subjects was "79.4±26.4%" using a refined model. There were "93" subjects, i.e., "54.7%", with 70% or greater differentiation accuracy, and "147" subjects, i.e., "86.5%", with a chance level of 50% or greater.

FIG. 31 shows pain occupancy. This is a concept indicating the certainty when a pain estimation value is differentiated as "having pain". The calculation method thereof is the following. i. Calculate an estimate for no pain (30 samples×81 subjects) and having pain (30 samples×81 subjects) by a differentiation model for 81 subjects (differentiation accuracy >70%) after refinement. ii. The minimum value (−1) and maximum value (2) of all pain estimation values are divided into, for example, 0.1 widths, and the occupancy of estimation value for having pain among each estimation value is calculated: "occupancy. (%) for having pain=number of estimation value for having pain/(number of estimation values for having pain+number of estimation values for no pain)". iii. This is fitted to a sigmoid function to obtain a "pain occupancy function" to create an occupancy model. An example of a pain occupancy function is shown below.

FIG. 32 shows an example of pain trend analysis. A feature of another experimental data was inputted into a pain model. Pain scores were "displayed as a pain trend" as a temporal change. EEG data was processed as follows. In the rest segment at 30 seconds from the start of recording, subsequent EEG features were standardized, and then inputted into a refined differentiation model. Estimation values increased in alignment with an increase in subjective evaluation and stimulation intensity. The occurrence rate (certainty) also increased. The correlation between estimation value and subjective evaluation of pain (COVAS) was as follows: r=0.45, and p≈0. The estimation value of a model increases as evaluation of discomfort increases with a double evaluation method of trends, and information supporting judgment on the degree of pain at the time (occupancy) is also obtained. The certainty of differentiation can be objectively judged by referring to the occupancy.

FIG. 33 shows an example of a high temperature stimulation paradigm used in Example 8 and the like. There were six levels of high temperature stimulation, and 3 stimulations were applied at each level. The time during which stimulation was applied was 15 seconds, and the time interval between level blocks was 100 seconds. The features were the mean frequency power ($\delta$, $\theta$, $\alpha$, $\beta$, and $\gamma$) and mean absolute amplitude of 3 stimulations at each level (15 seconds). The two levels to be differentiated are weak pain (levels 1 to 3) and strong pain (levels 4 to 6). The number of samples was strong/weak×3 levels×40 subjects=240.

FIG. 36 shows results of a comparative example. These are results (feature ranking and differentiation accuracy) of differentiation analysis with a process for contracting features (existing SVM-RFE: Support Vector Machine Recursive Feature Elimination: Guyon et al., (2002). Gene Selection for Cancer Classification using Support Vector Machine. Machine Learning 46: 389-422). The following is found from an economical pain differentiation/estimation model. 1) The top 4 types of features of an existing support vector machine (SVM) with contracting of features include the same types as the case using sigmoid contracting. 2) While the same differentiation accuracy of "71.3%" is materialized with a single feature, this is only a difference of one feature. 3) Calculation cost is high because leave-one-out cross validation is performed 240 times for SVM model construction, and this process is performed 24 times for ranking 24 features.

FIG. 37 shows the difference in calculation cost for sigmoid contracting and contracting in SVM-RFE. A shows a conventional SVM-RFE method. B shows an example of SVM with sigmoid contracting of the invention.

FIG. 38 shows a validation process of an economical differentiation model of the invention. 240 samples were divided into 10 (4 subjects×10 sets). 90% were used as data for creating a machine learning (SVM) model (36 subjects) to differentiate/estimate the pain level of the remaining 10% (4 subjects). Only the top two features were used.

FIG. 42A shows a pattern of change in differentiation accuracy as of the model creation, and FIG. 42B shows a pattern of change in differentiation accuracy of the final test data. As can be understood from both graphs, the change pattern has two step-like inflection areas. The extent of variation in the first inflection area is greater. Thus, sigmoid function approximation was applied to this inflection area to find a minimum feature exceeding the maximum value of the approximation function "63.7%". It was found that the differentiation model comprised 23 features (FIG. 42C). It was also found that the differentiation accuracy accounted for 54% of the overall improvement in differentiation accuracy due to the inflection (FIG. 42D).

FIG. 43 shows a list of 23 features included in a model exhibiting the maximum gain in improvement of differentiation accuracy. The brainwave features of Fp1 and Fp2 accounted for 9 out of a total of 23 (40%).

FIG. 44 shows differentiation model determination process 2 using a double contracting process upon section of a differentiation mode and features. The difference from the differentiation model determination process in FIG. 41 is in finding a value of difference (Diff) in differentiation accuracy of adjacent models, i.e., n−1 feature model (n≥2) and n feature model, after the first calculation of differentiation accuracy, and re-ranking features from a feature with a larger value of difference when inputted into a model. In such a case, a feature with the number 1 ranking in the first differentiation accuracy or a group of significantly correlated features is selected as the "main feature" and the rest are selected as "supporter features", where only the latter features are re-ranked. For example, differentiation accuracy exhibits a maximum gain of 1.4% in model creation from feature No. 14 to No. 15 in the list of features of FIG. 43. Thus, feature No. 15 is listed with a high ranking upon re-ranking excluding the number 1 ranking high gamma band feature in the Pz electrode, and inputted into a model at an early stage of model creation. By adding this process, the main feature that strongly approximates a differentiation function (e.g., sigmoid function or the like) is combined at an early stage with a supporter feature that has low approximation but fine tunes a model, so that a high differentiation accuracy is attained with few features.

FIG. 45 shows how differentiation accuracy changes by re-ranking of features using a value of difference (Diff) in differentiation accuracy of proximation models (n−1 feature model and n feature model) described in FIG. 44. A is the change in differentiation accuracy upon model validation by cross validation using learning data. B shows the change in accuracy upon validation of test data differentiation accuracy. For the change after two re-rankings, differentiation accuracy nearly reaches the ceiling at 10 to 15 features, indicating that this is the most economical differentiation model. This result suggests that re-ranking the number of features by the value of difference efficiently combines the main feature strongly approximating a differentiation function (e.g., sigmoid function or the like) with a supporter feature that fine tunes the model at an early stage to improve the differential accuracy.

FIG. 56 shows an outline of "tailor-made pain differentiation estimation method 1", in which a hyperparameter (C and γ for support vector machine (SVM)) is determined in all samples by cross validation (CV) as procedure 1, a model is created from all samples using the hyperparameter of procedure 1 to calculate differentiation accuracy at the individual level as procedure 2, a group of subjects with close differentiation accuracy is created from the ranking of differentiation accuracy at an individual level as procedure 3, a hyperparameter of each group is determined by CV as procedure 4, and a model is created from a sample of each group using the hyperparameter found in procedure 4, differentiation accuracy at an individual level is calculated, and a differentiation maximum model (displayed as "differentiation MAX model") is identified as procedure 5.

FIG. 62 summarizes differentiation accuracy of a differentiation maximum model ("differentiation MAX model") by demographics, i.e., by sex and age. It is predicted that a pain reaction property varies by sex and age. For example, differentiation accuracy of a single differentiation model using both sex and all ages did not reach 60% for males in their 60s, and the maximum accuracy was 70% for women in their 20s. Meanwhile, when a differentiation maximum (MAX) model is identified for each individual of each sex and each generation to perform differentiation and estimation, the differentiation accuracy improved 10% for males in their 60s, and the differentiation accuracy was 77% in women in their 20s, exhibiting a trend toward reaching 80%. This is an example demonstrating an effect of improving accuracy by tailor-made machine learning by grouping.

FIG. 63 shows an outline of "tailor-made pain differentiation estimation method 2" performed in Example 17. In addition to procedures 1 to 5 in Example 16, procedures 6 and 7 are performed. This is intended to improve differentiation accuracy by a differentiation model combination technology (ensemble method). Differentiation models are rearranged in descending order for each individual by differentiation accuracy using 62 models one at a time as procedure 6, and a differential model is increased one at a time, differentiation accuracy is calculated by "ensemble method (majority voting)", and the number of differentiation models with the highest differentiation accuracy is employed ("ensemble pruning") as procedure 7.

FIG. 64 shows a conceptual diagram 1 of the ensemble method. The diagram shows the relationship between a learning (training) data set and new validation (test) data and a process for outputting a final prediction. This is a process for separating a training data set into a plurality of subsets, sampling (grouping) the subsets, creating numerous individual differentiation models, and determining the final differentiation result for the test data by majority voting based on collection of individual model differentiation results.

FIG. 68 shows a summary of improvement in differentiation accuracy by ensemble method 1 performed in Example 17. Comparison of three differentiation methodologies of all objects is shown. The ensemble method improved accuracy about 16% more than the differentiation accuracy of a single differentiation model using all samples, and about 3% more than the single differentiation (maximum) MAX model.

FIG. 69 shows an outline of "tailor-made pain differentiation estimation method 3" performed in Example 18. This methodology strived to improve differentiation accuracy by a new differentiation model combination technology (ensemble method). This example rearranges models in descending order by differentiation accuracy using 62 models one at a time as procedure 6A, and a differentiation maximum (MAX) model with the highest differentiation accuracy thereamong is selected as the "main model", and the remaining "supporter models" are comprehensively added one by one, which is repeated to improve differentiation accuracy in stages as procedure 7A.

FIG. 70 shows a detailed description of the improved ensemble method performed in Example 18. Specifically, 1. A differentiation maximum (MAX) model is selected from all models (N models) as the "main model"; 2. N−1 models obtained from excluding the main model from all models are determined as "supporter models"; 3. Two model sets that improve differentiation accuracy the most by the ensemble method when one model is selected from N−1 supporter models and added to the main model are determined as the "updated main models"; 4. N−2 models obtained from excluding the updated main models from all models are determined as "updated supporter models"; 5. Procedures 3 to 4 are similarly repeated for the model set that improves differentiation accuracy the most by the ensemble method to update the updated main models and updated supporter models, and these procedures are repeated until there is no more updated supporter models.

FIG. 75 is a comparison of differentiation accuracy results with calibration for all 132 subjects. The slope of the percentage of correct answers of a reference differentiation model stabilizes by about 50 reference samples in the three models other than the single model of all samples (ensemble 1, ensemble 2, and differentiation maximum (MAX)) in a similar manner as individual patterns in FIG. 74. Test differentiation accuracy using a reference differentiation model exhibits a slow increase up to about 50 samples other than ensemble 1 and single model. The overall results show that application of reference stimulation before actual pain monitoring is, at most, about 50 times.

FIG. 76 shows how differentiation accuracy of the ensemble method with calibration changes when the number of references changes. The differentiation accuracy of test samples was similar even if the number of reference samples was increased to 10 to 50 for the single model and ensemble method 1, but differentiation accuracy improved 4 to 5% for ensemble method 2 and differentiation maximum (MAX) method.

FIG. 82 shows the results in Example 20, which are the results of differentiation analysis with a process of contracting features in FIG. 79 (feature ranking and differentiation accuracy).

FIG. 85 shows how differentiation accuracy changes by re-ranking of features using a value of difference (Diff) in differentiation accuracy of proximation models (n−1 feature model and n feature model) (see FIG. 80). The bottom left graph shows the change in accuracy upon validation of test data differentiation accuracy. For the change after two re-rankings, differentiation accuracy nearly reaches the ceiling at 10 to 15 features, indicating that this is the most economical differentiation model. This result suggests that re-ranking the number of features by the value of difference efficiently combines the main feature strongly approximating a differentiation function (e.g., sigmoid function or the like) with a supporter feature that fine tunes the model at an early stage to improve the differential accuracy. In other words, when re-ranking of features by a value of difference (Diff) in adjacent differentiation accuracies was repeated, features with high contribution tended to aggregate near the top of the ranking, so that differentiation accuracy nearly reached the ceiling with the second re-ranking as the earliest stage, with the fewest feature of 12. The standard deviation of differentiation accuracy up to ranks 1 to 12 was "1.4", exhibiting a property of improvement of "about 10-fold" of "0.11" of ranking 13 and thereafter (there is a number called DCV accuracy; SD of the top 12 and SD of ranking 13 and thereafter were calculated and compared).

FIG. 86 shows a distribution of object samples used in Example 22 by generation and sex.

FIG. 87 shows an example of a high temperature stimulation paradigm used in Example 21. There were six levels of high temperature stimulation, and 3 stimulations were applied for each level. The time during which stimulation was applied was 15 seconds, and the time interval between level blocks was 100 seconds. The correlation between features and brainwave features used are shown in FIG. 88. The two levels to be differentiated were weak pain (levels 1 to 3) and strong pain (levels 4 to 6). The number of samples was strong/weak×3 levels×158 subjects=948.

FIG. 88 shows the types of EEG features and correlation of features measured in Example 21.

FIG. 89 is a schematic diagram of calculation of multi-scale entropy (MSE) measured in Example 21. MSE is an improved version of sample entropy ($S_E$). First, time series data is divided by a time scale ($\tau$: number of divisions in data) to obtain coarse data. The solution is found by calculating, for each divided data, the percentage of data pair separated by a distance of m points being within r % of the standard deviation of data in the time frame of m and m+1, and calculating the negative natural logarithm of the ratio thereof (percentage of m+1 time frame/percentage of m time frame). Since activity in both time frames is often similar, the value is often "0", but the numerical value is high if the complexity of activity is high. Since there are the same number of $S_E$ as the number of divisions in the time scale, the sum is found as the complexity index (C). In general, m=2 and r=0.15 are used. $\tau$ can comprise 200 data points, and at most 600 points, in order to calculate a reliable MSE (Busa & Emmerik, Journal of Sport and Health Science 5 (2016) 44-51).

FIG. 91 shows a schematic diagram when curve fitting using a histogram of features. The numerical value where distributions of samples for no pain and having pain intersect is used as a differentiation threshold value. Samples less than the threshold value are converted to a category scale of "−1" and samples that are greater than the threshold value are converted to a category scale of "1". Poincare distribution or the like can also be used as the sample distribution for determining such a threshold value.

FIG. 92 shows extraction of dominant features (binomial classification). The features are rearranged by the magnitude of standardizing coefficient in descending order, and features containing 30% or more zero coefficients in 100 differentiations and estimations were eliminated to extract dominant features. This was able to extract six features. Such a feature set is known as "alternative integrated EEG features", which is called as such because the features are extracted by various signal processing methods from limited electrodes (Fp1, Fp2, or the like) worn upon monitoring and adaptively alternated depending on the monitoring environment or individual by the contracting process and "integrally" contributes to a pain differentiation model via, for example, a linear model. It was found as a result that frequency power at the parietal portion, frontal-parietal potential correlation, and MSE, frequency power, and mean amplitude at the frontal portion are especially useful as an EEG indicator for binomial classification of pain.

FIG. 94 shows differentiation accuracy from a generalized differentiation model comprising both high temperature and low temperature pain stimulation samples. A process of creating a differentiation model using n−1 samples, and estimating the pain level for the remaining one sample was repeated for the same number of times as the number of subjects. The differentiation accuracy of actually measured samples reached 74%, exceeding 56% of random samples by about 20%. In this Example, a feature correlation parameter for phase synchronization between electrodes of frequencies was also newly used in model creation.

DESCRIPTION OF EMBODIMENTS

Figure 1A:
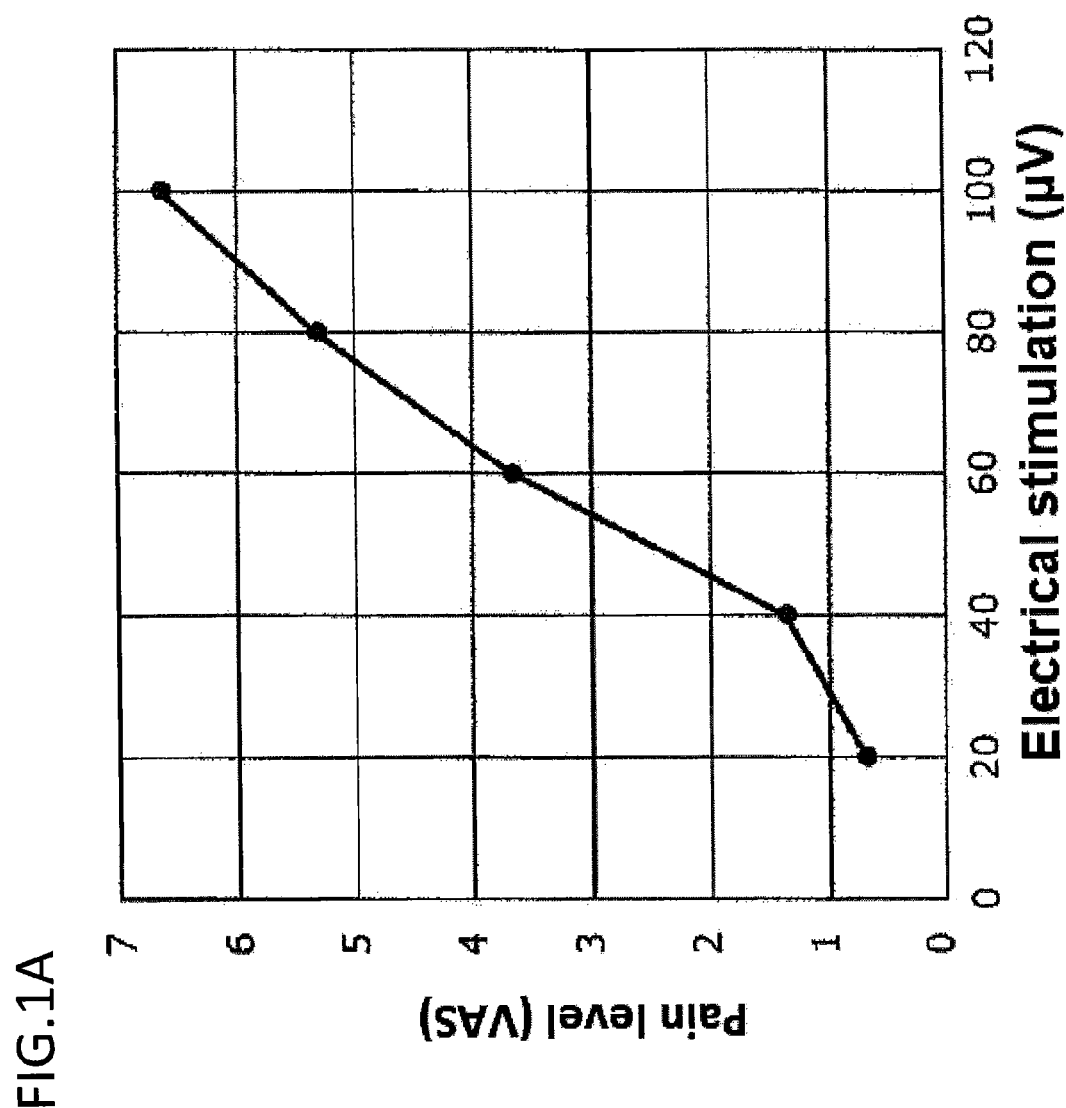
FIG. 1A is a graph showing the relationship between electrical stimulation and pain levels (VAS).

The present invention is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. The terms used herein should also be understood as being used in the meaning that is commonly used in the art, unless specifically noted otherwise. Thus, unless defined otherwise, all terminologies and scientific technical terms that are used herein have the same meaning as the general understanding of those skilled in the art to which the present invention pertains. In case of a contradiction, the present specification (including the definitions) takes precedence.

Definition

The terms and the general technologies used herein are first explained.

(Information Processing Related Matters)

As used herein, "machine learning" refers to a technology for imparting a computer the ability to learn without explicit programming. This is a process of improving a function unit's own performance by acquiring new knowledge/skill or reconfiguring existing knowledge/skill. Most of the effort required for programming details can be reduced by programming a computer to learn from experience. In the machine learning field, a method of constructing a computer program that enables automatic improvement from experience has been discussed. Data analysis/machine learning plays a role in elemental technology that is the foundation of intelligent processing along with field of the algorithms. Generally, data analysis/machine learning is utilized in conjunction with other technologies, thus requiring the knowledge in the cooperating field (domain specific knowledge; e.g., medical field). The range of application thereof includes roles such as prediction (collect data and predict what would happen in the future), search (find a notable feature from the collected data), and testing/describing (find relationship of various elements in the data). Machine learning is based on an indicator indicating the degree of achievement of a goal in the real world. The user of machine learning must understand the goal in the real world. An indicator that improves when an objective is achieved needs to be formularized. Machine learning has the opposite problem that is an ill-posed problem for which it is unclear whether a solution is found. The behavior of the learned rule is not definitive, but is stochastic (probabilistic). Machine learning requires an innovative operation with the premise that some type of uncontrollable element would remain. The tailor-made method of the invention can be considered as a solution to such a problem. It is useful for a user of machine learning to sequentially select data or information in accordance with the real world goal while observing performance indicators during training and operation.

Linear regression, logistic regression, support vector machine, or the like can be used for machine learning, and cross validation (CV) can be performed to calculate differentiation accuracy of each model. After ranking, a feature can be increased one at a time for machine learning (linear regression, logistic regression, support vector machine, or the like) and cross validation to calculate differentiation accuracy of each model. A model with the highest accuracy can be selected thereby. Any machine learning can be used herein. Linear, logistic, support vector machine (SVM), or the like can be used as supervised machine learning.

Machine learning uses logical reasoning. There are roughly three types of logical reasoning, i.e., deduction, induction, and abduction as well as analogy. Deduction, under the hypothesis that Socrates is a human and all humans die, reaches a conclusion that Socrates would die, which is a special conclusion. Induction, under the hypothesis that Socrates would die and Socrates is a human, reaches a conclusion that all humans would die, and determines a general rule. Abduction, under a hypothesis that Socrates would die and all humans die, arrives at Socrates is a human, which falls under a hypothesis/explanation. However, it should be noted that how induction generalizes is dependent on the premise, so that this may not be objective. Analogy is a probabilistic logical reasoning method which reasons that if object A has 4 features and object B has three of the same features, object B also has the remaining one feature so that object A and object B are the same or similar and close.

Impossible has three basic principles, i.e., impossible, very difficult, and unsolved. Further, impossible includes generalization error, no free lunch theorem, and ugly duckling theorem and true model observation is impossible, so that this is impossible to verify. Such an ill-posed problem should be noted.

Feature/attribute in machine learning represents the state of an object being predicted when viewed from a certain aspect. A feature vector/attribute vector combines features (attributes) describing an object being predicted in a vector form.

As used herein, "model" or "hypothesis" are used synonymously, which is expressed using mapping describing the relationship of inputted prediction targets to prediction results, or a mathematical function or Boolean expression of a candidate set thereof. For learning with machine learning, a model considered the best approximation of the true model is selected from a model set by referring to training data.

Examples of models include generation model, identification model, function model, and the like. Models show a difference in the direction of classification model expression of the mapping relationship between the input (object being predicted) x and output (result of prediction) y. A generation model expresses a conditional distribution of output y given input x. An identification model expresses a joint distribution of input x and output y. The mapping relationship is probabilistic for an identification model and a generation model. A function model has a definitive mapping relationship, expressing a definitive functional relationship between input x and output y. While identification is sometimes considered slightly more accurate in an identification model and a generation model, there is basically no difference in view of the no free lunch theorem.

Model complexity: the degree of whether mapping relationship of an object being predicted and prediction result can be described in more detail and complexity. Generally, more training data is required for a model set that is more complex.

If a mapping relationship is expressed as a polynomial equation, a higher order polynomial equation can express a more complex mapping relationship. A higher order polynomial equation is considered a more complex model than a linear equation.

If a mapping relationship is expressed by a decision tree, a deeper decision tree with more nodes can express a more complex mapping relationship. Therefore, a decision tree with more nodes can be considered a more complex model than a decision tree with less nodes.

Classification thereof is also possible by the principle of expressing the corresponding relationship between inputs and outputs. For a parametric model, the distribution or shape of the function is completely determined by parameters. For a nonparametric model, the shape thereof is basically determined from data. Parameters only determine smoothness.

Parameter: an input for designating one of a set of functions or distribution of a model. It is also denoted as Pr[y|x; θ], y=f(x; θ), or the like to distinguish from other inputs.

For a parametric model, the shape of a Gaussian distribution is determined by mean/variance parameters, regardless of the number of training data. For a nonparametric model, only the smoothness is determined by the number of bin parameter in a histogram. This is considered more complex than a parametric model.

For learning in machine learning, a model considered the best approximation of the true model is selected from a model set by referring to training data. There are various learning methods depending on the "approximation" performed. A typical method is the maximum likelihood estimation, which is a standard of learning that selects a model with the highest probability of producing training data from a probabilistic model set. Maximum likelihood estimation can select a model that best approximates the true model. KL divergence to the true distribution becomes small for greater likelihood. There are various types of estimation that vary by the type of form for finding a parameter or estimated prediction value. Point estimation finds only one value with the highest certainty. Maximum likelihood estimation, MAP estimation, and the like use the mode of a distribution or function and are most often used. Meanwhile, interval estimation is often used in the field of statistics in a form of finding a range within which an estimated value falls, where the probability of an estimated value falling within the range is 95%. Distribution estimation is used in Bayesian estimation or the like in combination with a generation model introduced with a prior distribution for finding a distribution within which an estimated value falls.

In machine learning, over-training (over-fitting) can occur. With over-training, empirical error (prediction error relative to training data) is small, but generalization error (prediction error relative to data from a true model) is large due to selecting a model that is overfitted to training data, such that the original objective of learning cannot be achieved. Generalization errors can be divided into three components, i.e., bias (error resulting from a candidate model set not including a true model; this error is greater for a more simple model set), variance (error resulting from selecting a different prediction model when training data is different; this error is greater for a more complex model set), and noise (deviation of a true model that cannot be fundamentally reduced, independent of the selection of a model set). Since bias and variance cannot be simultaneously reduced, the overall error is reduced by balancing the bias and variance.

As used herein, "ensemble (also known as ensemble learning, ensemble method, or the like)" is also referred to as group learning and attempts to perform the same learning as learning of a complex learning model by using a relatively simple learning model and a learning rule with a suitable amount of calculation, and selecting and combining various hypotheses depending on the difference in the initial value or weighting of a given example to construct a final hypothesis. Ensemble learning combines a plurality of individually learned learners to improve the generalization capability (prediction ability with respect to unlearned data) and create a single learner (FIG. 64). This is very broadly used, not only in simple use of ensemble learning itself as a methodology of algorithm of machine learning for regression or classification, but also in supplemental use such as when finding a learning coefficient of another machine learning algorithm. Since ensemble learning improves the performance by combining many hypotheses in this manner, the learning algorithm used in ensemble learning is known as a weak learning algorithm or weak learner, and the hypothesis is known as a weak hypothesis, weak discriminator, or weak differentiator.

As used herein, "pruning" is used in the ensemble method or the like, referring to pruning a branch of a tree that would overfit a model. Pruning can be performed by cross validation. The procedure is generally used only on a decision tree that operates as a single unit. Meanwhile, since a decision tree ensemble is generally comprised of sufficiently small trees, this functions as a self-defense mechanism against overfitting. Combining simple learners to make a complex learner has long been attempted in the field of neural networks. While terms such as combining predictor, combining learner, committee machine, modular network, voting network, ensemble learning, or the like is used to refer to a learner made in this manner or an algorithm thereof, the term ensemble learning is used herein.

When a plurality of different parameters are given by such learning, the final output is determined by a majority vote. In this regard, if hypothesis hi is weighted by weighting wi (generally the total sum of weightings is normalized to be 1), the weighting indicates which hypothesis output is prioritized. If the majority vote is configured based thereon, the vote is referred to as a weighted vote. If the weighting is uniform, the vote is referred to as equally vote. If outputs are quantitative, final outputs are hypothesis outputs that are weighted and added.

Machine learning obtained by ensemble learning is also referred to as a final hypothesis or strong discriminator, consisting of a large number of weak hypothesis and a coupler for combining them. This is classified into several learning algorithms depending on whether operation of a coupler is dynamic or static with respect to inputs, and whether generation method of weak hypotheses is parallel or sequential.

Examples of ensemble methodologies include boosting and bagging.

Boosting weights each supervisory data and generates a single weak learner by using all supervisory data. Weighting is reduced for supervisory data from which information has been correctly extracted by the generated weak learner, and weighting is increased for supervisory data from which information has been incorrectly extracted to update the weighting of supervisory data. All supervisory data with updated weighting is used to generate another weak learner. An information extraction apparatus with high accuracy is obtained thereafter by repeating the same processing to generate a plurality of weak learners and combine outputs of a plurality of generated weak learners at their respective weighting. Boosting is a methodology using, for example, several thousand detection targets and non-detection targets that have been labeled in advance called learning samples, such as samples (examples) consisting of facial images and non-facial images for generating and combining different learners (weak hypotheses) while sequentially changing the weighting of the examples to construct a learner (final hypothesis) with high accuracy. The term boosting is used to mean that the accuracy of the learning algorithm is boosted.

Bagging randomly samples a given number of data from all supervisory data to generate a supervisory data group and generates a weak learner by using the supervisory data group. By repeating this processing, a plurality of weak learners are generated and outputs of a plurality of the generated weak learners are combined to obtain an information extraction apparatus with high accuracy. This generates hypotheses in parallel. This can be considered as a method for learning by using a part of the information of learning data instead of all of the information and combining the data at the end. Boosting is the same as bagging in terms of using a part of learning data and combining at the end, but the difference is in boosting reusing data that has been used previously for literally boosting. For this reason, boosting is incapable of parallel processing as in bagging.

A bootstrap method can be used to improve the recognition performance. A bootstrap method is a method of selecting out weak learners and combining them into a final learner.

As used herein, "contract" refers to reducing or consolidating variables, i.e., features. For example, factor analysis refers to explaining, when there are a plurality of variable, the relationship between a plurality of variables with a small number of potential variables by assuming that there is a constituent concept affecting the variables in the background thereof. This is a form of conversion to a small number of variables, i.e., contracting. The potential variables explaining the constituent concept are referred to as factors. Factor analysis contracts variables that can be presume to have the same factors in the background to create new quantitative variables.

As used herein, "differentiation function" is a numerical sequence, i.e., a function, created to match the arrangement of samples to be differentiated by assigning continuous numerical values to the number of levels to be differentiated. For example, if samples to be differentiated are arranged to match the levels when there are two differentiation levels, the numerical sequence thereof, i.e., differentiation function, is generated, for example, to have a form of a sigmoid function. For three or more levels, a step function can be used. A model approximation index numerically represents the relationship between a differentiation function and differentiation level of samples to be differentiated. When a difference therebetween is used, the range of fluctuation is controlled. A smaller absolute value of a value of difference indicates higher approximation. When correlation analysis is performed, a higher correlation coefficient (r) indicates higher approximation. When regression analysis is used, a higher $R^2$ value is deemed to have higher approximation.

As used herein, "weighting coefficient" is a coefficient that is set so that an important element is calculated as more important in the calculation of the invention, including approximation coefficients. For example, a coefficient can be obtained by approximating a function to data, but the coefficient itself only has a description indicating the degree of approximation. When coefficients are ranked or chosen/discarded on the basis of the magnitude or the like, a difference in contribution within the model is provided to a specific feature, so that this can be considered a weighting coefficient. A weighting coefficient is used in the same meaning as an approximation index of a differentiation function. Examples thereof include $R^2$ value, correlation coefficient, regression coefficient, residual sum of squares (difference in feature from differentiation function), and the like.

As used herein, "differentiation function model" refers to a model of a function used for differentiation of pain or the like. Examples thereof include, but are not limited to, sigmoid function and step function.

As used herein, "hyperparameter" refers to a (hyper) parameter above machine learning, which is not learned by machine learning. A model used in machine learning has more or less parameters that need to be set by a person conducing the analysis. Machine learning generally involves such parameters. Each machine learning algorithm often has one or more hyperparameters for controlling the operation thereof. Unlike coefficients (parameters) contained in a model, the value of hyperparameters is not determined through machine learning. The value is given by solving an optimization problem before running a machine learning algorithm. Examples of hyperparameters include the number of generated decision trees in random forest, fitting accuracy of regression analysis, the degree of a polynomial equation contained in a model, and the like. A fixed value may be used as a value of a hyperparameter, or a user designated value may be used.

(Brainwave Related Matters)

As used herein, "object" is used synonymously with patient and subject and refers to any organism or animal which is subjected to the technology in the disclosure such as pain measurement and brainwave measurement. An object is preferably, but is not limited to, humans. As used herein, an object may be referred to an "object being estimated" when estimating pain, but this has the same meaning as object or the like. There may be a plurality of "objects". In such a case, each individual may be referred to as a "sample" (of objects).

As used herein, "brainwave" has the meaning that is commonly used in the art and refers to a current generated by a difference in potential due to neurological activity of the brain when a pair of electrodes is placed on the scalp. Brainwave encompasses electroencephalogram (EEG), which is obtained from deriving and recording temporal changes in the current. A wave with an amplitude of about 50 μV and a frequency of approximately 10 Hz is considered the primary component at rest. This is referred to as an α wave. During mental activity, α waves are suppressed and a fast wave with a small amplitude of 17 to 30 Hz appears, which is referred to as a β wave. During a period of shallow sleep, α waves gradually decrease and θ waves of 4 to 8 Hz appear. During a deep sleep, δ waves of 1 to 4 Hz appear. These brainwaves can be expressed by a specific amplitude, frequency, complexity index, correlation, or the like. Brainwaves can be represented by a specific, amplitude and frequency or analysis of amplitude.

As used herein, "brainwave data" is any data related to brainwaves (also referred to as "amount of brain activity", "brain feature", or the like), such as amplitude data (EEG amplitude), frequency property, or the like. "Analysis data" from analyzing such brainwave data can be used in the same manner as brainwave data, so that such data is collectively referred to as "brainwave data or analysis data thereof" herein. Examples of analysis data include mean amplitude and peak amplitude (e.g., Fz, Cz, C3, C4), frequency power (e.g., Fz(δ), Fz(θ), Fz(α), Fz(β), Fz(γ), Cz(δ), Cz(θ), Cz(α), Cz(β), Cz(γ), C3(δ), C3(θ), C3(α), C3(β), C3(γ), C4(δ), C4(θ), C4(α), C4(β), and C4(γ)) and the like of brainwave data. Of course, this does not exclude other data commonly used as brainwave data or analysis data thereof. For example, raw data sampled out for a certain period of time, when used for differentiation, is also a feature, so this can also be used in the present invention.

As used herein, "brainwave feature" or "feature of brainwave" refers to any feature of a brainwave, encompassing "brainwave data or analysis data thereof" such as amplitude, interrelation of brainwave features, frequency power, and complexity index. As examples thereof, the amplitude can comprise an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features can comprise potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power can comprise a spectral density, a power spectrum, or a subtype thereof, and the complexity index can comprise at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like)

As used herein, "amplitude data" is one type of "brainwave data" and refers to data for amplitudes of brainwaves. This is also referred to as simply "amplitude" or "EEG amplitude". Since such amplitude data is an indicator of brain activity, such data can also be referred to as "brain activity data", "amount of brain activity", or the like. Amplitude data can be obtained by measuring electrical signals of a brainwave and is indicated by potential (can be indicated by μV or the like). Amplitude data that can be used include, but are not limited to, mean amplitude.

As used herein, "frequency power" expresses frequency components of a waveform as energy and is also referred to as power spectrum. Frequency power can be calculated by extracting and calculating frequency components of a signal embedded in a signal contained in noise within a time region by utilizing fast Fourier transform (FFT) (algorithm for calculating discrete Fourier transform (DFT) on a computer at high speeds). FFT on a signal can, for example, use the function periodgram in MATLAB to normalize the output thereof and calculate the power spectrum density PSD or power spectrum, which is the source of measurement of power. PSD indicates how power of a time signal is distributed with respect to frequencies. The unit thereof is watt/Hz. Each point in PSD is integrated over the range of frequencies where the point is defined (i.e., over the resolution bandwidth of PSD) to calculate the power spectrum. The unit of a power spectrum is watt. The value of power can be read directly from power spectrum without integration over the range of frequencies. PSD and power spectrum are both real numbers, so that no phase information is included. In this manner, frequency power can be calculated with a standard function in MATLAB. As the analysis method, time frequency analysis can be used as exemplified in FIG. 25. For example, temporal change in frequency power can be found, for example, by determining a unit of time such as 1 second and shifting the point. As shown in FIG. 25, this elucidates the delay property of thermal pain. For example, a time segment where pain is sharp (e.g., 5 seconds after application of stimulation and thereafter) can be identified, and a feature that can be categorically distinguished from "delayed pain feature" among frequency features can be created. This was actually demonstrated in the Examples (see FIGS. 25 to 32).

As used herein, "complexity" refers to a situation where logically possible connection relationships among various elements are excessive, and one relationship must be selected therefrom. When used in the context of brainwaves, this refers to a state where the possible connection relationship of each brainwave is excessive. An index thereof is referred to as a "complexity index".

As used herein, "complexity index" refers to a scale of complex and superficially irregular appearing behavior due to the large number of constituent elements or nonlinearity. A complexity index can be represented with entropy or the like. Entropy refers to the scale of disorderliness of a system and refers to the mean value of the amount of information that is communicated by knowing which event has occurred from a limited complete event system. In informatics, entropy is also referred to as the amount of information, which is an indicator of complexity of activity. Thus, complexity is broader than the concept of entropy in the chaotic sense. Examples of entropy include, but are not limited to, multiscale entropy (MSE), sample entropy, self entropy, mean entropy, joint entropy, relative entropy, conditional entropy, and the like.

Multiscale entropy (MSE) is an analysis method that has drawn attention as a new nonlinear analysis method, which has overcome problems of existing nonlinear analysis methods (data stability, i.e., state where a property of the entire data (variance or the like) is not locally reproduced). MSE is vulnerable to artifacts and requires data from an extended period of time with high resolution, but was further improved upon from approximate entropy (ApEn; Pincus S M. Approximate entropy as a measure of system complexity. Proc Natl Acad Sci USA 1991; 88:2297-2301) and an improved version thereof, i.e., sample entropy (SampEn; Richman J S. Moorman J R. Physiological time-series analysis using approximate entropy and sample entropy. Am J Physiol Heart Circ Physiol 2000; 278: 2039-2049) as a practical nonlinear analysis method to overcome the fact that measurements meeting such conditions are challenging for actual measurement data in clinical settings. MSE was developed by Costa et al (Costa M. Goldberger A L. Peng C K. Multiscale entropy analysis of complex physiologic time series. Phys Rev Lett 2002; 89: 068102). MSE is found by reconstructing the original data from finding the arithmetic mean so that the data does not overlap and calculating each of ApEn/SampEn of the reconstructed data with a plurality of number of additions (time axis). With a low number of additions, complexity of a high frequency band is represented. With a high number of additions, complexity of a low frequency band is represented. Therefore, MSE analysis enables nonlinear extraction, which was challenging with existing nonlinear analysis methods. For example, Busa & Emmerik have recently published a report for brainwaves (Journal of Sport and Health Science Volume 5, Issue 1, March 2016, Pages 44-51).

As used herein, "interrelation of brainwave features" refers to the interrelation of two or more brainwave features. Any brainwave feature may be used as long as the feature is brainwave data or analysis data thereof. Examples thereof include, but are not limited to, amplitude (including mean amplitude and the like), frequency power, potential, complexity index (including MSE and the like), and the like.

As used herein, "interrelation" refers to any relationship between two features. Interrelation is a broad concept including the relationship of different features of the same electrode, relationship of the same features at different times, and the like, including correlation. There is a phase synchronization indicator, which retrieves multiple phases of activity to find synchronicity between periods. This is encompassed by a broadly defined concept of interrelation. In this manner, interrelation does not use a correlation coefficient, but encompasses the same type of relational indicator.

As used herein, "correlation" generally indicates a concept of association between two or more variable amounts or a value thereof in mathematical statistics and biological statistics. As an example of correlation, the statistical scale can be represented by a correlation coefficient (r, ρ, or the like). The value thereof is between −1 and +1. A value close to +1 means positive correlation, a value close to −1 means negative correlation, and a value close to 0 means non-correlation. For example, human body length/body weight has a positive correlation with a certain r value. If there is a positive or negative correlation, the functional relationship (empirical formula) between variables can be found in a form of a regression line, and this methodology can be expanded to nonlinear regression. Qualitative correlation for only large or small (+1 or −1) for each variable can be called association.

In one embodiment, interrelation encompasses correlation as well as indicators that cannot be considered correlation such as a phase synchronization indicator for finding synchronicity between periods. Examples of narrowly defined correlation, i.e., various forms of correlation (synchronicity, unrelatedness, delay, positive/negative, similarity, and match) include temporal correlation, spatial correlation, spatiotemporal synchronicity, spatial relationship or connectivity, unrelatedness or uncorrelatedness, delay or breakdown in temporal correlation, positive/negative or correlated property, similarity or level of correlation coefficient, and a match or complete correlation. In this manner, it can be understood that synchronicity is temporal correlation, connectivity is a spatial (e.g., parts of brain) relationship, unrelatedness is uncorrelatedness, delay is breakdown in temporal correlation, positive/negative is correlated property, similarity is having a high correlation coefficient, and match is complete correlation.

As used herein, "synchronicity" refers to the degree of synchronization. In this regard, synchronization refers to two periodically changing amounts having the same or different number of vibrations (frequencies), and a phase difference therebetween is constant or changes around a constant mean value. Examples of synchronicity include phase synchronization (phase locking value), coherence, and the like. The features of coherence are wide-ranging, such as cross power spectrum, cross bispectrum, high order cross spectrum, auto/cross bicoherence, auto/cross bispectral density, auto/cross real triple product, and auto/cross biphase corresponding to the frequency features of power spectrum, bispectrum, high order spectrum, auto power spectrum, auto bispectrum, and high order auto spectrum. These feature correlations have been understood as effective indicators for physiological and psychological conditions of an organism, wherein the numerical value decreases if the level of consciousness decreases. However, in contrast to expectation, the present invention demonstrated that a numerical value of potential feature correlation decreases even in a situation where a pain level becomes very strong such that the level of consciousness does not decrease but increases. Thus, not only the increasing pattern of the feature correlation described above, but also a decreasing pattern can be incorporated into a differentiation model as a "pain level inverse correlation feature parameter" in contrast to "pain level positive correlation feature parameter". In view of the above, a positive correlation parameter functions as an "accelerator", while an inverse correlation parameter functions as a "brake" for the adjustment thereof in a linear multiple regression model used in this embodiment, such that a more fine-tuned differentiation model can be created.

As used herein, similarity refers to the similarity (resemblance, affinity), dissimilarity, distance, and the like between objects obtained from trait data. Generally, the range of values of similarity and dissimilarity is a real number from "0 to 1" when the distance is scaled, but the range of values of distance can be a non-negative real number (0 to infinity). While a distance is close to infinity when considering the distance between stars at both ends in space, if this distance is scaled to a similarity index of "1", the distance would not be infinity. A distance is a difference between data, but this can be used as a similarity indicator by scaling and converting to 0 to 1. For a distance that can be used herein, any of Euclidean, block distance, Minkowski, Chebyshev, Mahalanobis, a value obtained by subtracting a correlation coefficient from 1, and the like can be used.

As used herein, "potential correlation" refers to correlation of two or more potentials, which are brainwave features. Since potential is represented by amplitude, this is also referred to as "amplitude correlation".

For a type of brainwave that is an event related potential, a negative potential reflecting automatic warning called N100 is observed at around 100 milliseconds after application of sensation stimulation. For example, since this component is readily affected by the internal condition of an organism such as familiarity or drowsiness, the amplitude decreases when consciousness decreases. Decrease in consciousness also affects high level cognition after N100. A decrease in positive potential such as P300 reflecting conscious evaluation or judgment is expected. Thus, if an object is applied with sensational stimulation 100 times and consciousness decreases with the progression of testing, it is expected that the negative potential of N100 decreases and positive potential of P300 decreases. If the relationship between 100 N100 potential (average or peak potential in a certain time frame) and P300 potential is analyzed by Pearson's correlation analysis, it is expected that a negative potential correlation is observed, i.e., the more the N100 potential is positive, P300 potential is more negative. Such a relationship between brain potential activities is determined herein as potential correlation.

As used herein, "brainwave feature" and "interrelation of brainwave features" are collectively referred to as a "parameter" associated with brainwaves.

As used herein, "alternative integrated EEG feature" refers to a feature extracted from limited electrodes (Fp1, Fp2, and the like in the front portion described above) by various signal processing methods, and is adaptively alternated depending on the monitoring environment or individual difference by a contracting process and integrally contributes to a pain determination model via, for example, the linear regression model in this Example.

As used herein, "pain" refers to a sensation that is generated as stimulation, generally upon intense injury such as damage/inflammation to a body part. Pain is not a disease but is a symptom. The state thereof is determined by the combination of three main properties, i.e., central nervous, nociceptive, and neuropathic pain. Acute pain and chronic pain are distinguished, which are different in terms of the associated cerebral site network (connectivity). Chronic pain is sometimes subjectively reported as painful when in fact it is not painful. Chronic pain includes psychogenic factors that cannot be explained by sensational intensity of pain stimulation.

In humans, pain is encompassed by common sensations as a sensation accompanying strong unpleasant feeling. In addition, cutaneous pain and the like also has an aspect as an external receptor to a certain degree, which plays a role in determining the quality such as hardness, sharpness, hotness (thermal pain), coldness (cold pain), or spiciness of an external object in cooperation with other skin sensation or taste. The sensation of pain of humans can occur at almost any part of the body (e.g., pleura, peritoneum, internal organs (visceral pain, excluding the brain), teeth, eyes, ears, and the like) other than the skin and mucous membrane, which can all be sensed as a brainwave or a change thereof in the brain. Additionally, internal sensation of pain represented by visceral pain is also encompassed by sensation of pain. The aforementioned sensation of pain is referred to as somatic pain relative to visceral pain. In addition to somatic pain and visceral pain, sensation of pain called "referred pain", which is a phenomenon where pain is perceived at a surface of a site that is different from a site that is actually damaged, is also reported. The present invention provides a methodology of expressing a temporal change in such various pain types as a trend and monitoring subjective pain levels, and other methodologies described herein.

For sensation of pain, there are individual differences in sensitivity (pain threshold), as well as qualitative difference due to a difference in the receptor site or how a pain stimulation occurs. Sensation of pain is classified into dull pain, sharp pain, and the like, but sensation of pain of any type can be measured, estimated, and classified in this disclosure. The disclosure is also compatible with fast sensation of pain (A sensation of pain), slow sensation of pain (B sensation of pain), (fast) topical pain, and (slow) diffuse pain. The present invention is also compatible with abnormality in sensation of pain such as hyperalgesia. Two nerve fibers, i.e., "Aδ fiber" and "C fiber", are known as peripheral nerves that transmit pain. For example, when a hand is hit, the initial pain is transmitted as sharp pain from a clear origin (primary pain: sharp pain) by conduction through the Aδ fiber. Pain is then conducted through the C fiber to feel throbbing pain (secondary pain; dull pain) with an unclear origin. Pain is classified into "acute pain" lasting 4 to 6 weeks or less and "chronic pain" lasting 4 to 6 weeks or more. Pain is an important vital sign along with pulse, body temperature, blood pressure, and breathing, but is difficult to express as objective data. Representative pain scales VAS (visual analogue scale) and faces pain rating scale are subjective evaluation methods that cannot compare pain between patients. Meanwhile, the inventors have focused on brainwaves which are hardly affected by the peripheral circulatory system as an indicator for objectively evaluating pain, arriving at the conclusion that pain can be differentiated and classified by observing the change during latency/amplitude in response to pain stimulation and performing trend analysis. In particular, instantaneous pain and throbbing sustained pain can also be distinguishable by the trend analysis of the invention. Since instantaneous pain is pain during a short time segment, associated brain activity can decrease if a time direction averaging method over at least several tens of seconds is used in trend analysis (e.g., significant correlation with pain evaluation is not observed). Meanwhile, sustained pain is continuous, so that significant correction with pain evaluation can be rather strengthened by a time direction averaging method. The inventors focused on brainwaves that are less susceptible to the effect of the peripheral circulatory system as an indicator for objective evaluation of pain. Observation of the change during latency/amplitude in response to pain stimulation lead to classification of types of pain (comfort/discomfort). Instantaneous stimulation and sustained stimulation can also be classified in this manner.

One of the important points of the present invention is in the ability to distinguish whether pain is pain "requiring therapy", rather than the intensity in itself. Therefore, it is important that "pain" can be clearly categorized based on the concept of "therapy". For example, this leads to "qualitative" classification of pain such as "pleasant/unpleasant" or "unbearable". For example, the position of a "pain classifier", baseline, and the relationship thereof can be defined. In addition to a case of n=2, cases where n=3 or greater can also be envisioned. When n is 3 or greater, pain can be separated into "not painful", "comfortable pain", and "painful". For example, pain can be differentiated as "unbearable, need therapy", "moderate", or "painful, but not bothersome". When the trend analysis of the invention is used, "unbearable" and "painful but bearable" pain can be distinguished by identifying a threshold value for long/short duration of a signal associated with strong pain.

As used herein, "subjective pain sensation level" refers to the level of sensation of pain of an object, and can be expressed by conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like.

As used herein, "trend analysis" refers to a methodology of analyzing the trend of changes in data by focusing on "chronological change" rather than data distribution. This is an attempt to pick up a characteristic change in parameters such as the slope of a change or ratio of change in the slope through comparison with expected change or the like to find some type of a cause of trend thereof. For this disclosure, a trend of changes in subjective pain is analyzed or estimated through trend analysis on electrical signals. In the present invention, a "temporal change" in subjective pain can be analyzed in detail and with accuracy through trend analysis of electrical signals.

As used herein, "mean potential in a time frame" refers to a mean value of potentials of brainwaves for a certain time frame (including, but not limited to, 30 seconds and the like). While mean generally uses the arithmetic mean, other means, such as the geometric mean can also be used. Other central tendencies (median or mode) can also be used. One or more peak amplitudes in a specific time frame can also be used. It is understood that any averaging methodology can be used herein (see for example FIG. 9).

Examples of the time frame that can be used herein include, but are not limited to, 10 seconds or greater, 15 seconds or greater, 20 seconds or greater, 25 seconds or greater, 30 seconds or greater, 35 seconds or greater, 40 seconds or greater, 45 seconds or greater, 50 seconds or greater, 55 seconds or greater, 60 seconds or greater, and the like. Even if the individual pattern of actual pain is unknown upon individual measurement, it is preferable to use a mean value using various time frames for the estimation thereof.

In a preferred embodiment, the time frame that can be used can be 30 seconds or greater or 40 seconds or greater. Examples of the upper limit include, but are not limited to, 20 seconds, 30 seconds, 40 seconds, 50 seconds, 60 seconds, 70 seconds, 80 seconds, 90 seconds, 100 seconds, 110 seconds, 120 seconds, and the like. Although not wishing to be bound by any theory, this is because a significant effect is observed at these values. However, a longer time frame for mean value calculation over 60 seconds (e.g., 70 seconds or greater, 80 seconds or greater, 90 seconds or greater, 100 seconds or greater, 110 seconds or greater, 120 seconds or greater, 150 seconds or greater, 180 seconds or greater, or the like) is effective particularly when the duration of pain exceeds several tens of minutes (see FIGS. 8 and 9).

In one embodiment, a time frame can be separated into 60 seconds and 120 seconds, but the time frame is not limited thereto. The time frame, when short, can be 10 to 120 seconds and, when long, can be 30 to 300 seconds, and a longer time frame of 120 seconds or longer can be included as needed.

Since a variety in pain monitoring times from short term to long term is expected in clinical settings, it is preferable to use the "hierarchical pain trend monitoring methodology". For the early stages of pain monitoring, pain is monitored time locally using, for example, a 10 second "short time base unit". With passage of time, the time unit is contracted in the direction of the time axis, which makes the trend (change) in medium term brain feature that is highly correlated with how pain is sensed visible. For long-term monitoring, the time unit is contracted to the level of several minutes, which makes the ultra-long term pain trend visible. With this methodology, local and broad changes in pain can be hierarchically monitored in parallel to materialize integrated monitoring of pain.

In this regard, examples of time frames for a "short time based unit" include 10 seconds as well as 5 seconds, 15 seconds, 20 seconds, 25 seconds, 30 seconds, 35 seconds, 40 seconds, 45 seconds, 50 seconds, 55 seconds, 60 seconds, and the like. This can be consolidated by contracting the time frame 2-fold, 3-fold, 4-fold, 5-fold, 6-fold, 7-fold, 8-fold, 9-fold, or the like (for example, 10 seconds can be contracted to 20 seconds, 30 seconds, 40 seconds, 50 seconds, 60 seconds, 70 seconds, 80 seconds, 90, seconds, or the like). The contracted time frame can be further contracted for observing a broader change in the level of several minutes (e.g., 2 minutes, 2.5 minutes, 3 minutes, 3.5 minutes, 4 minute, 4.5 minutes, 5 minutes, 6 minutes, 0.7 minutes, 8, minutes, 9 minutes, 10 minutes, 15 minutes, 20 minutes, 25 minutes, 30 minutes, and the like). For example, the time frame can be contracted 2 levels, 3 levels, or 4 or more levels. In such a case, each contracting can contract the time frame 2-fold, 3-fold, 4-fold, 5-fold, 6-fold, 7-fold, 8-fold, 9-fold, 10-fold, or the like, or a multiple therebetween.

As used herein, "non-overlapping block averaging method" refers to calculating a mean value for each time block, meaning the method is used only for a block having the values used for calculating the mean value (e.g., arithmetic/geometric mean potential). This is in contrast to "overlapping moving average method".

As used herein, "stimulation" refers to anything that causes some type of a reaction to an object. If the object is an organism, stimulation refers to a factor resulting in a temporarily change in the physiological activity of the organism or a portion thereof.

Events related to sensation of pain presented as specific examples of "stimulation" includes any stimulation that can cause sensation of pain. Examples thereof include electrical stimulation, cold stimulation, thermal stimulation, physical stimulation, chemical stimulation, and the like. In the present invention, stimulation can be any stimulation. Evaluation of stimulation can be matched with subjective pain sensation levels using, for example, conventional technology such as computerized visual analog scale (COVAS) or other known technologies such as Support Team Assessment Schedule (STAS-J), Numerical Rating Scale (NRS), Faces Pain Scale (FPS), Abbey pain scale (Abbey), Checklist of Nonverbal Pain Indicators (CNPI), Non-communicative Patient's Pain Assessment Instrument (NOPPAIN), Doloplus 2, or the like. Examples of values that can be employed as stimulation intensity include nociceptive threshold (threshold for generating neurological impulses in nociceptive fiber), pain detection threshold (intensity of nociceptive stimulation that can be sensed as pain by humans), pain tolerance threshold (strongest stimulation intensity among nociceptive stimulation that is experimentally tolerable by humans), and the like.

As used herein, "classification" of pain can be performed from various viewpoints. Representative examples include classification by whether pain is "painful" or "not painful" for the object being estimated, but a methodology of classification for pain felt by whether pain is strong pain or weak pain, or "bearable" pain or "unbearable" pain can be envisioned. Other examples include a methodology of classification between "painful and unpleasant" and "painful but pleasant". The present disclosure can be used to chronologically differentiate/estimate whether an object feels unbearable strong pain or weak pain by observing monotonous increase or monotonous decrease.

As used herein, "pain index" refers to an index obtained by appropriately processing brainwave data or analysis data thereof. As long as an explanation is provided for the provided index, any processing method can be used, but a methodology that can visualize and track a property (trend) of temporally sustained or changing pain is important. The disclosure also shows such a methodology. A pain index can also be referred to as a "pain level index". The term "pain indicator"" refers to subjective evaluation, stimulation intensity, associated brain feature, or the like.

As used herein, "baseline" refers to a standard or reference for facilitating the reading of pain levels, such as a feature associated with strong pain level at the start of monitoring, mean value or normalized value thereof, or a method using a pain index as zero, and a calculated numerical value.

As used herein, "headset" refers to equipment used for obtaining brainwaves from the head. A headset can have any shape. Any obtaining method can be used as long as brainwaves can be directly or indirectly obtained. A headset can be preferably shaped to be worn on the head, but the shape is not limited thereto. Examples thereof include those in a shape of a wireless head gear as well as existing shapes such as a hat, net, or band type headsets. With further improvement, the shape can be of any form, as long as brainwaves are obtained directly from the head via electrodes such as a hair pin form. Brainwaves can also be obtained without contact from the outside. The above forms can be collectively called headsets.

As used herein, "base unit" refers to a part that obtains information such as brainwave signals from a headset and performs action such as analysis, differentiation, communication, and display. A base unit can comprises a process, which is configured mainly to extract a quantitative feature such as a brainwave feature from brain electrical activity data (brainwave data, analysis data thereof or the like) of an object, and further generate and apply a differentiation model, differentiate pain, and the like. A base unit may include an input device for input into a memory device that is operably connected to a processor.

Preferred Embodiments

The preferred embodiments of the present invention are described hereinafter. It is understood that the embodiments provided hereinafter are provided to facilitate better understanding of the present invention, so that the scope of the invention should not be limited by the following descriptions. Thus, it is apparent that those skilled in the art can refer to the descriptions herein to make appropriate modifications within the scope of the invention. It is also understood that the following embodiments of the invention can be used individually or as a combination.

Each of the embodiments described below provides a comprehensive or specific example. The numerical values, shapes, materials, constituent elements, positions of arrangement and connection forms of the constituent elements, steps, order of steps, and the like in the following embodiments are one example, which is not intended to limit the Claims. Further, the constituent elements in the following embodiments that are not recited in the independent claims showing the most superordinate concept are described as an optional constituent element.

In this regard, the inventors elucidated the relationship between pain and brainwaves by evaluating a plurality of types of pain by a plurality of method. The relationship between pain and brainwaves elucidated by the inventors are described hereinafter with reference to the drawings.

First, the relationship between pain due to electrical stimulation and brainwaves is described. The data provided hereinafter shows data for one representative subject from a plurality of subjects.

Figure 1C:
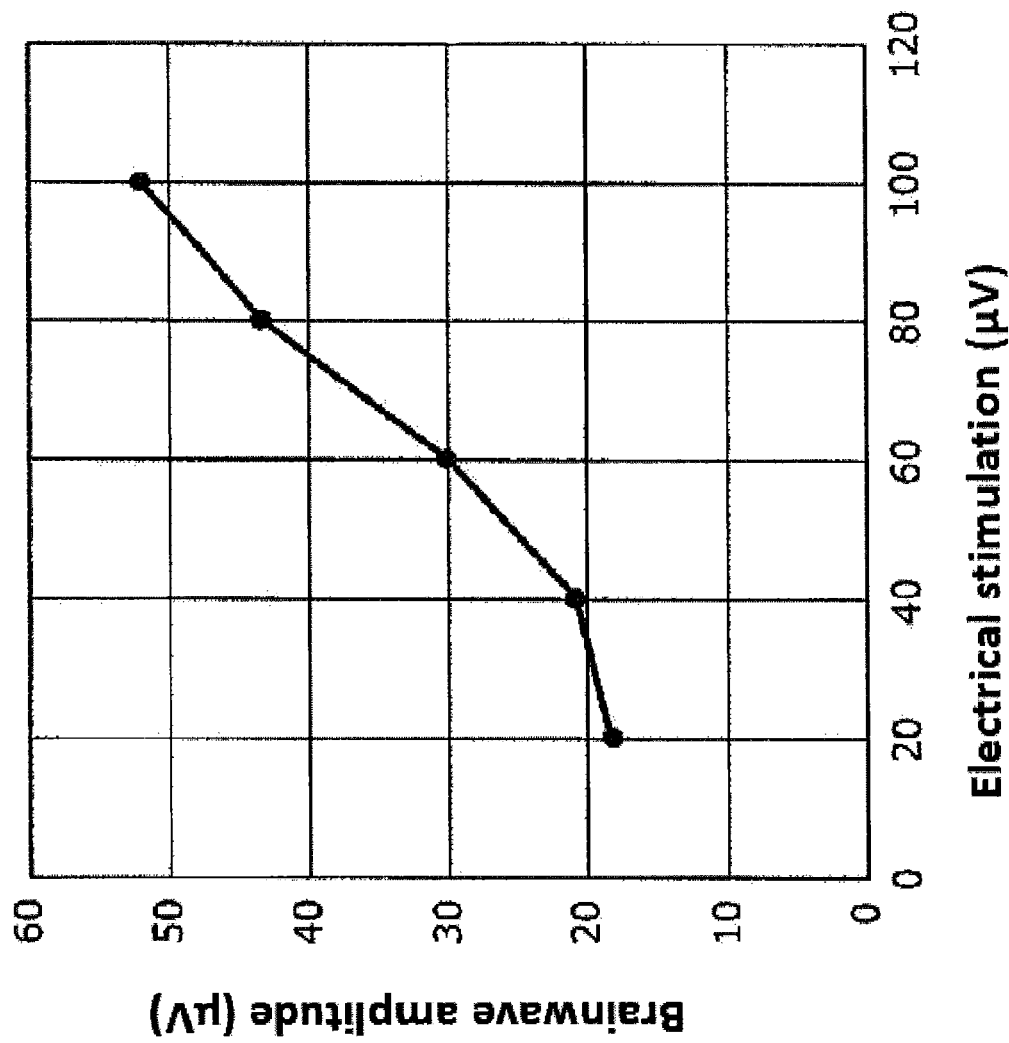
FIG. 1C is a graph showing the relationship between electrical stimulation and brainwave amplitude.

FIG. 1A is a graph showing the relationship between electrical stimulation and pain level (VAS). FIG. 1B is a graph showing the relationship between electrical stimulation and pain level (paired comparison). FIG. 1C is a graph showing the relationship between electrical stimulation and brainwave amplitude. FIG. 1D is a graph showing an example of a waveform of a brainwave.

Figure 4:
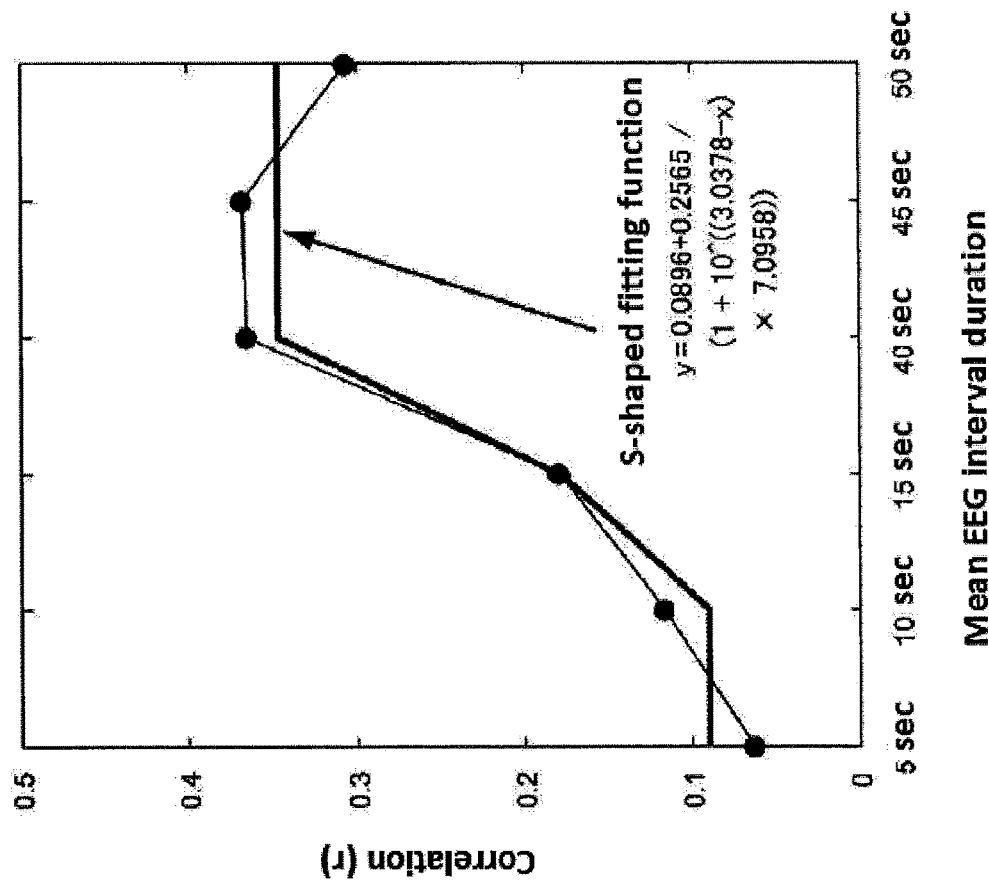
FIG. 4 shows the difference between a duration of less than about 15 seconds and a long duration over 40 seconds. In particular, a disparity is observed in the correlation coefficient values approximating a sigmoid function between the mean interval duration sections of less than 15 seconds and 40 second or greater. The vertical axis indicates the correlation coefficient, and the horizontal axis indicates the mean EEG interval duration. The thick line indicates an S-shaped fitting function.

The horizontal axes of FIGS. 1A, 1B, and 1C indicate the value of current of electrical stimulation. The vertical axis of FIG. 1A indicates the pain level reported by the subject in accordance with VAS. The vertical axis of FIG. 1B indicates the pain level reported by the subject in accordance with paired comparison. The vertical axis of FIG. 1C indicates the value of brainwave amplitude. In FIG. 4, the horizontal axis indicates time, and the vertical axis indicates signal levels.

Paired comparison is a method of using two magnitudes of electrical stimulation as a set and having a subject report which electrical stimulation is how much more painful by a numerical value for each of a plurality of sets of electrical stimulation. In such a case, pain levels are reported by comparing two pains, so that the effect of past experience of a subject with respect to pain levels can be mitigated.

As shown in FIGS. 1A and 1B, the relationship between the value of current of electrical stimulation (i.e., intensity of stimulation) and pain level is represented roughly by a sigmoid (S-shaped) curve, regardless of which of VAS or paired comparison method is used. The shape of the sigmoid curve (e.g., the upper limit value and lower limit value, and the like) varies depending on the subject.

As shown in FIG. 1C, the relationship between the value of current of electrical stimulation and the value of brainwave amplitude is also roughly represented by a sigmoid curve. In this regard, the difference between the maximum peak value and minimum peak value (i.e., peak-to-peak value) is used as the value of brainwave amplitude. For example in FIG. 1D, the maximum value of difference (N1–P1) among three differences (N1–P1, N2–P2, and N1–P2) is used as the value of amplitude.

In this manner, the relationship between the intensity of electrical stimulation and pain level and the relationship between the intensity of electrical stimulation and the value of brainwave amplitude are both represented by a sigmoid curve. In other words, pain levels and brainwave amplitude both have an upper limit and lower limit to electrical stimulation and exhibit a similar change with respect to the intensity of electrical stimulation. In this regard, the relationship between the value of brainwave amplitude and pain level, when analyzed, was represented as shown in FIGS. 1E and 1F.

Figure 1E:
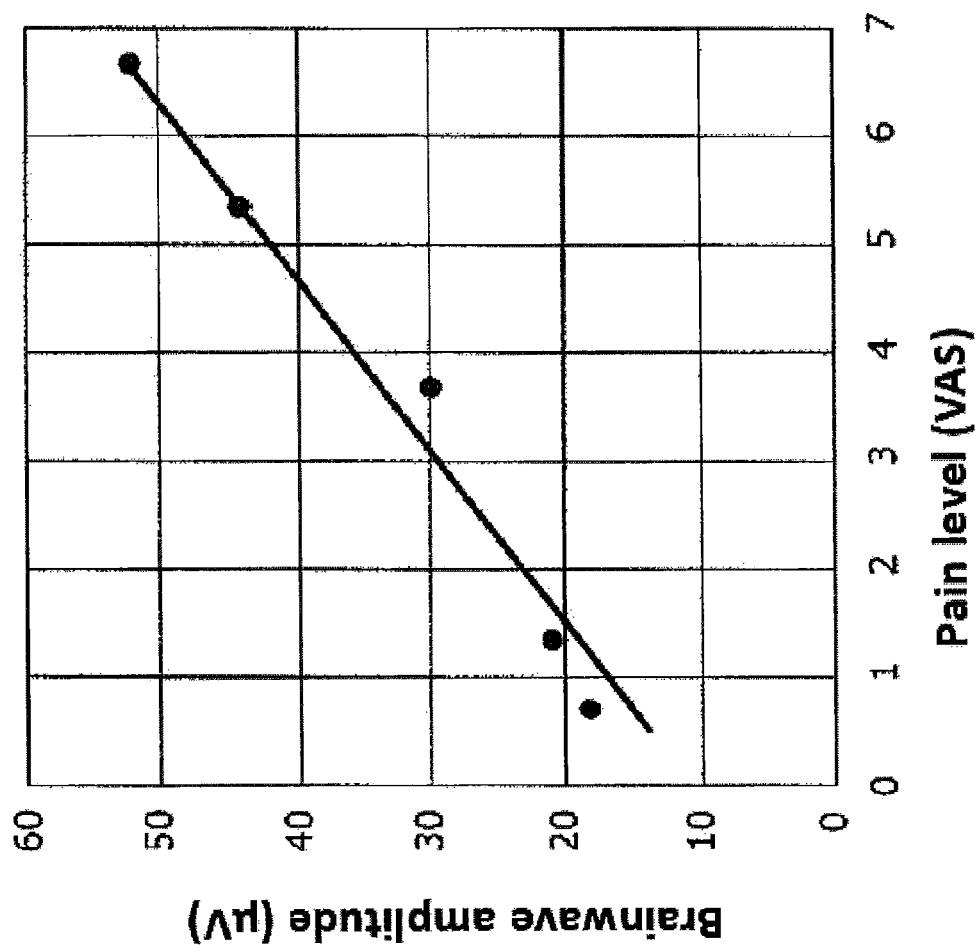
FIG. 1E is a graph showing the relationship between pain level due to electrical stimulation (VAS) and brainwave amplitude.

FIG. 1E is a graph showing the relationship between pain level due to electrical stimulation (VAS) and brainwave amplitude. FIG. 1F is a graph showing the relationship between pain level due to electrical stimulation (paired comparison) and brainwave amplitude. In FIGS. 1E and 1F, the horizontal axis indicates the brainwave amplitude, and the vertical axis indicates the pain level.

Figure 1F:
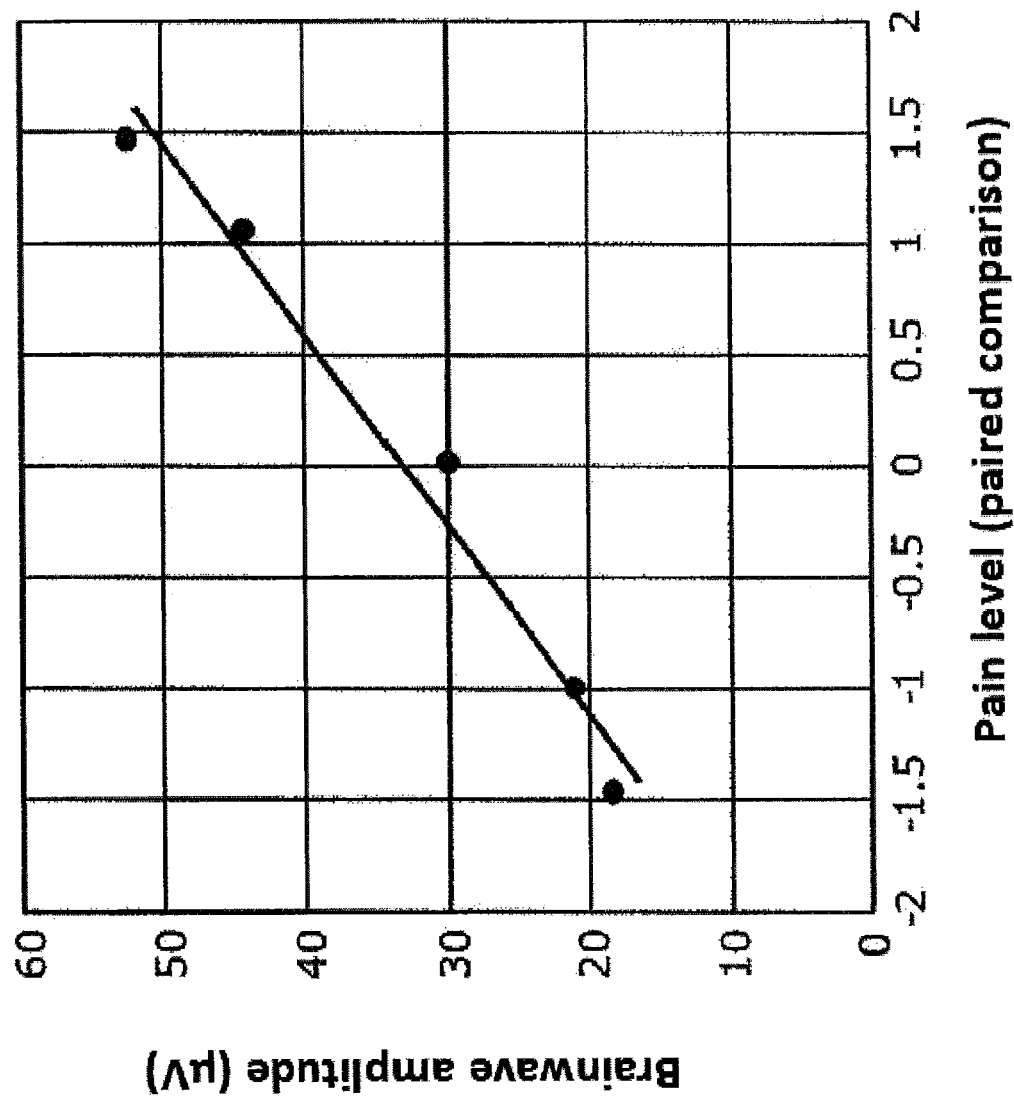
FIG. 1F is a graph showing the relationship between pain level due to electrical stimulation (paired comparison) and brainwave amplitude.

As shown in FIGS. 1E and 1F, the pain level due to electrical stimulation and the value of brainwave amplitude have linearity for both VAS and paired comparison. In other words, the value of brainwave amplitude is proportional to the pain level.

As used herein, linearity includes strict linearity as well as substantial linearity. In other words, linearity includes relationships that can be approximated to linearity within a given range of error. A given range of error is defined, for example, by a coefficient of determination $R^2$ in regression analysis. The coefficient of determination $R^2$ is a value found by subtracting 1 from a result of dividing the Residual Sum of Squares by total Sum of Squares of the difference in the observed value from the mean value. The give range of error is, for example, a range where $R^2$ is 0.5 or greater.

For the relationship between pain due to thermal stimulation and brainwaves, the pain level and brainwave amplitude also have linearity in the same manner as electrical stimulation.

Figure 1H:
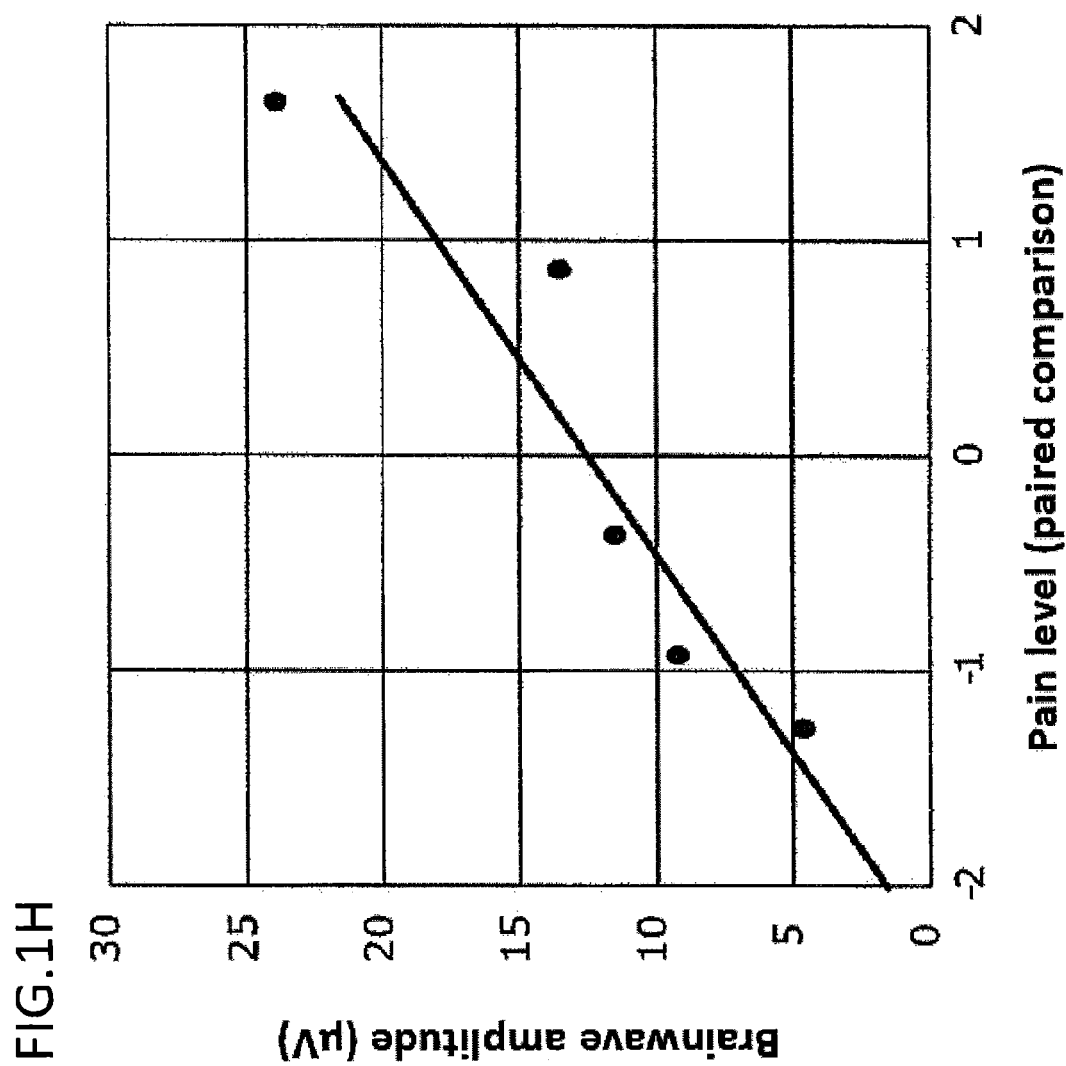
FIG. 1H is a graph showing the relationship between pain level due to hot stimulation (paired comparison) and brainwave amplitude.

FIG. 1G is a graph showing the relationship between the pain level due to thermal stimulation (VAS) and brainwave amplitude. FIG. 1H is a graph showing the relationship between the pain level due to thermal stimulation (paired comparison) and brainwave amplitude. In FIGS. 1G and 1H, the horizontal axis indicates the brainwave amplitude, and the vertical axis indicates the pain level.

As shown in FIGS. 1G and 1H, the pain level due to thermal stimulation and the value of brainwave amplitude have linearity for both VAS and paired comparison. While the upper limit value and lower limit value of the value of brainwave amplitude have variations depending on the subject, the inventors found through experiments that the upper limit value of amplitude does not exceed about 60 µV.

In this manner, the inventors have elucidates that brainwave amplitudes and pain have a specific relationship as a result of analyzing the relationship between values of brainwave amplitude and pain levels from evaluation of a plurality of types of pain by a plurality of methods. In addition, the present invention found that a pain classification value for estimating the magnitude of pain can be calculated based on the specific relationship between brainwave amplitudes and pain.

(Trend Analysis Method)

In one aspect, the present invention provides a method of monitoring pain of an object being estimated based on a brainwave of the object being estimated. The method comprises: a) measuring or obtaining from the object being estimated brainwave data or analysis data thereof by measuring a brainwave in response to stimulation; b) obtaining a temporal change of a mean value of the brainwave data and analysis data thereof in a specific time frame; and c) monitoring a level of pain of the object being estimated from the brainwave data or analysis data thereof based on the temporal change of the mean value.

More specifically, the method can optionally use a pain index (e.g., degree of feature indicating strong pain level or the like) for chronologically evaluating or monitoring a pain level of the object being estimated from the brainwave data, or set of baseline for monitoring pain for a) measuring or obtaining from the object being estimated brainwave data or analysis data thereof by measuring a brainwave in response to stimulation; b) obtaining a temporal change of a mean value (e.g., arithmetic/geometric mean potential) of the brainwave data or analysis data thereof in a specific time frame, comprising b-1) extracting a feature for the mean value and b-2) plotting the temporal change of the mean value (e.g., arithmetic/geometric mean potential) of the feature in the specific time frame; and c) evaluating or monitoring a level of pain of the object being estimated from the brainwave data or analysis data thereof based on the temporal change of the mean value. The "pain index" can be separately calculated by appropriately analyzing the feature of brainwave data or analysis data thereof.

A pain index can be expressed by various methods. For example, the obtained feature itself or a mean value can be used directly to express a pain level. If it is known that "mean value is high=strong pain level", the mean value can itself be a pain index. The mean value can also be digitally expressed after conversion into a numerical range of "0 to 100". The feature itself or the mean value thereof can be used as a pain index after standardization or normalization.

A "baseline" used herein provides a reference for reading the change in pain levels by using the pain index described above. For example, a zero line, i.e., a baseline, is determined using a pain index for a strong level of pain with a pain level differentiated by a pain reading/estimation apparatus. The understanding of changes in pain level is facilitated thereby. If the pain level is unknown, not any external stimulation is applied. A certain section of a stable state or a "resting (rapid) state" that is close thereto can be used as a baseline. For example, a baseline can be obtained (sometimes referred to as baseline correction) as follows (this calculation method is also referred to as a baseline determination process).

Baseline correction for a pain index (for brainwave feature (EEG)) can be expressed by $$\text{EEG} - \text{BS} \qquad \text{[Numeral 1]}$$

wherein BS=mean value of most intense pain EEG (normalized) or the like, or $$(\text{EEG} - \text{BS})/\text{SD}(\text{BS}) \qquad \text{[Numeral 2]}$$

wherein SD (BS)=standard deviation of BS.

Trend analysis has enabled a more accurate evaluation of changes in subjective pain. As another feature, the present invention also measures a mean amplitude for each block over several tens of seconds instead of changes of each small data point such as each second, resulting in an effect of eliminating randomly included external noise and organism derived internal noise. Thus, the present invention has enabled more accurate evaluation of a pattern, i.e., trend, of temporal changes in pain levels (improvement in correlation between subjective pain evaluation and brain feature).

The method of the invention further comprises referencing pain occupancy, wherein the pain occupancy indicates certainty when a pain estimation value is differentiated as having pain. Such pain occupancy can be calculated by: (a) calculating an estimation value for differentiating having pain and no pain by a differentiation model; (b) dividing a pain estimation value into sectional ranges and calculating occupancy of an estimation value for having pain of each estimation value in the sectional range; and (c) generating a pain occupancy function by functionalizing the occupancy and calculating the pain occupancy with the pain occupancy function. The pain occupancy can be calculated, for example, by the specific processing shown in the Examples. Pain occupancy (%) is calculated by the following equation.

$$PO_i = \text{number}_i \text{ of estimation values of samples for having pain}/(\text{number}_i \text{ of estimation values of samples for no pain} + \text{number}_i \text{ of estimation values of samples for having pain}) \times 100$$

i: number of divisions in the pain estimation value range (i is generally a positive integer).

In one embodiment, the pain can be judged to be strong if the temporal change of the mean value (e.g., arithmetic/geometric mean potential) is a monotonic increase, and the pain can be judged to be weak if the temporal change is a monotonic decrease. For example, it was found that correlation for 20 seconds was significantly higher than 15 seconds when correlation coefficients of EEG and subjective evaluation or stimulation intensity were calculated, applied a paired t-test, and compared between 15 seconds and proximate 20 seconds upon stimulation under conditions of 60 second stimulation and 60 second rest in one embodiment. This trend was similarly observed even if 20 seconds was increased to 30 second and 30 seconds was increased to 40 seconds. Thus, it can be concluded that a time frame of preferably 20 seconds or greater, more preferably 30 seconds or greater, and still more preferably 40 seconds or greater is used. This methodology is highly effective especially for monitoring sustained pain over a long period of time. Even for common pain, unpleasant pain may be continuous or intermittent for over several tens of seconds. Thus, monitoring using a time frame of 20 seconds or greater is highly effective. In fact, it has been elucidated that the methodology of the invention can be used effectively for analyzing unpleasant pain. Thus, it can be understood the time frame that can be used in the present invention is, for example, 10 seconds or greater, more preferably 15 seconds or greater, still more preferably 20 seconds or greater, 25 seconds or greater, 30 seconds or greater, 35 seconds or greater, 40 seconds or greater, 45 seconds or greater, 50 seconds or greater, 55 seconds or greater, and 60 seconds or greater in order of preferred embodiments. Further, a "hierarchical pain trending monitoring methodology" is used in accordance with a change from a short term to long term pain monitoring time. A trend (temporal change) of medium term brain feature with increasingly higher correlation with how pain is sensed is made visible by using a short time unit of about 10 seconds and contracting the time unit with the passage of monitoring time. For a long period of monitoring, the unit is contracted to the level of several minutes to show an ultra-long term pain trend.

In one embodiment, it is understood that a change in mean value (e.g., arithmetic/geometric mean potential) can be judged as "strong pain" for a monotonically increasing pattern as a result of such a trend analysis, while the change can be judged as "weak pain" for a monotonically decreasing pattern. In some cases, "pain index" can be optionally converted and set to an indicator indicating strong pain when greater than 0 and weak pain when less than 0 (process of "baseline" correction) to facilitate monitoring. When EEG potential monotonically increases with an increase in the pain level, a waveform can be directly used without inversing so that activity of strong pain would be 0. Meanwhile, for monotonic decrease, an inverse of waveform can be calculated so that pain would be stronger for a larger number to facilitate intuitive understanding of the change in pain levels. The present invention can be applied regardless of the method of calculation of an index.

In one embodiment, baseline correction of a pain index can be represented by $$EEG^{-1}-BS \qquad \text{[Numeral 3]}$$

wherein $^{-1}$ indicates the inverse, and BS=standard value calculated using the most intense pain EEG (normalized). In such a case, in another embodiment, the pain index can be calculated by $$EEG-BS \qquad \text{[Numeral 4]}$$

wherein BS=standard value which is the most intense pain EEG (normalized) In such a case, pain would be intense for a smaller number, and the activity of intense pain would be 0. Since data is already normalized before the baseline correction, normalization is not required at this stage.

As used herein, "pain index" or "baseline" of the pain index is an index introduced with a standard taking into consideration qualitative judgment of a change in feature related to continuous pain such as "painful" or "not painful", or pain is "decreasing" or "increasing" based on a feature reflecting a specific pain level (e.g., intense pain level). Such an index is understood in the same manner as the distinction of an aqueous solution such as "alkaline", "neutral", and "acidic" based on pH 7.

In this disclosure, any time frame for computing a mean value (e.g., arithmetic/geometric mean potential) or absolute value of potential, and other mean value of a feature can be used. Examples include a moving average method, non-overlapping block averaging method, sparse averaging method (averaging of hopped data points), method of obtaining and averaging a plurality of peak amplitudes, and the like. The mean value (e.g., arithmetic/geometric mean potential) in a specific time frame is preferably calculated by the non-overlapping block averaging method if statistically better. Although not wishing to be bound by any theory, this is because a moving average method, due to high temporal continuity of mean data, can encounter more difficulty in capturing a change in pain levels discretely, such that use of a non-overlapping block averaging method is considered as the base. A time direction averaging method is advantageous in that time varying noises can be expected to be offset and/or reduced in view of comprising more data in the time direction to leave pain related signals, such that an effect of a noise such as a sporadic large burst can be reduced with more data in the time direction.

The following schematic diagram is used to describe a pain level monitoring methodology (FIG. 11). a) step S100 for measuring or obtaining brainwave data or analysis data thereof by measuring brainwaves in response to stimulation from an object being estimated, b) step S200 for extracting a feature for plotting a temporal change in a mean value (e.g., arithmetic/geometric mean potential) of the brainwave data or analysis data thereof in a specific time frame, and optionally step S300 for calculating a pain index (e.g., degree of feature indicating strong pain level) for chronologically evaluating or monitoring a level of pain of the object being estimated from the brainwave data to calculate a baseline of monitoring based on the pain index, and c) optionally step S400 for monitoring a level of pain of the object being estimated from the brainwave data based on the baseline or pain index.

Step a), which is a step (S100) for measuring or providing brainwave data or analysis data thereof by measuring brainwaves in response to stimulation from an object being estimated, is a step of obtaining brainwave data or analysis data thereof (e.g., amplitude data) of an object being estimated by any method. Such brainwave data or analysis data thereof (e.g., amplitude data) can be obtained using any methodology that is well known in the art. The exemplified amplitude data can be obtained by measuring electrical signals of brainwaves and displayed as potential (can be displayed by μV or the like).

Step b), which is a step for b) obtaining a temporal change in the mean value (e.g., arithmetic/geometric mean potential) of the brainwave data or analysis data thereof (e.g., amplitude data) in a specific time frame, extracts a feature for obtaining the mean value, and calculates a mean value of the extracted feature over a certain time frame (e.g., 40 seconds or the like) (S200). In this regard, preprocessing such as reduction in eye movement, correction of oscillation of the baseline, artifact removal (absolute value of amplitude >100 μV), normalization of absolute value of amplitude, or standardization can be applied.

Step b) is a step (S200) for extracting a feature for plotting a temporal change in the mean value (e.g., arithmetic/geometric mean potential) of the brainwave data in a specific time frame. This step creates data for change in the mean value by using the amplitude data obtained in step a. A mean value (mean value (e.g., arithmetic/geometric mean potential), absolute value of potential, and other mean values of feature) can be obtained using any methodology known in the art. Examples of such a specific methodology include, but are not limited to, a moving average method, non-overlapping block averaging method, sparse averaging method, method of obtaining and averaging a plurality of peak amplitudes, as well as other types of central tendency values including mean value (median and mode). A methodology statistically indicating approximation or high correlation with subjective change in pain (e.g., non-overlapping block averaging method herein) particularly is highly prioritized in view of the fact that a trend of pain levels is more discretely expressed.

Optionally, a baseline of monitoring can be determined using a pain index (e.g., degree of feature indicating strong pain level or the like) for chronologically evaluating or monitoring a level of pain of the object being estimated from the brainwave data (S300). A pain index can be calculated in advance with a pain differentiation/estimation model and determined by the start of monitoring for each individual. Therefore, S300 is not particularly an essential step in the trend analysis method of the invention. A pain index and/or baseline given in advance can also be used. Step c) optionally evaluates or monitors pain online by referring to a baseline of monitoring, based on a temporal change in the mean value (e.g., arithmetic/geometric potential) (S400). In this regard, the pain level can be displayed or evaluated by an appropriate methodology. In this regard, various evaluations can be performed in accordance with the method of displaying the presented data (display of a trend or an individual number method). For example, a pain level of the object being estimated can be differentiated from the brainwave data based on the plot. In particular, the main objective of a pain differentiation/estimation apparatus is to monitor pain levels that change with each passing moment due to a sedative in clinical settings. Therefore, the pain trend analysis and visualizing method herein are important constituent technologies.

A pain level differentiation/estimation apparatus 1110 for monitoring pain of an object being estimated based on a brainwave of the object being estimated of the invention comprises: A) a brainwave data measurement unit 1111 for obtaining brainwave data or analysis data thereof of the object being estimated; B) a feature extraction unit 1112 for retrieving a mean value (e.g., arithmetic/geometric mean potential) to obtain a temporal change of a mean value (e.g., arithmetic/geometric mean potential) of the brainwave data and analysis data thereof in a specific time frame, and optionally a pain index generation unit 1113, and optionally a pain monitoring standard determination unit 1114 for determining a baseline of monitoring using a pain index (e.g., degree of feature indicating a strong level of pain or the like) for chronologically evaluating or monitoring a level of pain of the object being estimated from the brainwave data; and C) a pain level monitoring unit 1115 for monitoring a level of pain of the object being estimated from the brainwave data or analysis data thereof based on the temporal change of the mean value. The brainwave data obtaining unit A) performs step a). The feature (including mean value (e.g., arithmetic/geometric mean potential) data) extraction unit B) performs step b), and the pain index generation unit optionally generates a pain index, and a standard determination unit optionally determines a standard. The pain level monitoring unit C) performs step c). B) and C) and optional pain index generation unit and standard determination unit may be configured so that the same part has three functions, or configured as separate parts. A pain index generation unit and standard determination unit are optional parts, so that a pain index and/or a standard value (baseline) can be introduced or received from an external source.

Figure 12:
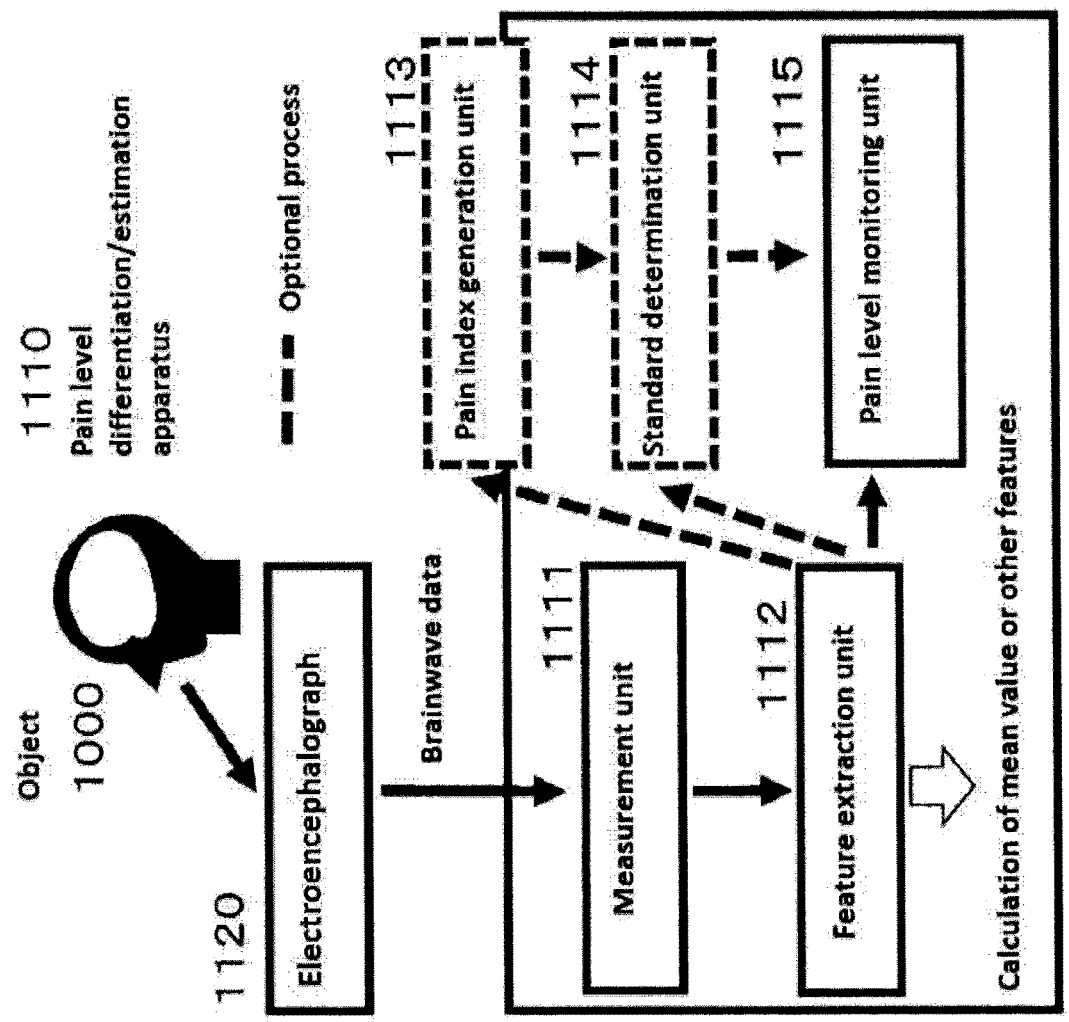
FIG. 12 is a block diagram of the configuration of the apparatus of the invention.

FIG. 12 is a block diagram showing the functional configuration of the system 1100 comprising a pain level differentiation/estimation apparatus of one embodiment. The system 1100 comprises the pain level differentiation/estimation apparatus 1110 and an electroencephalograph 1120. An electroencephalograph can be configured to be separate from the pain level differentiation/estimation apparatus in this manner.

The apparatus 1110 comprises the measurement unit 1111, the feature extraction unit 1112, the standard determination unit 1114, and the pain level monitoring unit 1115. The apparatus 1110 is materialized by, for example, a computer comprising a processor and a memory. In such a case, the apparatus 1110 makes the processor function as the measurement unit 1111 and the feature extraction unit 1112, and optionally the pain index generation unit 1113 and the standard determination unit 1114 when a program stored in the memory is implemented by the processor. The apparatus 1110 can also be materialized by, for example, a dedicated electrical circuit. A dedicated electrical circuit can be a single integrated circuit or a plurality of electrical circuits. The amplitude data measurement unit 1111 and the pain index generation unit 1113 for providing a pain index to the standard determination unit can be configured internally or externally.

The measurement unit 1111 obtains a plurality of brainwave data by measuring a brainwave from an object being estimated 1000 via the electroencephalograph 1120. The object being estimated 1000 is an organism in which a change in brainwave is induced by pain, which can be an organism having a pain sensing nerve (e.g., vertebrae such as mammals and avian (including livestock animals, pet animals, and the like) and is not limited to humans.

The feature extraction unit 1112 generates a mean value of brainwave data in an appropriate time frame. The unit optionally provides a feature to the pain index generation unit 1113 and the pain monitoring standard determination unit 1114 for a higher level model based pain level differentiation/estimation (machine learning or the like) or online monitoring of pain level. A mean value can be calculated by a methodology that is well known in the art. An algorithm for such a calculation method can be stored in advance in the feature extraction unit 1112 or inputted upon use via a medium or a communication function. In other words, the feature extraction unit 1112 can generate a feature for pain trend monitoring including mean data. The pain level monitoring unit 1115 tracks a feature including calculated mean data to contribute to a supervisor monitoring or evaluating subjective pain of an object. The monitoring unit 1115 can express the output results of the standard determination unit 1114 as individual number (pain level of 0 to 100 or the like) or a change in numbers.

The electroencephalograph 1120 measures the electrical activity generated in the brain of an object being estimated with an electrode on the scalp. The electroencephalograph 1120 then outputs brainwave data, which is the result of measurement in concert with the measurement unit 1111.

Figure 11:
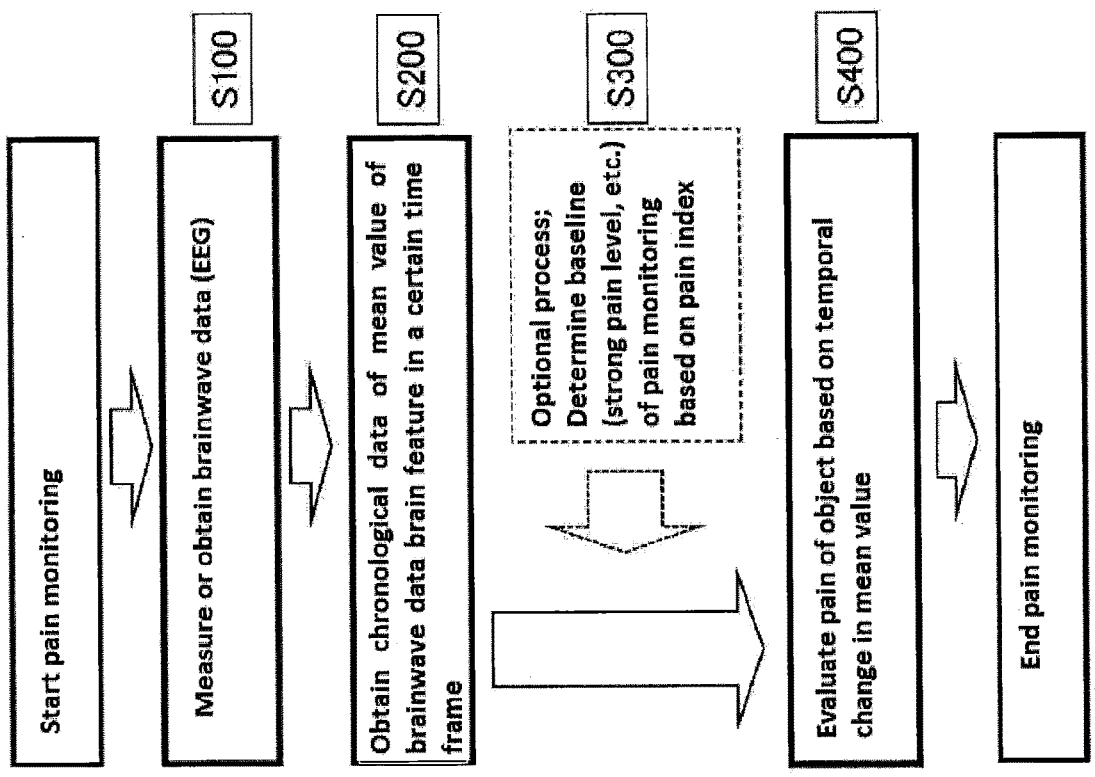
FIG. 11 is a diagram of a scheme of the invention.

The process or method of the apparatus configured in such a manner can execute the flow chart showing the series of processes exemplified in FIG. 11. In other words, S100 to S400 can be executed with the apparatus shown in FIG. 12.

Figure 13:
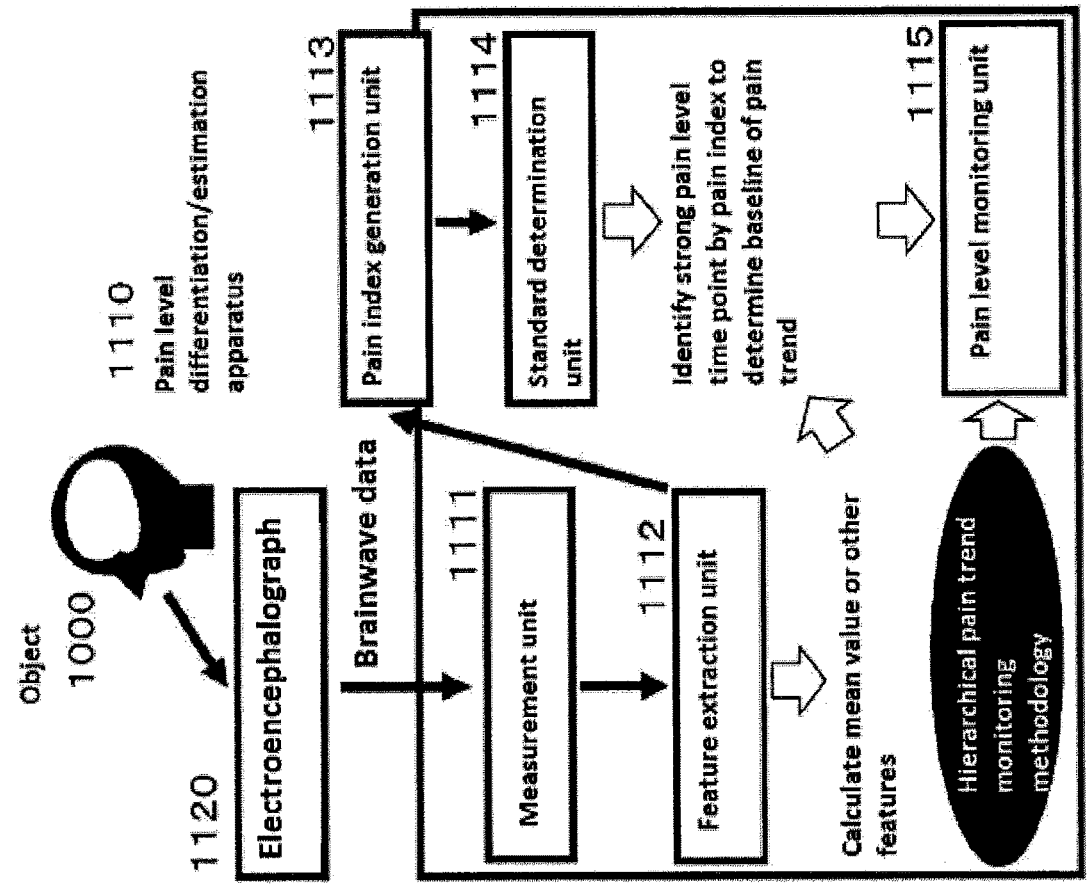
FIG. 13 is a block diagram incorporating the "hierarchical pain trend monitoring methodology" into the configuration of the apparatus in FIG. 12.

FIG. 13 is a block diagram incorporating the "hierarchical pain trend monitoring methodology" and the details of optional processes for baseline correction into the configuration of the apparatus in FIG. 12.

The present invention can be utilized as a medical apparatus with the configuration exemplified in FIGS. 12, 13, and the like. For example, data is obtained from a subject undergoing pain evaluation and the mean is calculated. The method of calculating the mean value in such a case can be performed while monitoring the data or performed after accumulation of data to a certain degree, or both. In FIG. 13, use of a hierarchical pain trend monitoring is implemented, wherein a mean value or another feature is calculated, and the point of time where the pain level is strong is identified based on a pain index, so that a baseline of pain trend can be determined. In other words, brainwave data (or analysis data thereof) is obtained from the electroencephalograph 1120 and measured at the measurement unit 1111. A feature the like is extracted from the measurement value at the feature extraction unit 1112. Optionally, a pain index can be generated at the pain index generation unit 1113 from the feature, and a baseline to be used as the standard for pain level monitoring can be determined using the index at the standard determination unit 1114. With a hierarchical pain trend monitoring methodology, a trend of pain levels can be monitored online as soon as a baseline is obtained or determined.

Other Embodiments

The pain estimation apparatus according to one or more embodiments of the invention has been described based on the embodiments, but the present invention is not limited to such embodiments. Various modifications applied to the present embodiments and embodiments constructed by combining constituent elements in different embodiments that are conceivable to those skilled in the art are also encompassed within the scope of one or more embodiments of the invention as long as such embodiments do not deviate from the intent of the inventions.

Some or all of the constituent elements of the pain estimation apparatus in each of the above embodiments can be comprised of a single system LSI (Large Scale Integration). For example, the apparatus 1110 can be comprised of system LSI having the measurement unit 1111, mean data obtaining unit 1112, the pain monitoring standard determination unit 1114 and pain level monitoring unit 1115.

System LSI is ultra-multifunctional LSI manufactured by integrating a plurality of constituents on a single chip, or specifically a computer system comprised of a microprocessor, ROM (Read Only Memory), RAM (Random Access Memory), and the like. A computer program is stored in a ROM. The system LSI accomplishes its function by the microprocessor operating in accordance with the computer program.

The term system LSI is used herein, but the term IC, LSI, super LSI, and ultra LSI can also be used depending on the difference in the degree of integration. The methodology for forming an integrated circuit is not limited to LSI. An integrated circuit can be materialized with a dedicated circuit or universal processor. After the manufacture of LSI, a programmable FPGA (Field Programmable Gate Array) or reconfigurable processor which allows reconfiguration of the connection or setting of circuit cells inside the LSI can be utilized.

If a technology of integrated circuits that replaces LSI by advances in semiconductor technologies or other derivative technologies becomes available, functional blocks can obviously be integrated using such technologies. Application of biotechnology or the like is also a possibility.

One embodiment of the invention can be not only such a pain index generation, pain differentiation/classification apparatus, but also a pain index generation, pain level monitoring method using characteristic constituent units in the pain differentiation/estimation apparatus as steps. Further, one embodiment of the invention can be a computer program for implementing each characteristic step in the pain index generation, pain level monitoring method on a computer. Further, one embodiment of the invention can be a computer readable non-transient recording medium on which such a computer program is recorded.

In each of the embodiments described above, each constituent element can be comprised of a dedicated hardware or materialized by implementing software program that is suited to each constituent element. Each constituent element can be materialized by a program implementation unit such as a CPU or a processor reading out and implementing a software program recorded on a recording medium such as a hard disk or semiconductor memory. In this regard, software materializing the pain differentiation/estimation apparatus of each of the embodiments described above is a program such as those described below.

Specifically, this program makes a computer implement a method of monitoring pain of an object being estimated based on a brainwave of the object being estimated, comprising: a) measuring or obtaining brainwave data or analysis data thereof by measuring brainwaves in response to stimulation from the object being estimated, b) obtaining a temporal change of a mean value (e.g., arithmetic/geometric mean potential) of the brainwave data or analysis data thereof in a specific time frame (and optionally extracting a feature for temporal change in the mean value), and optionally generating a pain index (e.g., degree of feature indicating a strong pain level) for chronologically evaluating or monitoring a level of pain of the object being estimated from brainwave data and optionally determining a baseline of monitoring, and c) optionally monitoring a level of pain of the object being estimated from the brainwave data based on the baseline determination process.

The present invention provides a recording medium storing a program for implementing a method of monitoring pain of an object being estimated based on a brainwave of the object being estimated on a computer. The program makes the computer implement the method of monitoring pain of an object being estimated based on a brainwave of the object being estimated, comprising: a) measuring or obtaining from the object being estimated brainwave data or analysis data thereof by measuring a brainwave in response to stimulation; b) obtaining and plotting a temporal change of a mean value (e.g., arithmetic/geometric mean potential) of the brainwave data or analysis data thereof in a specific time frame (and extracting a feature for obtaining a temporal change of the mean value when appropriate), and optionally generating a pain index (e.g., degree of feature indicating a strong pain level) for chronologically evaluating or monitoring a level of pain of the object being estimated from brainwave data and optionally determining a baseline of monitoring; and c) monitoring a level of pain of the object being estimated from the brainwave data or analysis data thereof based on a change in the mean value over time.

It is understood that the method implemented therein can use one or a combination of a plurality of any of the embodiments described in the section of (Trend analysis method) of the present invention.

In another aspect, the present invention provides a method for generating a model for differentiating pain of an object, comprising:

a) obtaining brainwave data or analysis data thereof from the object;
b) contracting features based on the brainwave data or analysis data thereof with respect to the pain after determining feature coefficients associated with the pain;
c) creating a differentiation and analysis model by machine learning and validation based on the features that have been weighted after the contracting or a combination thereof; and
d) determining a differentiation and analysis model that attains a given accuracy.

In one embodiment, the present invention is characterized by performing the contraction, after determining the feature coefficient, by repeating differentiation and estimation, calculating a mean of and ranking the feature coefficients for the differentiation and estimation, and selecting a feature based on a given threshold value in step b). The feature coefficients are determined by, preferably but not limited to, machine learning.

Examples of machine learning include Support Vector Machine (SVM), neutral network, deep learning, logistic regression, reinforcement learning, and the like.

In another embodiment, the present invention comprises, upon determining the feature coefficients in b), determining a hyperparameter resulting in the highest differentiation accuracy, and determining the feature coefficients based on the hyperparameter, and excluding a feature which has no effect or a low ratio of contribution for differentiation. The feature coefficients and the hyperparameter are determined by, preferably but not limited to, machine learning.

In another embodiment of the present invention, b) to d) comprise: (C1) dividing the features and data corresponding to the pain corresponding to the features into data for learning and data for testing; (C2) performing machine learning using the learning data to create a differentiation model and calculating an optimal X value (and a partial regression coefficient, a regression equation, and a model intercept); (C3) calculating differentiation accuracy of the differentiation model by using the data for testing; (C4) if there is a target sample with the differentiation accuracy at or below a chance level in the objects, repeating steps C1 to C3 after excluding the sample, and if there is no sample at or below a chance level, ending the steps to determine a differentiation model, wherein the chance level is a numerical value obtained by dividing 100% by the number of classifications. In this regard, the chancel level refers to a value obtained by dividing 100% by the number of classifications. This is verification to avoid accidental match. Such a backward elimination method is also useful for generation of a differentiation model in the present invention.

A model created based on the method of the invention, albeit just one example, can materialize 70% accuracy even with few features, such that the significance thereof is high. There are several method of ranking and selecting features other than the methodologies of the invention. For example, machine learning (SVM-RFE) disclosed as a comparative example is a more complex method of actually creating a differentiation model using features while calculating and ranking a weighting coefficient of each feature. Unlike such a method, one of the feature of the present invention is in first finding the robustness of a change pattern of brainwave features before differentiating and analyzing by contracting (e.g., using the neuron firing principle, the "all-or-none" law, as the selection criteria) based on the most basic property of classification instead of ranking features by differentiation.

With regard to contracting before or after, it is more advantageous to perform the contracting of the invention first. As a reason thereof, the present invention is characterized by fitting features by contracting (e.g., sigmoid function) and then extracting an all-or-none feature, and determining select few differentiation models by machine learning, such that calculation can be simple. Meanwhile, if fitting such as sigmoid fitting is performed after, sigmoid would be used to identify how many all-or-none patterns the features used in a differentiation pattern have (or approximate) rather than used for contracting. In such a case, machine learning is performed, individual feature or a plurality of features are used to determine the feature or differentiation model with the highest accuracy, a sigmoid function is fitted to the feature with high differentiation accuracy, the robustness of the feature is found, and if it is desirable to make an economical differentiation model, only features with a high degree of fit are selected to re-run machine learning. Thus, the calculation cost would be high and the learning process would be inefficient. In this manner, if sigmoid fitting of features or the like additively materialize previous to "machine learning process with contracting of the number of features", an addition procedure for futilely performing machine learning would be required so that the calculation cost would be high. In view of the above, it is more advantageous to perform the contracting of the invention first.

For contracting, for example correlation between features can be studied to consolidate those with high correlation, or a primary factor can be found by deleting one of the features or performing factor analysis or the like (e.g., 10 factors from 100 data or the like). Contracting can also be materialized as in the above example by using a sigmoid function or the like to find only features that are in accordance with a specific reaction pattern model and use the features in the model. While various specific patterns can be set, differentiation of "0 or 1" such as having pain or no pain can be used for pain. In this regard, a sigmoid function (example of logistic regression) or step function can be used for 0 or 1. A sigmoid function is created with "0, 1" and approximated. If a statistically significant approximation is observed, this can be used in a model. "All-or-none", in other words, can be expressed as reacting at two values of "0 or 1" to specific stimulation, which can be considered a feature indicating a digital discrete reaction. When contracting, contracting can be kept within a certain range by determining the target objective. For example, contracting can be expressed as "contracting with respect to pain" or "contracting with respect to pain stimulation".

Figure 42:
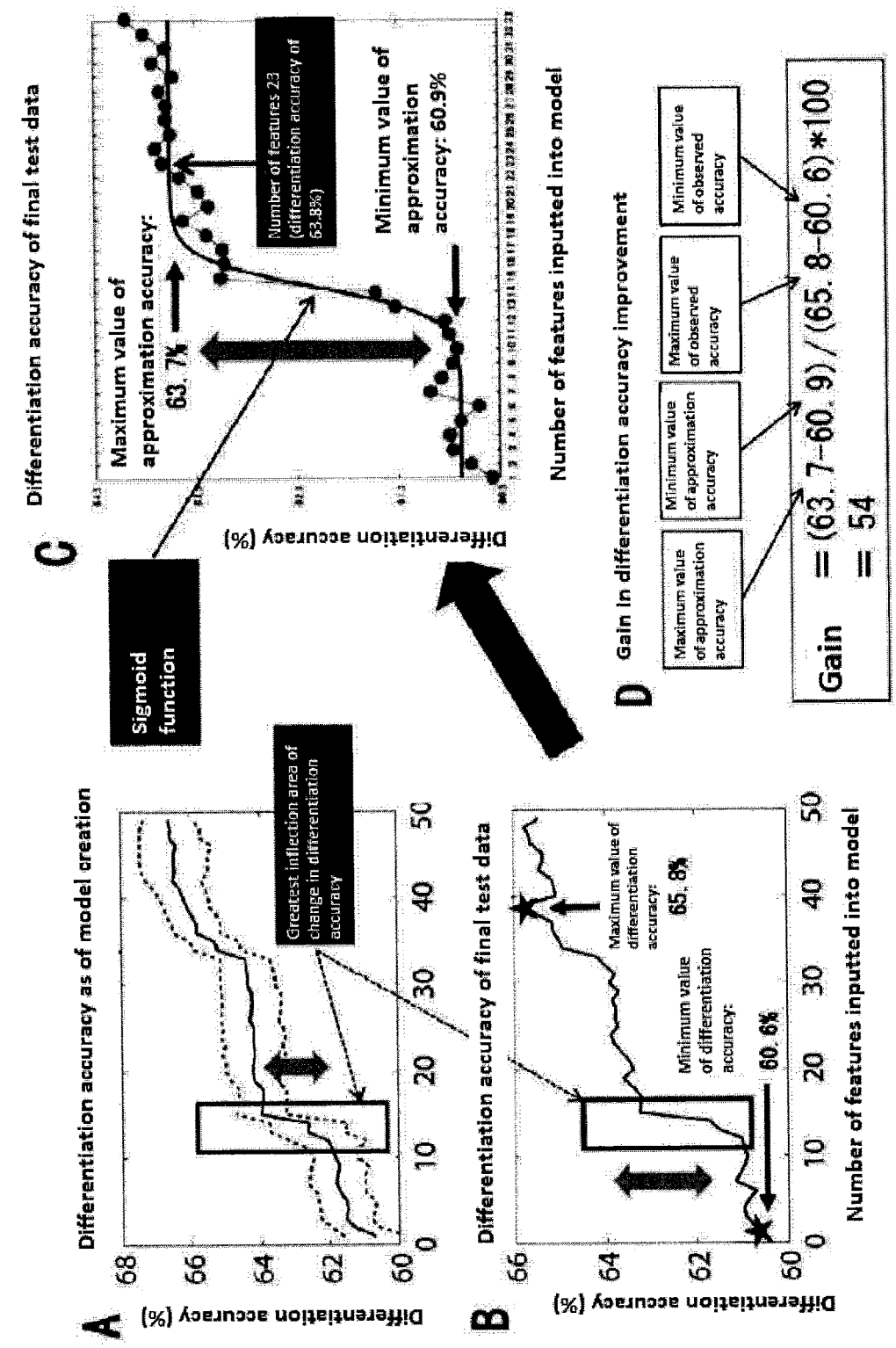
FIG. 42 shows patterns of change in differentiation accuracy of all 49 differentiation models.

The example described above is function approximation for the purpose of contracting features. Meanwhile, for identification of an optimal differentiation model, a change in differentiation accuracy of a plurality of differentiation models (from a model with few features to a model with the maximum number of features) can be approximated to a function to select an economical model, as shown in Example 10 of the present invention. For example, the sigmoid function materializing binomial classification described above can be used for function approximation. A sigmoid function is an elemental function used at various levels, which can certainly be a neuron firing principle, as well a pain reaction function, pain differentiator, or pain occurrence function (see FIG. 31), a feature contracting tool described above (see FIG. 34), or can be related to the selection process of a differentiation model described herein. For example, as shown in FIG. 42A, a change curve of differentiation accuracy of a differentiation model is observed to have patterns including two inflection areas. Therefore, in a preferred embodiment, an asymptote of the minimum value and maximum value is derived by sigmoid approximation by first limiting the inflection area to that with a relatively large inflection range (amplitude). Next, the variation in differentiation accuracy is expressed as a representative value (minimum value, maximum value), and the value of improvement in differentiation accuracy (maximum value−minimum value) is calculated, and with the maximum value as the threshold value, the number of features that first exceeds this value can be presented as an economical differentiation model attaining the maximum gain in the percentage of improvement.

The step of differentiating and analyzing by machine learning and cross validation from top of ranking of weighting coefficients (including approximation coefficients; e.g., regression coefficients) of each feature after the contracting or combination thereof can differentiate and analyze by creating a ranking of features after contracting (or combination thereof) and weighting coefficients and performing cross validation thereon by machine learning or the like.

In one embodiment, the present invention further comprises, after step c), calculating a value of difference (Diff) of adjacent models in differentiation accuracy obtained by differentiating and analyzing, wherein the adjacent models are models comprising n−1 features and n features, wherein n is 2 or greater, and wherein judgment of a differentiation model in step d) takes into consideration the difference. In this regard, the value of difference is implemented in software such as the MATLAB function Diff or the like as is well known in the art. This is a function for "continuously subtracting adjacent numerical values". In other words, the Diff function is one of the functions implemented in MATLAB for finding the value of difference of adjacent values while shifting by one point. This function mathematically corresponds to "differentiation" and mechanically corresponds to "speed". While the usage varies, for signal processing, this can be used to find a rapid or discontinuous (or stepwise) inflection point in a time series or spatial data distribution. For sigmoid functions, the Diff function is effective for finding an inflection area. The function can also be used to find a temporal or spatial point where the feature dramatically changes in brainwaves.

In one embodiment, taking into consideration of the value of difference comprises a process of re-ranking features from values with a greater value of difference and recalculating differentiation accuracy to generate a model with higher differentiation accuracy.

In one embodiment, the judgment based on the value of difference comprises classifying the features into a main feature and supporter features and re-ranking the supporter features. In this regard, a feature with a number one ranking or a feature with significant correlation thereto can be selected as the main feature and others can be selected as supporter features for re-ranking based on a value of difference of n feature model and n−1 feature model when supporter features are inputted. For example, the function Diff implemented in MATLAB or the like can be used. For example, the number 1 ranking can be fixed and the rest can be used as supporters. Therefore, the single main feature, or the combination of the main feature and other supporter features can be used.

As used herein, the number 1 ranking feature after rearranging by $R^2$ values is referred to as the single main feature. Since top ranking features exhibiting significant correlation with the single main feature have a similar differentiation pattern, such a group of features that is not limited to one single main feature can also be collectively the main feature. In such a case, number 1 ranked feature and features that exhibit significant correlation thereto can be the main feature.

In one embodiment, the method of the invention comprises, after the re-ranking, changing the features and repeating step c).

In another embodiment of the invention, the method comprises, after the re-ranking, changing the features and performing machine learning (linear, logistic regression, support vector machine, or the like) and cross validation to calculate differentiation accuracy of each model. After re-ranking, a feature is increased one at a time to perform machine learning (linear, logistic regression, support vector machine, or the like) and cross validation to calculate differentiation accuracy of each model. The most accurate model can be selected thereby. In the present invention, any machine learning can be used. Linear, logistic, support vector machine (SVM) or the like can be used as supervised machine learning.

In one embodiment, the step described above can be repeated at least once. In this regard, the ranking of features has changed, so that only the inputted feature would be different.

Once model candidates are calculated, a model attaining a given accuracy can be optionally determined to generate a model of interest.

A given accuracy can be appropriately determined in accordance with the objective. A model with the highest accuracy and fewest number of features, a model with the highest accuracy, or the like can be determined. For example, if there are a plurality of differentiation models that attain the same or same degree of differentiation accuracy, it is preferable to select a model comprising the fewest number of features (this is referred to as the economical standard).

Thus, one embodiment comprises selecting a model with fewer types of features among models that attain a give accuracy.

In another embodiment, the given differentiation accuracy comprises the highest accuracy. Contracting can be characterized by extracting an effective feature. More specifically, contracting is characterized by selecting a feature close to all or none corresponding to having pain or no pain, i.e., two value feature. To extract a feature associated with a subordinate classification within having pain or no pain, the same process can be repeated to further recursively perform contracting.

In one embodiment, the weighting coefficient is used in the same meaning as an approximation index of a differentiation function, and is selected from the group consisting of an $R^2$ value, a correlation coefficient, a regression coefficient, a residual sum of squares (difference between differentiation function and feature), and the like.

In another embodiment, a differentiation function (model) is selected from the group consisting of a sigmoid function, step function, and the like.

In still another embodiment, a model approximation index is a subset of weighting coefficients, and is selected from the group consisting of an $R^2$ value, a correlation coefficient, a regression coefficient, a residual sum of squares, and a subset thereof.

In still another embodiment, the effective feature, for binomial classification, is presence or absence corresponding to having pain or no pain, i.e., a 2 value feature, or a feature with higher approximation to a differentiation function.

In another aspect, the present invention provides a method of differentiating pain of an object, comprising: a) obtaining brainwave data or analysis data thereof from a reference object; b) contracting features in the brainwave data or analysis data thereof with respect to the pain; c) differentiating and analyzing by machine learning and cross validation from top of ranking of weighting coefficients (also referred to as a model approximation index; e.g., $R^2$ value) of each feature; d) determining a model that attains a given accuracy; e) obtaining brainwave data or analysis data thereof from a test object; and f) differentiating pain by fitting the model to the test object.

In another aspect, the present invention provides a method of differentiating pain of an object, comprising: e) obtaining brainwave data or analysis data thereof from a test object; and f) differentiating pain by fitting a model for differentiating pain to the test object, wherein the model is generated by: a) obtaining brainwave data or analysis data thereof from a reference object; b) contracting features of the brainwave data or analysis data thereof with respect to the pain; c) differentiating and analyzing by machine learning and cross validation from top of ranking of weighting coefficients (also referred to as a model approximation index; e.g., $R^2$ value) of each feature; d) determining a model that attains a given differentiation accuracy.

In one preferred embodiment, the present invention further comprises filtering the brainwave data or analysis data thereof.

In one preferred embodiment, the filtering used in the present invention comprises filtering for at least one selected from the group consisting of eye movement elimination and attenuation of myogenic potential.

In one preferred embodiment, the brainwave data or analysis data thereof used in the present invention comprises at least one selected from the group consisting of a mean amplitude, interelectrode (frontal-parietal etc.) signal (potential, frequency, amount of information, or the like) correlation, frequency power, and a complexity index (multiscale entropy), and phase synchronicity (phase locking value, coherence).

(Backward Sampling)

In one aspect in the present invention, b) to d) comprise: (C1) dividing the feature and data corresponding to the pain corresponding to the feature into data for learning and data for testing; (C2) performing machine learning using the learning data to create a differentiation model and calculating an optimal λ value (and a partial regression coefficient, a regression equation, and a model intercept); (C3) calculating differentiation accuracy of the differentiation model by using the data for testing; (C4) if there is a target sample with the differentiation accuracy at or below a chance level in the objects, repeating steps C1 to C3 after excluding the sample, and if there is no sample at or below a chance level, ending the steps to determine a differentiation model, wherein the chance level is a numerical value obtained by dividing 100% by the number of classifications. In this regard, the chancel level refers to a value obtained by dividing 100% by the number of classifications. This is verification to avoid accidental match.

With such backward sampling, an "exemplary model" can be created based on an object for which a change in a brainwave feature is observed when pain is sensed for the creation of a prototype of a differentiation model used in the initial pain differentiation apparatus. For example, as shown in the Examples, data for a healthy object with regard to two levels ("painful, not painful") of acute neurological pain (electrical pain) was differentiated and estimated by machine learning (LASSO) one object at a time. When the process including an object with a chance level or greater in a model is repeated, the differentiation accuracy that was not at a very high level of "62%" or the like in the early stages exhibited an improvement to a relatively high level of "81%" or the like at the final 5th stage, as shown in the Examples. It was found that objects included in a model had higher sensitivity to neurological pain relative to objects that were not included, demonstrating that an exemplary model based on a sample which is sensitive to neurological pain by refining can be created. Progressive sampling is a methodology for differentiating with few samples, and increasing the differentiation accuracy by gradually increasing the samples. Such a methodology is also useful for refining and is considered as one of the important aspects of the invention. For example, there is a method of rearranging based on the degree of clarity in the difference in the feature of "painful, not painful" of individual samples and progressively inputting the samples in order in model creation. The difference between progressive and backward elimination is in progressive having reduced load for calculation time because progressive transitions "few→many samples". Meanwhile, the advantage of backward elimination, which is another embodiment of the invention, is in being comprehensive, albeit time consuming, because a model is refined with information on differentiation accuracy of individual samples.

(Novel Feature of Pain Differentiation)

In another aspect, the present invention provides a method of differentiating pain of an object, comprising differentiating pain of an object using a model for differentiating pain of an object, comprising a feature in at least two electrodes at Fz, Fpz, or a vicinity thereof. It should be noted that specific information of electrodes is not required in contracted learning of the invention. Since a procedure for creating a differentiation model is important, the type of feature that is inputted is considered secondary information.

In one embodiment, the vicinity comprises at least one of F3, F4, Fp1, and Fp2.

The present invention provides model formation with low calculation cost. In addition, it was found that a feature that was not considered effectively usable for conventional differentiation of pain can be unexpectedly used for differentiation of pain. Due to the nature of brainwaves, potential activity is conducted in the brain in a wavelike manner and further attenuated at the skull. Thus, if the amplitude of Fz is important, the amplitude of electrodes in the vicinity such as Fpz or FCz can be a substitute. Since existing monitoring apparatuses are not worn on the scalp with hair, it was common to attach two electrodes (Fp1 and Fp2) for recording brainwaves around the forehead. The present invention has shown that "two electrodes" are the most effective in the process of contracting features, and Fz and Fpz or the vicinity thereof due to the possibility of propagation/diffusion of potential can also be effective. A result of "two electrodes" and "vicinity of the forehead" was obtained from data analysis for determining the performance of an apparatus, i.e., differentiation accuracy. Since it is reported that the frequency power in the γ band of the front portion of the prefrontal portion can be associated with pain (Schulz et al., (2015). Prefrontal Gamma Oscillations Encode Tonic Pain in Humans. Cerebral Cortex 25: 4407-4414), the pain analysis method using Fz or Fpz or the vicinity thereof as the feature of the invention should be recognized as a new differentiation means.

Each step is described hereinafter.

Figure 34:
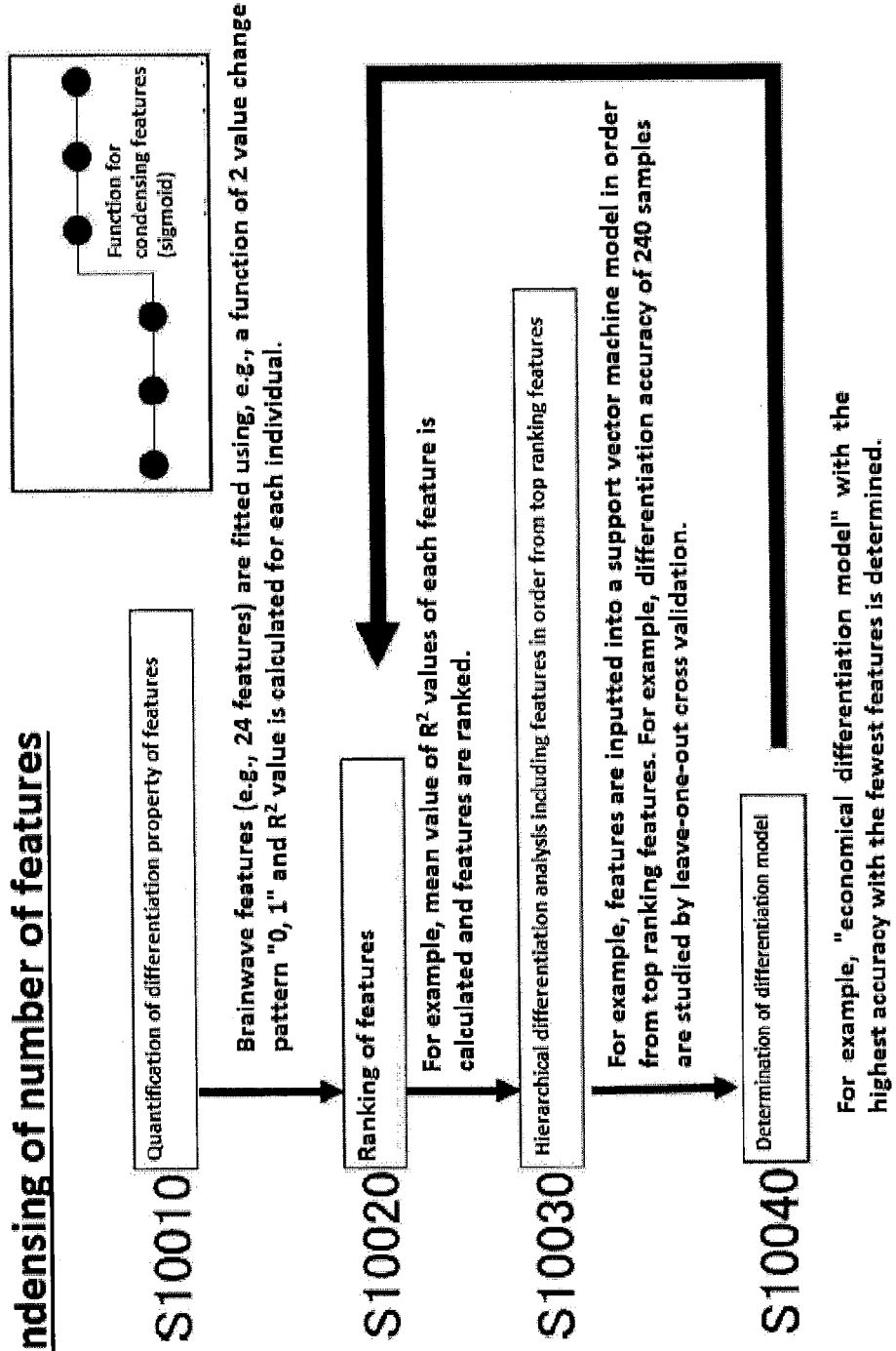
FIG. 34 shows the flow of differentiation analysis with a process for contracting the number of features.

A differentiation and analysis method with contracting of the number of features is described hereinafter using the following schematic diagram (FIG. 34).

a) First, differentiation properties of features of brainwave data or analysis data thereof or the like is quantified (S10010). In other words, this step fits a brainwave feature using a sigmoid function of two value changing pattern "0, 1" to calculate a model approximation index (e.g., $R^2$ value) for each individual. This step can be considered a step for contracting features in brainwave data or analysis data thereof with respect to pain. This step can be used as a step for determining a threshold value or differentiation index in a model curve obtained by fitting when the objective is to differentiate or estimate for individual features. In other words, a threshold value can be determined as a numerical value such as a threshold potential and used as a determination index. More specifically, a differentiation/estimation model is created for 2, 3, or 4 classifications or more in accordance with conditional parameters using a brainwave feature. As one method, a plot diagram is created and applied (fitted) to an appropriate fitting function such as a sigmoid function pattern or a step function. Any methodology that is known in the art can be used for fitting. Specific examples of such fitting functions include, but are not limited to, the functions described above, as well as a Boltzmann function, double Boltzmann function, Hill function, logistic dose response, sigmoid Richards function, sigmoid Weibull function, and the like. A standard logistic function is particularly called a sigmoid function. A standard function or a modified form thereof is common and preferred.

If a regression coefficient for fitting to an appropriate function pattern such as the sigmoid function pattern is greater than a given level, a threshold value for determining pain can be optionally be set based on the sigmoid curve or the like. In this regard, the value can be generated based on an inflection point for sigmoid curves, but this is not limited thereto. As needed, a pain classification value can be calibrated to maximize the pain level classification.

b) Next, features are ranked (S10020). In this regard, a weighting coefficient can be used. The mean value of $R^2$ values of each feature or the like can be used as the weighting coefficient. Once calculation is completed, features are ranked.

c) Next, hierarchical differentiation analysis that includes features in order from top ranking features is performed (S10030). Examples thereof include inputting features in order from top ranking features into a machine learning model such as support vector machine and studying the differentiation accuracy of the entire sample by leave-one-out cross validation and the like. b) and c) correspond to steps for differentiating and analyzing by machine learning and cross validation after inputting the weighted feature after contracting or a combination thereof from top of the ranking.

d) Next, a differentiation model is determined (S10040). This corresponds to a step of determining a model that attains a given accuracy. For example, a model with the highest accuracy or an "economical differentiation model" with the fewest feature for models with the same accuracy can be determined. However, a setting such as select any model that attains a give accuracy (e.g., 70% differentiation accuracy) can be provided. In the present invention, steps c) and d) can be performed in a model generation unit. If it is expected that a model is predetermined using a known database, pain data may be input into the model during actual monitoring to perform differentiation and estimation. Black arrows can be assumed as the envisioned flow of actual monitoring.

A method of re-ranking features shown in Example 11 can also be used in a different optimal model selection procedure. In such a case, a differentiation model is determined in S10040, and then regressed to the feature ranking in S10020, features are re-ranked by a value of difference in differentiation accuracy of an n−1 feature model (n≥2) and n feature model, and top features in S10030 are inputted into the model one at a time to recalculate the differentiation accuracy. A differentiation model is then determined through the 2nd model determination process in S10040. These steps are as follows when using the symbols in FIG. 44. Specifically, a differentiation model is determined then regressed to the feature ranking in S10060, and features are re-ranked by a value of difference in differentiation accuracy of an n−1 feature model (n≥2) and n feature model (S10070-1), and top features in S10070-2 are inputted into the model one at a time to recalculate the differentiation accuracy. A differentiation model is then determined through the model determination process in S10080.

Figure 35:
FIG. 35 shows results (feature ranking and differentiation accuracy) of differentiation analysis with a process for contracting features (Example 8). This is an economical pain differentiation/estimation model with low calculation cost. While all 24 features were used up to this point for differentiation, it was found here that differentiation accuracy for 2 levels of pain of "71.3%" was exhibited by using only the top two features with higher sigmoid function approximation.

A feature can be a feature that is obtained in response to some type of stimulation (e.g., low temperature stimulation, electrical stimulation, or the like) or obtained in a natural environment, or various brainwave data, brain activity data, amount of brain activity, amplitude data (EEG amplitude), frequency property, and the like can be used. Such brainwave data can be obtained using any methodology that is well known in the art. Brainwave data can be obtained by measuring electrical signals of a brainwave and is displayed by potential (can be displayed by μV or the like) as amplitude data or the like. Frequency properties are displayed as power spectrum density or the like. After basic signal processing of brainwave data such as filtering, eye movement correction, or artifact removal, the data can be associated with a conditional parameter and a signal of the corresponding portion is extracted to create a brainwave feature. This includes mean value (arithmetic mean or geometric mean), other representative value (median or mode), entropy, frequency power, wavelet, mean and single run event related potential component, and the like. FIG. 35 and FIG. 36 show a comparison of an example of the present invention with a comparative example. The difference in calculation cost is evident.

In a preferred embodiment, brainwave data is preferably collected by a simple method, which can 1) use electrodes at a number that is required for analysis, 2) avoid the scalp with hair as much as possible, and 3) record while sleeping, to carry out the invention. Exemplary number of electrodes used is, but not limited to, 24, but the number can be 12 to 24, 24 to 36, 6 to 12, or fewer (e.g., 3, 4, 5, or the like).

For contracting, sigmoid fitting, or a step function with stepwise inflection, a linear function with a continuous stepwise change, or the like can be used.

As a weighting coefficient, a regression coefficient, or an $R^2$ value, correlation coefficient, residual sum of squares (difference between differentiation function and feature), or the like can be used. However, it is important that pain or stress sensed by an individual can be distinguished with as much accuracy as possible for differentiation of pain, so that efficacy which is different from detection of statistical significance difference can be required or intended.

In one embodiment, brainwave data or analysis data thereof comprises, as data recording positions, frontal-parietal portions such as F3, F4, C3, C4, P3, and P4 in compliance with the international 10-20 system or expanded standard thereof, and positions on the scalp over the occipital portion as electrode positions. Alternatively, a position at a specific uniform distance (e.g., 2.5 cm or the like) can be covered. The duration of recording and analysis can be, for a short period of event related potential activity, 0 to 100, 100 to 200, 200 to 300, 300 to 400, 400 to 500, 500 to 600, 600 to 700, 700 to 800 milliseconds (ms), a shorter time segment (10 milliseconds or the like), or a longer time frame (sometimes spanning several seconds). The brainwave data or analysis data thereof comprises at least one brainwave feature selected from combinations thereof.

In still another embodiment, a brainwave feature comprises at least one selected from the group consisting of Fp1, Fp2, Fpz, F3, F4, Fz, C3, C4, Cz, P3, P4, and Pz, such as mean amplitudes Fz, C3, and C4, and frequencies Fz ($\delta$), Fz($\beta$), Cz($\delta$), C3($\theta$), and C4($\beta$). It is preferable that the feature comprises, but not limited to, Cz (amplitude), C3($\alpha$), Cz($\beta$), Fz($\delta$), and Cz($\gamma$).

Figure 47:
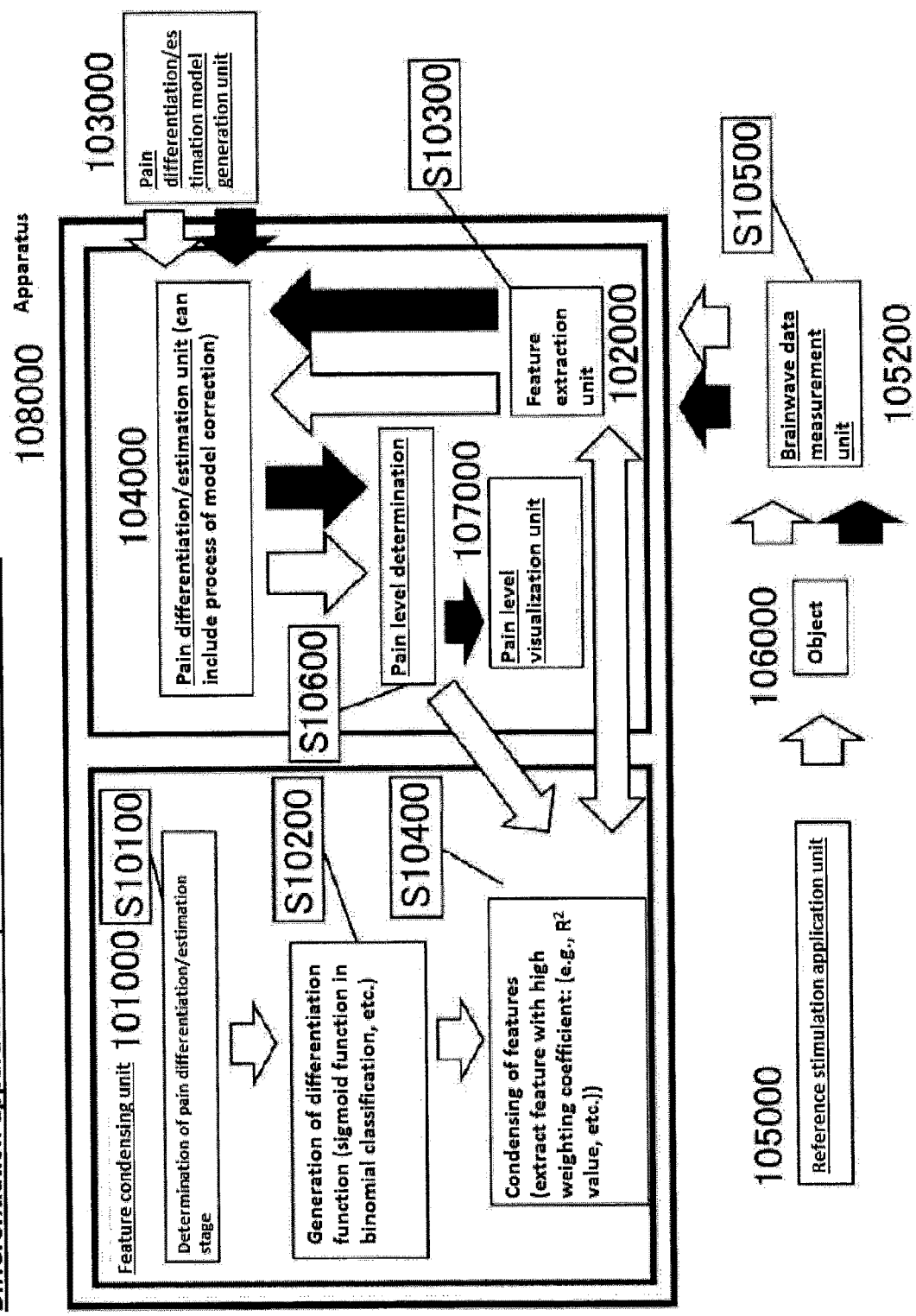
FIG. 47 shows a schematic diagram of a differentiation apparatus with a process for contracting features.
Figure 48:
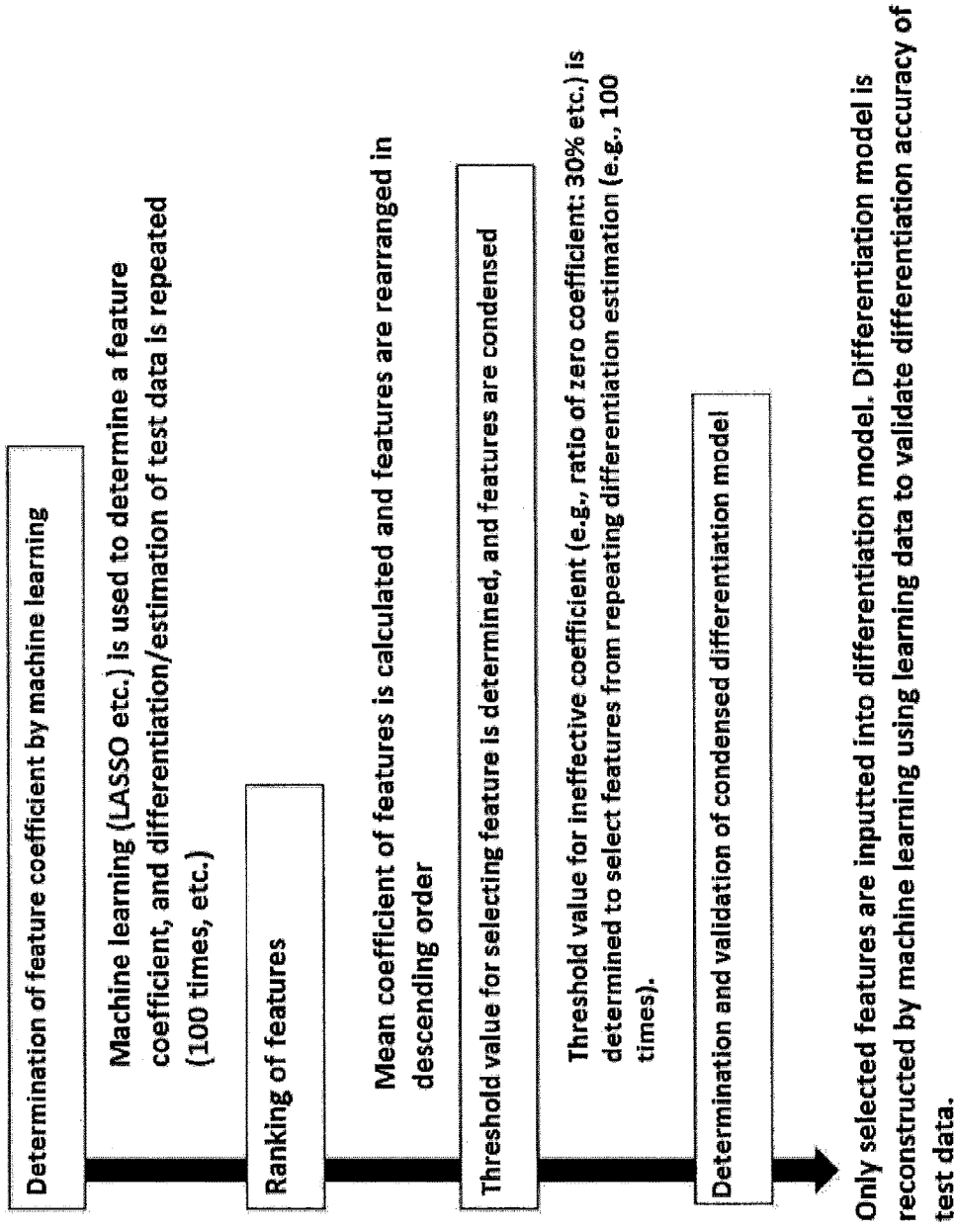
FIG. 48 shows a schematic diagram of another example of a contracting process based on a feature coefficient. All numerical values in the figure are exemplary.

FIG. 47 describes a schematic diagram of the apparatus of the invention (differentiation apparatus with a process of contracting features) (101000 to 108000) (it should be noted that some of the configuration diagrams are optional constituents that can be omitted). In this schematic diagram, each step is described when appropriate (S10100 to S10600).

This apparatus is comprised of a feature contracting unit 101000, feature extraction unit 102000, pain differentiation/estimation model generation unit 103000, pain differentiation/estimation unit (can comprise a model correction process) 104000, reference stimulation application unit 105000, brainwave data measurement unit 105200, and pain level visualization unit 107000. An object is denoted as 106000.

In such differentiation with a process of contracting, the number of pain differentiation/estimation stages (2 stages, 3 stages, or the like) is determined (S10100), and a differentiation function is generated (examples include sigmoid functions in binomial classification and the like; S10200). A feature is obtained after a reference stimulation (electrical stimulation or the like) is applied to the object 106000 from the reference stimulation application unit 105000 in accordance with the differentiation stage determined at S10100, and a feature related to a pain stage is collected (S10300) and contracted (S10400). The collected feature is approximated by a differentiation function generated at S10200 and ranked in accordance with the magnitude of the obtained approximation coefficient (regression coefficient or the like). Features are used in order from the top features. The pain level of reference stimulation is differentiated and estimated with the pain differentiation/estimation unit 104000, and a differentiation model with the number of features with the highest differentiation accuracy is used for monitoring pain. This is one embodiment of the process of contracting features S10400. A differentiation model (algorithm) installed in a pain differentiation/estimation unit used in the process of contracting (white arrows) and actual pain monitoring process (black arrows) is created at the pain differentiation/estimation model generation unit 103000, and installed in the pain differentiation/estimation unit 104000. After completion of the preprocessing described above at the feature contracting unit 101000, actual pain related brainwave data is collected from the object 106000 at the brainwave data measurement unit 105200 comprising an electroencephalograph or the like (S10500). This is transmitted to the feature extraction unit 102000 and converted to a feature selected in the process of contracting amplitudes or frequencies (e.g., specific amplitude or frequency band of specific electrodes or the like). The extracted feature is taken into the pain differentiation/estimation unit 104000 (can comprise a model correction process) from the feature extraction unit 102000, and a pain level is determined (S10600). The result of the determination is indicated as a trend of changes or numerical value (e.g., 1 to 100) at the pain level visualization unit 107000.

The determination of pain differentiation/estimation stages at S10100 determines the number of levels to be differentiated or estimated (e.g., 2 stages, 3 stages, or the like).

The generation of a differentiation function at S10200 creates a differentiation function used in accordance with the number of differentiation levels of S10100 (sigmoid function or step function in binomial classification or the like).

The collection of pain stage related features at S10300 applies reference stimulations (electrical stimulation or the like) a plurality of times from the reference stimulation application unit 105000 to the object 106000 in accordance with the number of levels determined at S10100 to collect related brainwave features.

In contracting of features at S10400, features obtained at S10300 are approximated with a differentiation function, features with a high approximation index (e.g., $R^2$ value or the like) are ranked, and features are inputted into the pain differentiation/estimation unit 4104000 in order from top ranking features to differentiate and estimate a level of reference stimulation. A model with a number of features with the highest differentiation accuracy thereamong is used for actual pain differentiation/estimation.

For collection of pain related brainwave data at S10500, actual pain related brainwave data subjected to monitoring of pain is collected after completion of the contracting process at the feature contracting unit 101000. This step is data collection in an actual pain monitoring process.

For pain level determination at S10600, actual pain related data obtained at S10500 is processed at the feature extraction unit 102000 to obtain a feature set and then differentiated and estimated at the pain differentiation/estimation unit 104000, a pain level is quantified from an estimated value, and a pain level is determined and made visible at the pain level visualization unit 107000.

The apparatus 108000 is configured to comprise or to be connected to an electroencephalograph that is or can be connected to the object (106000), so that brainwave data synchronized with stimulation emitted from the reference stimulation application unit 105000 to the object (106000) is obtained at the brainwave data measurement unit 105200. This is the summary of the apparatus 108000.

The apparatus 108000 can comprise a brainwave measurement unit, which internally comprises or externally connects to a brainwave recording sensor and optionally a brainwave amplification unit, and process signals of a pain related brainwave and differentiate/estimate pain in the apparatus 108000.

In the apparatus 108000, collected brainwave signals are processed to extract a brainwave feature at the feature extraction unit 102000. Upon extraction, a feature contracted in advance at the feature contracting unit 101000 is selected. Further, pain is (optionally) made visible at the pain level visualization unit 107000. The apparatus internally or externally comprises the reference stimulation application unit 105000, which applies reference stimulation such as electrical stimulation a plurality of times in accordance with the pain level determined at S10100 in order to contract features that are effective for monitoring pain of the object 106000. Brainwave data related thereto is recorded at the brainwave data measurement unit 105200, the related brainwave feature is obtained at the feature extraction unit 102000, a pain level of reference stimulation is differentiated and estimated from the feature at the pain differentiation/estimation unit 104000, and the feature is contracted S10400 from the result thereof. The reference stimulation application unit 105000 also transmits pain stimulation information (stimulation type, environmental information, or the like) for differentiating an actual unknown pain level and differentiator creation. The reference stimulation application unit 105000 optionally comprises a stimulation information visualization unit in addition to the reference stimulation application unit 105000 and may display information such as an image or number associated with stimulation or environment. The apparatus 108000 can also internally or externally comprise the pain differentiation/estimation unit 104000 for generating a determination value or differentiator.

In this manner, the apparatus 108000 comprises the brainwave data measurement unit 105200 and the pain differentiation/estimation unit 104000 and optionally the reference stimulation application unit 105000. The apparatus 108000 is materialized, for example, by a computer comprising a processor and a memory. In such a case, the apparatus 108000 makes the processor function as the feature contracting unit 101000, feature extraction unit 102000, pain differentiation/estimation model generation unit 103000, pain differentiation/estimation unit 104000, or the like as needed when a program stored in the memory is implemented by the processor. The processor is also made to make stimulation or environmental information visible as needed. The apparatus 108000 of the invention can be materialized, for example, by a dedicated electronic circuit. A dedicated electronic circuit can be a single integrated circuit or a plurality of electrical circuits. A brainwave data obtaining unit and pleasant/unpleasant determination value generation unit can have the same configuration as a pleasant/unpleasant determination apparatus.

The feature extraction unit 102000 can also obtain a plurality of brainwave data by measuring a brainwave a plurality of times from an object being estimated via an electroencephalograph (included in the brainwave data measurement unit 105200). An object is an organism in which a change in brainwave is induced by stimulation or environment, which does not need to be limited to humans.

The pain differentiation/estimation unit 104000 differentiates/estimates the degree of unpleasantness using a determination value, and also generates a differentiator of determination value if not generated in advance externally or internally. The apparatus 108000 can comprise a part generating a differentiator or determination value externally or internally as the pain differentiation/estimation unit 104000. A differentiation value used for differentiation/estimation of pain is for estimating or classifying the degree of unpleasantness from amplitudes of a plurality of brainwave data. In other words, the pain differentiation/estimation unit 104000 or the pain differentiation/estimation model generation unit 103000 can generate a determination value for estimating or classifying the degree of unpleasantness of an object from brainwave data.

A brainwave recording sensor contained in the brainwave data measurement unit 105200 measures electrical activity generated inside the brain of an object being estimated with an electrode on the scalp. The brainwave recording sensor also outputs the result of measurement, brainwave data. Brainwave data can be amplified as needed.

Other Embodiments

The differentiation apparatus with a process of contracting features according to one or more embodiments of the invention has been described based on the embodiments, but the present invention is not limited to such embodiments. Various modifications applied to the present embodiments and embodiments constructed by combining constituent elements in different embodiments that are conceivable to those skilled in the art are also encompassed within the scope of one or more embodiments of the invention as long as such embodiments do not deviate from the intent of the inventions.

For example, a peak to peak value can be used as the amplitude value of brainwave data in each of the embodiments described above, but the amplitude value is not limited thereto. For example, a simple peak value can be used as the amplitude value.

In the embodiment described above, the range of the value of magnitude of the degree of unpleasantness is envisioned to be set so that the value of Pmax, which is the magnitude of the degree of unpleasantness corresponding to the upper limit value Amax of a feature such as brainwave amplitude or a combination thereof, would be 1, or the value of Pmin, which is the magnitude of pain corresponding to the lower limit value Amin of the feature or combination thereof, would be 0, but the range of values is not limited thereto. For example, the magnitude of pain can be represented by 0 to 100. In such a case, the pain differentiation/estimation unit 104000 can estimate the value Px of magnitude of pain, when shown by the pain level visualization unit 107000, by the following equation.

$$Px = P\max \times (Ax - A\min)/(A\max - A\min)$$

Curve fitting including sigmoid fitting was described above as an example of generating a pleasant/unpleasant determination value by analyzing a plurality of brainwave data, but this is not a limiting example. A predetermined value can also be used as the upper limit value of a brainwave amplitude. The predetermined value (absolute value) is for example 50 μV to 100 μV, which can be experimentally or empirically determined. In such normal analysis, data from about plus or minus 50 μV to 100 μV is eliminated as an artifact removal method. Such artifact removal can also be performed in the present invention as needed.

Any type of stimulation can be applied as stimulation applied to the object 106000 by the reference stimulation application unit 105000 (see FIG. 47) as long as the magnitude of the degree of unpleasantness sensed by the object 106000 changes in accordance with the type of stimulation or application environment.

Some or all of the constituent elements of the apparatus of the invention in each of the embodiments described above can be comprised of a single system LSI (Large Scale Integration). For example, as shown in FIG. 47, the apparatus 108000 can be comprised of the feature contracting unit 101000, pain differentiation/estimation model generation unit 103000, pain differentiation/estimation unit 104000, and pain level visualization unit 107000, as well as a system LSI having the feature extraction unit 102000 and the reference stimulation application unit 105000.

System LSI is ultra-multifunctional LSI manufactured by integrating a plurality of constituents on a single chip, or specifically a computer system comprised of a microprocessor, ROM (Read Only Memory), RAM (Random Access Memory) and the like. A computer program is stored in a ROM. The system LSI accomplishes its function by the microprocessor operating in accordance with the computer program.

The term system LSI is used herein, but the term IC, LSI, super LSI, and ultra LSI can also be used depending on the difference in the degree of integration. The methodology for forming an integrated circuit is not limited to LSI. An integrated circuit can be materialized with a dedicated circuit or universal processor. After the manufacture of LSI, a programmable FPGA (Field Programmable Gate Array) or reconfigurable processor which allows reconfiguration of the connection or setting of circuit cells inside the LSI can be utilized.

If a technology of integrated circuits that replaces LSI by advances in semiconductor technologies or other derivative technologies becomes available, functional blocks can obviously be integrated using such technologies. Application of biotechnology or the like is also a possibility.

One embodiment of the invention can be not only such a pain differentiation/estimation model generation, sustained pain differentiation/estimation unit, but also a pain classifier generation, pain differentiation/classification method using characteristic constituent units contained in a pain estimation apparatus as steps. Further, one embodiment of the invention can be a computer program for implementing each characteristic step in feature contracting, feature extraction, pain differentiation/estimation model generation, and pain differentiation/estimation on a computer. One embodiment of the invention can also be a computer readable non-transient recording medium on which such a computer program is recorded.

In each of the embodiments described above, each constituent element can be materialized by being configured with a dedicated hardware or by implementing software program that is suited to each constituent element. Each constituent element can be materialized by a program implementation unit such as a CPU or a processor reading out and implementing a software program recorded on a recording medium such as a hard disk or semiconductor memory. In this regard, software materializing the pain estimation apparatus of each of the embodiments described above or the like can be a program such as those described below.

Embodiment Using Cloud, IoT, and AI

Figure 50:
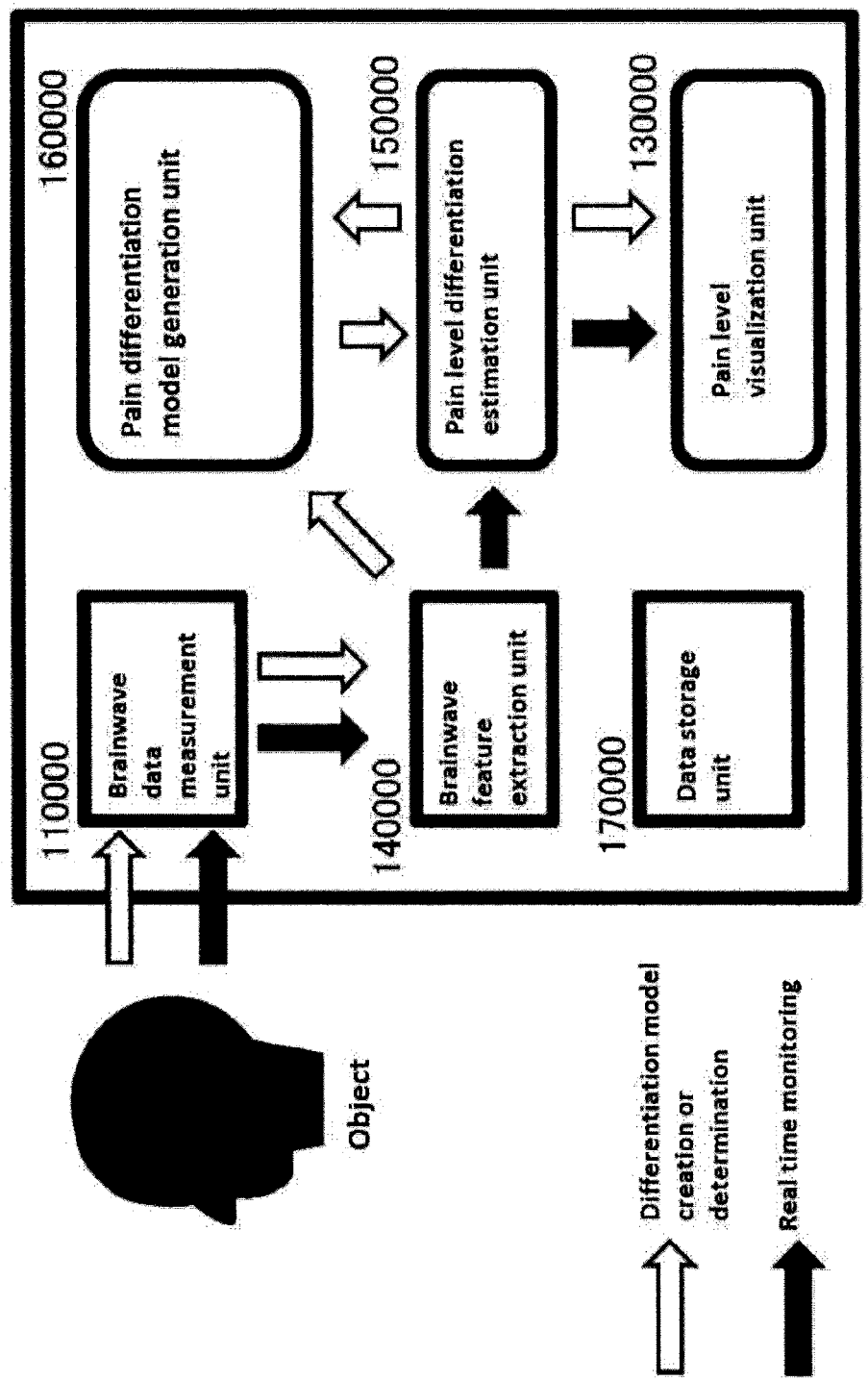
FIG. 50 is a schematic diagram of the device of the invention. This presumes an example equipped with all parts.

The pain determination technology of the invention can be provided in a form comprising all constituents as a single system or apparatus (see FIG. 50). Alternatively, a pain differentiation apparatus can also be envisioned in a form of mainly measuring brainwaves and displaying results while calculation or differentiation model calculation are performed on a server or cloud (see FIGS. 51, 52, and 53). Some or all of them can be performed using IoT (Internet of Things) and/or artificial intelligence (AI).

Figure 53:
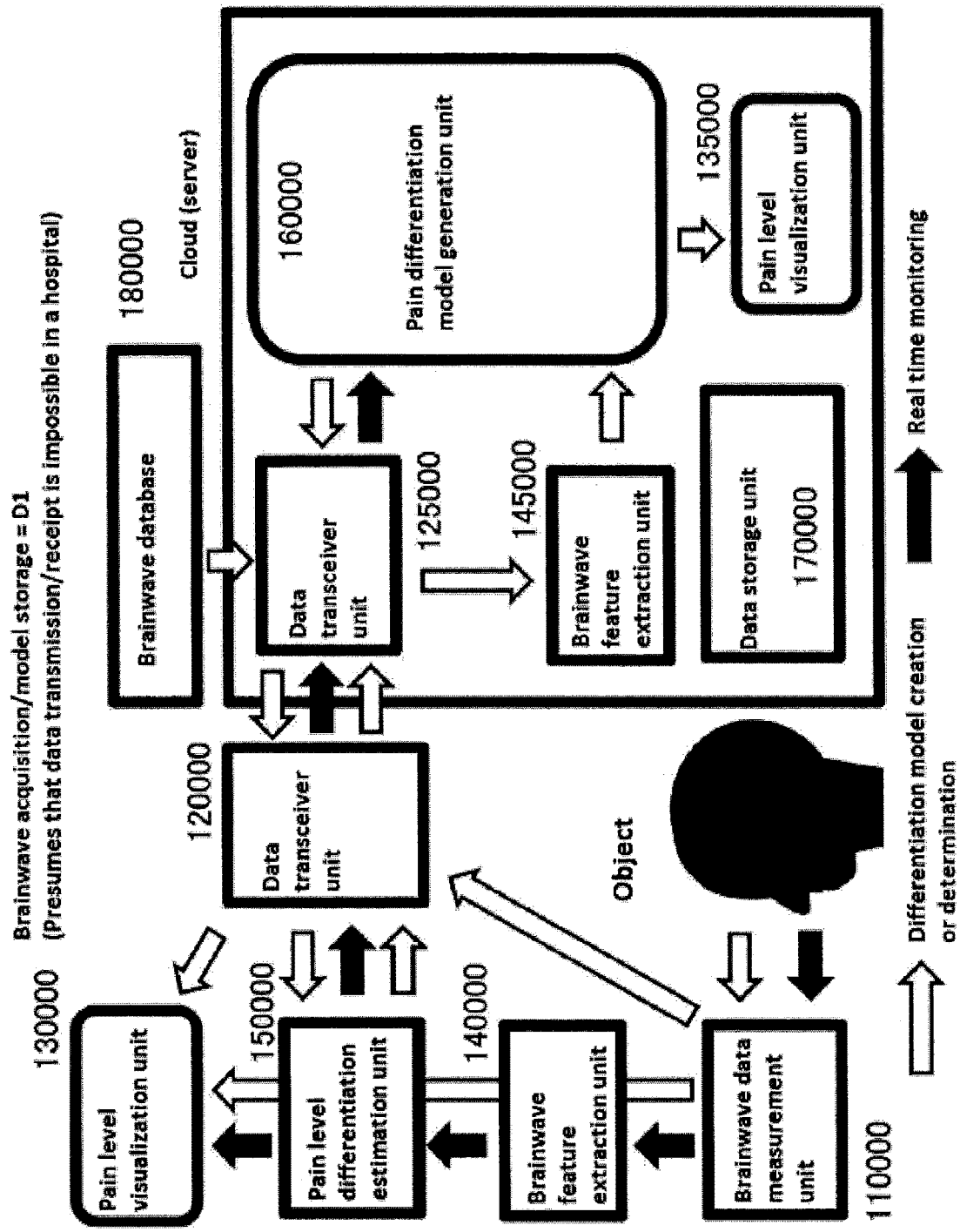
FIG. 53 is a schematic diagram of the device of the invention, showing an embodiment of the device portion (left side) having a function for obtaining brainwaves, transmitting/receiving data, enabling on-site differentiation by storing a differentiation model, and making them visible. Such an embodiment presumes use at a facility or location where it is difficult to transmit/receive radio waves such as a hospital. This is an embodiment where a determination/differentiation model is generated on the cloud or server, and actual measurement data is actually fitted to a model at a device. The brainwave feature (analysis data) can be extracted at a terminal or on the server side.

Alternatively, a pain differentiation apparatus can also be envisioned in a semi-standalone form where a differentiation model is stored and performs differentiation therein, but main calculation such as calculation of a differentiation model is performed on a server or cloud (FIG. 53). Since transmitting/receiving is not necessarily always possible at some locations where the apparatus is implemented such as hospitals, this is a model envisioned for use when communication is blocked.

Therefore, in one aspect, the present invention provides a program for implementing a method of differentiating pain of an object on a computer, the method comprising: a) obtaining brainwave data or analysis data thereof from the object; b) generating a differentiation model based on the brainwave data or analysis data thereof; and c) differentiating pain by fitting the brainwave data or analysis data thereof from the object to the differentiation model, and a recording medium, system, and apparatus storing the same.

A system that materializes such a program is materialized in an embodiment that deems the entirety as a system. In this aspect, the present invention is a system for differentiating pain of an object, the system comprising: X) a brainwave data obtaining unit for obtaining brainwave data or analysis data thereof from an object; Y) a pain differentiation/estimation model generation unit for generating a differentiation model based on the brainwave data or analysis data thereof; and Z) a pain differentiation/estimation unit for differentiating pain by fitting the brainwave data or analysis data thereof from the object to the model. In such a case, the brainwave data obtaining unit is illustrated as a brainwave data measurement unit 110000 and brainwave feature extraction unit 140000, as schematically exemplified in FIG. 50. The pain differentiation/estimation model generation unit is depicted as a pain differentiation model generation unit 160000. Furthermore, the pain differentiation/estimation unit is depicted as a pain level differentiation estimation unit 150000. In FIG. 50, a pain level visualization unit 130000 and data storage unit 170000 are also depicted. Such a visualization unit and storage unit are not necessarily essential, but it is preferable that they are comprised when provided as a medical equipment.

A visualization unit can be any unit, as long as a user can recognize the result of differentiating pain. An input/output apparatus, display, television, monitor, or the like can be used. Instead of a visualization unit, another recognition means can be used such as audio. A sound generation apparatus (e.g., speaker), vibration apparatus, electrode, or other apparatuses that can present a challenge to a subject can be comprised.

A storage unit can be a recording medium such as a CD-R, DVD, Blueray, USB, SSD, or hard disk. A storage unit can be stored in a server or an appropriate recording form on the cloud.

As schematically exemplified in FIG. 50, the present apparatus can be used when creating or determining a differentiation model (white arrow) and when monitoring actual pain. When creating/determining a model, the brainwave data measurement unit 110000 obtains brainwaves when a plurality of pain stimulations is applied to an object. Recorded data is transmitted to the brainwave feature extraction unit 140000 to create a plurality of features. The features are transmitted to the pain differentiation model generation unit 160000 to generate a differentiation algorithm. The differentiation algorithm is transmitted to the pain level differentiation estimation unit 150000, and differentiation results from the created model are transmitted to the pain level visualization unit 130000 and displayed for reviewing the appropriateness of pain level differentiation results. After the differentiation model is determined, real-time monitoring of actual pain levels occurs through the flow of black arrows. Specifically, once pain monitoring starts, brainwave data is obtained by the brainwave data measurement unit 110000 from an object, and the brainwave data is transmitted to the brainwave feature extraction unit 140000 to extract a plurality of brainwave features. The created features are transmitted to the pain level differentiation estimation unit 150000, and the differentiation results are displayed on the pain level visualization unit 130000. The processes can be combined. If differentiation results are not appropriate upon real-time monitoring, results of the pain level differentiation estimation unit 150000 are fed back to the pain differentiation model generation unit 160000. After the model is corrected, the corrected model is retransmitted to the pain level differentiation estimation unit 150000.

Figure 51:
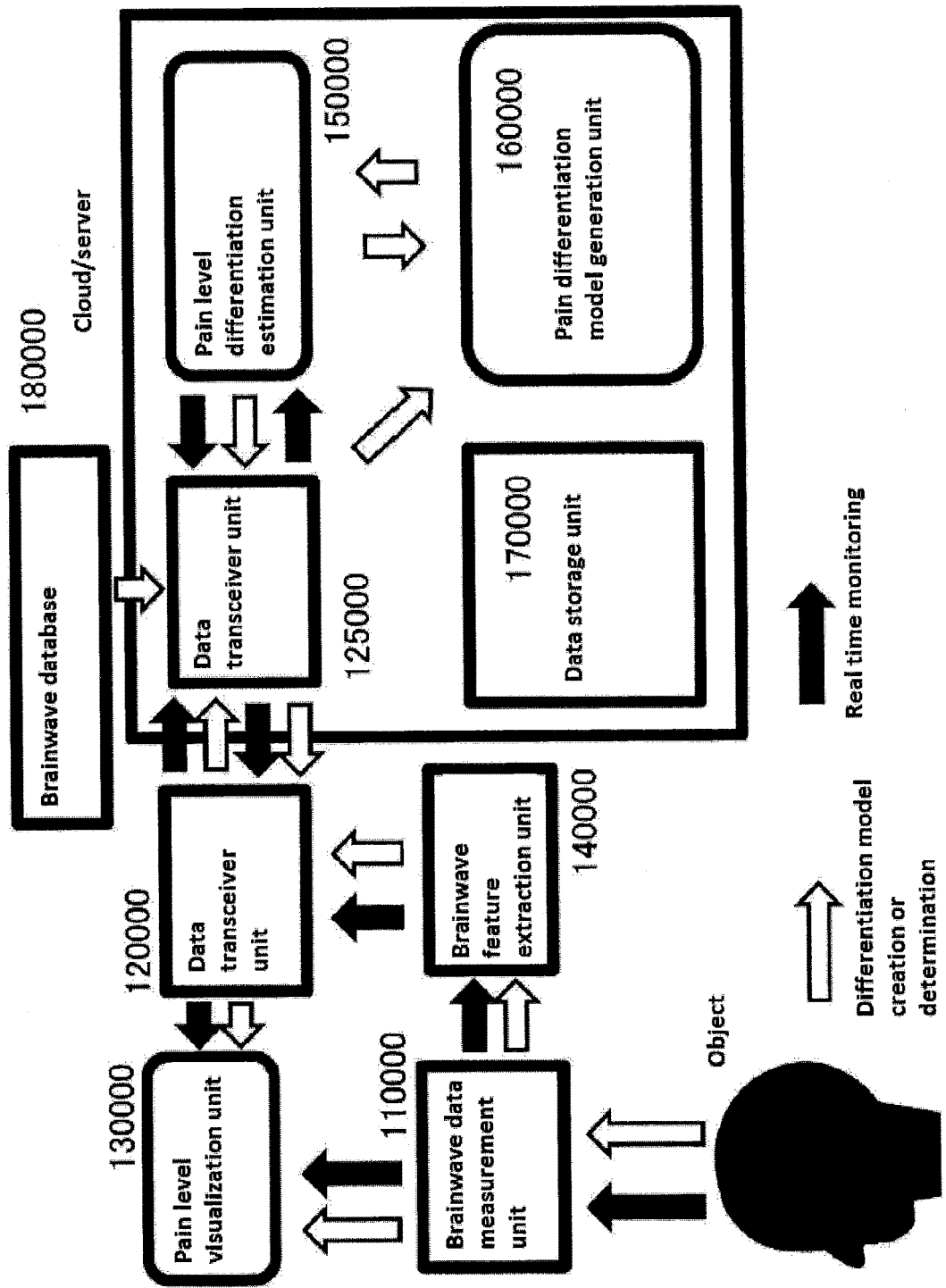
FIG. 51 is a schematic diagram of the device of the invention, showing an embodiment of the device portion (left side) having only a function for obtaining brainwaves, transmitting/receiving data, and making them visible. This is an embodiment presuming that analysis and determination/differentiation model generation and the like are performed on the cloud or a server. A brainwave feature (analysis data) is extracted on the terminal side in this model.

In one aspect, based on FIG. 51, a terminal only obtains brainwaves, and the present invention is a system for differentiating pain of an object, the system comprising X) a pain differentiation terminal and Y) a pain differentiation/estimation server, wherein the pain differentiation terminal comprises: X-1) a brainwave data obtaining terminal for obtaining brainwave data or analysis data thereof from an object; and X-2) a module for transmitting and receiving the brainwave data or analysis data thereof and a differentiation result to a pain differentiation/estimation server, wherein the pain differentiation/estimation server comprises: Y-1) a pain differentiation/estimation model generation module for generating a differentiation model based on the brainwave data or analysis data thereof; Y-2) a pain differentiation/estimation module for generating a differentiation result from differentiating pain by fitting the brainwave data or analysis data thereof from the object to the model; and Y-3) a differentiation result transceiver module for transmitting and receiving the brainwave data or analysis data thereof and the differentiation result.

As schematically exemplified in FIG. 53, the present apparatus can be used when creating or determining a differentiation model (white arrow) and when monitoring actual pain. When creating/determining a model, the brainwave data measurement unit 110000 obtains brainwaves when a plurality of pain stimulations is applied to an object. Recorded data is displayed online at the pain level visualization unit 130000 and transmitted to the brainwave feature extraction unit 140000 to create a plurality of features. The created features are transmitted, through a data transceiver unit 120000, to a data transceiver unit 125000 of a cloud/server and to the pain differentiation model generation unit 160000. The created model is ultimately stored in the pain level differentiation estimation unit. At this time, the outputted differentiation/estimation results are transmitted to the external data transceiver unit 120000 through the data transceiver unit 125000 and displayed at the pain level visualization unit 130000 for reviewing. After the differentiation model is determined, real-time monitoring of actual pain levels occurs through the flow of black arrows. Specifically, once pain monitoring starts, brainwave data is obtained by the brainwave data measurement unit 110000 from an object, and the brainwave data is displayed at the pain level visualization unit 130000 and simultaneously transmitted to the brainwave feature extraction unit 140000 to extract a plurality of brainwave features. The created features are transmitted to the pain level differentiation estimation unit 150000 through the data transceiver units 120000 and 125000 for differentiation and estimation of pain levels. The differentiation results are displayed on the pain level visualization unit 130000 through the data transceiver units 120000 and 125000. The processes can be combined. If differentiation results are not appropriate upon real-time monitoring, results of the pain level differentiation estimation unit 150000 are fed back to the pain differentiation model generation unit 160000. After the model is corrected, the corrected model is retransmitted to the pain level differentiation estimation unit 150000. The recorded data or created feature or differentiation model is stored in the data storage unit 170000 when appropriate.

In another aspect, "brain feature"=analysis data extracting module is in a separated form based on FIG. 51. A feature is presumed to be calculated on the terminal side. In this regard, the present invention provides a system for differentiating pain of an object, the system comprising X) a pain differentiation terminal and Y) a pain differentiation/estimation server, wherein the pain differentiation terminal comprises: X-1) a brainwave data obtaining terminal for obtaining brainwave data from an object; and X-2) a module for transmitting and receiving the brainwave data and a differentiation result to the pain differentiation/estimation server, wherein the pain differentiation/estimation server comprises: Y-1) a pain differentiation/estimation model generation module for generating a differentiation model based on the brainwave data or analysis data thereof; Y-1') a brainwave feature extraction module for extracting analysis data from the brainwave data; Y-2) a pain differentiation/estimation module for generating a differentiation result from differentiating pain by fitting the brainwave data or analysis data thereof from the object to the model; and Y-3) a differentiation result transceiver module for transmitting and receiving the brainwave data or analysis data thereof and the differentiation result As schematically exemplified in FIG. 52, the present apparatus can be used when creating or determining a differentiation model (white arrow) and when monitoring actual pain. When creating/determining a model, the brainwave data measurement unit 110000 obtains brainwaves when a plurality of pain stimulations is applied to an object. Recorded data is displayed online at the pain level visualization unit 130000 and transmitted to the data transceiver unit 125000 of a cloud server through the data transceiver unit 120000 and to the brainwave feature extraction unit 140000 to create a plurality of features. The created features are transmitted to the pain differentiation model generation unit 160000. The created model is ultimately stored in the pain level differentiation estimation unit 150000. At this time, the outputted differentiation/estimation results are transmitted to the external data transceiver unit 120000 through the data transceiver unit 125000 and displayed at the pain level visualization unit 130000 for reviewing. After the differentiation model is determined, real-time monitoring of actual pain levels occurs through the flow of black arrows. Specifically, once pain monitoring starts, brainwave data is obtained by the brainwave data measurement unit 110000 from an object, and the brainwave data is displayed at the pain level visualization unit 130000 and simultaneously transmitted to the brainwave feature extraction unit 140000 through the data transceiver units 120000 and 125000 to extract a plurality of brainwave features. The created features are transmitted to the pain level differentiation estimation unit 150000 for differentiation or estimation of pain levels. The differentiation results are displayed on the pain level visualization unit 130000 through the data transceiver units 120000 and 125000. The processes can be combined. If differentiation results are not appropriate upon real-time monitoring, results of the pain level differentiation estimation unit 150000 are fed back to the pain differentiation model generation unit 160000. After the model is corrected, the corrected model is retransmitted to the pain level differentiation estimation unit 150000. The recorded data or created feature or differentiation model is stored in the data storage unit 170000 when appropriate.

In still another aspect, an embodiment of a terminal obtaining brainwaves and fitting the brainwaves to a stored model is provided. In this aspect, the present invention provide a system for differentiating pain of an object, the system comprising X) a pain differentiation terminal and Y) a pain differentiation/estimation server, wherein the pain differentiation terminal comprises: X-1) a brainwave data obtaining terminal for obtaining brainwave data or analysis data thereof from an object; X-2) a module for transmitting and receiving the brainwave data or analysis data thereof and a differentiation model to the pain differentiation/estimation server; and X-3) a differentiation model module for storing a differentiation model, wherein pain is differentiated by fitting the brainwave data or analysis data thereof from the object to the differentiation model, wherein the pain differentiation/estimation server comprises: Y-1) a pain differentiation/estimation model generation module for generating a differentiation model based on the brainwave data or analysis data thereof; Y-2) a model transmission module for transmitting the differentiation model to the pain differentiation terminal; and optionally a brainwave feature extraction module for extracting analysis data from the brainwave data.

As schematically exemplified in FIG. 53, the present apparatus can be used when creating or determining a differentiation model (white arrow) and when monitoring actual pain. When creating/determining a model, the brainwave data measurement unit 110000 obtains brainwaves when a plurality of pain stimulations is applied to an object. Recorded data is displayed online at the pain level visualization unit 130000 and transmitted, through the data transceiver unit 120000, to the data transceiver unit 125000 of a cloud server and to a brainwave feature extraction unit 145000 in a cloud server to create a plurality of features. The created features are transmitted to the pain differentiation model generation unit 160000. The created model is ultimately stored in the pain level differentiation estimation unit 150000. At this time, the outputted differentiation/estimation results are transmitted to the external data transceiver unit 120000 through the data transceiver unit 125000 and displayed at the pain level visualization unit 130000 for reviewing. After the differentiation model is determined, real-time monitoring of actual pain levels occurs through the flow of black arrows. Specifically, once pain monitoring starts, brainwave data is obtained by the brainwave data measurement unit 110000 from an object transmitted to the brainwave feature extraction unit 140000 to extract a plurality of brainwave features. The created features are transmitted to the pain level differentiation estimation unit 150000 for differentiation or estimation of pain levels and displayed at the pain level visualization unit 130000. The processes can be combined. If differentiation results are not appropriate upon real-time monitoring, results of the pain level differentiation/estimation unit 150000 are fed back to the pain differentiation model generation unit 160000. After the model is corrected, the corrected model is retransmitted to the pain level differentiation estimation unit 150000. The recorded data or created feature or differentiation model is stored in the data storage unit 170000 when appropriate.

"Software as service (SaaS)" mostly falls under such a cloud service. Since a pain differentiation apparatus at the early stages is understood to be installed with a differentiation algorithm made from data in a laboratory environment, the apparatus can be provided as a system comprising two or three features of these embodiments.

For example, the following is contemplated.

1. A function for incorporating brainwave data is included on the terminal side (brainwave data measurement unit 110000 in FIGS. 50 to 53).

2. An apparatus can have a function for extracting a feature, or the feature can be included on the terminal side (e.g., brainwave data itself is the responsibility of another equipment, which provides a feature to a terminal by transmission/receipt.) In this regard, the brainwave feature extraction unit 140000 or 145000 (FIGS. 50 to 53) can be on the terminal side or the server side, or integrated with the brainwave data measurement unit or provided separately. FIGS. 50 to 53 show embodiments comprising them separately.

For example, basic features such as potential, frequency, potential correlation, and entropy can be stored as standard specification, and other features for increasing differentiation accuracy or the like can be stored as options.

A pain differentiation model is generated in the pain differentiation model generation unit 160000. At the pain differentiation model generation unit, a pain differentiation model is generated based on brainwave data or analysis data thereof, and the pain differentiation model is transmitted to a pain level differentiation estimation unit.

For example, a standard (general differentiation model with stand installation) as well as options can be included in a pain differentiation model generation unit. For example, the pain differentiation model generation unit can comprise option 1 (tailor-made differentiation model, where price changes depending on the extent of model creation), option 2 (creation of a facility dedicated differentiation model), option 3 (client requested setting), option 4 (model creatable by the clients themselves), option 5 (increase in the number of created differentiation models), or the like.

A preferred embodiment may comprise a function for improving a differentiation model. This function can be in a pain differentiation model generation unit, or comprised as a separate module. Such a differentiation model improving function can comprise options such as option 1 (period of 1 year, 1 to 2 times a year), option 2 (period of 1 year, once every 1 or 2 months), option 3 (extended period, once or twice a year), or option 4 (extended period+1, once every 1 or 2 months).

Data can be stored as needed. Data storage is generally equipped on the sever side (data storage unit 170000 in FIGS. 51 to 53), but data storage can be at the terminal side for not only fully equipped models but also for cloud models (not shown due to being optional). When a service is provided on the cloud, options such as standard (e.g., up to 10 Gb on the cloud), option 1 (e.g., additional 1 Tb on the cloud), option 2 (parameter is set for divided storage on the cloud), and option 3 (stored by differentiation model on the cloud) can be provided for data storage. Data is stored, and data is imported from all sold apparatuses to create big data (e.g., brainwave database 180000), and a differentiation model is continuously updated or a new model is constructed so that new differentiation model software such as "burn pain differentiation model" can be provided.

There can also be data analysis options. In this regard, a pattern classification of patients (search for a patient cluster based on a change in patters of feature or differentiation accuracy) or the like can be provided. In other words, this can be envisioned as an option for a calculation method of the pain differentiation model generation unit 160000.

(Tailor-Made Machine Learning)

In still another aspect, the present invention provides a method of improving machine learning, comprising: A) generating a determination model by machine learning; B) determining a hyperparameter in all samples by cross validation; C) generating a differentiation model by using the hyperparameter to calculate differentiation accuracy for each sample; D) grouping each sample based on the differentiation accuracy; E) determining an individual hyperparameter for each of the groups; and F) generating an individual differentiation model for each group using the individual hyperparameter and calculating differentiation accuracy of each sample to generate a differentiation maximum (MAX) model from thereamong. In this regard, it was found that hyperparameters can be optimized by grouping based on differentiation accuracy. Such improvement in accuracy is significant, which was not found in conventional processing methods.

One of the features of the present invention is that the present invention can be called a "Single-algorithm-based multi-classifier tailor-made method" for creating multiple models within a single algorithm and selecting the maximum model or combining the models with the ensemble method. It is important that this is different from a concept of using the best after using various algorithm, or in other words, using only "multi-algorithm tailor-made method". In one embodiment, it is possible to initially prepare a plurality of algorithms, and determine the algorithm with the highest accuracy with the entire model, and then transition to the tailor-made method of the invention.

In the present invention, one of the features is in performing analysis using a hyperparameter and grouping this as in F). It is notable that this enables more accurate machine learning. It is further notable that such analysis is used in determination of pain and more accurate differentiation results are exhibited.

In one embodiment, selection of the optimal hyperparameter resulting in the highest differentiation accuracy can use any means known in the art such as the LASSO function or SVM function of MATLAB. One of the features of the present invention is in first determining a hyperparameter using the entire data, rearranging individual samples based on differentiation accuracy, grouping individual samples, and recalculating a hyperparameter for each group. In other words, this has significance in terms of how detailed a hyperparameter is calculated and presenting a methodology that can be deemed as a tailor-made calculation methodology for a hyperparameter of a differentiation model. It is understood that such grouping allows individualization and enables customization.

A preferred embodiment disclosed below is a method of combining thereafter a plurality of models determined for each group to attain the highest differentiation accuracy, which can be referred to as a tailor-made combination methodology of differentiation models. Tailor-made machine learning can be further refined with two such elemental methodologies.

Differentiation models targeted by the present invention are not limited to the medical field (e.g., differentiation of pain), audio, electronic, motion pictures, transport equipment, stock trading, commercial activity (presentation of products), client analysis, shape detection, education (student training), personnel decisions (hiring judgment), politics (dispute prediction, election prediction), public transportation (congestion analysis or the like), or public order (event trouble prediction). In addition, the type of model can be of any type. LASSO, logistic, support vector, neural network, random forest, Bayes, or decision tree can be used.

In one embodiment in the present invention, the step of generating the differentiation maximum (MAX) model comprises an ensemble method and pruning thereof.

Pruning used in the present invention is a well-known concept in the field of algorithms, which is a concept that is also commonly used in machine learning. This is also a processing methodology that can be implemented in game theory or the like.

One of the features provided by the present invention is an improvement method for increasing a model one at a time and selecting a model set resulting in the highest differentiation accuracy using a majority vote on results differentiated by individual models in the ensemble method. Such a methodology was not provided by conventional art, such that the method corresponds to a significantly improved ensemble method. It should be noted that a higher differentiation accuracy is provided.

One embodiment in the present invention provides a methodology, wherein the maximum model is selected as a main model and the rest are selected as supporter models, and the supporter (support) models are added one at a time to improve differentiation accuracy. In such a case, it is possible to select the differentiation maximum (MAX) model as a main model and the rest are selected as supporter models, and the supporter models are comprehensively added one at a time to the main model to improve differentiation accuracy stepwise. This method includes a method of ranking differentiation models and including top ranking models in order of differentiation accuracy as shown in FIG. 63, and a method of comprehensively inputting all models other than the differentiation maximum (MAX) and inputting only models resulting in the highest differentiation accuracy stepwise as shown in FIG. 69.

In a preferred embodiment, the stepwise improvement of the differentiation accuracy comprises: A) selecting two model sets that improve differentiation accuracy the most by an ensemble method when selecting and adding one of N−1 supporter models to the main model as updated main models; B) selecting N−2 models resulting from taking out the updated main models from all N models as updated supporter models; and C) repeating steps A) to B) in the same manner for a model set that improves differentiation accuracy the most by an ensemble method to update updated main models and updated supporter models until there is no more updated supporter model.

In one embodiment, the present invention can further comprise dividing all the samples into a reference sample and a test sample, determining the differentiation maximum (MAX) model or an optimal differentiation model from a plurality of differentiation model sets including the maximum model as a reference differentiation model by using the reference sample, differentiating and estimating with the test sample using the reference differentiation model to test the reference differentiation model, and determining a final preferred differentiation model based on a result of the differentiating and estimating. If a differentiation maximum model of reference stimulation has a high ratio alone such as 95%, test differentiation may be performed only with a single model. If the accuracy of a differentiation maximum model is not so high, such as about 70%, and the ensemble method is used to increase accuracy, a differentiation model comprising two or more individual models can be used.

In one embodiment, the present invention can apply reference stimulation (preferably a plurality of times) to obtain brainwave data or analysis data thereof or extract a feature, and create a reference differentiation model for each individual using the tailor-made method (e.g., ensemble method) of the invention to differentiate and estimate actual pain monitoring data using a tailor-mode differentiation model.

Validation can be performed by the following procedure: individual differentiation model→reference stimulation differentiation maximum model or set→reference differentiation model→model validation using test data→determination of final model. The following is an example of the procedures thereof.

1. There are a plurality of individual differentiation models, which include the differentiation maximum mode and others.
2. only the differentiation maximum model or a model set comprising the same is selected.
3. The reference differentiation model is validated.
4. If sufficient accuracy is attained, this is deemed the "final differentiation model".

The method of the invention can validate how this is used in actual pain monitoring (e.g., Example 19). In an actual setting, reference brainwave data can be obtained by, for example, applying reference stimulation (preferably a plurality of times) before monitoring. A differentiation model suitable for unknown individual's pain sensation, i.e., tailor-made differentiation model, can be created using such reference brainwave data. This model can be used and applied to actual settings by monitoring various types of pain. The present invention also provides such a pain differentiation apparatus.

In one embodiment, to show this procedure in Examples, data in possession can be virtually divided into reference portion and online monitoring samples, a model can be created with an estimation method (e.g., estimation methods 1 to 3 in the Examples) using the reference portion, and test data can be fitted. The number of reference samples can be changed to test how many references are required (see Examples 19).

While sample data can be divided into reference and test, this is not a limiting example. In such a case, data can be handled as those virtually reproducing actual measurements.

Before starting an aspect of actual pain monitoring, reference brainwave data (sample) can be collected for application of reference stimulation and a feature can be extracted to create the optimal differentiation model using individual differentiation models. For the model determination process, a method of determining a single differentiation MAX model with maximum differentiation accuracy (differentiation maximum model), a method of further improving differentiation accuracy by combining a single differentiation MAX model (differentiation maximum model) and the rest of the models based on differentiation ranking, a method of finding the optimal combination by comprehensively combining a single differentiation MAX model that is the main model and the rest of the supporter models, or the like described herein can be used. A change in pain such as when an object actually feels pain, when pain is no longer felt, or when pain has started to alleviate can be differentiated and estimated with brainwave data and extracted feature using a differentiation model determined in this manner.

In one embodiment, the present invention applies reference stimulation a plurality of times to record brainwave data, extracts a feature, and creates a reference differentiation model for each individual using the ensemble method described above. Actual pain monitoring data is differentiated and estimated using the tailor-made differentiation model. This is the expected method of use of estimation methods 1 to 3 (see Examples 16 to 18) in actual environment.

One of the intended field of application of the machine learning is, but not limited to, differentiation of pain. Examples of other fields include the medical field, as well as audio, electronic, motion pictures, transport equipment, stock trading, commercial activity (presentation of products), client analysis, shape detection, education (student training), personnel decisions (hiring judgment), politics (dispute prediction, election prediction), public transportation (congestion analysis or the like), and public order (event trouble prediction).

In one embodiment, if the objective of the machine learning is differentiation of pain, the sample is brainwave data of a subject in response to experimental stimulation, and the differentiation model is calculated based on the brainwave data. In a preferred embodiment, the determination model is calculated based on the brainwave data, wherein the method can further comprise dividing all the samples into a reference sample and a test sample, determining the differentiation maximum (MAX) model or an optimal differentiation model from a plurality of differentiation model sets including the maximum model as a reference differentiation model by using the reference sample, differentiating and estimating with the test sample using the reference differentiation model to test the reference differentiation model, and determining a final preferred differentiation model based on a result of the differentiating and estimating. In a preferred embodiment, the earliest section of brainwave data of the sample is selected as the reference sample, and others are selected as the test sample.

Alternatively, in actual monitoring, step A) comprises providing a reference sample of a brainwave obtained by applying reference stimulation to a brain of an object, and generating the differentiation model based on the reference sample.

Thus, in one aspect, the present invention provides a method of differentiating pain, comprising: A) generating a differentiation model by machine learning; B) determining a hyperparameter in all samples by cross validation; C) generating a pain differentiation model by using the hyperparameter to calculate differentiation accuracy for each sample; D) grouping each sample based on the differentiation accuracy; E) determining an individual hyperparameter for each of the groups; and F) generating an individual pain differentiation model for each group using the individual hyperparameter and calculating differentiation accuracy of pain of each sample to generate a pain differentiation maximum (MAX) model from thereamong.

Any differentiation model can be used therein. Supervised machine learning including LASSO, logistic, support vector, neural network, random forest, Bayes, or decision tree, and unsupervised machine learning including deep learning can be used.

(Tailor-Made Machine Learning System, Program, Etc.)

In one aspect, the present invention provides a program for implementing a method of improving machine learning on a computer, the method comprising: A) generating a differentiation model by machine learning; B) determining a hyperparameter in all samples by cross validation; C) generating a differentiation model by using the hyperparameter to calculate differentiation accuracy for each sample; D) grouping each sample based on the differentiation accuracy; E) determining an individual hyperparameter for each of the groups; and F) generating an individual differentiation model for each group using the individual hyperparameter and calculating differentiation accuracy of each sample to generate a differentiation maximum (MAX) model from thereamong. In this regard, the embodiment that can be run at each step can comprise one or more appropriate combination of characteristics described in (Tailor-made machine learning).

In another aspect, the present invention provides a recording medium storing a program for implementing a method of improving machine learning on a computer, the method comprising: A) generating a differentiation model by machine learning; B) determining a hyperparameter in all samples by cross validation; C) generating a differentiation model by using the hyperparameter to calculate differentiation accuracy for each sample; D) grouping each sample based on the differentiation accuracy; E) determining an individual hyperparameter for each of the groups; and F) generating an individual differentiation model for each group using the individual hyperparameter and calculating differentiation accuracy of each sample to generate a differentiation maximum (MAX) model from thereamong. In this regard, the embodiment that can be run at each step can comprise one or more appropriate combination of characteristics described in (Tailor-made machine learning).

In still another aspect, the present invention provides a system providing the method of the invention with an individual module, i.e., a system implementing a method of improving machine learning, the system comprising: A) a differentiation model generation module for generating a differentiation model by machine learning; B) a hyperparameter determination module for determining a hyperparameter in all samples by cross validation; C) a differentiation accuracy calculation module for generating a differentiation model by using the hyperparameter to calculate differentiation accuracy for each sample; D) a grouping module for grouping each sample based on the differentiation accuracy; E) an individual hyperparameter module for determining an individual hyperparameter for each of the groups; and F) a differentiation maximum (MAX) model generation module for generating an individual differentiation model for each group using the individual hyperparameter and calculating differentiation accuracy of each sample to generate a differentiation maximum (MAX) model from thereamong. In this regard, the specific embodiment of steps that can be run in each module can comprise one or more appropriate combination of characteristics described in (Tailor-made machine learning).

In still another aspect, the present invention provides a system with the premise that a CPU performs every step for executing a method of improving machine learning, the system comprising a machine learning execution module, wherein the machine learning execution module executes a method comprising A) generating a differentiation model by machine learning; B) determining a hyperparameter in all samples by cross validation; C) generating a differentiation model by using the hyperparameter to calculate differentiation accuracy for each sample; D) grouping each sample based on the differentiation accuracy; E) determining an individual hyperparameter for each of the groups; and F) generating an individual differentiation model for each group using the individual hyperparameter and calculating differentiation accuracy of each sample to generate a differentiation maximum (MAX) model from thereamong. In this regard, the embodiment that can be run at each step can comprise one or more appropriate combination of characteristics described in (Tailor-made machine learning).

Each step is described hereinafter in more detail.

Figure 55:
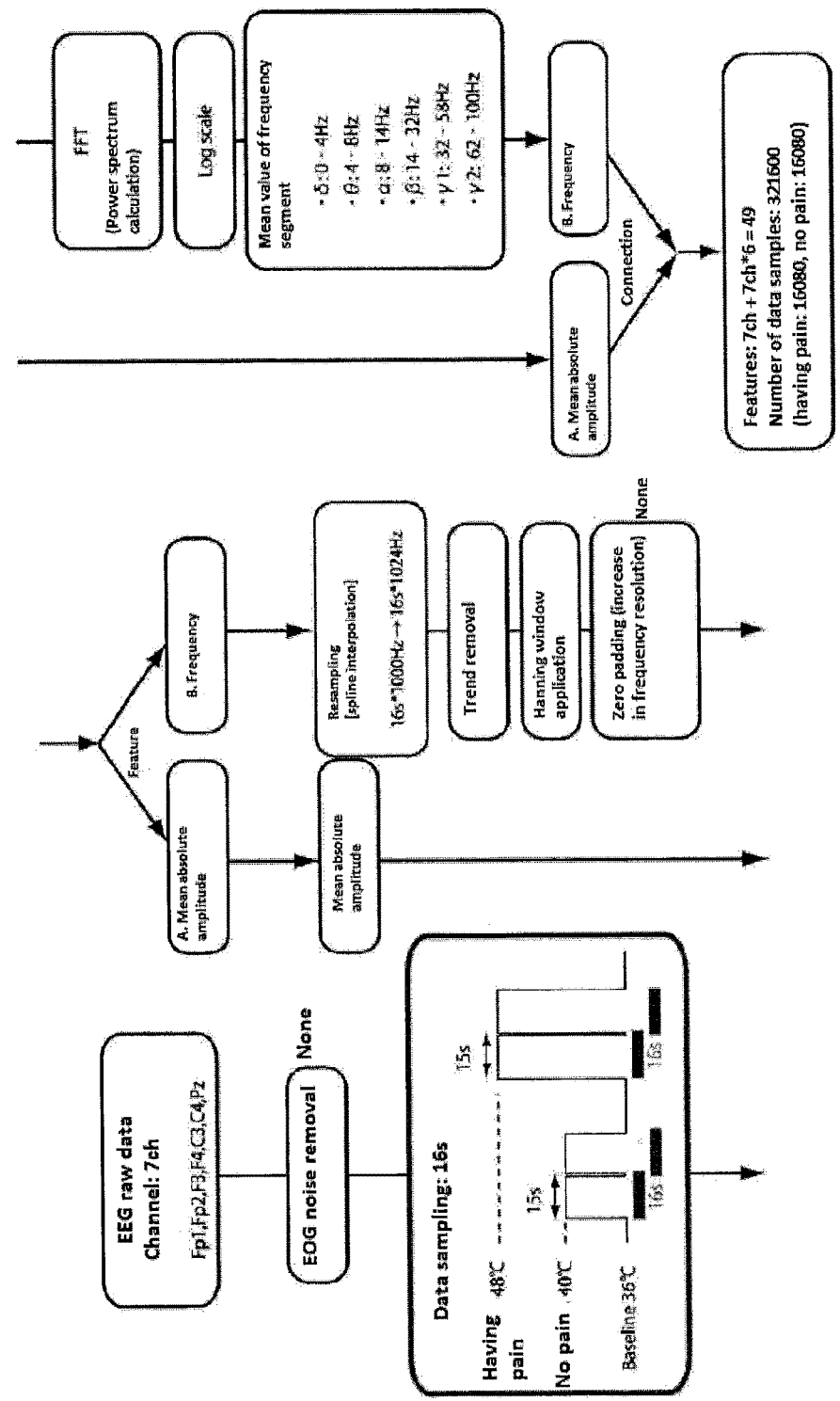
FIG. 55 shows a process of extracting a feature used in a differentiation model. The process includes 1) brainwave (EEG) data collection, 2) data sampling, 3) selection of two types of features, and 4) connection of features. A total of 49 features were obtained through these processes.

First, an embodiment of tailor-made pain differentiation estimation method 1 is described (FIG. 56)

a) First, features such as brainwave data or analysis data thereof is quantified/extracted (FIG. 55). Specifically, EEG raw data is obtained, noise is removed, and data is sampled to extract features in this step (mean absolute amplitude and frequency). When extracting a frequency feature, resampling (spline interpolation) is performed using a power of 2 to increase the calculation speed of discrete Fourier transform (1000→1024 Hz in the Example), a brainwave baseline trend is removed, and Hanning window is applied for zero padding (increase in frequency resolution). FFT (power spectrum calculation) is then performed, and the result is converted to a log scale to find the mean value in the frequency segment. Finally, the mean absolute amplitude and frequency are connected to form a feature set for differentiation. In this example, there were 49 features, 32160 data samples, 16080 having strong pain, and 16080 with no pain.

Next, the outline of tailor-made pain differentiation estimation method 1 (FIG. 56) is explained (procedures 1 to 5).

Procedure 1:

Hyperparameters in all samples (C and $\gamma$ for SVM) are determined by cross validation. Specifically, the following procedures are performed: As an example, Support Vector Machine (SVM) can be used as the machine learning method, but the example is not limiting. Other machine learning methods can also be used. SVM is a type of supervised sample classification method. SVM, as shown in the Examples, can find a hyper plane separating a vector labeled having pain and a vector labeled no pain. Other machine learning methods can also be appropriately used in accordance with the methodology of SVM. In such a case, a labeled vector known as a support vector is searched. SVM finds a support vector that would maximize the distance (margin) between the classifier, i.e., hyper plane, and support vector (margin maximization). As a classifier, linear, Gaussian, sigmoid function or the like is commonly used as a kernel function. A methodology for linear separation by mapping a vector to a feature space is used. This is known as a kernel trick, but the methodology is not limited thereto. The Examples shown use a Gaussian (radial basis function) function as the kernel.

An example of the algorithm of SVM when using a hyper plane f(x) is shown below.

Hyper plane:

$$f(x)=x'\beta+b=0$$

Optimization problem:

$$\min(\tfrac{1}{2}\beta^T\beta+C\Sigma\xi)$$

Conditions:

$$y_j f(x_j) \geq 1-\xi_j$$

$$\xi_j \geq 0$$

$\beta$: weighting coefficient
C: penalty term
$x_j$: support vector
$y_j$: category label
$\xi_j$: slack function
Kernel function
Gaussian (radial basis) function $$K(x_1,x_2)=\exp(-\gamma\|x_1-i_2\|^2)$$

$x_1$: class 1 vector
$x_2$: class 2 vector

While the following are exemplary procedures, those skilled in the art can implement the procedures by making appropriate changes based on this example. This section shows an example for scaling all data, selecting a kernel function (Gaussian function herein), and determining the optimal penalty term (C) and $\gamma$ parameter using cross validation (5-fold cross validation in this example) (regularization). These parameters are used to create a differentiation model.

Procedure 2:

A model is created from all samples to calculate differentiation accuracy at the individual level using the hyperparameter of Procedure 1 (C and γ in this example). Specifically, the following procedures are performed: the pain level is differentiated and estimated for each individual using the SVM model from all samples obtained in procedure 1 to calculate the percentage of correction answers. The differentiation accuracy of all subjects (132 in this example) is calculated thereby. Those skilled in the art can appropriately create models in accordance with this example.

Procedure 3:

A group of subjects with close differentiation accuracy is created based on an appropriate standard (e.g., differentiation accuracy ranking at the individual level). Specifically, the following procedures are performed: Differentiation accuracy of 132 subjects calculated in procedure 2 is rearranged in descending order. With 10 subjects as a set in order, 62 groups are created by shifting the set by two subjects. When features are contracted concurrently, features are ranked which can use weighting coefficients. As the weighting coefficients, the mean value of $R^2$ of each feature or the like can be used. In this regard, ranking of features is optional. Alternatively, features can be contracted at each model upon creation of a differentiation model of each group.

Procedure 4:

A hyperparameter (e.g., C and γ) for each group is determined using the same procedure as procedure 1 (SVM in this example). For example, the following procedures are specifically performed: After grouping in procedure 3, machine learning (SVM in this example) is performed for each group. In other words, a hyperparameter (C and γ) is determined by cross validation (5-fold cross validation in this example) using all samples of each group (e.g., regularization), and the parameter is tuned to be suitable for individual groups. Those skilled in the art can perform procedure 4 with appropriate modification in accordance with this example.

Procedure 5:

By using the hyperparameter found in procedure 4, a differentiation model is created from a sample of each group and differentiation accuracy at the individual level is calculated to identify the "differentiation MAX model" ("differentiation maximum model" herein). Specifically, the following procedures are performed: Individual SVM differentiation models are created with procedure 4 (e.g., total of 62 models). Differentiation accuracy results (%) for each individual (62 individual differentiation accuracy results in this example) are obtained using each model. A model outputting the highest differentiation accuracy among them is selected as the differentiation maximum (MAX) model. When contracting features in the process of identifying the differentiation maximum (MAX) model, an "economical differentiation maximum (MAX) model" can be determined if the model has the highest accuracy and fewest features, but this is not a limiting example. In such a case, differentiation/estimation models are created for 2, 3, or 4 classifications or more in accordance with conditional parameters using brainwave features for feature contracting. As one method, a plot diagram is created and fitted to an appropriate fitting function such as a sigmoid function pattern or step function to obtain weighting coefficients ($R^2$ values or regression coefficients). Fitting can be performed using any methodology that is known in the art. Specific examples of such fitting functions include, but are not limited to, those described above, as well as a Boltzmann function, double Boltzmann function, Hill function, logistic dose response, sigmoid Richards function, sigmoid Weibull function, and the like. A standard logistic function is particularly called a sigmoid function. A standard function or a modified form thereof is common, but the function is not limited thereto. If weighting coefficients ($R^2$ values or regression coefficients) for fitting to an appropriate function pattern such as the sigmoid function pattern is equal to or greater than a predetermined value, this can be optionally selected and inputted before the SVM in procedure 1, i.e., as of the differentiation model creation.

Tailor-made pain differentiation estimation method 2 is now described.

Up to procedures 1 to 5, the same procedures as tailor-made pain differentiation estimation method can be performed. Differentiation accuracy is improved thereafter by a differentiation model combination technology (ensemble method) (FIG. 63).

In procedure 6, models are rearranged in descending order by differentiation accuracy using a differentiation model set (62 sets in this example) one at a time. Specifically, the following procedures are performed: Since differentiation and estimation is performed using each model for each individual sample, the same number of differentiation accuracy results as the number of models is obtained (62 in the Example). Models are rearranged in order of higher differentiation accuracy to obtain ranking of the models, which has the differentiation maximum (MAX) model at the top.

Procedure 7: Differentiation accuracy is calculated by the "ensemble method" (see FIGS. 64 and 65) while increasing the differentiation models one at a time. The number of differentiation models with the highest differentiation accuracy is employed ("ensemble pruning") (see FIGS. 66 and 67). Specifically, the following procedures are performed: Since models with decreasing differentiation accuracy from the differentiation maximum (MAX) model are ranked in order by procedure 6, models are increased one at a time for model ensemble, and individual samples are differentiated and estimated by a majority vote on differentiation results. A differentiation model group with the highest differentiation accuracy is identified for each individual by this process (i.e., tailor-made differentiation method).

Tailor-made pain differentiation/estimation method 3 is now shown (FIG. 69; procedures 6A and 7A). This estimation method also improves differentiation accuracy by a differentiation model combination technology (ensemble method), but the model inputting method is different from procedure 2.

In this method, procedures 1 to 5 are the same as the preceding estimation methods. In other words, a single differentiation model is created by machine learning using all samples, and differentiation accuracy is calculated for each individual. Individuals are ranked and grouped by differentiation accuracy to obtain a differentiation model set. Estimation method 1 selected a model with the highest differentiation accuracy as the differentiation MAX model of an individual ("differentiation maximum model" herein). This is a tailor-made method at an early stage before employing the ensemble method. If this differentiation model has sufficiently high accuracy, this can be used as a differentiator. Estimation method 2 ranks differentiation accuracy for each individual, increases differentiation models stepwise from top models, and determines differentiation results using the ensemble method, i.e., majority vote on differentiation results. Unlike these methods, estimation method 3 is new in terms of conceptually distinguishing a differentiation model set into a "main model" and "supporter model" to perform the ensemble method. In this regard, models are rearranged in descending order by differentiation accuracy using models (e.g., 62 models) one at a time as procedure 6. Alternatively, it is sufficient to identify only the differentiation maximum (MAX) model that materializes the highest differentiation accuracy because models are comprehensively combined with the differentiation maximum (MAX) model to study the degree of improvement in differentiation accuracy by ensemble. However, the possibility of improving the overall differentiation level is higher by trying combinations from those with higher differentiation accuracy, so that models are ranked in this procedure. As procedure 7, a differentiation MAX model is selected as the "main model" and the rest of the "supporter models" are comprehensively added one at a time for processing to improve the differentiation accuracy stepwise. Such processing using main-supporter models is a novel methodology that is not used in conventional ensemble methods.

The details of the main-supporter model integrated processing is shown below (FIG. 70).

Main-Supporter Procedure 1

From all models (N models), the MAX model (differentiation maximum model) is selected as the "main model" (for example, the MAX model (differentiation maximum model) can be selected based on procedures 1 to 5 described above). Specifically, the following procedures are performed: In other words, a single differentiation model is created using all samples and differentiated for each individual to rank all subjects. Next, the subjects are grouped, and a hyperparameter (e.g., C and γ) is identified for each group to obtain an individual differentiation model set. Furthermore, an individual differentiation model set is applied to each individual to obtain a differentiation accuracy result for each individual. For example, 62 differentiation accuracy output results are obtained in the Examples, while a model with the highest differentiation accuracy among them is the differentiation maximum (MAX) model, which is referred to as the main model.

Main-Supporter Procedure 2

N−1 models excluding the main model from all models are the "supporter models". In other words, the procedure of 1 describes above identifies only one main model, so that all of the rest would be supporter models. However, if a plurality of main models have the same differentiation accuracy or the difference in accuracy is very small, the plurality of main models can be collectively the "main model set".

Main-Supporter Procedure 3

A model set with the most improved differentiation accuracy by the ensemble method when a supporter model is selected from N−1 supporter models and added to the main model is the "updated main model". As described in additional procedure 2, when m main models are initially included in the main model set, a model set with m+1 models is the updated main model (when an expression of "two models" is used, this refers to a model set with the main model and a selected supporter model).

Main-Supporter Procedure 4

N−2 models excluding the updated main models from all models are the "updated supporter models". If the initial main model consists of m models, the remaining N−(m+1) models are the updated supporter models.

Main-Supporter Procedure 5

The procedures of 3 to 4 described above are repeated in the same manner for the model set with the most improved differentiation accuracy by the ensemble method. This is repeated until the updated supporter model becomes a null set while updating the updated main model and updated supporter model.

Figure 73:
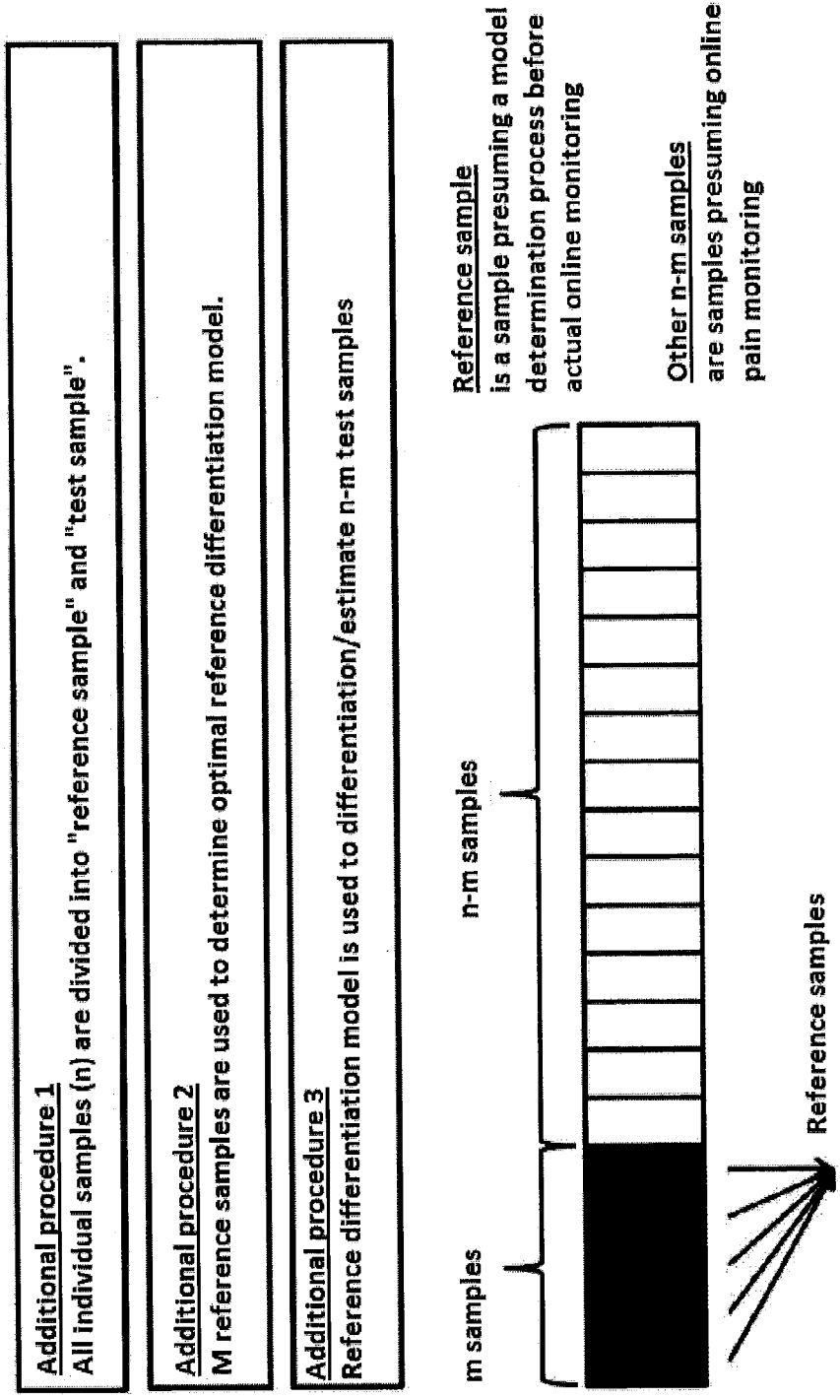
FIG. 73 is an outline of tailor-made pain differentiation estimation method 4 with calibration. While presuming actual pain monitoring, individual samples (total of n samples) are separated into references (m samples) and test (n−m samples), and a reference differentiation model is created to perform differentiation/estimation of test samples that presume online monitoring samples. The reference samples are samples presuming a model determination process before actual online monitoring, and other n−m samples are samples that presumes online pain monitoring.

Lastly, tailor-made pain differentiation/estimation method 4 is shown (FIG. 73).

A differentiation method taking into consideration actual online pain differentiation monitoring is described in this section. The procedures are the same as the preceding estimation methods (procedures 1 to 5) until the addition procedure. In other words, a single differentiation model is created by machine learning using all samples, and differentiation accuracy for each object contained in the sample is calculated. Objects are ranked by differentiation accuracy and grouped into a specific number of samples to create a differentiation model for individual groups. In an actual differentiation apparatus, grouping information and prototypes of individual differentiation models can be stored in a database or a data storage unit.

Reference Addition Procedure 1:

All individual samples (N) are separated into "reference samples" and "test samples". Such division using existing samples assumes the following aspect of actual pain monitoring. Specifically, a pain reaction characteristic of an individual is unknown when monitoring an object with some type of pain in a clinical setting. Thus, "reference stimulation" such as electrical stimulation must be applied a plurality of times to determine what pain differentiation model is optimal. Reference samples in addition procedure 1 corresponds to preparatory data before online monitoring.

Reference Addition Procedure 2:

An optimal differentiation model is determined using m reference samples by estimation 1, estimation method 2, or estimation method 3. Estimation method 1 uses a differentiation MAX model alone, and estimation methods 2 and 3 use a model set of main model+supporter models, but any of the methods can be used depending on the situation. In other words, for differentiation of m reference samples, the differentiation MAX model or a model set comprising the differentiation MAX main model with the highest differentiation accuracy is used for actual online pain monitoring.

Reference Addition Procedure 3:

The reference differentiation model determined in reference addition procedure 2 is used to study test samples. Test samples in this procedure presume features and brainwave data recorded upon actual unknown pain monitoring. In this Example, N−m samples from excluding reference samples (m samples) from all samples (N samples) are used as dummy pain monitoring samples. When the examples (total of 132) shown in the Examples were tested with 10 and 50 reference samples to test the degree at which estimation methods 1, 2, and 3 can accurately differentiate test samples (N−m samples), it was confirmed that up to 50 samples are tolerable. Meanwhile, the range of number of references that can be differentiated varies depending on various conditions such as the total number. This can be appropriately determined by those skilled in the art.

In a preferred embodiment, brainwave data is preferably collected by a simple method, which can 1) use a number of electrodes that is required for analysis, 2) avoid the scalp with hair as much as possible, and 3) record while sleeping, to carry out the invention with respect to pain. Exemplary number of electrodes used is, but not limited to, 24, but the number can be 12 to 24, 24 to 36, 6 to 12, or fewer (e.g., 3, 4, 5, or the like).

For contracting, sigmoid fitting, or a step function with stepwise inflection, a linear function with a continuous stepwise change, or the like can be used.

As a weighting coefficient, a regression coefficient, or an $R^2$ value, correlation coefficient, residual sum of squares (difference between differentiation function and feature), or the like can be used. However, it is important that pain or stress sensed by an individual can be distinguished with as much accuracy as possible for differentiation of pain, so that efficacy which is different from detection of a statistically significant difference can be required or intended.

In one embodiment when targeting pain, brainwave data or analysis data thereof can comprise, as data recording positions, frontal-parietal portions such as F3, F4, C3, C4, P3, and P4 in compliance with the international 10-20 system or expanded standard thereof, and positions on the scalp over the occipital portion as electrode positions. Alternatively, a position at a specific uniform distance (e.g., 2.5 cm or the like) can be covered. The duration of recording and analysis can be, for a short period of event related potential activity, 0 to 100, 100 to 200, 200 to 300, 300 to 400, 400 to 500, 500 to 600, 600 to 700, 700 to 800 milliseconds (ms), a shorter time segment (10 milliseconds or the like), or a longer time frame (sometimes spanning several seconds). The brainwave data or analysis data thereof comprises at least one brainwave feature selected from combinations thereof.

In still another embodiment, a brainwave feature comprises at least one selected from the group consisting of Fp1, Fp2, Fpz, F3, F4, Fz, C3, C4, Cz, P3, P4, and Pz, such as mean amplitude Fz, C3, and C4, and frequency Fz($\delta$), Fz($\beta$), Cz($\delta$), C3($\theta$), and C4($\beta$). It is preferable that the feature comprises, but not limited to, Cz (amplitude), C3($\alpha$), Cz($\beta$), Fz($\delta$), and Cz($\gamma$).

Figure 77:
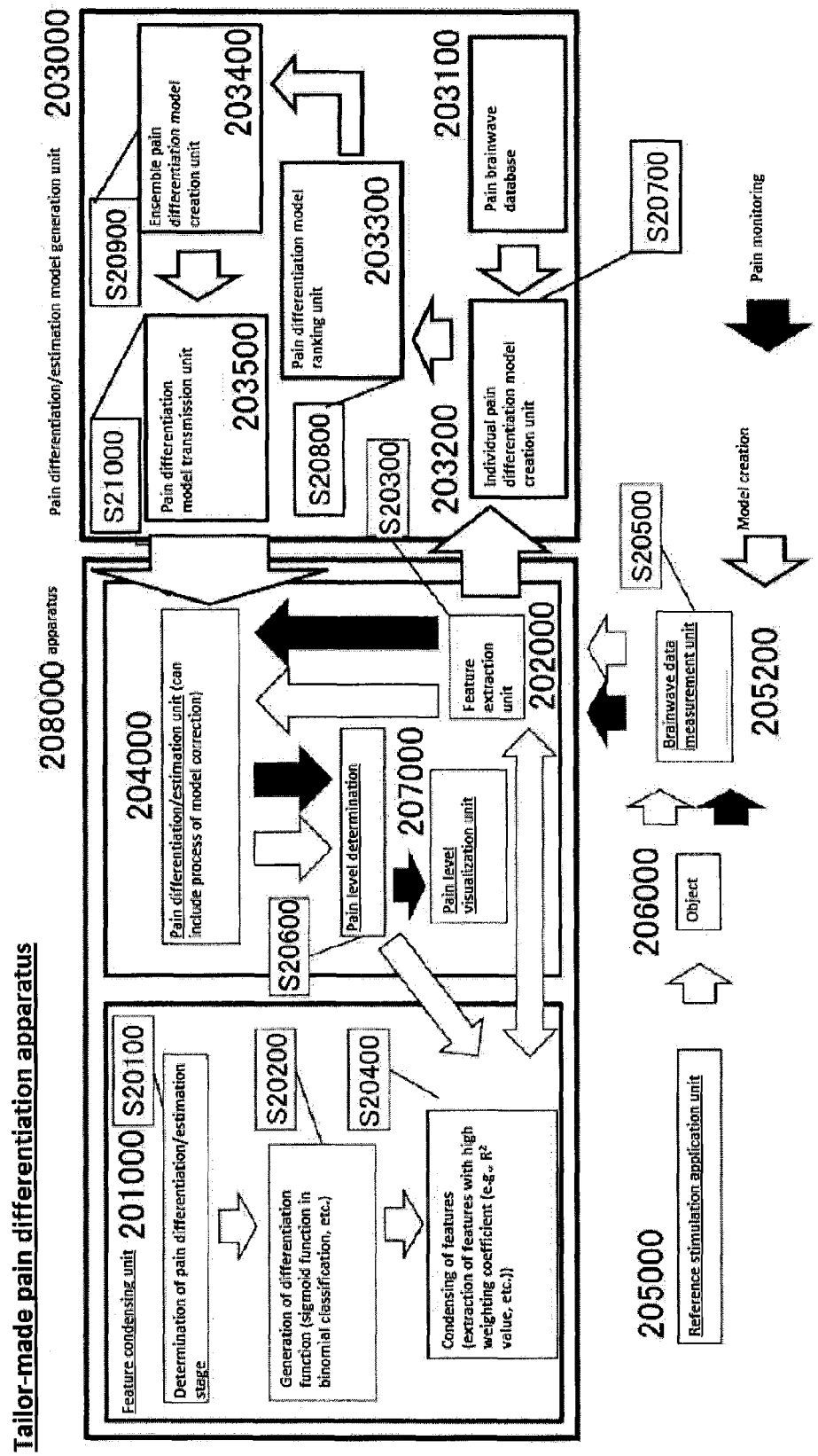
FIG. 77 is a schematic diagram of a tailor-made pain differentiation apparatus with the tailor-made differentiation model creation method using machine learning of the invention installed therein.
Figure 78:
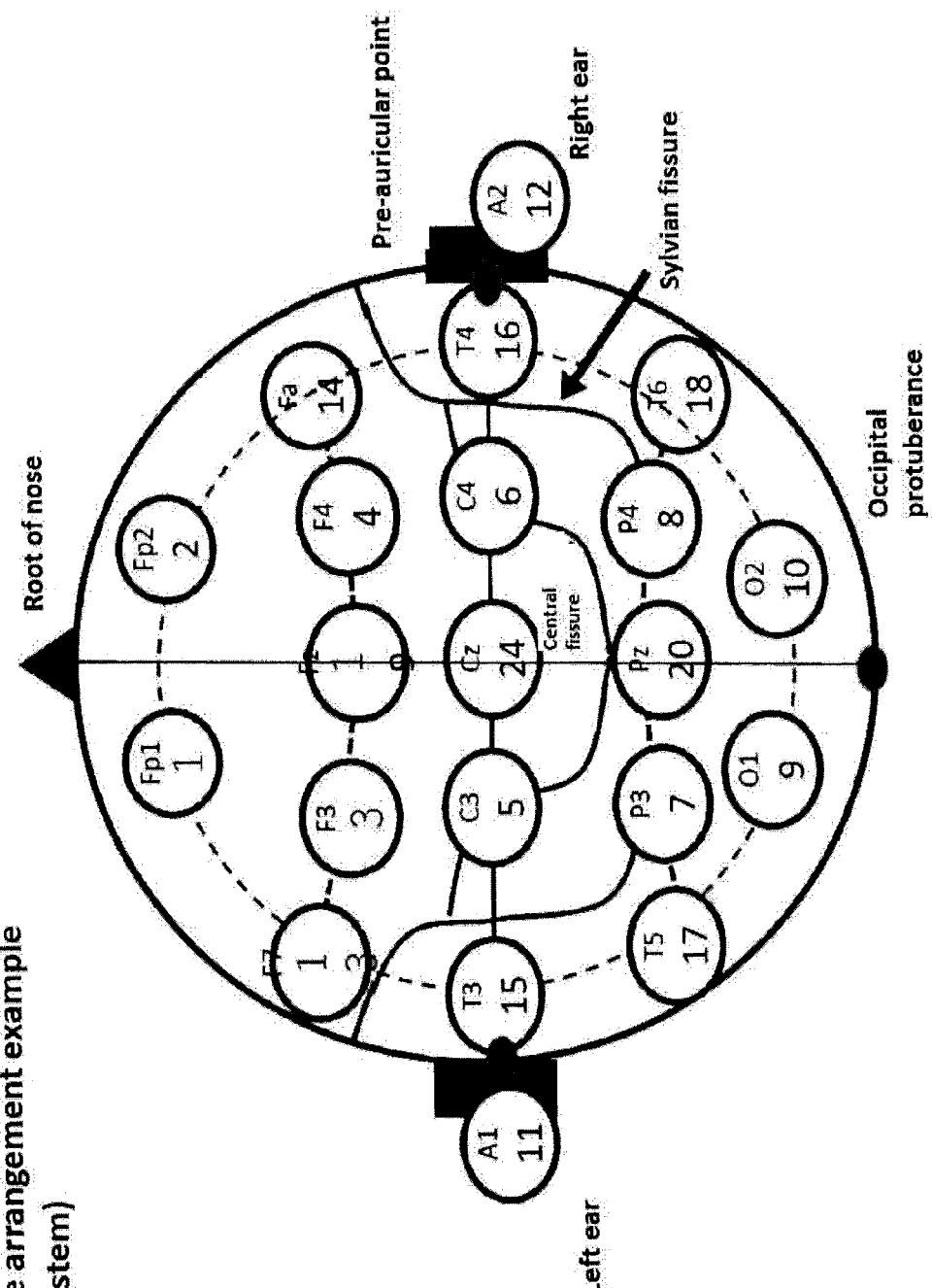
FIG. 78 is a schematic diagram viewing the head from above, showing a representative arrangement of electrodes. The boundary between the front portion and the back portion starting at the auricle is also shown.

FIG. 77 describes a schematic diagram of the apparatus of the invention (tailor-made pain differentiation apparatus) (201000 to 208000) (It should be noted that some of the configuration are optional constituents that can be omitted). In this schematic diagram, each step is described when appropriate (S20100 to S20600).

The apparatus 208000 is comprised of a feature contracting unit 201000, a feature extraction unit 202000, a pain differentiation/estimation model generation unit 203000, a pain differentiation/estimation unit (can comprise a model correction process) 204000, a reference stimulation application unit 205000, a brainwave data measurement unit 205200, and a pain level visualization unit 207000. An object is denoted as 206000. The pain differentiation/estimation model generation unit 203000 is comprised of lower level parts 203100 to 203500 in accordance with the tailor-made differentiation estimation technology of the invention. In such differentiation with a process of contracting, the number of pain differentiation/estimation stages (2 stages, 3 stages, or the like) is determined (S20100), and a differentiation function is generated (examples include sigmoid functions in binomial classification and the like; S20200). A differentiation apparatus comprises a tailor-made differentiation model creation procedure (white arrow) and actual pain level monitoring procedure (black arrow). In the model creation procedure (white arrow), a feature is obtained after reference stimulation (electrical stimulation or the like) is applied to the object 206000 from the reference stimulation application unit 205000 in accordance with the differentiation stage determined at S20100, a feature related to a pain stage is collected (S20300) and contracted (S20400). The collected feature is approximated by a differentiation function generated at S20200 and ranked in accordance with the magnitude of the obtained approximation coefficient ($R^2$ value, regression coefficient, or the like). Features are used in order from the top features. The pain level of a reference stimulation is differentiated and estimated with the pain differentiation/estimation unit 204000, and the number of features with the highest differentiation accuracy is used. This is one embodiment of the process of contracting features S20400. The contracted feature information is transmitted from the feature extraction unit 202000 to the individual pain differentiation model creation unit 203200 and stored. Further, the individual pain differentiation model creation unit 203200 collects brainwave data or analysis data thereof or feature data from the pain brainwave database (or storage unit) 203100 based on contracted feature information (quantity or the like) to create a plurality of individual differentiation models. At this time, the number of individual differentiation models is predetermined, but the number can be configured to be correctable at a later time. Such a case can be readily envisioned. The pain differentiation model ranking unit 203300 differentiates features transmitted from the feature extraction unit 202000 with an individual differentiation model to create ranking of models. The ensemble pain differentiation model creation unit 203400 determines an ensemble differentiation model resulting in the maximum differentiation accuracy by adding a supporter model to the top ranking main model. However, if the main model materializes sufficiently high differentiation accuracy alone, the main model can be used alone. The pain differentiation model transmission unit 203500 transmits the resulting ensemble differentiation model to the pain differentiation/estimation unit 204000.

In an actual pain level monitoring process that can be implemented as one embodiment (black arrow), actual pain related brainwave data is collected from the object 206000 at the brainwave data measurement unit 205200 comprising an electroencephalograph or the like (S20500). This is transmitted to the feature extraction unit 202000 and converted to a feature selected in the process of contracting amplitudes or frequencies (e.g., specific amplitude or frequency band power of specific electrodes or the like). The extracted feature is taken into the pain differentiation/estimation unit 204000 from the feature extraction unit 202000, and a pain level is determined (S20600). The result of the determination is indicated as a trend of changes or numerical value (e.g., 1 to 100) at the pain level visualization unit 207000.

The determination of the pain differentiation/estimation stages at S20100 determines the number of levels to be differentiated or estimated (e.g., 2 stages, 3 stages, or the like).

The generation of a differentiation function at S20200 creates a differentiation function used in accordance with the number of differentiation levels at S20100 (sigmoid function or step function in binomial classification or the like).

In the collection of pain stage associated features at S20300, reference stimulation (electrical stimulation or the like) is applied from the reference stimulation application unit 205000 to the object 206000 a plurality of times in accordance with the number of levels determined at S20100 to collect related brainwave features.

In contracting of a feature at S20400, a feature obtained at S20300 is approximated with a differentiation function, features with a high approximation index (e.g., $R^2$ value or the like) are ranked, and features are inputted into the pain differentiation/estimation unit 204000 in order from top ranking features to differentiate and estimate a level of reference stimulation. A model with a number of features with the highest differentiation accuracy is used for actual pain differentiation/estimation.

For collection of pain related brainwave data at S20500, actual pain related brainwave data subjected to monitoring of pain is collected after completion of the contracting process at the feature contracting unit 201000. This step is data collection in an actual pain monitoring process.

For pain level determination at S20600, actual pain related data obtained at S20500 is processed at the feature extraction unit 202000 to obtain a feature set and then differentiated and estimated at the pain differentiation/estimation unit 204000. A pain level is quantified from an estimated value, and a pain level is determined and made visible at the pain level visualization unit 207000.

In the processing procedure at the individual differentiation model creation unit in S20700, an individual differentiation model is created based on contracted feature information transmitted from the feature extraction unit 202000 and sample from the pain brainwave database 203100.

In the processing procedure at the pain differentiation model ranking unit 203300 in S20800, models are ranked based on differentiation accuracy of reference stimulation by individual differentiation models.

In the processing procedure at the ensemble pain differentiation model creation unit 203400 at S20900, models are divided into the top ranking main model with maximum (MAX) differentiation and other differentiation models to create a differentiation model set resulting in maximum differentiation accuracy, i.e., ensemble differentiation model, using the ensemble method. If the main model with maximum (MAX) differentiation materializes sufficient differentiation accuracy, the model can be used alone. The ensemble method can be either estimation method 2 or 3.

The processing procedure at the pain differentiation model transmission unit 203500 at S21000 transmits the determined differentiation model to the pain differentiation/estimation unit 204000.

The apparatus 208000 is configured to comprise or to be connected to an electroencephalograph that is or can be connected to the object (206000), so that brainwave data synchronized with stimulation emitted from the reference stimulation application unit 205000 to the object (206000) is obtained at the brainwave data measurement unit 205200. This is a summary of the apparatus 208000.

The apparatus 208000 can comprise a brainwave measurement unit, which internally comprises or externally connects to a brainwave recording sensor and optionally a brainwave amplification unit, and processes signals of a pain related brainwave and differentiates/estimates pain in the apparatus 208000.

In the apparatus 208000, collected brainwave signals are processed to extract a brainwave feature at the feature extraction unit 202000. Upon extraction, a feature contracted in advance at the feature contracting unit 201000 is selected. Further, pain is (optionally) made visible at the pain level visualization unit 207000. The apparatus internally or externally comprises the reference stimulation application unit 205000, which applies a plurality of reference stimulations such as electrical stimulations in accordance with the pain level determined at S20100 in order to contract features that are effective for monitoring pain of the object 206000. Brainwave data related thereto is recorded at the brainwave data measurement unit 205200, the associated brainwave features are obtained at the feature extraction unit 202000, a pain level of reference stimulation is differentiated and estimated from the features at the pain differentiation/estimation unit 204000, and the features are contracted S20400 from the result thereof. The reference stimulation application unit 205000 also transmits pain stimulation information (stimulation type, environmental information, or the like) for differentiating an actual unknown pain level and creating a differentiator. The reference stimulation application unit 205000 optionally comprises a stimulation information visualization unit in addition to the reference stimulation application unit 205000 and may display information such as an image or number associated with the stimulation or environment. The apparatus 208000 can also internally or externally comprise the pain differentiation/estimation model generation unit 203000 for generating a determination value or differentiator.

The apparatus 208000 externally or internally comprise the pain differentiation/estimation model generation unit 203000 for creating a tailor-made differentiation model, which consists of the following lower level modules. A database (or storage unit) comprises sufficient sample data and feature data upon delivery of the initial model of apparatus, and samples are group by default for creating tailor-made model because a plurality of individual models are required for the ensemble method. At the individual pain differentiation model creation unit 203200, individual differentiation models are created based on contracted feature information transmitted from the feature extraction unit 202000. For example, even if 200 features are stored in the pain brainwave database 203100, if the number of contracted features is 10, the 10 features are used by the individual pain differentiation model creation unit 203200 to create individual pain differentiation models. At the pain differentiation model ranking unit 203300, the created individual models are used one at a time to differentiate and estimate reference stimulation transmitted from the feature extraction unit 202000, and individual models are ranked based on the differentiation accuracy. The ensemble pain differentiation model creation unit 203400 separates models into the main model with maximum (MAX) differentiation or main model set and other supporter model set based on ranking information. The supporter models are combined stepwise with the main model, and pain level of reference stimulation is differentiated and estimated by majority vote on differentiation results. The combining and majority vote are the so-called ensemble method. The ensemble model with the highest differentiation accuracy is the differentiation model used in actual pain monitoring. If sufficient differentiation accuracy can be materialized with the main model alone, the main model can be used alone. In such a case, this is called a single ensemble differentiation model. The pain differentiation model transmission unit 203500 transmits the final ensemble differentiation model to the pain differentiation/estimation unit 204000.

In this manner, the apparatus 208000 comprises the brainwave data measurement unit 205200 and the pain differentiation/estimation unit 204000 and optionally the reference stimulation application unit 205000 and the pain differentiation/estimation model generation unit 203000. The apparatus 208000 is materialized, for example, by a computer comprising a processor and a memory. In such a case, the apparatus 208000 makes the processor function as the feature contracting unit 201000, feature extraction unit 202000, pain differentiation/estimation model generation unit 203000, pain differentiation/estimation unit 204000, or the like as needed when a program stored in the memory is implemented by the processor. Stimulation or environmental information is also made visible as needed. The apparatus 208000 of the invention can be materialized, for example, by a dedicated electronic circuit. A dedicated electronic circuit can be a single integrated circuit or a plurality of electrical circuits. The brainwave data obtaining unit and pleasant/unpleasant determination value generation unit can have the same configuration as the pleasant/unpleasant determination apparatus.

The feature extraction unit 202000 can also obtain a plurality of brainwave data by measuring a brainwave a plurality of times from an object being estimated via an electroencephalograph (included in the brainwave data measurement unit 205200). An object is an organism in which a change in a brainwave is induced due to stimulation or environment, which does not need to be limited to humans.

The pain differentiation/estimation unit 204000 differentiates/estimates the degree of unpleasantness using a determination value, and also generates a differentiator of determination value if not generated in advance externally or internally. The part generating a differentiator or determination value can be comprised external or internal to the apparatus 208000 as the pain differentiation/estimation unit 204000. A differentiation value used for differentiation/estimation of pain is for estimating or classifying the degree of unpleasantness from amplitudes of a plurality of brainwave data. In other words, the pain differentiation/estimation unit 204000 or the pain differentiation/estimation model generation unit 203000 can generate a determination value or determination model for estimating or classifying the degree of unpleasantness of an object from brainwave data.

A brainwave recording sensor contained in the brainwave data measurement unit 205200 measures electrical activity generated inside the brain of an object being estimated with an electrode on the scalp. The brainwave recording sensor also outputs the result of measurement, i.e., brainwave data. Brainwave data can be amplified as needed.

Other Embodiments

The differentiation apparatus with a process of contracting features according to one or more embodiments of the invention has been described based on the embodiments, but the present invention is not limited to such embodiments. Various modifications applied to the present embodiments and embodiments constructed by combining constituent elements in different embodiments that are conceivable to those skilled in the art are also encompassed within the scope of one or more embodiments of the invention as long as such embodiments do not deviate from the intent of the inventions.

For example, a peak to peak value can be used as the amplitude value of brainwave data in each of the embodiments described above, but the amplitude value is not limited thereto. For example, a simple peak value can be used as the amplitude value.

In the embodiment described above, the range of the value of magnitude of the degree of unpleasantness is envisioned to be set so that the value of Pmax, which is the magnitude of the degree of unpleasantness corresponding to the upper limit value Amax of a feature such as brainwave amplitude or a combination thereof, would be 1, or the value of Pmin, which is the magnitude of pain corresponding to the lower limit value Amin of the feature or combination thereof, would be 0, but the range of values is not limited thereto. For example, the magnitude of pain can be represented by 0 to 100. In such a case, the pain differentiation/estimation unit 204000 can estimate the value Px of magnitude of pain, when shown by the pain level visualization unit 207000, by the following equation.

$$Px = P\max \times (Ax - A\min)/(A\max - A\min)$$

Curve fitting including sigmoid fitting was described above as an example of generating a pleasant/unpleasant determination value by analyzing a plurality of brainwave data, but this is not a limiting example. A predetermined value can also be used as the upper limit value of a brainwave amplitude. The predetermined value (absolute value) is for example 50 μV to 100 μV, which can be experimentally or empirically determined. In such normal analysis, data from about plus or minus 50 μV to 100 μV is eliminated as an artifact removal method. Such artifact removal can also be performed in the present invention as needed.

Any type of stimulation can be applied as stimulation applied to the object 206000 by the reference stimulation application unit 205000 (see FIG. 77) as long as the magnitude of the degree of unpleasantness sensed by the object 206000 changes in accordance with the type of stimulation or application environment.

Some or all of the constituent elements of the apparatus of the invention in each of the embodiments described above can be comprised of a single system LSI (Large Scale Integration). For example, as shown in FIG. 77, the apparatus 208000 can be comprised of the feature contracting unit 201000, pain differentiation/estimation model generation unit 203000, pain differentiation/estimation unit 204000, and pain level visualization unit 207000, as well as a system LSI having the feature extraction unit 202000, the pain differentiation/estimation model generation unit 203000, and the reference stimulation application unit 205000.

System LSI is ultra-multifunctional LSI manufactured by integrating a plurality of constituents on a single chip, or specifically a computer system comprised of a microprocessor, ROM (Read Only Memory), RAM (Random Access Memory) and the like. A computer program is stored in a ROM. The system LSI accomplishes its function by the microprocessor operating in accordance with the computer program.

The term system LSI is used herein, but the term IC, LSI, super LSI, and ultra LSI can also be used depending on the difference in the degree of integration. The methodology for forming an integrated circuit is not limited to LSI, but can be materialized with a dedicated circuit or universal processor. After the manufacture of LSI, a programmable FPGA (Field Programmable Gate Array) or reconfigurable processor which allows reconfiguration of connection or setting of circuit cells inside the LSI can be utilized.

If a technology of integrated circuits that replaces LSI by advances in semiconductor technologies or other derivative technologies becomes available, functional blocks can obviously be integrated using such technologies. Application of biotechnology or the like is also a possibility.

One embodiment of the invention can be not only such a pain differentiation/estimation model generation, sustained pain differentiation/estimation unit, but also a pain classifier generation, pain differentiation/classification method using characteristic constituent units contained in a pain estimation apparatus as steps. Further, one embodiment of the invention can be a computer program for implementing each characteristic step in feature contracting, feature extraction, pain differentiation/estimation model generation, and pain differentiation/estimation on a computer. One embodiment of the invention can also be a computer readable non-transient recording medium on which such a computer program is recorded.

In each of the embodiments described above, each constituent element can be materialized by being configured with a dedicated hardware or by implementing software program that is suited to each constituent element. Each constituent element can be materialized by a program implementation unit such as a CPU or a processor reading out and implementing a software program recorded on a recording medium such as a hard disk or semiconductor memory. In this regard, software materializing the pain estimation apparatus of each of the embodiments described above or the like can be a program such as those described below.

(Priority Feature)

In still another aspect, the present invention provides a method of determining pain using one or more features of a brainwave.

Any feature of a brainwave can be used in the present invention. Typically, the feature comprises, for example, at least one selected from an amplitude, interrelation of brainwave features, frequency power, and a complexity index. In one embodiment the amplitude comprises an amplitude distribution property value such as a mean amplitude (e.g., absolute mean amplitude, relative mean amplitude, or the like), an amplitude median value, an amplitude mode, an amplitude maximum value, a peak amplitude, or a quartile amplitude, the interrelation of brainwave features comprises potential correlation (e.g., frontal-parietal potential correlation (a correlation coefficient, a partial correlation coefficient, Connectivity, Causality, and subtypes thereof)) or phase synchronization between electrodes (e.g., coherence, Phase locking value, and subtypes thereof), the frequency power comprises a spectral density, a power spectrum, or a subtype thereof, and the complexity index comprises at least one selected from entropy (e.g., multiscale entropy (MSE), sample entropy, self entropy, mean entropy, joint entropy, relative entropy, conditional entropy, and the like), and a biological potential feature manifested in association with an event in conjunction with occurrence of pain (eye movement potential reflecting eye movement such as a blink reflex or the like).

In one embodiment, the method of determining pain of the invention comprises creating a determination model using the features.

(Complexity Index)

In still another embodiment, the present invention provides a method of differentiating or determining pain using a complexity index.

In one embodiment, a value based on entropy can be used as an exemplary "complexity index" that can be used in the present invention. Examples of a method of calculating a value based on entropy include, but are not limited to, multiscale entropy (MSE), sample entropy, self entropy, mean entropy, joint entropy, relative entropy, conditional entropy, Shannon entropy, and the like. There are many other types of entropy. It is understood that any of them can be used. For example, diverse entropy described above falls under such entropy, which can be used.

In a specific example, multiscale method makes time series data coarse and grainy to make a plurality of divided time series data (coarse graining) and calculates the sample entropy thereof. The technology of coarse graining time series can be advantageous for extracting local activity properties.

Multiscale method has many known methods for calculating entropy of input data series and derivative data series. Examples thereof include normal entropy, Kolmogorov-Sinai (KS) entropy, Eckmann-Ruelle (ER) entropy, Fourier entropy, Wavelet entropy, Renyi entropy, Lyapunov spectrum, Hausdorff dimension, correlation dimension, and the like. See Pincus, 1991, Approximate entropy as a measure of system complexity, Proc. Natl. Acad. Sci. USA 88: 2297-2301.

Another preferred entropy calculation method is "sample entropy ($S_E$)" which is a method incorporated into MSE in the Examples herein. Sample entropy is a method of correcting a certain bias (due to including self-matches) that is present in approximate entropy (see Richman et al, 2000, Am. J. Physiol. Heart Circ. Physiol. 278: H2039-H2049). This entropy is expressed by calculating the percentage of number of points within the range of r % of the standard deviation of data, which is the similarity threshold value of activity, in specific time point frames m and m+1, and finding the negative natural logarithm of the ratio of percentages for both time frames (m+1/m). The calculation equation is the following.

$$S_E(m,r,N) = -\ln(A(k)/B(k-1))$$

m: number of distance points
n: number of data points
A: percentage of points within similarity threshold value (SD×r) of m+1 point time frame
B: percentage of points within similarity threshold value (SD×r) of m point time frame
ln: natural logarithm Preferred and commonly used parameters are the following. Tolerance r is desirably set to about 20 or 15% of standard deviation of the input data series, and the length (distance between points) m is set to 2 (Busa & Emmerik (2016). Multiscale entropy: A tool for understanding the complexity of postural control. Journal of Sport and Health Science 5:44-51).

As the analysis method thereof, see for example Manolakis D. G et al., 2005, Artech House Signal Processing Library and David R. Brillinger Time Series Data Analysis and Theory 2001 as well as Press et al, Numerical Recipes in C 1992 Cambridge Press.

In this manner, many types of entropy are known. Any of the entropy methodologies can be used in the analysis of pain of the invention.

As used herein, the complexity index used can be, but not limited to, at least one selected from the group consisting of electrode Fp1, electrode Fp2, electrode F3, electrode F4, electrode C3, electrode C4, and electrode Pz.

In another aspect, the present invention provides a method of differentiating pain of an object, comprising differentiating pain of an object using a model for differentiating pain of an object, comprising a feature in at least two electrodes comprising at least one electrode at a front portion of a head.

A potential amplitude and primary processed feature (absolute value or arithmetic/geometric mean) are essential for extraction of a derivative feature. The frequency, amount of information (complexity index), wavelet, and interrelation between features (correlation, phase synchronization, coherence) are derived therefrom. This is referred to as the "mother feature". A feature that is adaptively alternated depending on the situation by the feature contracting process is conceptually essential and is referred to as the "alternative integrated EEG feature". This feature set is extracted by various signal processing methods from limited electrodes (Fp1 or Fp2 at the front portion described above), and adaptively alternated depending on the monitoring environment or individual difference by the contracting process and integrally contributes to a pain differentiation model via the linear regression model in this Example. Due to such a characteristic, the present invention achieves an effect of being able to cover not only the pattern of "increase in pain→increase in EEG feature", but also the pattern of "increase in pain→decrease in EEG feature" by efficiently applying interrelation of brainwave features (phase synchronization, coherence, connectivity, or causality) for differentiating pain. The ability to cover phenomena where pain cannot be comprehensively differentiated with a single feature is a worthy discovery. The feature known as the "integrated EEG feature" of the invention attains such an effect. Those skilled in the art can adaptively implement the feature as appropriate depending on the situation in the contraction process by referring to the descriptions herein.

In a preferred embodiment, a method for differentiating pain of an object, comprising differentiating pain of an object using a model for differentiating pain of an object, comprising a feature in at least two electrodes at Fz or Fpz or the vicinity thereof is provided. It should be noted that specific information of electrodes is not required in contracted learning of the invention. Since a procedure for creating a differentiation model is important, the type of feature that is inputted is considered secondary information.

In one embodiment, the vicinity comprises at least one of F3, F4, Fp1, and Fp2. The property of a temporal change in the frequency feature (β band) exhibiting the property of delayed pain sensation of C fiber is illustrated (displayed by temporal frequency analysis). In particular, the frequency power is increased compared to other levels with a delay of 5 seconds after applying stimulation of level 6 (see FIG. 25).

The present invention provides model formation with low calculation cost. In addition, it was found that a feature that was not considered effectively usable for conventional differentiation of pain can be unexpectedly used for differentiation of pain. Due to the nature of brainwaves, potential activity is conducted in the brain in a wavelike manner and further attenuated at the skull. Thus, if the amplitude of Fz is important, the amplitude of electrodes in the vicinity such as Fpz or FCz can be a substitute. Since existing monitoring apparatuses are not worn on the scalp with hair, it was common to attach two electrodes (Fp1 and Fp2) for recording brainwaves around the forehead. The present invention has shown that "two electrodes" are the most effective in the process of contracting features, and Fz and Fpz or the vicinity thereof due to the possibility of propagation/diffusion of potential can also be effective (see FIGS. 25 to 30). A result of "two electrodes" and "vicinity of the forehead" was obtained from data analysis for determining the performance of an apparatus, i.e., differentiation accuracy. Since it is reported that the frequency power in the γ band of the front portion of the prefrontal portion can be associated with pain (Schulz et al., (2015). Prefrontal Gamma Oscillations Encode Tonic Pain in Humans. Cerebral Cortex 25: 4407-4414), the pain analysis method using Fz or Fpz or the vicinity thereof as the feature of the invention should be recognized as a new differentiation means.

In a preferred embodiment, the complexity index used in the present invention can be multiscale entropy. In a specific embodiment, multiscale entropy (MSE) can be, but not limited to, entropy at 7 electrodes (Fp1, Fp2, F3, F4, C3, C4, and Pz).

In one embodiment, the method of the invention comprises generating a determination model by machine learning using the complexity feature.

In one embodiment, the present invention provides a method of generating a model for determining pain of an object, comprising: a) obtaining complexity index of brainwave features from an object; b) contracting the complexity index with respect to the pain after determining a feature coefficient associated with the pain; c) creating a differentiation and analysis model by machine learning and validation based on each feature after the contracting or a combination thereof; and d) determining a differentiation and analysis model that attains a given accuracy.

In another embodiment, the present invention provides a method of differentiating pain of an object, comprising: a) obtaining a complexity index from a reference object; b) contracting the complexity index with respect to the pain after determining a feature coefficient for the pain; c) creating a differentiation and analysis model by machine learning and validation based on each feature coefficient after the contracting or a combination thereof; d) determining a differentiation and analysis model that attains a given accuracy; e) obtaining a complexity index from a test object; and f) differentiating pain by fitting the complexity index of the test object to the model.

In still another embodiment, the present invention provides a method of differentiating pain of an object, comprising: e) obtaining a complexity index from a test object; and f) differentiating pain by fitting the complexity index of the test object to the model; wherein the model is generated by: a) obtaining a complexity index from a reference object; b) contracting the complexity index with respect to the pain after determining a feature coefficient for the pain; c) creating a differentiation and analysis model by machine learning and validation based on each feature coefficient after the contracting or a combination thereof; and d) determining a differentiation and analysis model that attains a given accuracy.

In still another embodiment, the present invention provides a program for implementing the method of generating a model for differentiating pain of an object or method of differentiating pain of an object of the invention on a computer, and a recording medium storing the same, and an apparatus or system comprising the same.

(Brainwave Feature Correlation)

In another aspect, the present invention provides a method of differentiating or determining pain using brainwave feature correlation. Examples of brainwave features targeted for correlation include, but are not limited to, raw brainwave data and analysis data thereof (also referred to as processed feature) such as potential, frequency power, amplitude (e.g., mean amplitude, complexity index (entropy or the like)) and the like. It was found that any of them can be used as an indicator of functional connectivity by studying the correlation between electrodes. A more desirable method estimates the intracranial source from scalp data and studying the correlation between sites. If recording electrodes are limited, it is inferred from the correlation between electrodes described above. While "brainwave feature correlation" is also referred to as "brainwave relation feature", they have the same meaning. Examples of features that can be used for brainwave feature correlation or the like include, but are not limited to, "potential correlation", "phase synchronization (phase locking value)" and the like. Coherence and the like can also be used.

It was found in the present invention that correlation of processed features such as frequencies and entropy can also be used, besides brainwave potential correlation, in differentiating pain. Since they can be used as an indicator of function connectivity by observing correlation between electrodes, "brainwave feature correlation" itself can be used more broadly in differentiating pain.

As correlation, "potential correlation", "phase synchronization (phase locking value)" or the like can be preferably used in the Examples, but coherence that has been used conventionally or the like can also be used.

In one embodiment, the brainwave feature used in the present invention can be a plurality of brainwave features from the same electrode or brainwave features from different electrodes when calculating correlation. Thus, the brainwave feature correlation used in the present invention is correlation between brainwave features at the same or different electrodes. When brainwave features at the same electrode are used, features can be from the same category (e.g., frequency power, mean amplitude, complexity index, or the like) of features from different categories. When using brainwave features at different electrodes, features can be from the same category (e.g., frequency power, mean amplitude, complexity index, or the like) of features from different categories. Brainwave features that can be used may be simply the extracted raw brainwave data itself or processed data thereof. Examples of brainwave features that can be used include, but are not limited to, potential, frequency power, mean amplitude, complexity index (e.g., MSE), and the like. Examples of correlation include, but are not limited to, potential frequency and phase synchronization (phase locking value). Coherence can also be used. Coherence and phase synchronization (phase locking value) are phase synchronicity of the same frequency or different frequencies between or in electrodes, and they can be used in the same manner. Coherence is a phase synchronization indicator that is calculated based on the premise of signals being stable (overall activity property is also consistently materialized locally) and linear. However, prior art is not used after verifying the premises in many cases. Meanwhile, phase synchronization (phase locking value (PLV)) can detect phase synchronization properties more strongly, with no premise presumed by coherence. Thus, in one embodiment herein, phase synchronization (PLV) can be more preferable than coherence. Alternatively, coherence and PLV can both be used, where they can be used as a multiple choice system that uses one that better approximates a binomial classification pattern of sigmoid or step function or uses both alternatingly (Coh×PLV).

Figure 91:
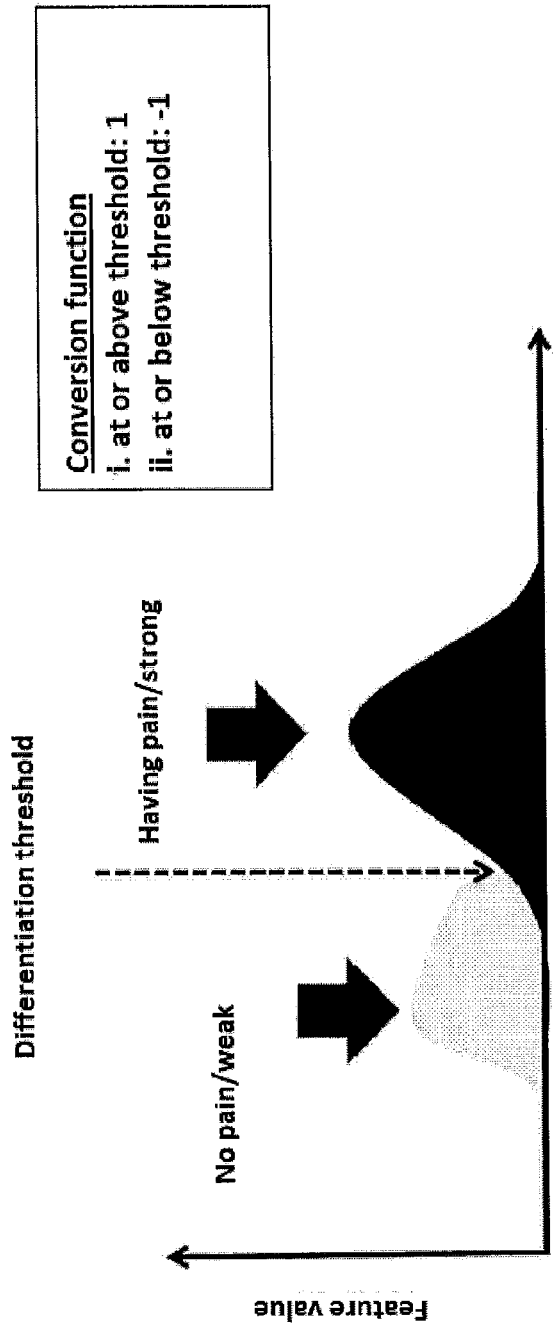
FIG. 91 is another embodiment of "discrete feature" comprising the sigmoidal feature shown in FIG. 90. Prior to pain monitoring, pain test stimulation is applied multiple times to an object to find the distribution property of features for no pain and having pain.

A feature exhibiting a binomial classification pattern (e.g., sigmoidal feature) is a form of "discrete feature", i.e., feature exhibiting a binomial distribution property. Such a double-peak distribution is also observed in pain estimation values (see FIG. 29), so that this is involved in the principal mechanism of pain differentiation. In actual pain monitoring, a distribution property of features for no pain and having pain can be studied by applying a plurality of pain test stimulations to an object. FIG. 91 shows a schematic diagram from function or curve fitting to plotting of a histogram of a feature. The numerical value where distributions of samples for no pain and having pain intersect is used as a "differentiation threshold value". Samples less than the threshold value are converted to a category scale of "−1" and samples that are greater than the threshold value are converted to a category scale of "1" using this threshold value for each feature. The converted samples can be inputted into a differentiation model. Poincare distribution or the like can also be used as the distribution for determining such a threshold value.

In various embodiments, the present invention is intended to be directed to broadly defined "interrelation" including synchronicity and narrowly defined relation expressed by a correlation coefficient (r or ρ). In this regard, correlation can include various embodiments such as synchronicity, connectivity, unrelatedness, delay, positive/negative, similarity, and match. Examples thereof include temporal correlation, spatial correlation, spatiotemporal synchronicity, special relationship or connectivity, unrelatedness or uncorrelatedness, delay or breakdown in temporal correlation, positive/negative or correlated property, similarity or level of correlation coefficient, and match or complete correlation. It can be understood that synchronicity is temporal correlation, connectivity is spatial (e.g., parts of brain) relationship, unrelatedness is uncorrelated, delay is breakdown in temporal correlation, positive/negative is correlated property, similarity is high correlation coefficient, and match is complete correlation.

In one embodiment, the brainwave feature correlation used in the present invention is correlation of brainwave features between different electrodes. It was not conventionally known that correlation of brainwave features between different electrodes is useful for differentiation or determination of pain. The frontal-occipital potential correlation is between electrodes. In addition for correlation of frequency power, correlation between different frequencies in the same electrodes can be the feature correlation.

It has been elucidated that anesthesia and pain can be distinguished by observing the correlation between different electrodes in the present invention. In this regard, it is generally understood that functional connectivity decreases when consciousness decreases due to the effect of anesthesia. Meanwhile, as demonstrated in the present invention, it was found that the frontal-parietal potential correlation decreases when pain at the highest level of Level 6 (50° C.) exemplified in the Examples becomes unbearable. This is understood to explain functional connectivity. It was found that activity correlation breaks down with a decrease in consciousness while activity correlation breaks down when pain is strong, which was unexpected. It can be understood as a result of further study thereon that activity is fragmented from a decrease in consciousness due to anesthesia: decrease in overall cortex activity, and consciousness is extremely focused on pain if pain is excessive, resulting in fragmentation due to excessive local increase in the intensity of activity of the front portion of the prefrontal portion. In this manner, this can be interpreted as break down in correlation due to "Hypo-activity" for anesthesia and "Hyper-activity" for excessive pain. The differentiation of the invention can distinguish such a difference between hypo and hyper. For example, functional connectivity breaks down and correlation decreases due to anesthesia, so that it is inconsistent to predict that a strong pain level similarly results in decreased correlation. Thus, the findings in the present invention would not have been readily expected. In other words, increased pain generally elicits attention so that functional connectivity between sites should rather be understood to increase. Despite of the above, a decrease in frontal-parietal potential correlation when pain is excessive in the present invention is different from intuition. In this regard, the present invention is interpreted so that a "similar" correlation decrease can be understood with vectors in different directions based on the concept of hyper and hypo.

In one embodiment, if correlation of brainwave features at two or more different electrodes is used, the different electrodes preferably have a relationship of being positioned relatively in front and back of a head. Pain can be more effectively differentiated by observing the interrelation of brainwave features with such a positional relationship. The relative back and front relationship can be determined by the relationship that is generally understood in the art. When an absolute positional relationship is to be identified, a line connecting ear lobes can be used for the determination.

In one embodiment, at least one of the different electrodes is at a front portion of a head. In another embodiment, at least one of the different electrodes is at a back portion of a head. In still another embodiment, at least one of the different electrodes is at a front portion of a head, and another electrode is at a back portion of the head. The "front portion" of the head refers to an area in front of a line connecting the left and right ear lobes, and "back portion" of the head refers to an area behind a line connecting the left and right ear lobes. Electrodes at the center portion on the scalp with a name of C or T alone can be included in either or both the front and back portions. In a preferred embodiment, electrodes at the center portion on the scalp on a line connecting earlobes with a name of C or T alone are excluded, but if the electrode in the center portion is relatively behind the electrode in the front portion, or relatively in front of the electrode in the back portion, the electrodes can be used for extraction of a correlation feature. This is not a limiting example.

In one preferred embodiment, the correlation used in the present invention comprises correlation between an electrode in a front portion of a head and an electrode in a back portion of the head. In another preferred embodiment, the correlation used in the present invention comprises correlation between an electrode in a frontal portion and an electrode in a parietal portion.

In one specific embodiment, the brainwave features used in correlation used in the present invention comprise at least one feature at the frontal portion such as the frontal pole Fp1, frontal pole Fp2, frontal portion F3, frontal portion F4, anterior-temporal portion F7, anterior-temporal portion F8, and midline frontal portion Fz and adjacent sites, and at least one feature at the parietal portion such as midline parietal portion Pz, parietal portion P3, and parietal portion P4. In one specific embodiment, the electrodes used can comprise, but not limited to, electrodes at at least one of the frontal pole Fp1, frontal pole Fp2, frontal portion F3, and frontal portion F4 and parietal electrode Pz.

In one embodiment, "front-back signal correlation" can be used, which uses a brainwave recording electrode worn at the front portion from a line connecting the left and right ear lobes as an electrode at the front portion, and uses a brainwave recording electrode warn at the back portion from the line connecting the left and right ear lobes as an electrode at the back portion. As an embodiment of such a "front-back signal correlation", electrodes comprising an "electrode at the frontal portion" and an "electrode at the parietal portion" are used. The "parietal portion" is encompassed by "back portion", and "back" can include the parietal portion as well as the central portion and occipital portion, but this can be only the parietal portion and the occipital portion. Alternatively, mid-temporal and posterior temporal portions can also be encompassed by back portion.

In one embodiment, the brainwave feature comprises at least one selected from the group consisting of a potential (mean amplitude or the like), frequency power, and a complexity index. In a preferred embodiment, potential is included as a brainwave feature. In such a case, the brainwave feature correlation is also referred to as potential correlation.

In one embodiment, the mean amplitude that can be used in the present invention is dependent on a stimulation application time or pain duration, but can be a mean value of an absolute value of amplitude during 15 seconds after application of stimulation as shown in the Examples. When seven electrodes are used, there would be a mean of seven amplitude absolute values for each level of stimulation.

In one embodiment, the frequency power comprises at least one of 5 bandwidths δ, θ, α, β, and γ in Fp1, Fp2, F3, F4, C3, C4, and Pz.

In one embodiment, the method of the invention comprises generating a differentiation model by machine learning using the brainwave feature. The machine learning used can use any algorithm used in the art.

For example, differentiation model creation using machine learning can be provided by a method comprising: a) obtaining brainwave data or analysis data thereof from the object; b) contracting features in the brainwave data or analysis data thereof with respect to the pain; c) differentiating and analyzing by machine learning and cross validation from top of ranking of weighting coefficient (including approximation coefficient; e.g., regression coefficient) of each feature after the contracting or combination thereof; and d) determining a model that attains a given accuracy.

(Medical Apparatus/System/Program)

In one aspect, the present invention provides an apparatus for evaluating or determining pain experienced by an object, the apparatus comprising: A) a headset comprising at least one electrode for obtaining a brainwave signal; and B) a base unit, wherein the base unit calculates a parameter comprising at least one selected from the group consisting of brainwave feature correlation and/or a complexity index of a brainwave, wherein a differentiation model correlating the parameter with a pain level of the object is generated, and wherein the pain level of the object is calculated and displayed by applying the parameter of the object to the differentiation model.

Any headset can be used herein, as long as the headset can be worn on the head and measure brainwaves. Examples thereof include, but not limited to, wireless head gear shaped headsets with electrodes attached thereto. Any base unit can be used, as long as the function described above can be materialized. The base unit used can have any shape used in normal medical equipment or device. For example, a base unit can comprise portions that receive, analyze, differentiate, and display brainwave signals from a headset.

In one aspect, the present invention provides a computer program for making an apparatus implement a process for evaluating or determining pain experienced by an object, the process: calculating a parameter comprising at least one selected from the group consisting of correlation of brainwave features of a brainwave and/or a complexity index of a brainwave; generating a differentiation model for correlating the parameter with a pain level of the object; and calculating and displaying the pain level of the object by applying the parameter of the object to the differentiation model.

In another aspect, the present invention provides a recording medium storing a computer program for making an apparatus implement a process for evaluating or determining pain experienced by an object, the process: calculating a parameter comprising at least one selected from the group consisting of correlation of brainwave features of a brainwave and/or a complexity index of a brainwave; generating a differentiation model for correlating the parameter with a pain level of the object; and calculating and displaying the pain level of the object by applying the parameter of the object to the differentiation model.

In still another aspect, the present invention provides a method of evaluating or determining pain experienced by an object, the method comprising: calculating a parameter comprising at least one selected from the group consisting of correlation of brainwave features and/or a complexity index of a brainwave; generating a differentiation model for correlating the parameter with a pain level of the object; and calculating and displaying the pain level of the object by applying the parameter of the object to the differentiation model.

It is understood that each of the brainwave feature correlation and complexity index of a brainwave used in the apparatus, program, recording medium, and method of the invention can use any embodiment described in the sections of (Brainwave feature correlation) and (Complexity index).

Each step for differentiation of pain using correlation of brainwave features or a complexity index of brainwave is described hereinafter.

Figure 79:
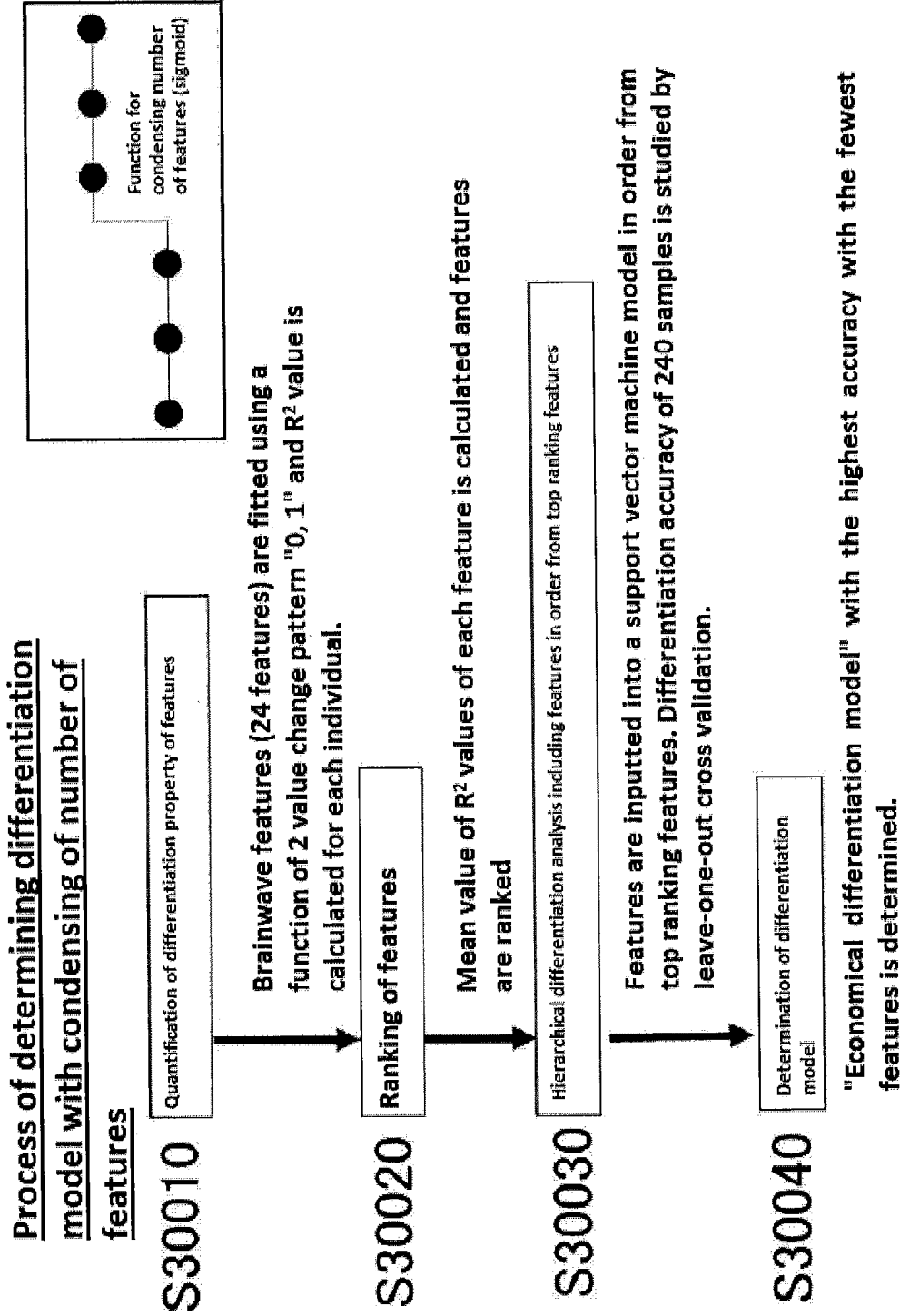
FIG. 79 shows an example of the flow of a determination process in differentiation analysis with a process of contracting the number of features. This is an example for 1) quantifying the feature differentiation properties, 2) ranking features, 3) performing hierarchical differentiation analysis with features included in order from the top feature, and 4) determining a differentiation model. All numerical values in the figure are exemplary.

A method of differentiating and analyzing using correlation of brainwave features or a complexity index is described hereinafter using a schematic diagram (FIG. 79).

a) First, the differentiation properties of features of brainwave data or analysis data thereof or the like or brainwave feature correction or complexity index are quantified (S30010). Specifically, this step fits a feature, or brainwave feature correction or complexity index, using a sigmoid function of two value change pattern "0, 1" to calculate a model approximation index (e.g., $R^2$ value) for each individual. This step can be considered a step for contracting features, or brainwave feature correction or complexity index, with respect to pain. This step can be used as a step for determining a threshold value or determination index in a model curve obtained by fitting when the objective is to differentiate or estimate individual features, or brainwave feature correction or complexity index. In other words, a threshold value can be determined by a numerical value such as a threshold potential and used as a determination index. More specifically, a differentiation/estimation model is created for 2, 3, or 4 classifications or more in accordance with conditional parameters using a feature, or brainwave feature correction or complexity index. As one method, a plot diagram is created and applied (fitted) to an appropriate fitting function such as a sigmoid function pattern or a step function. Any methodology that is known in the art can be used for fitting. Specific examples of such fitting functions include, but are not limited to, the functions described above, as well as a Boltzmann function, double Boltzmann function, Hill function, logistic dose response, sigmoid Richards function, sigmoid Weibull function, and the like. A standard logistic function is particularly called a sigmoid function. A standard function or a modified form thereof is common and preferred.

If a regression coefficient for fitting to an appropriate function pattern such as the sigmoid function pattern is at or greater than a given value, a threshold value for determining pain can optionally be determined based on the sigmoid curve or the like. In this regard, this can be generated based on an inflection point for sigmoid curves, but this is not limited thereto. As needed, pain classification values can be calibrated to maximize the pain level classification.

b) Next, features such as brainwave feature correction or complexity index are ranked (S30020). In this regard, a weighting coefficient can be used. The mean value of $R^2$ values of each parameter or the like can be used as the weighting coefficient. Once calculation is completed, features such as brainwave feature correction or complexity index are ranked.

Next, c) hierarchical differentiation analysis that includes features such as brainwave feature correction or complexity index in order from top ranking features is performed (S30030). Examples thereof include inputting features in order from top ranking features into a machine learning model such as support vector machine and studying the differentiation accuracy of all samples by leave-one-out or 10-fold cross validation and the like. b) and c) correspond to steps for differentiating and analyzing by machine learning and cross validation after inputting the weighting coefficients of each feature after contracting or a combination thereof from top of the ranking.

d) Next, a differentiation model is determined (S30040). This corresponds to a step of determining a model that attains a given accuracy. For example, a model with the highest accuracy or an "economical differentiation model" with the fewest feature for a model with the same accuracy can be determined. However, a setting such as select any model that attains a give accuracy (e.g., 70% differentiation accuracy) or the like can be provided. In the present invention, steps c) and d) can be performed in a model generation unit. If it is expected that a model is predetermined using a known database, pain data may be inputted during actual monitoring to perform differentiation and estimation. Black arrows are the envisioned flow of actual monitoring.

Figure 80:
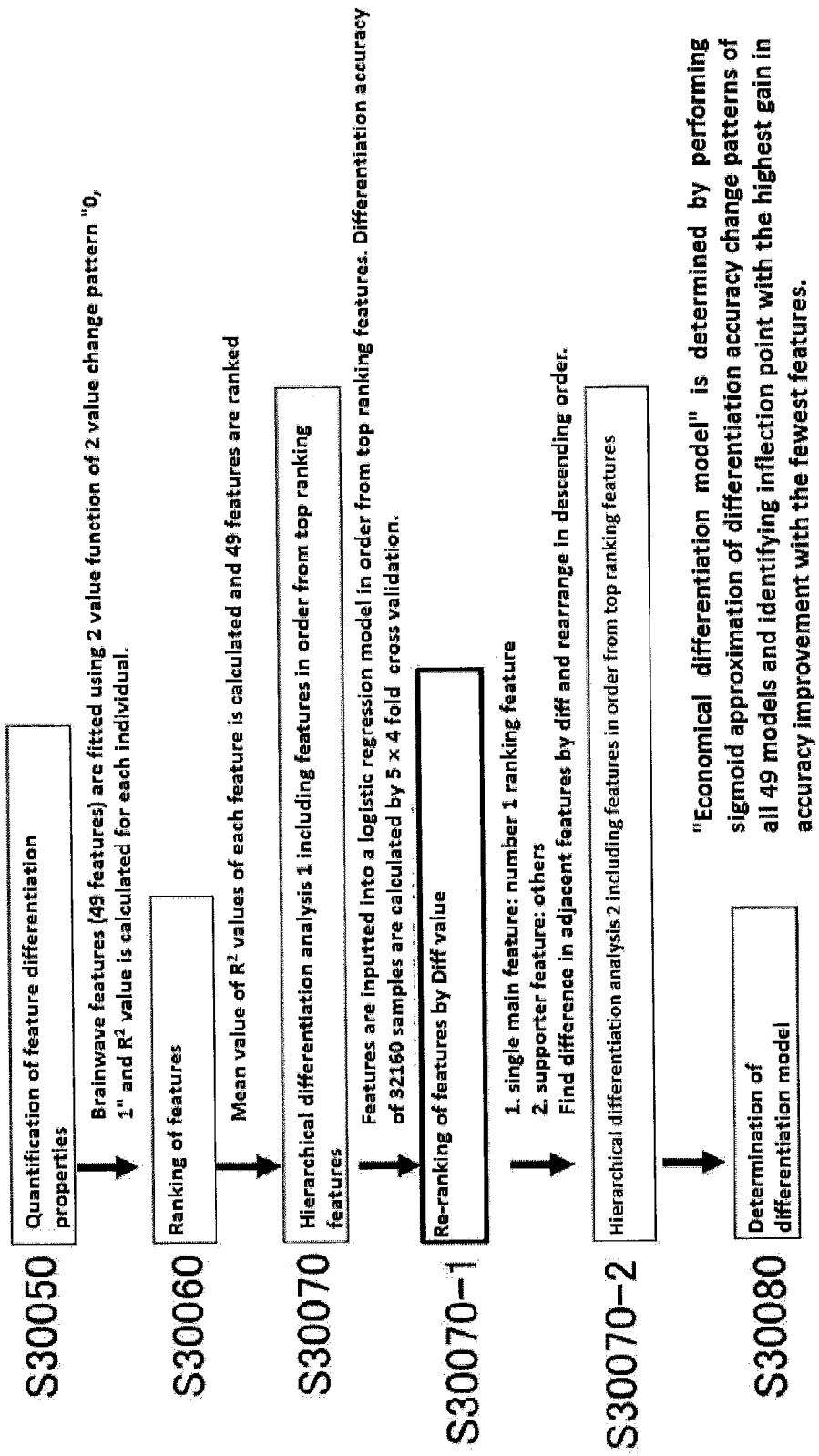
FIG. 80 shows a differentiation model determination process using double contracting process upon selecting a differentiation model and features. The differentiation model determination process in FIG. 79 includes the same processes up to 1) quantification of feature differentiation properties, 2) ranking of features, and 3) hierarchical differentiation analysis with features included in order from the top feature. Meanwhile, approximation of a change in differentiation accuracy using a sigmoid function or the like to select an economical differentiation model is newly included as of the final differentiation model selection. All numerical values in the figure are exemplary.

A method of re-ranking features such as correlation of brainwave features and a complexity index can also be used in a different optimal model selection process (see FIG. 80). In such a case, a differentiation model is determined in S30040 and then regressed to the feature ranking in S30020, features are re-ranked by a value of difference in differentiation accuracy of n−1 feature model (n≥2) and n feature model, and features are inputted into the model one at a time from the top features in S30030 to recalculate the differentiation accuracy. A differentiation model is then determined through the 2nd model determination process in S30040. These steps are as follows when using the symbols in FIG. 80. Specifically, a differentiation model is determined then regressed to the feature ranking in S30060, and features are re-ranked by a value of difference in differentiation accuracy of n−1 feature model (n≥2) and n feature model (S30070-1), and features are inputted into the model one at a time from top features in S30070-2 to recalculate the differentiation accuracy. A differentiation model is then determined through the model determination process in S30080.

A feature can be a feature that is obtained in response to some type of stimulation (e.g., low temperature stimulation, electrical stimulation, or the like) or obtained in a natural environment, or various brainwave data, brain activity data, amount of brain activity, amplitude data (EEG amplitude), frequency property, or the like can be used. It was found in the present invention that brainwave feature correction, complexity index, and the like are prioritized. Such brainwave data can be obtained using any methodology that is well known in the art. Brainwave data can be obtained by measuring electrical signals of a brainwave and is displayed by potential (can be displayed by μV or the like) as amplitude data or the like. Frequency properties are displayed as power spectrum density or the like (also referred to as frequency power or the like). A complexity index can also be calculated. After basic signal processing of brainwave data such as filtering, eye movement correction, or artifact removal, the data can be associated with a conditional parameter and a signal of the corresponding portion is extracted to create a brainwave feature. This includes mean value (arithmetic mean or geometric mean), other representative value (median or mode), entropy, frequency power, wavelet, mean and single run event related potential component, and the like. Further, the correlation of brainwave features can be calculated from such brainwave features.

In a preferred embodiment, brainwave data is preferably collected by a simple method, which can 1) use electrodes at a number that is required for analysis, 2) avoid the scalp with hair as much as possible, and 3) record while sleeping, to carry out the invention. Exemplary number of electrodes used is, but not limited to, 24, but the number can be 12 to 24, 24 to 36, 6 to 12, or fewer (e.g., 3, 4, 5, or the like). When brainwave feature correlation is used, brainwave feature correlation at any preferred positions described herein can be used.

For contracting, sigmoid fitting, or a step function with stepwise inflection, a linear function with a continuous stepwise change, or the like can be used.

As a weighting coefficient, a regression coefficient, or an $R^2$ value, correlation coefficient, residual sum of squares (difference between differentiation function and feature), or the like can be used. However, it is important that pain or stress sensed by an individual can be distinguished with as much accuracy as possible for differentiation of pain, so that efficacy which is different from detection of statistically significant difference can be required or intended.

In one embodiment, brainwave data or analysis data thereof for obtaining the brainwave feature correction or complexity index used in the present invention comprises, as data recording positions, frontal-parietal portions such as F3, F4, C3, C4, P3, and P4 in compliance with the international 10-20 system or expanded standard thereof, and positions on the scalp over the occipital portion as electrode positions. Alternatively, a position at a specific uniform distance (e.g., 2.5 cm or the like) can be covered. The duration of recording and analysis can be, for a short period of event related potential activity, 0 to 100, 100 to 200, 200 to 300, 300 to 400, 400 to 500, 500 to 600, 600 to 700, 700 to 800 milliseconds (ms), a shorter time segment (10 milliseconds or the like), or a longer time frame (sometimes spanning several seconds).

In still another embodiment, features such as correlation of brainwave features or a complexity index that can be used comprises a feature in an electrode at at least one selected from the group consisting of Fp1, Fp2, Fpz, F3, F4, Fz, C3, C4, Cz, P3, P4, and Pz, such as mean amplitude Fz, C3, and C4, and frequency $Fz(\delta)$, $Fz(\beta)$, $Cz(\delta)$, $C3(\theta)$, and $C4(\beta)$. A feature can comprise Cz (amplitude), $C3(\alpha)$, $Cz(\beta)$, $Fz(\delta)$, and $Cz(\gamma)$. In a preferred embodiment, any feature described in the sections of (Complexity index) and (Brainwave feature correlation) can be used herein.

Figure 96:
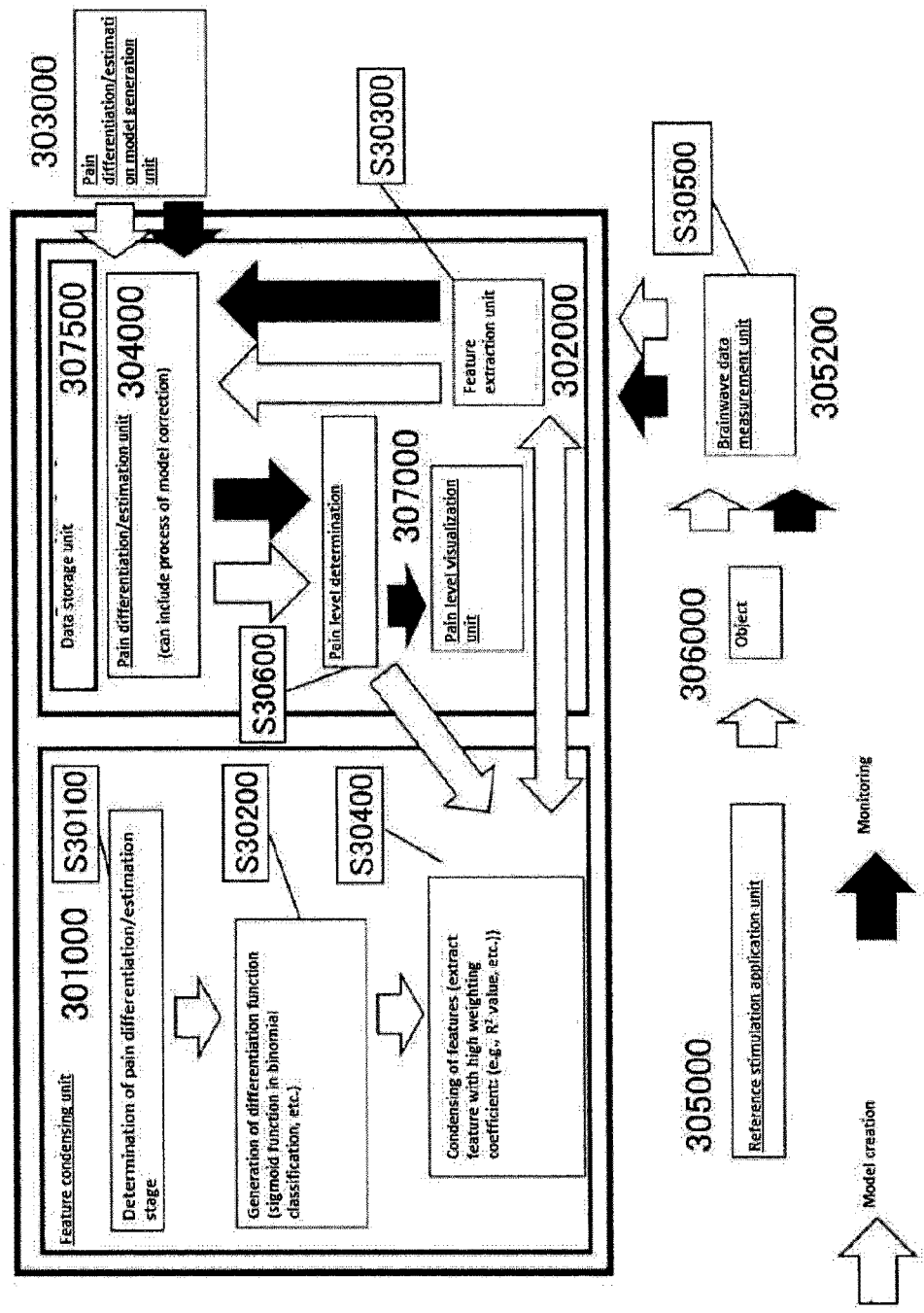
FIG. 96 is a schematic diagram of a differentiation apparatus with a feature contracting process. As of the model creation (white arrow), a differentiation function matching the number of classification levels is created and fitted to each feature, and a feature is selected with a weighting coefficient such as R square value to create a differentiation model. This information is stored in a feature extraction unit and a differentiation estimation unit. A pain level is differentiated and estimated online in actual pain monitoring (black arrow).

FIG. 96 describes a schematic diagram of the apparatus of the invention (differentiation apparatus with a process of contracting features) (301000 to 308000) (it should be noted that some of the configuration diagrams are optional constituents that can be omitted). In this schematic diagram, each step is described when appropriate (S30100 to S30600).

As shown in FIG. 96, this apparatus is comprised of a feature contracting unit 301000, a feature extraction unit 302000, pain differentiation/estimation model generation unit 303000, pain differentiation/estimation unit (can comprise a model correction process) 304000, a reference stimulation application unit 305000, a brainwave data measurement unit 305200, and a pain level visualization unit 307000. An object is denoted as 306000. A data storage unit 307500 can be optionally installed.

In such differentiation with a process of contracting, the number of pain differentiation/estimation stages (2 stages, 3 stages, or the like) is determined (S30100), and a differentiation function is generated (examples include sigmoid functions in binomial classification and the like; S30200). A feature is obtained after a reference stimulation (electrical stimulation or the like) is applied to the object 306000 from the reference stimulation application unit 305000 in accordance with the differentiation stage determined at S30100, and a feature related to a pain stage is collected (S30300) and contracted (S30400). The collected feature is approximated by a differentiation function generated at S30200 and ranked in accordance with the magnitude of the obtained approximation coefficient (regression coefficient or the like). Features are used in order from the top features. The pain level of reference stimulation is differentiated and estimated with the pain differentiation/estimation unit 304000, and a differentiation model with the number of features with the highest differentiation accuracy is used for monitoring pain. This is one embodiment of the process of contracting features S30400. A differentiation model (algorithm) installed in a pain differentiation/estimation unit used in the process of contracting (white arrows) and actual pain monitoring process (black arrows) is created at the pain differentiation/estimation model generation unit 303000, and installed in the pain differentiation/estimation unit 304000. After completion of the preprocessing described above at the feature contracting unit 301000, actual pain related brainwave data is collected from the object 306000 at the brainwave data measurement unit 305200 comprising an electroencephalograph or the like (S30500). This is transmitted to the feature extraction unit 302000 and converted to a feature selected in the process of contracting amplitudes, frequencies, or the like (e.g., can be complexity index, brainwave feature correlation, or the like of specific electrodes). The extracted parameter is taken into the pain differentiation/ estimation unit 304000 (can comprise a model correction process) from the feature extraction unit 302000, and a pain level is determined (S30600). The result of the determination is indicated as a trend of changes or numerical value (e.g., 1 to 100) at the pain level visualization unit 307000.

The determination of the pain differentiation/estimation stages at S30100 determines the number of levels to be differentiated or estimated (e.g., 2 stages, 3 stages, or the like).

The generation of a differentiation function at S30200 creates a differentiation function used in accordance with the number of differentiation levels at S30100 (sigmoid function or step function in binomial classification or the like).

In the collection of pain stage associated features at S30300, reference stimulation (electrical stimulation or the like) is applied a plurality of times from the reference stimulation application unit 305000 to the object 306000 in accordance with the number of levels determined at S30100 to collect related features such as brainwave feature correction and complexity index.

In contracting of a feature at S30400, a feature obtained at S30300 is approximated with a differentiation function, features with high approximation index (e.g., $R^2$ value or the like) are ranked, and features are inputted into the pain differentiation/estimation unit 304000 in order from top ranking features to differentiate and estimate a level of reference stimulation. A model with a number of features with the highest differentiation accuracy thereamong is used for actual pain differentiation/estimation.

For collection of pain related brainwave data at S30500, actual pain related brainwave data subjected to monitoring of pain is collected after completion of the contracting process at the feature contracting unit 301000. This step is data collection in an actual pain monitoring process.

For pain level determination at S30600, actual pain related data obtained at S30500 is processed at the feature extraction unit 302000 to obtain a feature set, which is then differentiated and estimated at the pain differentiation/estimation unit 304000, and a pain level is quantified from an estimated value, and a pain level is determined and made visible at the pain level visualization unit 307000.

The apparatus 308000 is configured to comprise or to be connected to an electroencephalograph that is or can be connected to the object (306000), so that brainwave data synchronized with stimulation emitted from the reference stimulation application unit 305000 to the object (306000) is obtained at the brainwave data measurement unit 305200. This is a summary of the apparatus 308000.

The apparatus 308000 can comprise a brainwave measurement unit, which internally comprises or externally connects to a brainwave recording sensor and optionally a brainwave amplification unit, and processes signals of a pain related brainwave and differentiates/estimates pain in the apparatus 308000.

In the apparatus 308000, collected brainwave signals are processed to extract a brainwave feature at the feature extraction unit 302000. Upon extraction, a feature contracted in advance at the feature contracting unit 301000 is selected. Further, pain is (optionally) made visible at the pain level visualization unit 307000. The apparatus internally or externally comprises the reference stimulation application unit 305000, which applies reference stimulation such as electrical stimulation a plurality of times in accordance with the pain level determined at S30100 in order to contract features that are effective for monitoring pain of the object 306000. Brainwave data related thereto is recorded at the brainwave data measurement unit 305200, a related brainwave feature is obtained at the feature extraction unit 302000, a pain level of reference stimulation is differentiated and estimated from the feature at the pain differentiation/ estimation unit 304000, and the feature is contracted S30400 from the result thereof. The reference stimulation application unit 305000 also transmits pain stimulation information (stimulation type, environmental information, or the like) for differentiating an actual unknown pain level and creating a differentiator. The reference stimulation application unit 305000 optionally comprises a stimulation information visualization unit in addition to the reference stimulation application unit 305000 and may display information such as an image or number associated with the stimulation or environment. The apparatus 308000 can also internally or externally comprise the pain differentiation/estimation unit 304000 for generating a determination value or differentiator.

In this manner, the apparatus 308000 comprises the brainwave data measurement unit 305200 and the pain differentiation/estimation unit 304000 and optionally the reference stimulation application unit 305000. The apparatus 308000 is materialized, for example, by a computer comprising a processor and a memory. In such a case, the apparatus 308000 makes the processor function as the feature contracting unit 301000, feature extraction unit 302000, pain differentiation/estimation model generation unit 303000, pain differentiation/estimation unit 304000, or the like as needed when a program stored in the memory is implemented by the processor. Stimulation or environmental information is also made visible as needed. The apparatus 308000 of the invention can be materialized, for example, by a dedicated electronic circuit. A dedicated electronic circuit can be a single integrated circuit or a plurality of electrical circuits. The brainwave data obtaining unit and pleasant/ unpleasant determination value generation unit can have the same configuration as a pleasant/unpleasant determination apparatus.

The feature extraction unit 302000 can also obtain a plurality of brainwave data by measuring a brainwave a plurality of times from an object being estimated via an electroencephalograph (included in the brainwave data measurement unit 305200). An object is an organism in which a change in a brainwave is induced due to stimulation or environment, which does not need to be limited to humans.

The pain differentiation/estimation unit 304000 differentiates/estimates the degree of unpleasantness using a determination value, and also generates a differentiator of determination value if not generated in advance externally or internally. The part generating a differentiator or determination value can be comprised external or internal to the apparatus 308000 as the pain differentiation/estimation unit 304000. A differentiation value used for differentiation/ estimation of pain is for estimating or classifying the degree of unpleasantness from amplitudes of a plurality of brainwave data. Specifically, the pain differentiation/estimation unit 304000 or the pain differentiation/estimation model generation unit 303000 can generate a determination value for estimating or classifying the degree of unpleasantness of an object from brainwave data.

A brainwave recording sensor contained in the brainwave data measurement unit 305200 measures electrical activity generated inside the brain of an object being estimated with an electrode on the scalp. The brainwave recording sensor also outputs the result of measurement, i.e., brainwave data. Brainwave data can be amplified as needed.

Other Embodiments

The differentiation method, program, and apparatus according to one or more embodiments of the invention has been described based on the embodiments, but the present invention is not limited to such embodiments. Various modifications applied to the present embodiments and embodiments constructed by combining constituent elements in different embodiments that are conceivable to those skilled in the art are also encompassed within the scope of one or more embodiments of the invention as long as such embodiments do not deviate from the intent of the inventions.

For example, a peak to peak value can be used as the amplitude value of brainwave data in each of the embodiments described above, but the amplitude value is not limited thereto. For example, a simple peak value can be used as the amplitude value.

In the embodiment described above, the range of the value of magnitude of the degree of unpleasantness is envisioned to be set so that the value of Pmax, which is the magnitude of the degree of unpleasantness corresponding to the upper limit value Amax of a feature such as brainwave amplitude or a combination thereof, would be 1, or the value of Pmin, which is the magnitude of pain corresponding to the lower limit value Amin of the feature or combination thereof, would be 0, but the range of values is not limited thereto. For example, the magnitude of pain can be represented by 0 to 100. In such a case, the pain differentiation/estimation unit 304000 can estimate the value Px of magnitude of pain, when shown by the pain level visualization unit 307000, by the following equation.

$$Px = P\max \times (Ax - A\min)/(A\max - A\min)$$

Curve fitting including sigmoid fitting was described above as an example of generating a pleasant/unpleasant determination value by analyzing a plurality of brainwave data, but this is not a limiting example. A predetermined value can also be used as the upper limit value of a brainwave amplitude. The predetermined value (absolute value) is for example 50 μV to 100 μV, which can be experimentally or empirically determined. In such normal analysis, data from about plus or minus 50 μV to 100 μV is eliminated as an artifact removal method. Such artifact removal can also be performed in the present invention as needed.

Any type of stimulation can be applied as stimulation applied to the object 306000 by the reference stimulation application unit 305000 (see FIG. 96) as long as the magnitude of the degree of unpleasantness sensed by the object 306000 changes in accordance with the type of stimulation or application environment.

Some or all of the constituent elements of the apparatus of the invention in each of the embodiments described above can be comprised of a single system LSI (Large Scale Integration). For example, as shown in FIG. 96, the apparatus 308000 can be comprised of the feature contracting unit 301000, pain differentiation/estimation model generation unit 303000, pain differentiation/estimation unit 304000, and pain level visualization unit 307000, as well as a system LSI having the feature extraction unit 302000 and the reference stimulation application unit 305000.

System LSI is ultra-multifunctional LSI manufactured by integrating a plurality of constituents on a single chip, or specifically a computer system comprised of a microprocessor, ROM (Read Only Memory), RAM (Random Access Memory) and the like. A computer program is stored in a ROM. The system LSI accomplishes its function by the microprocessor operating in accordance with the computer program.

The term system LSI is used herein, but the term IC, LSI, super LSI, and ultra LSI can also be used depending on the difference in the degree of integration. The methodology for forming an integrated circuit is not limited to LSI, but can be materialized with a dedicated circuit or universal processor. After the manufacture of LSI, a programmable FPGA (Field Programmable Gate Array) or reconfigurable processor which allows reconfiguration of connection or setting of circuit cells inside the LSI can be utilized.

If a technology of integrated circuits that replaces LSI by advances in semiconductor technologies or other derivative technologies becomes available, functional blocks can obviously be integrated using such technologies. Application of biotechnology or the like is also a possibility.

One embodiment of the invention can be not only such a pain differentiation/estimation model generation, sustained pain differentiation/estimation unit, but also a pain classifier generation, pain differentiation/classification method using characteristic constituent units contained in a pain differentiation/estimation apparatus as steps. Further, one embodiment of the invention can be a computer program for implementing each characteristic step in feature contracting, feature extraction, pain differentiation/estimation model generation, and pain differentiation/estimation on a computer. One embodiment of the invention can also be a computer readable non-transient recording medium on which such a computer program is recorded.

In each of the embodiments described above, each constituent element can be materialized by being configured with a dedicated hardware or by implementing software program that is suited to each constituent element. Each constituent element can be materialized by a program implementation unit such as a CPU or a processor reading out and implementing a software program recorded on a recording medium such as a hard disk or semiconductor memory. In this regard, software materializing the pain estimation apparatus of each of the embodiments described above or the like can be a program such as those described below.

As used herein, "or" is used when "at least one or more" of the listed matters in the sentence can be employed. When explicitly described herein as "within the range of two values", the range also includes the two values themselves.

Reference literatures such as scientific literatures, patents, and patent applications cited herein are incorporated herein by reference to the same extent that the entirety of each document is specifically described.

As described above, the present invention has been described while showing preferred embodiments to facilitate understanding. The present invention is described hereinafter based on Examples. The above descriptions and the following Examples are not provided to limit the present invention, but for the sole purpose of exemplification. Thus, the scope of the present invention is not limited to the embodiments or the Examples specifically described herein and is limited only by the scope of claims.

EXAMPLES

Examples are described hereinafter. The objects used in the following Examples were handled, as needed, in compliance with the standards of the Osaka University, and the Declaration of Helsinki and ICH-GCP in relation to clinical studies.

Example 1: EEG Trend Analysis

This Examples conducted EEG trend analysis. This demonstrates that determination of subjective pain, which has difficult with simple association of data of conventional art, can be conducted more accurately in line with temporal changes.

(Materials and Methods)
(Participants)

Separate groups of 32 healthy adult subjects in their 20s to 70s participated in the low temperature pain and high temperature pain experiments. Most participants overlapped in the two groups. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

A temperature stimulation system (Pathway; Medoc Co., Ltd., Ramat Yishai, Israel) was used to apply high temperature stimulation and low temperature stimulation to the right forearm of the participants. High temperature stimulation and low temperature stimulation were independently applied in separate tests. Each test included six levels of temperature intensities. Under high temperature pain conditions, the temperature was decreased by 2° C. each for six temperature levels in the range of 40° C. to 50° C. Each temperature level consisted of three stimulations with a 5 second inter-stimulus interval (ISI). Each stimulation lasted 15 seconds, and waiting period for increase and decrease from the standard temperature (35° C.) was about 5 seconds. After three stimulations at each level, the intervals between blocks lasted 100 seconds. Under low temperature pain conditions, the temperature was decreased by 5° C. each for six temperature levels in the range of 15° C. to −10° C. Each level consisted of three stimulations with a 5 second ISI and maintained 15 second plateau with a waiting period for increase and decrease for about 5 seconds. The intervals between blocks were fixed at 100 seconds. The participants continuously evaluated pain intensities in the range of 0 to 100 (0: "no pain"; 100: "unbearable pain") on a computerized visual analog scale (COVAS). COVAS data was simultaneously recorded with changes in stimulation intensities.

(EEG Data Record)

Commercially available Bio-Amplifier (EEG 1200: Nihon Koden) was used to record EEG from four scalp Ag/AgCI scalp electrodes (Fz, Cz, C3, and C4). The frontmost electrode Fp1 was used for recording EOG activity. Reference electrodes for guiding brainwaves were attached to both earlobes, and an earth electrode was placed on the center portion of the forehead. The sampling rate was 1000 Hz and amplified in the frequency band range of 0.3 to 120 Hz. The impedance of all electrodes was less than 15 kΩ.

(EEG Analysis)

Continuous EEG data under low temperature pain and high temperature pain conditions was sampled from the start of first stimulation to 40 seconds after the start of last stimulation. Since therapy is administered in the direction of reducing pain from strong to weak in clinical settings, EEG data was rearranged in the opposite direction in terms of time. To reduce VEOG noise, the following regression filter was applied to raw EEG data:

Raw EEG=β×EOG+$C$

EEG estimate=raw EEG−β×EOG        [Numeral 5]

β: partial regression coefficient
$C$: intercept
EEG estimate: estimated EEG

Fp1 was the closest to the left eye and affected heavily by the eye movement, so that Fp1 data was used as EOG data. After VEOG was diminished, by using various time windows from 10 seconds to 60 seconds in 10 second increment, absolute values of EEG amplitudes were continuously averaged with a non-overlapping method, and standardized using the maximum mean amplitude. Analysis in 5 second units was also conducted to study the effect of time direction averaging method for a short time frame as needed.

To find which mean time interval of EEG trend is the most sensitive to detection of change in subjective pain intensity and temperature intensity, the inventors studied the relationship between individual participant's EEG data and temperature intensity, or EEG data and subjective pain intensity under both high temperature stimulation conditions and low temperature stimulation conditions by Pearson's correlation analysis. The absolute value of correlation coefficient (rs) were studied between adjacent mean intervals (e.g., 10 seconds vs 20 seconds) by paired t-test with an α level of $p<0.05$ as the baseline.

FIG. 1I simultaneously plots the averaged EEG amplitude change and change in low temperature intensity (A) or change in subjective pain evaluation (B) for each of 10, 20, and 40 second intervals for one of the participants. In FIG. 1-A, changes in temperature intensity and EEG exhibit the opposite patterns. When a change in temperature was stronger and biased upward, EEG amplitude was weaker and biased downward. The negative correlation coefficient in the method with a mean interval of 40 seconds was stronger than other mean time interval. As shown in FIG. 1-B, the relationship between changes in subjective pain intensity and EEG amplitudes also exhibited the same trend. When subjective pain evaluation is greater and tends upward, the EEG amplitude was weaker. The negative correlation coefficient was also observed most strongly for 40 second mean interval.

Figure 2:
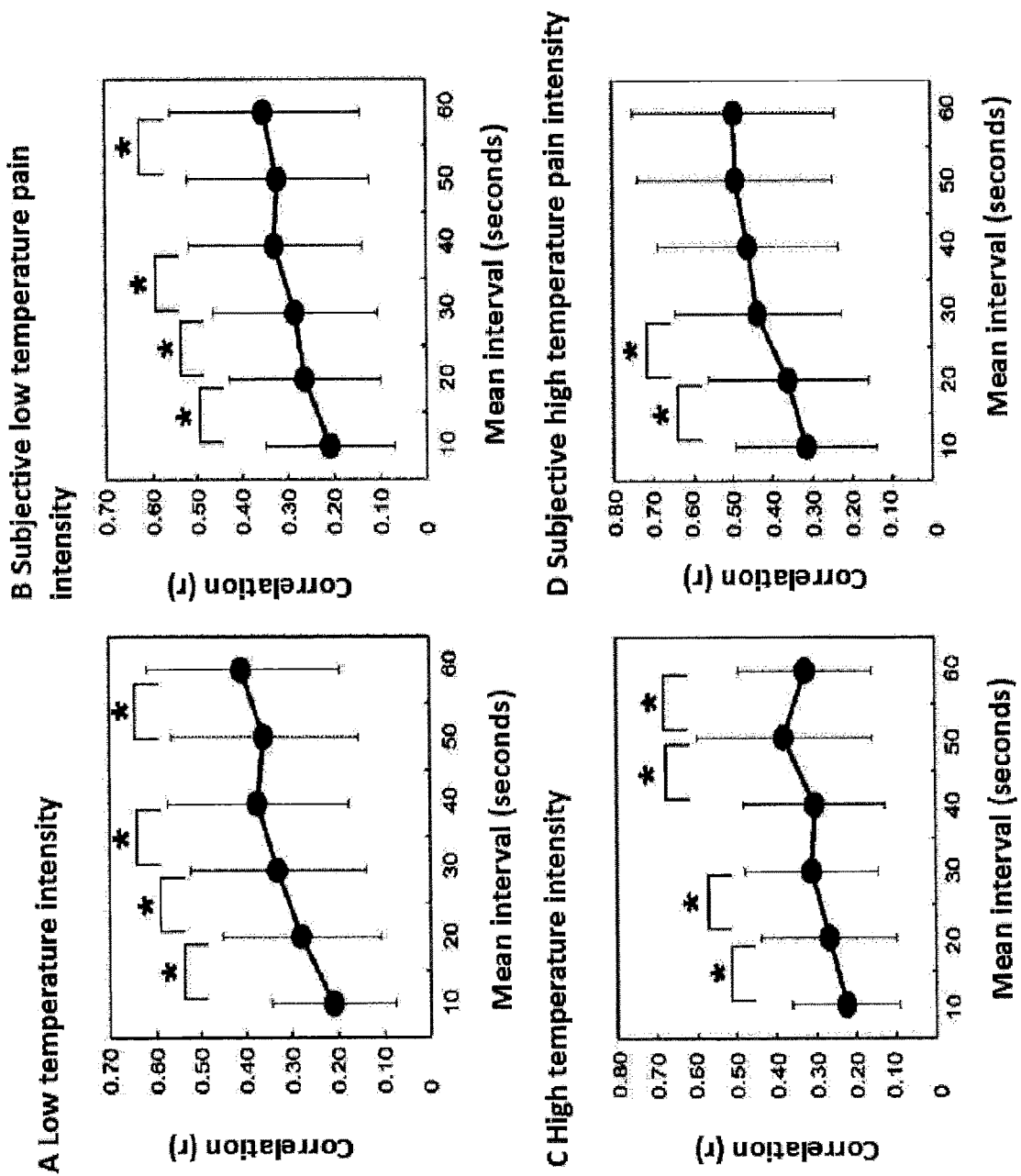
FIG. 2 shows a comparison of mean correlation coefficients (n=32) between a change in EEG (converted to absolute value and standardized) under high temperature pain stimulation conditions and low temperature pain stimulation conditions and temperature, or a change in EEG and change in pain evaluation. A statistical difference in correlation coefficients is observed between adjacent time intervals around 30 to 40 seconds under both high temperature and low temperature stimulation conditions. A shows low temperature intensity, B shows subjective low temperature pain intensity, C shows high temperature intensity, and D shows subjective high temperature pain intensity. The vertical axis indicates the correlation coefficient, and the horizontal axis indicates the mean interval (seconds). * indicates statistical significance ($p<0.05$).

The inventors calculated correlation coefficients between change in pain evaluation and temperature intensity and change in EEG for 6 mean intervals from 10 seconds to 60 seconds for all participants (32 participants for each stimulation type). The mean correlation coefficient between mean time interval and change in pain evaluation and temperature intensity was then studied by a paired t-test using an α level of $p<0.05$ under both high temperature pain conditions and low temperature pain conditions. FIG. 2 shows the summary of results. In general, there was a trend of a longer mean interval resulting in a greater correlation coefficient. For low temperature stimulation intensity (FIG. 2A), the correlation coefficient gradually increased up to a mean time interval of 40 seconds. A similar pattern was also observed when judging subjective pain from low temperature stimulation (FIG. 2B). For high temperature stimulation intensity (FIG. 2C), the correlation coefficient gradually increased up to a mean time interval of 30 seconds. A similar pattern was also observed when judging subjective pain from high temperature stimulation (FIG. 2D). These results indicate that accurate monitoring of the trend of EEG overtime requires at least a 30 second time interval in the time direction averaging method.

Figure 3:
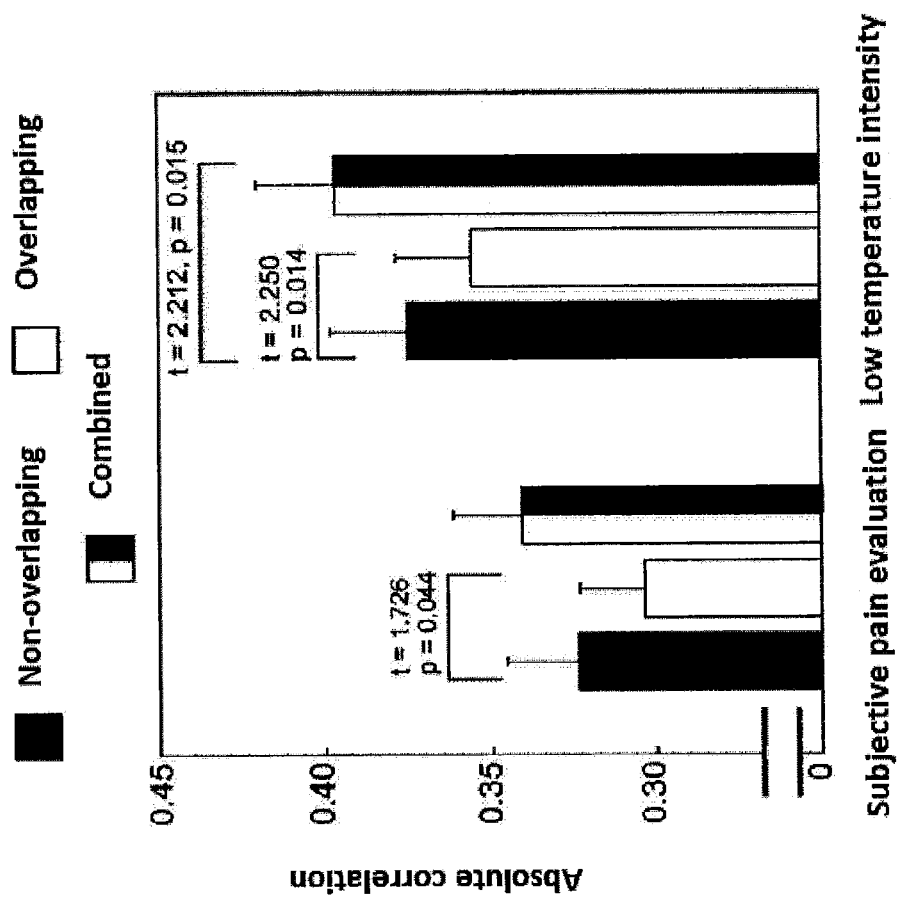
FIG. 3 shows a comparison of mean correlation coefficient values between non-overlapping time direction averaging method and overlapping time direction averaging method. For non-overlapping, overlapping (moving average), or combined method (moving average, and then non-overlapping average), the correlation coefficient for a pain indicator (subjective evaluation, low temperature intensity) is higher using the non-overlapping method compared to the overlapping method. The vertical axis indicates the absolute correlation coefficient. The left panel shows the subjective pain evaluation, and the right panel shows the low temperature intensity. Black bars indicate non-overlapping, white bars indicate overlapping, and mixture of black and white indicates combined.

Next, the inventors compared the strength of correlation coefficient of an averaging method combining both the non-overlapping block averaging method and overlapping moving average method using 40 second mean time intervals. The combined averaging method first applied an overlapping moving average method and then the non-overlapping block averaging method. As shown in FIG. 3, the combined averaging method exhibited a tendency of being significantly higher or higher among all methods.

Furthermore, the change in the correlation coefficient of a short mean time interval (5 seconds, 10 seconds, and 15 seconds) and long mean time interval (40 seconds, 45 seconds, and 50 seconds) was continuously plotted to find the difference in the correlation coefficients (absolute value) between the mean time interval of less than about 15 seconds used in prior data and a longer time interval used by the inventors. As can be seen in FIG. 4, the change in the mean correlation coefficient is approximated by an S-shaped function ($\beta=0.978$, $p=0.0007$), showing that a rapid change in the strength of correlation relationship occurs between mean time intervals of 15 seconds and 40 seconds.

Example 2: Differentiation of Strong Pain and Weak Pain Using Pain Intensity

This Example demonstrated that strength and weakness of pain can be differentiated from the circumstances such as monotonic increase or monotonic decrease by using pain intensity.

Figure 5:
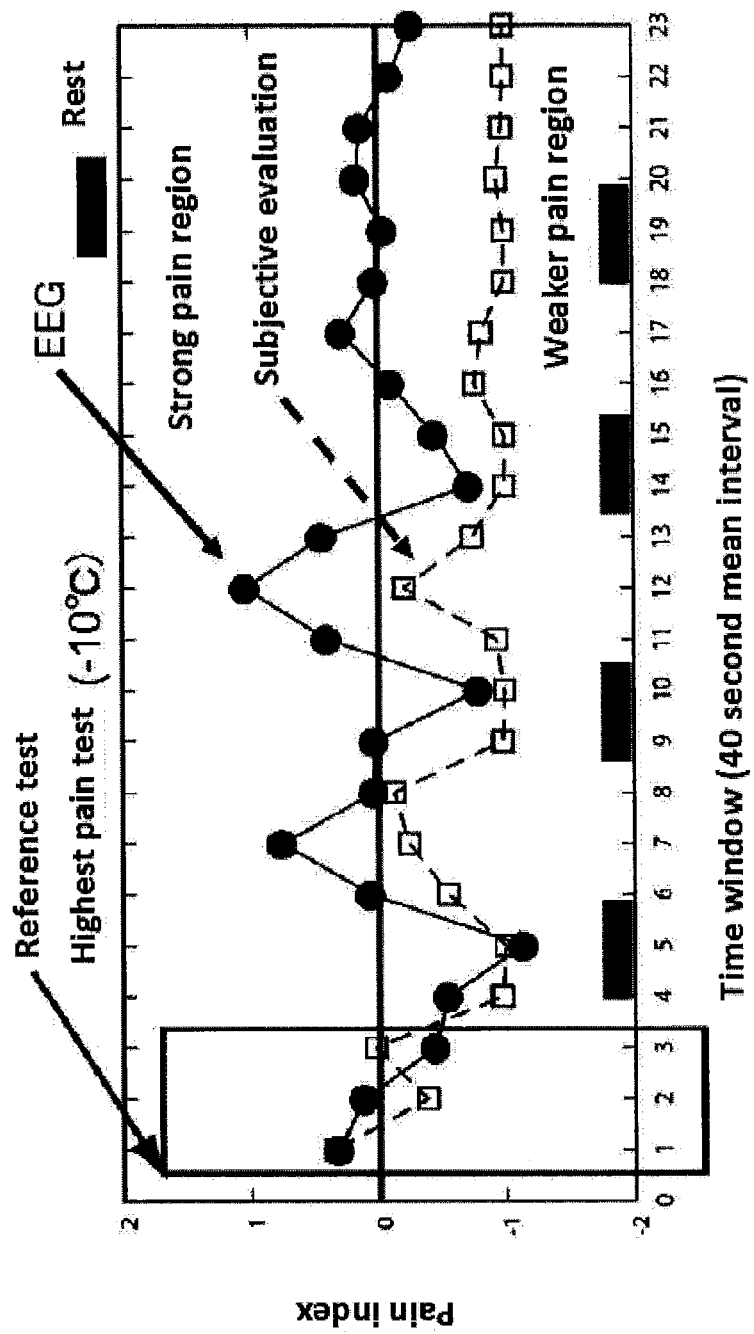
FIG. 5 shows a pain index based on EEG. A change in pain levels with an analgesic or sedative in a clinical setting is expected to mainly progress in the direction of strong to weak. In this regard, a pain index is created while using the feature (mean of amplitude absolute values (standardized)) under condition with the highest pain level as the baseline, and the trend is expressed by 40 second non-overlapping time averaging method. The vertical axis indicates the pain index, and the horizontal axis indicates the time window (40 second mean interval). The black dots indicate change in EEG, and the dotted line with white squares indicates the change in subjective evaluation.

The trend of mean EEG amplitude and subjective pain evaluation of one participant, using the 40 second averaging method (FIG. 1I) was converted to a pain index. Since a low temperature pain paradigm exhibited a negative correlation between EEG and subjective pain evaluation, the function of the trend of EEG was first inversed, and baseline correction was applied to a reference value by using the mean value for the first three most intense pain stimulations. FIG. 5 shows the results. The zero line (baseline) is strong pain intensity. A negative value indicates alleviation of pain intensity, whereas a positive value indicates increase in pain intensity.

The pain used in this case is pain that is considered as subjectively "unbearable" pain.

Pain index=EEG$^{-1}$-BS     [Numerical 6]

$^{-1}$=inverse function
BS=reference value calculated using the strongest pain EEG.

(Results and Discussion)

A pain index converted from the amount of brain activity exhibits a pattern that is similar to subjective pain evaluation. Specifically, there is a tendency for the line to lean above the zero line when pain stimulation is applied to a subject, and lean below the zero line when pain stimulation is eliminated. This tendency is more prominent in the early stages of a time window. It should be noted that a pain index is not necessarily the highest in a test with the highest pain. Specifically, throbbing sustained pain such a high temperature pain stimulation exhibits a delayed increase in a pain related brainwave feature or a pain index derived therefrom (see the delayed pain feature in FIG. 25), and the relative difference from a case of no pain increases. This is an example showing that the index value as well as the fluctuation range thereof are important for accurate understanding of a pain trend.

Example 3: Comparison of Superiority of Evaluation Depending on Difference in Mean Time Interval (Seconds)

This Example demonstrated that a difference due to a time interval leads to a significant difference for actually evaluating the difference in subjective pain.

While 15 seconds and 20 seconds were compared in this Example, the same experiment can be conducted by using other interval of seconds, such as 20 seconds, 30 seconds, and 40 seconds, and the same result is obtained. In particular, 15 seconds was used as an object of comparison because 15 seconds is used in prior studies, while the relationship between pain related brain feature and pain level is understood to exhibit a large inflection around 15 seconds as shown herein.

(Materials and Methods)

In this Example, data for 15 seconds and 20 seconds was calculated based on the methodology described in Example 1.

(Results)

The results obtained are shown below.

TABLE 1

|  | 15 second mean | 20 second mean | t value | p value |
|---|---|---|---|---|
| Subjective pain evaluation | 0.235 | 0.264 | 4.062 | 0.00012 |
| Stimulation intensity | 0.256 | 0.284 | 4.008 | 0.00015 |

As described above, correlation coefficients of EEG and subjective evaluation and stimulation intensity were calculated for 73 subjects. A paired t-test was performed for the correlation coefficients, and the results were compared between 15 seconds and proximate 20 seconds. It can be concluded as a result that a time frame of 20 seconds or more is preferably used in view of the correlation coefficient (absolute value) being higher for 20 seconds than 15 seconds. It is unexpected that a difference in effect is observed discontinuously even with such a difference of 5 seconds. Selection of a long mean time interval of 40 seconds or more unexpectedly resulted in showing a higher correlation with subjective pain evaluation by the analysis of the invention.

Example 4: Trend Analysis Using Various Mean Time Intervals

This Example studied how the correlation between pain index (subjective pain evaluation, pain stimulation intensity) and mean brain feature changes when a time direction averaging method is performed using a long mean time interval under cold stimulation conditions.

(Methods)

The subjects, testing method, and analysis method are in accordance with Example 1. The mean time frame, after 10 seconds, was extended by 20 seconds each, such as 20, 40, 60, 80, 100, and 120 seconds.

(Results and Discussion)

FIG. 6A shows the change in mean correlation coefficient r (absolute value) of the mean (e.g., arithmetic mean potential) amplitude (absolute value) with subjective evaluation of pain, and FIG. 6B shows that with cold temperature stimulation intensity. The correlation coefficient significantly increases up to 40 seconds for both cases. While a significant difference in stimulation intensity is observed between 60 seconds and 80 seconds, intensity was maintained until 100 seconds. Meanwhile, for the maximum length of 120 seconds, the correlation coefficient significantly increased compared to preceding time intervals especially for subjective evaluation. This testing paradigm has six pain levels that increase in a stepwise manner. Thus, it is understood that features for low pain levels and high pain levels (absolute value of mean amplitude in this case) can be consolidated more discontinuously when the mean time interval is extended, so that the correlation coefficient is high.

Example 5: Trend Analysis 2 Using Various Pain Stimulation Durations

In the preceding Examples, the duration of high temperature and low temperature pain stimulation was constant at 15 seconds and the testing time was short, which was about 10 minutes. This Example further studied the relationship between the length of mean time interval and subjective evaluation of pain using a testing paradigm where thermal stimulation lasts randomly from 15 seconds to 4 minutes.

(Participants)

12 healthy adult subjects in their 20s to 70s participated in the high temperature pain experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Procedure)

Figure 7:
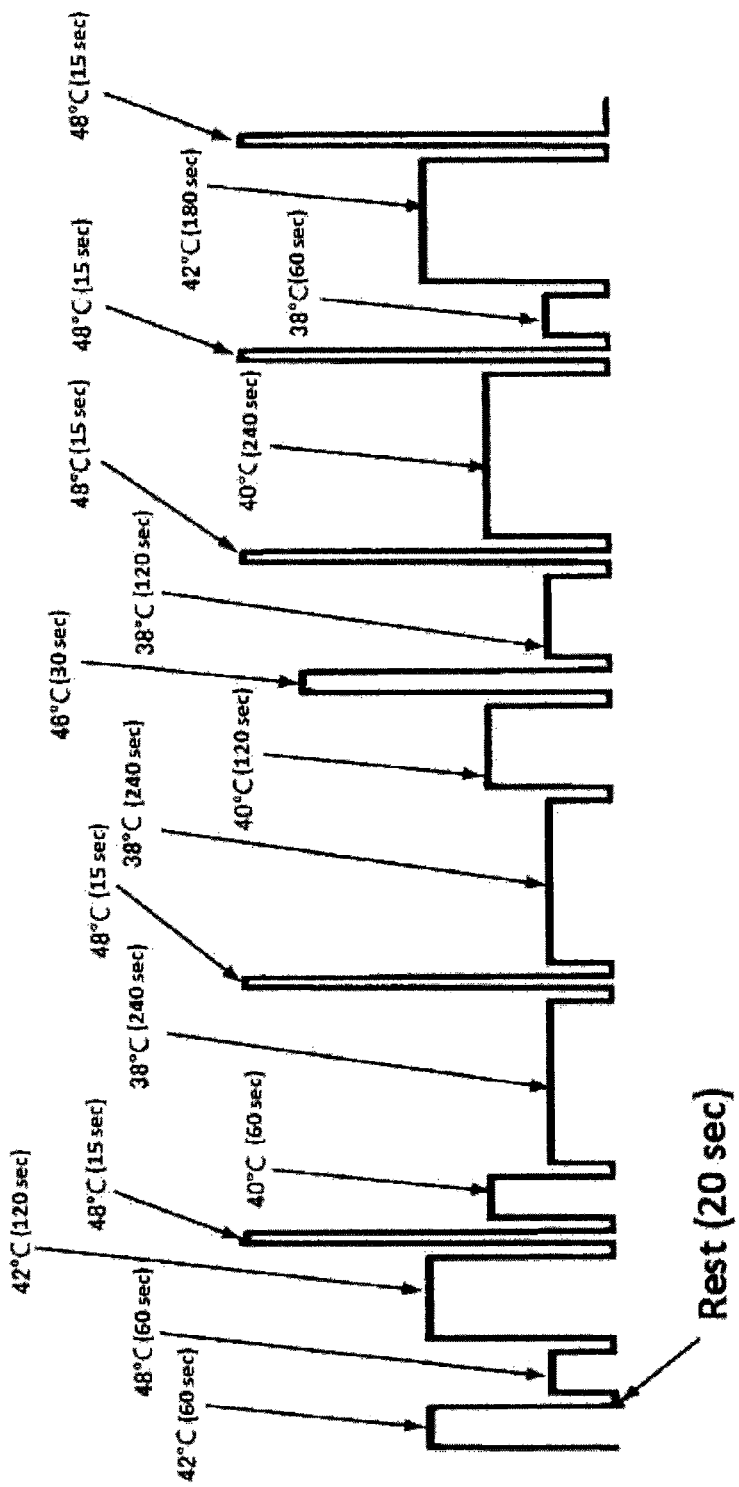
FIG. 7 is a random high temperature stimulation test paradigm with varied temperatures and stimulation durations. The temperature changes in the range of 38° C. to 48° C., and the duration changes in the range of 15 seconds to 240 seconds.

A temperature stimulation system (Pathway; Medoc Co., Ltd., Ramat Yishai, Israel) was used to apply high temperature stimulation to the right forearm of the participants. High temperature stimulation from 38° C. and 48° C. was randomly applied 17 times for a duration of 15 seconds to 240 seconds (see FIG. 7). The interval between stimulations was 20 seconds. Stimulation was independently applied in separate tests. The subjects continuously evaluated pain intensities in the range of 0 to 100 (0: "no pain"; 100: "unbearable pain") on a computerized visual analog scale (COVAS). COVAS data was simultaneously recorded with changes in stimulation intensities.

(EEG Data Record)

Commercially available Bio-Amplifier (EEG 1200: Nihon Koden) was used to record from seven scalp Ag/AgCI electrodes (Fp1, Fp2, F3, F4, C3, C4, and Pz). Reference electrodes for guiding brainwaves were attached to both earlobes, and an earth electrode was placed on the center portion of the forehead. The sampling rate was 1000 Hz and amplified in the frequency band of 0.3 to 120 Hz. The impedance of all electrodes was less than 15 kΩ.

(EEG Analysis)

F3 and F4 were used for EEG data analysis. Data was sampled from the start of first stimulation to 40 seconds after the start of last stimulation for each subject. To reduce VEOG noise, the following regression filter was applied to raw EEG data:

$$\text{Raw EEG} = \beta \times \text{EOG} + C$$

$$\text{EEG estimate} = \text{raw EEG} - \beta \times \text{EOG} \quad \text{[Numeral 7]}$$

β: partial regression coefficient
C: intercept
EEG estimate: estimated EEG

Fp1 and Fp2 were the closest to both eyes and affected heavily by the eye movement, so that both data were added and used as EOG data. After VEOG was diminished, 60 Hz of external electrical noise was removed with a filter. After converting amplitudes to their absolute values and removing artifacts exceeding 100 μV, the mean amplitude was calculated by time direction averaging method in 10 seconds, and 20 second intervals from 20 seconds to 120 seconds to consolidate F3 and F4 with a mean value. This Example calculated the arithmetic mean and the geometric mean for comparison of different mean value types. Subjective pain evaluation data was also consolidated using the time direction averaging method. The Pearson's correlation coefficients of subjective pain evaluation and EEG mean data of each subject was calculated and converted into their absolute values, then the levels of correction coefficients were compared based on the α standard of p<0.05 between adjacent mean time intervals (e.g., 10 seconds vs 20 seconds).

(Results and Discussion)

FIGS. 8A and 8B show the change in correlation coefficient between arithmetic mean amplitude (absolute value) and subjective pain evaluation and high temperature stimulation intensity. As can be understood from visual inspection, the correlation coefficient tended to be higher with longer mean time interval in a more complex random application method of this Example. For subjective pain evaluation (FIG. 8A), 120 second interval is longer than the immediately preceding 100 second interval, so that a local improvement in the correlation was observed (t=1.81, p=0.049). Meanwhile, for high temperature intensity (FIG. 8B), improvement was observed in the correlation at a lower stages between 40° C. and 60° C. (t=2.07, p=0.031). FIGS. 9A and 9B show changes in the correlation coefficient between the geometric mean amplitude (absolute value) and subjective pain evaluation and high temperature stimulation intensity. Similarly, a trend of higher correlation coefficient is observed for longer mean time interval. However, the increase is more gradual, so that a significant difference is not found in adjacent time intervals. 120 seconds also had a significantly higher correlation coefficient for subjective pain evaluation from comparison by leave-one-out t-test (t=3.034, p=0.011). For stimulation intensity, a statistically significant difference was found between a shorter 80 second interval and 40 second interval (t=2.271, p=0.044). It is understood in view of these results that the correlation coefficient tends to be higher for longer mean time interval even for a change in pain stimulation which is more complex with a long duration, so that a longer mean time interval in accordance with the duration of pain stimulation results in more discretely contracted feature of pain level and higher correlation.

Example 6: Hierarchical Pain Trend Monitoring Methodology

After extracting a feature by the time direction averaging method at the feature extraction unit in FIG. 12, a change in the pain level is expressed as a trend at the pain level monitoring unit, thus enabling a clinician to monitor pain over time. This requires at least the following three procedures:

1. obtaining brainwave data upon pain from a subject (electroencephalograph 1120 and measurement unit 1111);

2. determining a specific time interval and calculating a mean feature by the time direction averaging method "online" (feature extraction unit 1112).

3. selecting and changing the method of displaying a trend of a mean feature by elapsed time of online monitoring by the "hierarchical pain trend monitoring methodology" (pain level monitoring unit 1115).

Figure 10:
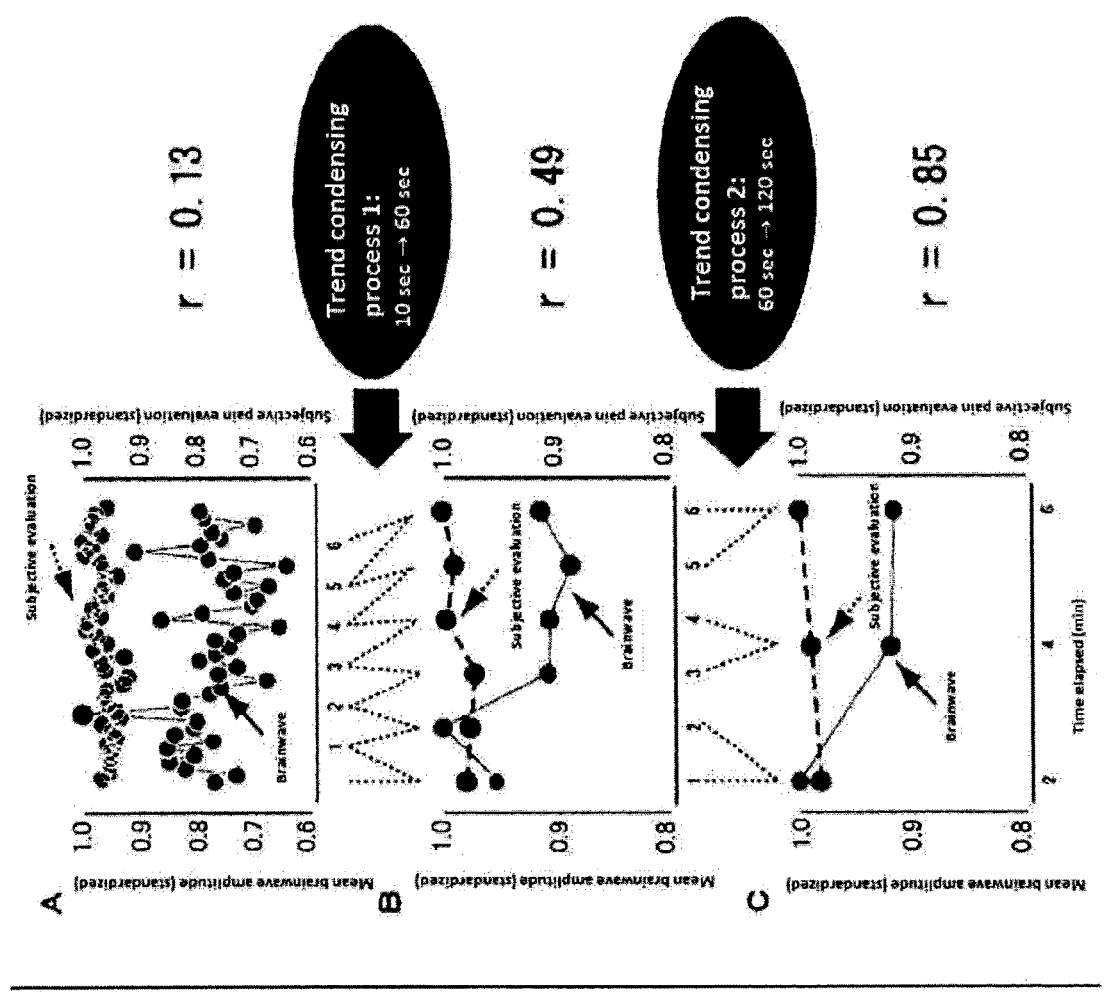
FIG. 10 shows an example of a trend contracting process in the "hierarchical pain trend monitoring methodology" used in pain level trend monitoring (in this example, 10 seconds→60 seconds, 60 seconds→120 seconds). This is a method covering local monitoring from broad monitoring by contracting a trend unit (10 seconds in this example) with passage of time.

Optionally, a procedure for identifying a time point with a strong pain level (standard (baseline) determination unit 1114) and determining a monitoring baseline for a pain trend may be performed between procedures 2 and 3. The details of the procedure are additionally described in FIG. 13 that expands FIG. 12. In such a case, trends of a mean amplitude or other features and the time area differentiated/estimated as "strong pain level" by a differentiation model (machine learning such as support vector machine, regression model using sparse model analysis or sigmoid function) are collated to determine the baseline of monitoring pain levels, and the pain index is corrected as shown in FIG. 5. In procedure 4, a method of making a pain trend visible, i.e., the "hierarchical pain trend monitoring methodology", is used. An example thereof is shown in FIG. 10. Since the elapsed time is short at the start of pain monitoring, it is difficult to use a long mean time interval. Thus, a feature such as a mean value for each 10 seconds (e.g., arithmetic/geometric mean potential) or other features is obtained by the non-overlapping averaging method as a "pain trend unit". A plurality of units are contracted continuously or discontinuously with the passage of time for a correction to a broader trend expression. Six adjacent 10 second units in FIG. 10A are consolidated and corrected to a one minute unit in FIG. 10B. This improves the correlation between brainwave feature (mean value (e.g., arithmetic/geometric mean potential) absolute value) and subjective pain evaluation and facilitates a more objective differentiation/estimation of a change in pain level. FIG. 10C further reconstruct the units into 2 minute units to enable monitoring of a broader pain trend. The correlation of brainwave feature and subjective pain evaluation is also significantly improved. In this manner, a local and broader change in pain levels can be comprehensively monitored by hierarchical trend monitoring.

(Example 7: Refinement of Trend Analysis) <FIGS. 14 to 24>

(Example of Refining Trend Analysis 1)

This Example analyzed brainwave data during application of pain stimulation with a differentiation model (multiple regression model) using the mean amplitude.

(Method)

(Participant)

158 healthy adult male and female subjects in their 20s to 70s participated in hot stimulation paradigm and cold stimulation paradigm experiments (151 subjects) (total of 309 subjects). Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

The summary of the experiment is illustrated in FIG. 14. A temperature stimulation system (Pathway; Medoc Co., Ltd., Ramat Yishai, Israel) was used to apply hot and cold stimulation to the right forearm of the participants. Hot and cold stimulation each included six levels of temperature intensities (hot: increased by 2° C. from 40° C. to 50° C.; cold: decreased by 5° C. from 15° C. to −10° C.). Each temperature level consisted of three stimulations with about a 5 second inter-stimulus interval (ISI). Each stimulation lasted about 15 seconds, and the waiting period for increase and decrease from the standard temperature (36° C.) was about 10 seconds. After three stimulations at each level, the intervals between blocks lasted 100 seconds. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Recording)

Brainwaves were continuously recorded during the test from seven poles at the frontal, mid, and parietal portions (Fp1, Fp2, F3, F4, C3, C4, and Pz), with the reference electrodes to both earlobes, the electrode in the left hemisphere to the left earlobe, and the electrode in the right hemisphere to the right earlobe. An earth electrode was placed on the forehead. The sampling frequency was 1000 Hz. The band filter was 0.3 to 120 Hz. The impedance was 15 kΩ or less.

(EEG Analysis)

(Extraction of Feature of Amplitude)

First, the eye movement noise (EOG) in the EEG data recorded in the hot stimulation and cold stimulation experiments was diminished. Main component analysis was performed using data from seven electrodes, and the first component was extracted as an EOG component. To leave only the EOG component, data was passed through a 30 Hz band pass filter. The following regression filter was then applied to remove the EOG component from EEG.

Raw EEG=β×EOG+$C$

EEG estimate=raw EEG−β×EOG     [Numeral 8]

β: regression coefficient
C: intercept
EEG estimate: estimated EEG

After EOG correction, a 30 Hz high pass filter was applied to an EEG waveform to reduce the myogenic potential. Data was sampled from the time of applying stimulation to 15 seconds after application of stimulation for each electrode and each level of stimulation to obtain a total of 18 epochs (3 stimulations×6 levels) for each electrode. After converting the amplitudes of each epoch to an absolute value, the mean potential was calculated, and a z value was calculated using the mean amplitude and standard deviation in all time segments of 18 stimulations at each electrode.

(Pain Differentiation Model Creation by Machine Learning)

Having pain (hot: level 6, cold: level 5 (due to subjects who could not complete level 6)) and no pain (level 1) from thermal stimulation on a total of 309 hot and cold stimulation participants were differentiated using machine learning of linear multiple regression models. Seven brainwave features (standardized among individuals) obtained by the extraction method described above were used. For each individual, the pain level for three samples of having pain and three samples of no pain for each stimulation was differentiated and estimated by the following procedure. First, all 3708 samples were divided into learning data for 308 subjects and test data for the remaining one subject. 10-fold cross validation was performed using the learning data, and the intercept of a model function and a partial regression coefficient of seven features contained in a linear differentiation model were determined. The coefficient was used to estimate the pain level of test data for 12 samples of one subject. This process was repeated 309 times for the number of subjects. Subjects with differentiation accuracy less than the chance level were excluded from the data. The accuracy of the differentiation model was increased by continuing this process until there was no subject with differentiation accuracy less than the chance level to obtain the "differentiation model for both hot and cold pain".

The final differentiation model was used to differentiate and estimate test data obtained in a different hot stimulation experiment (40° C., 44° C., and 48° C. were randomly applied) in accordance with temporal changes (trend analysis). The test data was from seven electrodes at the frontal, mid, and parietal portions in the same manner as the data for creating a differentiation model. The 15 second absolute mean amplitude was calculated by the moving average method in the same manner for model creation. The feature was inputted into the differentiation model for both hot and cold pain to calculate the temporal change in pain estimation values. The correlation coefficient of estimation value and COVAS value was calculated to find the degree of match of the temporal change in the estimation value with subjective evaluation.

(Results and Discussion)

Figure 15:
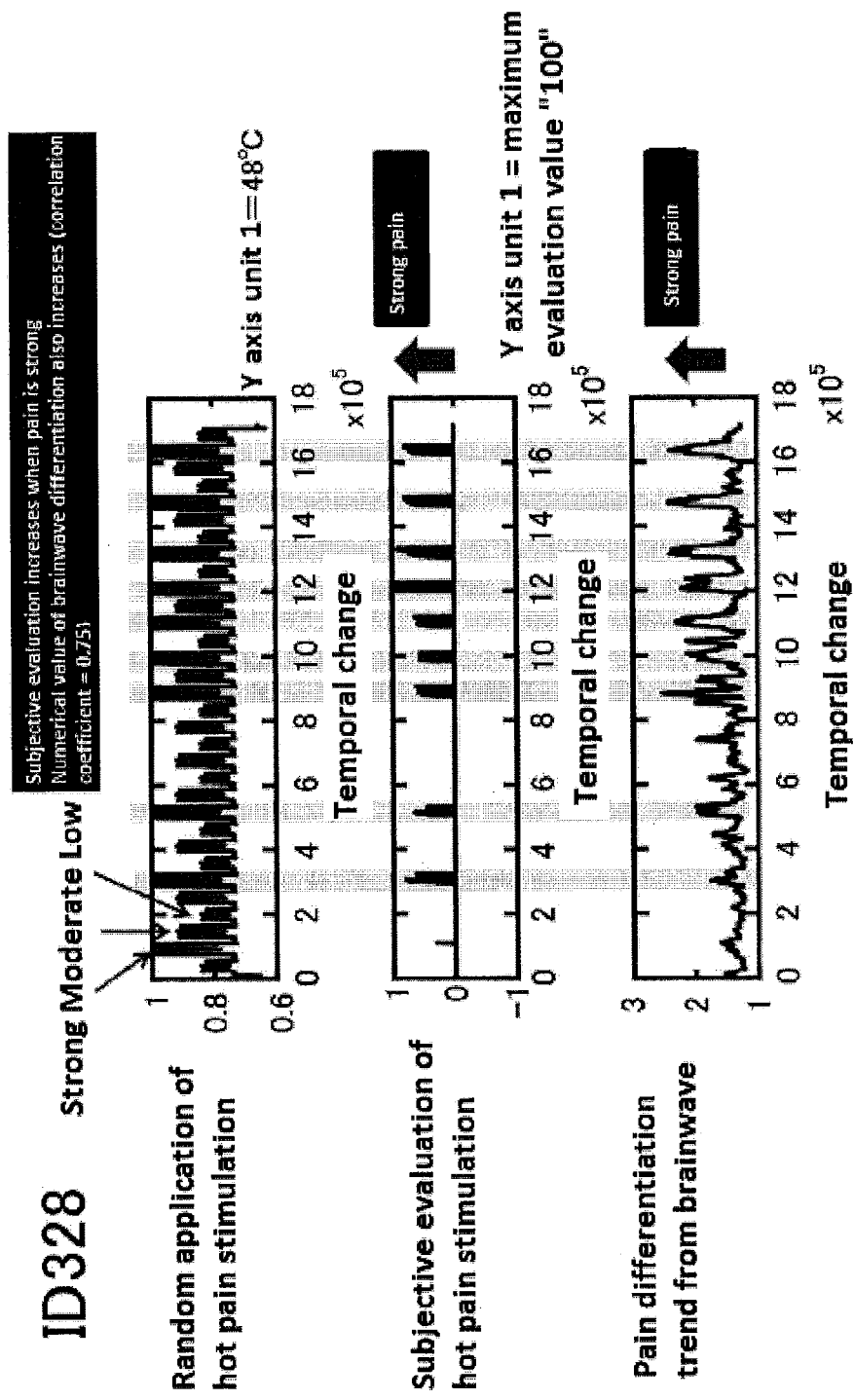
FIG. 15 shows an Example for ID328.
Figure 16:
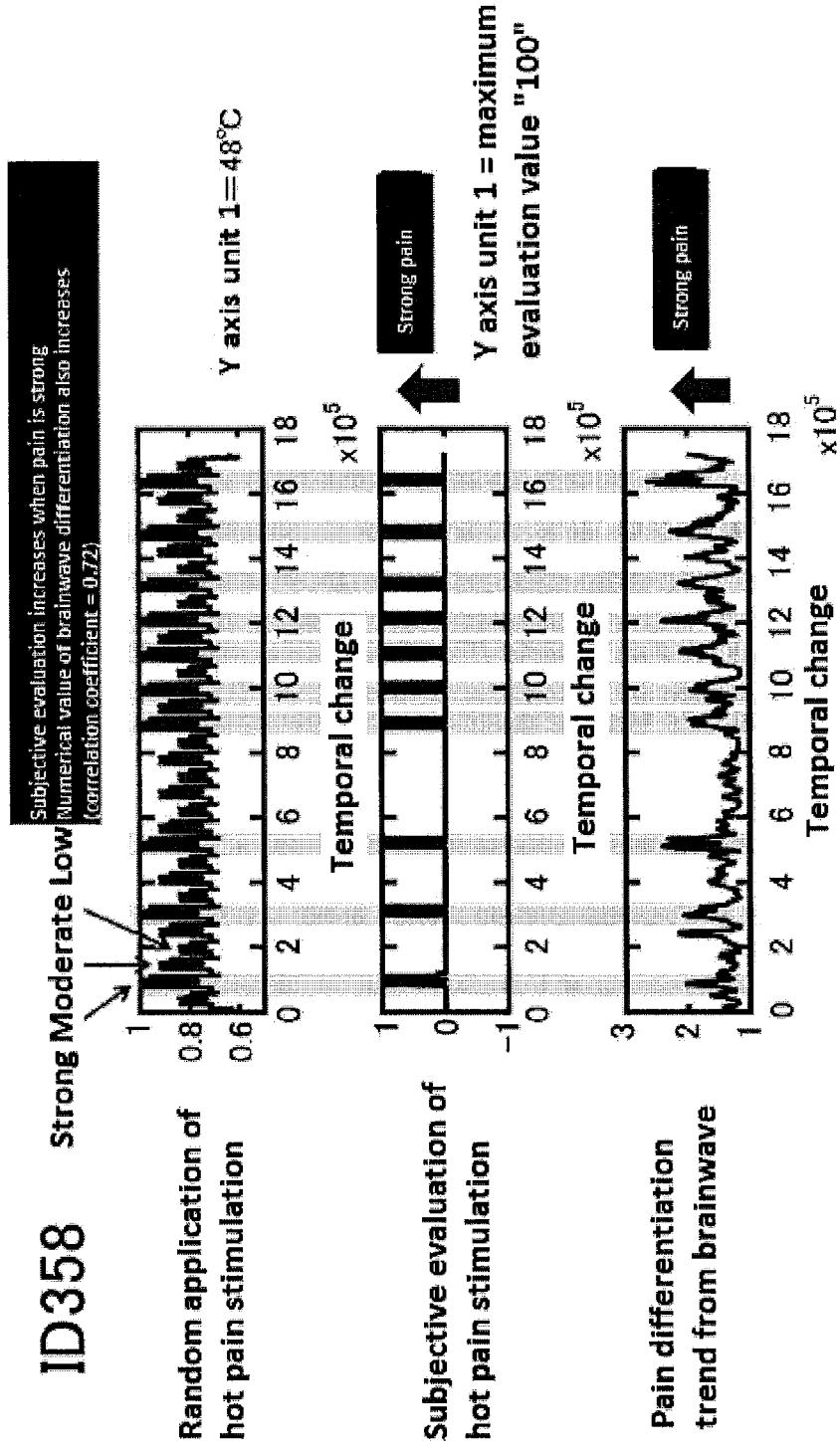
FIG. 16 shows an Example for ID358.
Figure 17:
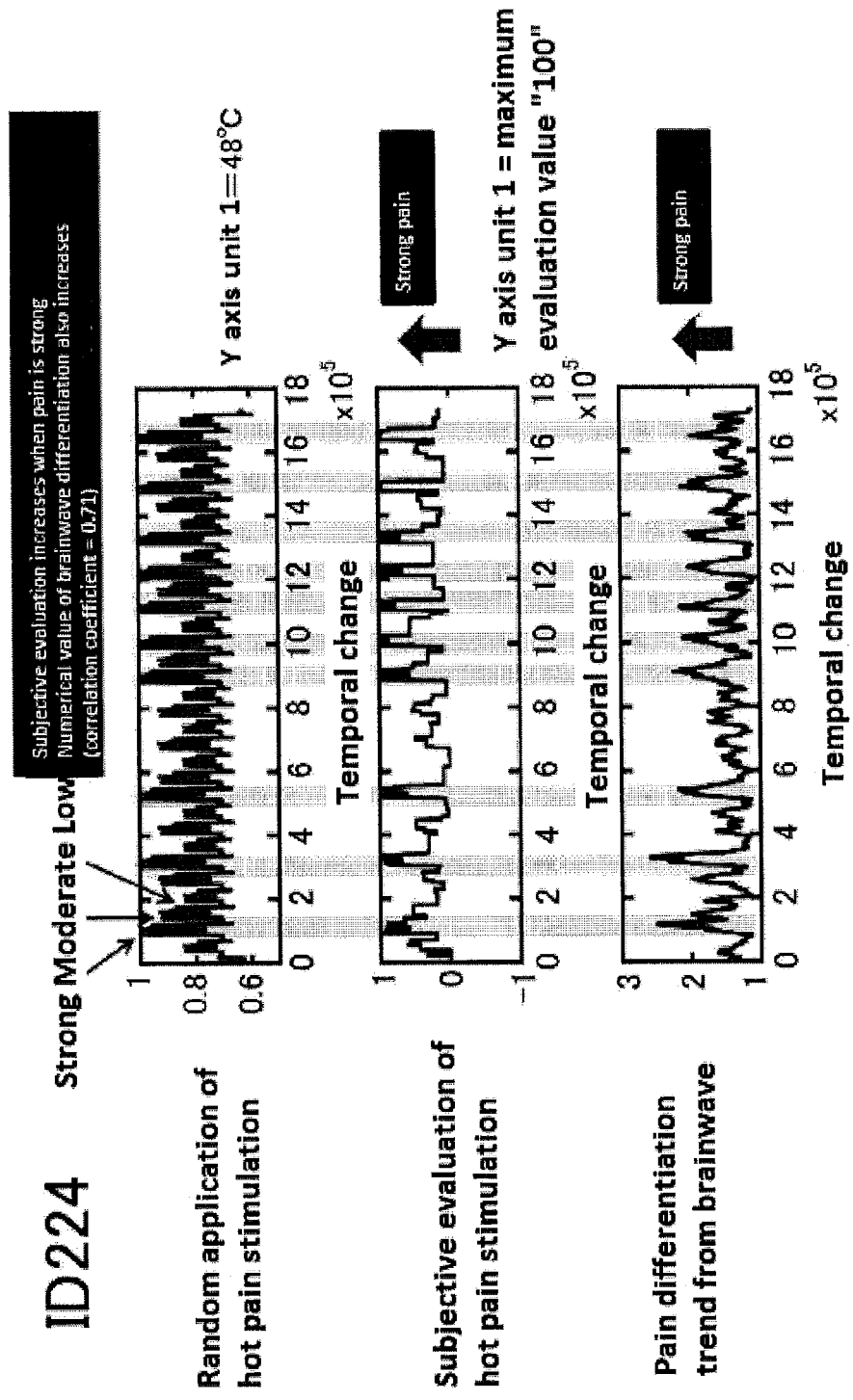
FIG. 17 shows an Example for ID224.
Figure 18:
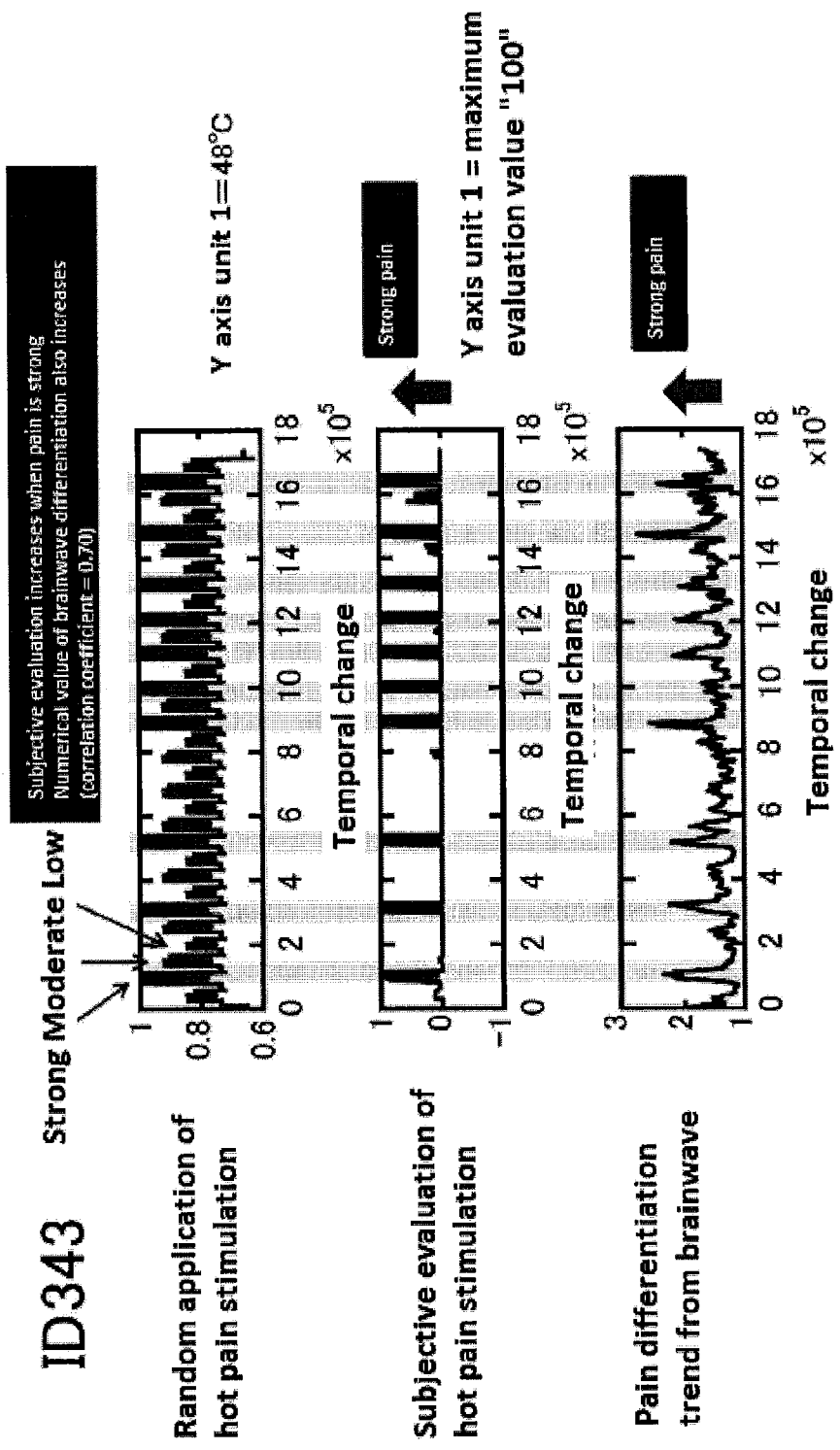
FIG. 18 shows an Example for ID343.
Figure 19:
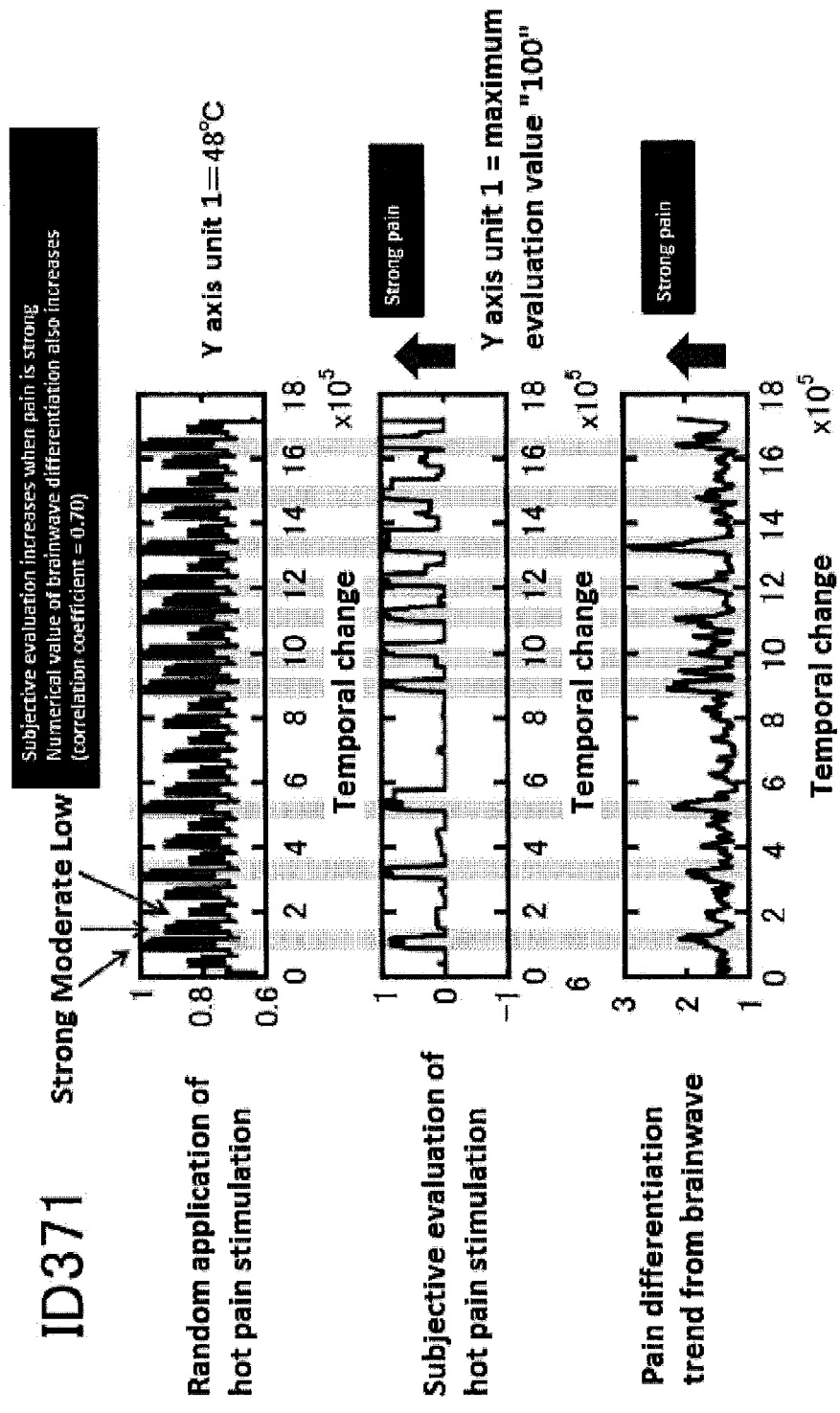
FIG. 19 shows an Example for ID371.
Figure 20:
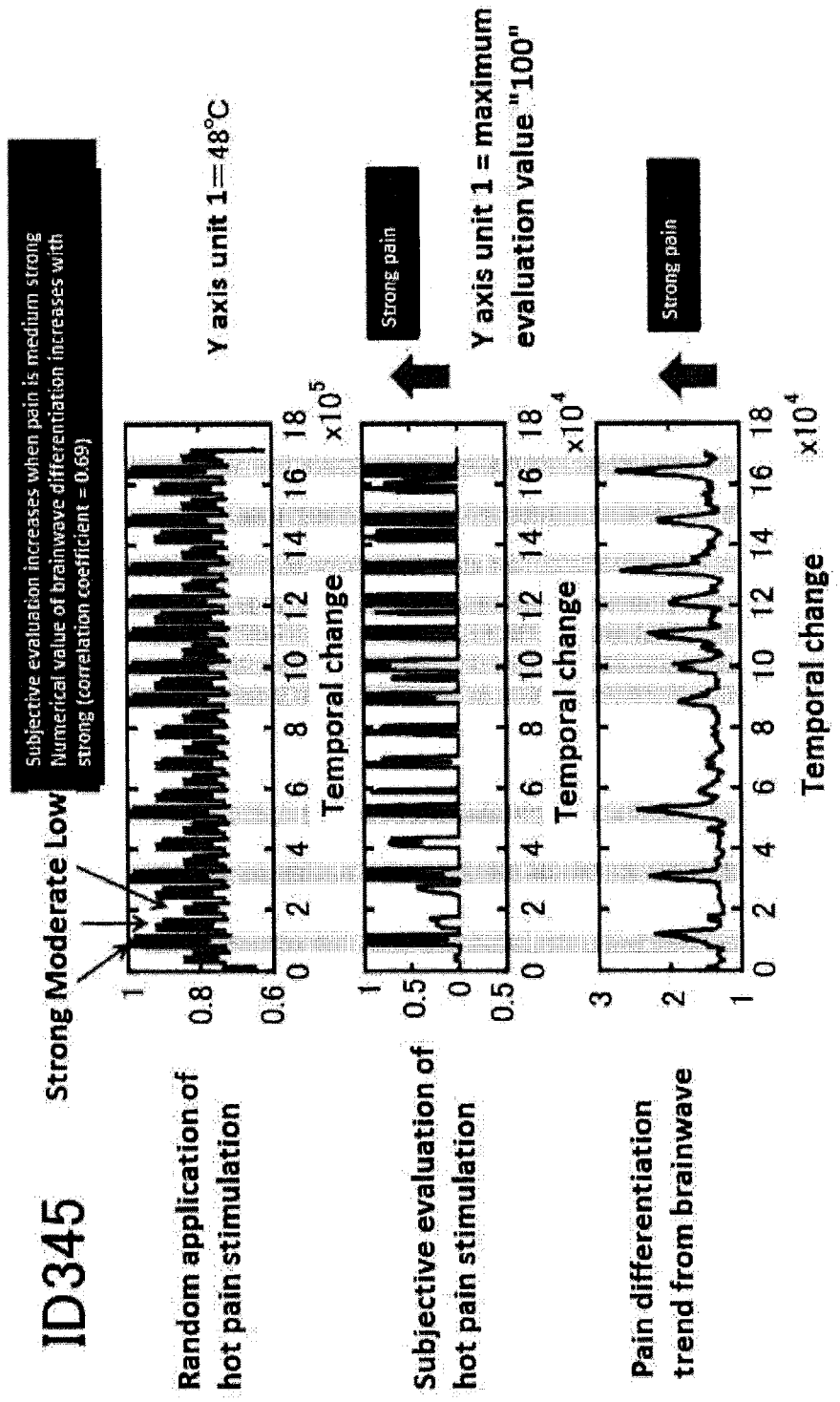
FIG. 20 shows an Example for ID345.
Figure 21:
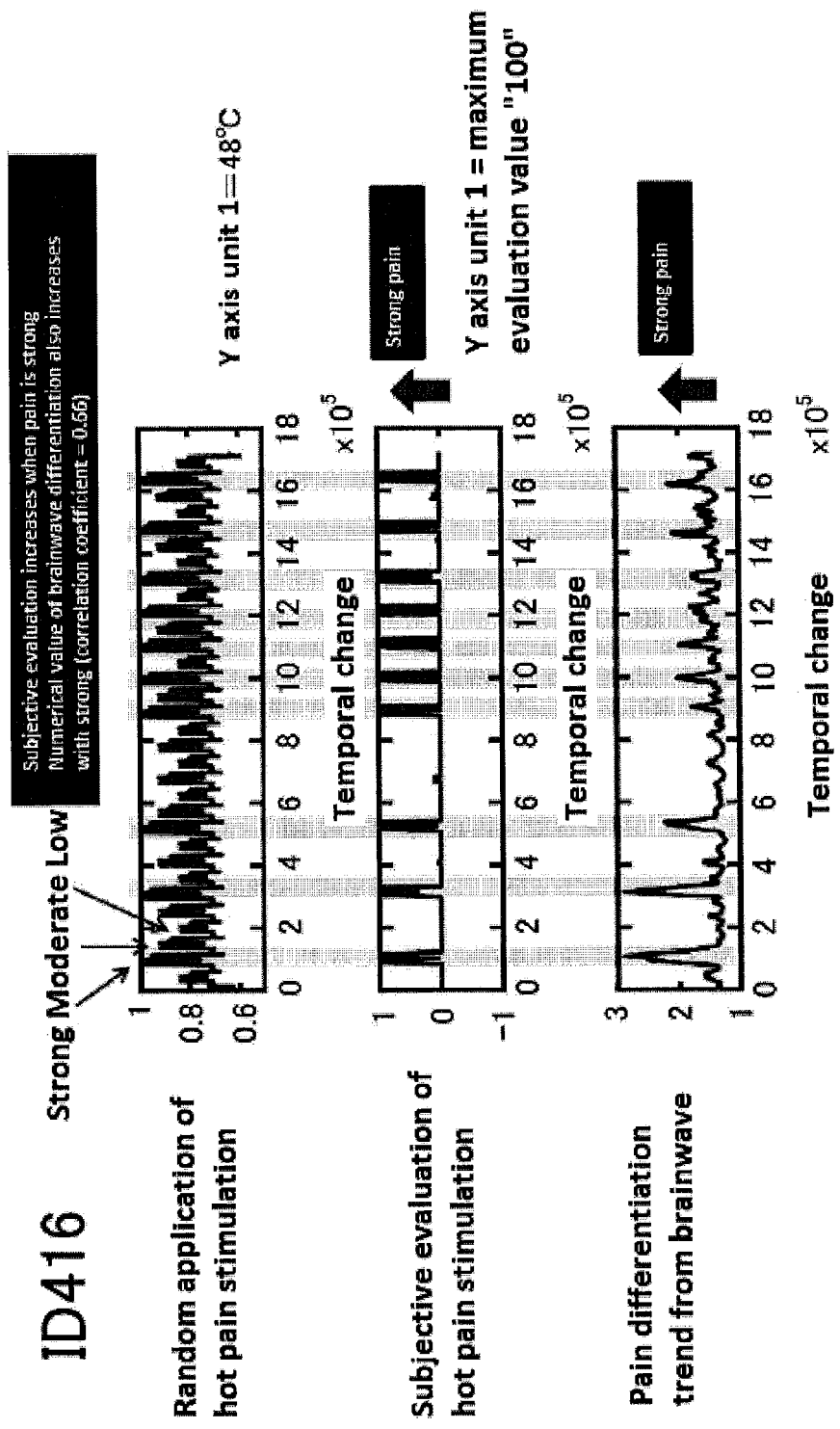
FIG. 21 shows an Example for ID416.
Figure 22:
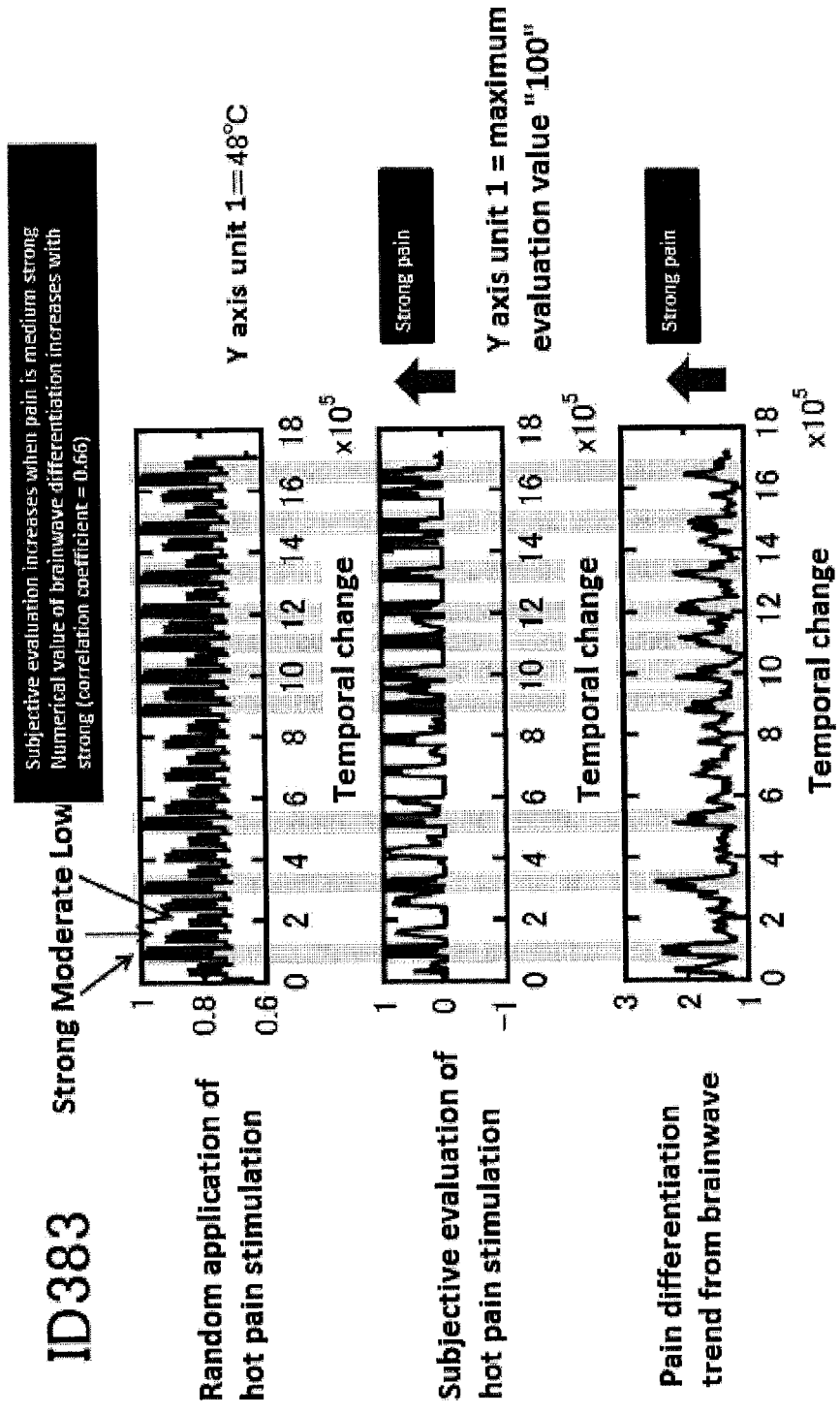
FIG. 22 shows an Example for ID383.
Figure 23:
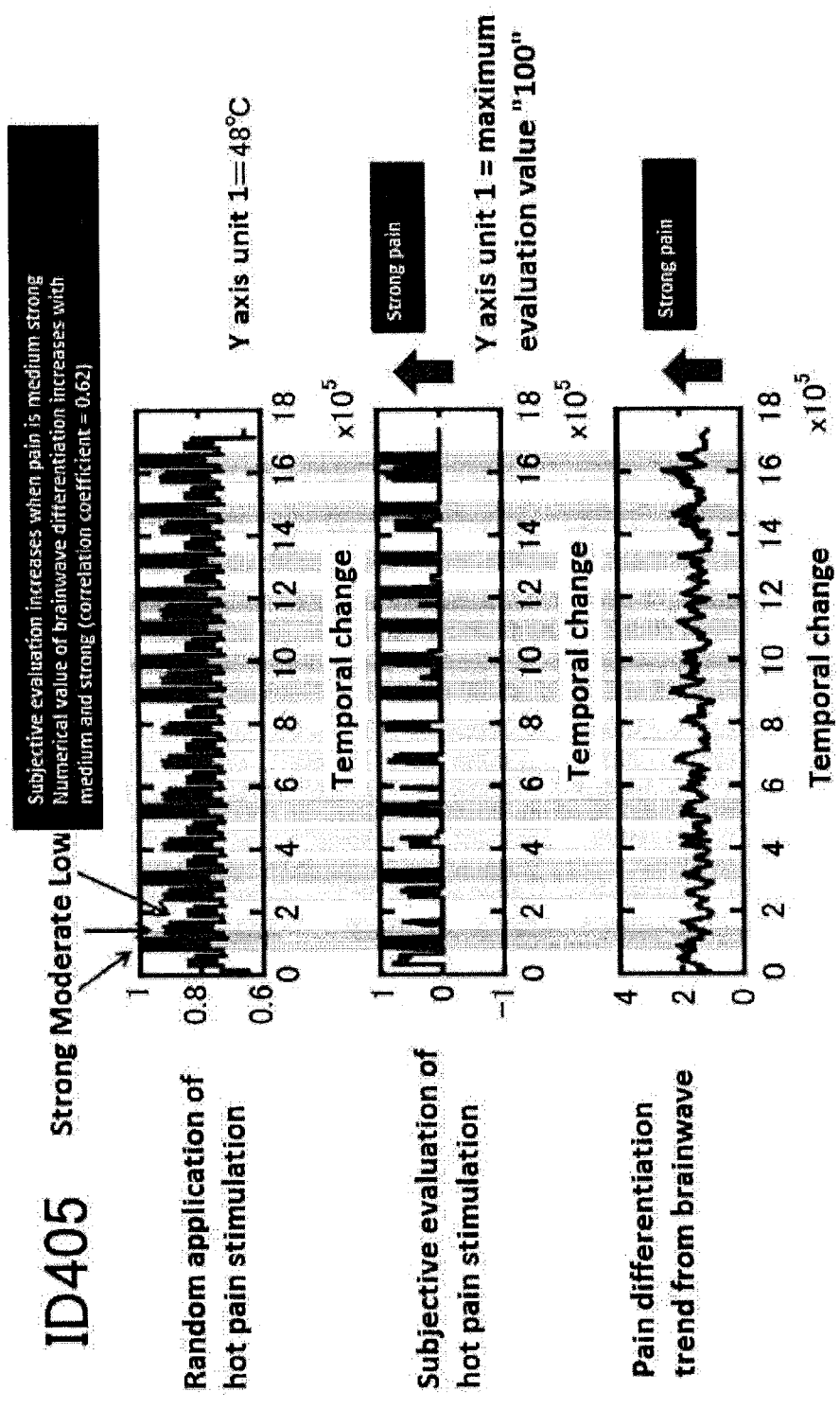
FIG. 23 shows an Example for ID405.
Figure 24:
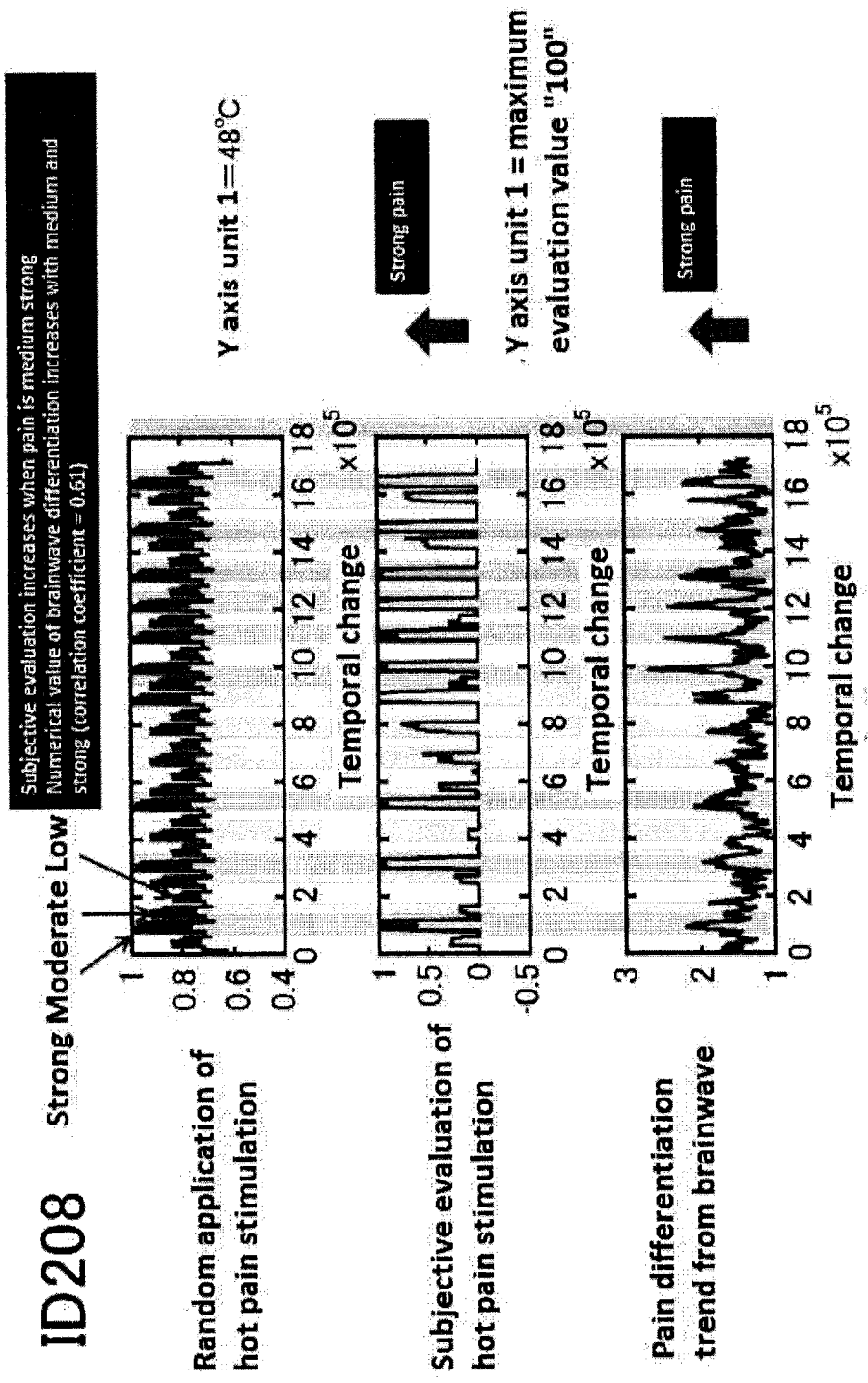
FIG. 24 shows an Example for ID208.

The number of subjects in the differentiation model for both hot and cold pain after refinement was "total of 216 (70%)", and the differentiation accuracy was "84.3±17%". The mean feature coefficients of all 216 models were Fp1=0.092, Fp2=0.058, F3=0.082, F4=0.067, C3=0.055, C4=−0.050, and Pz=−0.005, and the intercept was 1.51. The following differentiation model for both hot and cold pain was obtained therefrom.

$$Y=0.092 \times x1+0.058 \times x2+0.082 \times x3+0.067 \times x4+0.055 \times x5-0.050 \times x6-0.005 \times x7+0.151$$

x1: Fp1 feature
x2: Fp2 feature
x3: F3 feature
x4: F4 feature
x5: C3 feature
x6: C4 feature
x7: Pz feature Pain estimation values were chronologically calculated from independent data of the hot stimulation experiment which randomly applied 40° C., 44° C., and 48° C. stimulation by using the model for both hot and cold pain described above. FIGS. 15 to 24 show results for 10 subjects whose correlation coefficient between the pain estimation value and pain subjective evaluation value (COVAS) was r>0.6. The result for subject ID 328 in FIG. 15 is explained as an example. The graph on the top row shows the method of applying three stimulations used in the experiment. The highest numerical value is 48° C., and the lowest numerical value is 40° C. Three types of stimulation were randomly applied. The second row is the subjective evaluation value of pain to hot stimulation. When the numerical value is "0", the subject does not feel any pain. A higher numerical value indicates that the subject feels a stronger unpleasant pain. The bottom row shows pain estimation values calculated by a differentiation model for both hot and cold pain using seven brainwave amplitude features. As can be understood from visual inspection, a pain estimation value is elevated for a higher subjective evaluation value. It can be understood that particular, in the latter half of estimation segments, subjective evaluation is high for only the 48° C. stimulation, and pain estimation values selectively increase significantly at the time. The goodness of fit of the subjective evaluation and estimation value had a correlation coefficient of 0.75, indicating that the match therebetween is also statistically high.

The results in this Example use only one of the simplest features, i.e., brainwave amplitude. The fact that there are cases where a pain estimation value and subjective evaluation exhibit high fit as shown in FIG. 15 despite of the above means that if a better differentiation model is used, a temporal change in pain can be monitored with more accuracy. FIGS. 15 to 24 show data for ID328, ID358, ID224, ID343, ID371, ID345, ID416, ID383, ID405, and ID208, respectively. Figures other than FIG. 15 also demonstrated that a temporal change in pain can be monitored with the same accuracy.

In this manner, it was demonstrated that pain can be measured efficiently with application of pain stimulation by using a differentiation model (multiple regression model) that uses a mean amplitude.

(Example of Refining Trend Analysis 2)

In this Example, trend analysis was improved by using hot stimulation experimental data, increasing features, and refining a differentiation model. (FIG. 25) shows the outline of the method of improvement.

This is explained in detail hereinafter.
(Method)
(Participant)

170 healthy adult male and female subjects in their 20s to 70s participated in a high temperature stimulation paradigm experiment. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

A temperature stimulation system (Pathway; Medoc Co., Ltd., Ramat Yishai, Israel) was used to apply high temperature stimulation to the right forearm of the participants. High temperature stimulation included six levels of temperature intensities (increased by 2° C. from 40° C. to 50° C.). Each temperature level consisted of three stimulations with about a 5 second inter-stimulus interval (ISI). Each stimulation had a plateau that lasted for 5 seconds, and a waiting period for increase and decrease from the standard temperature (35° C.) was about 10 seconds. After three stimulations at each level, the intervals between blocks lasted 100 seconds. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Recording)

Brainwaves were continuously recorded during the test from four poles at the frontal portions (Fp1, Fp2, F3, and F4), with the reference electrodes to both earlobes, the electrode in the left hemisphere to the left earlobe, and the electrode in the right hemisphere to the right earlobe. An earth electrode was placed on the forehead. The sampling frequency was 1000 Hz. The band filter was 0.3 to 120 Hz. The impedance was 15 kΩ or less.

(EEG Analysis)
(Extraction of Feature of Amplitude)

First, the eye movement noise (EOG) in the continuous EEG data recorded under high temperature stimulation conditions was diminished. Main component analysis was performed using data from four electrodes, and the first component was extracted as an EOG component (procedure 1 in FIG. 26). To leave only the EOG component, data was passed through a 1 to 30 Hz band pass filter. The following regression filter was then applied to remove the EOG component from EEG (procedure 2 in FIG. 26).

Raw EEG=β×EOG+C

EEG estimate=raw EEG−β×EOG [Numeral 9]

β: regression coefficient
C: intercept
EEG estimate: estimated EEG

Figure 27:
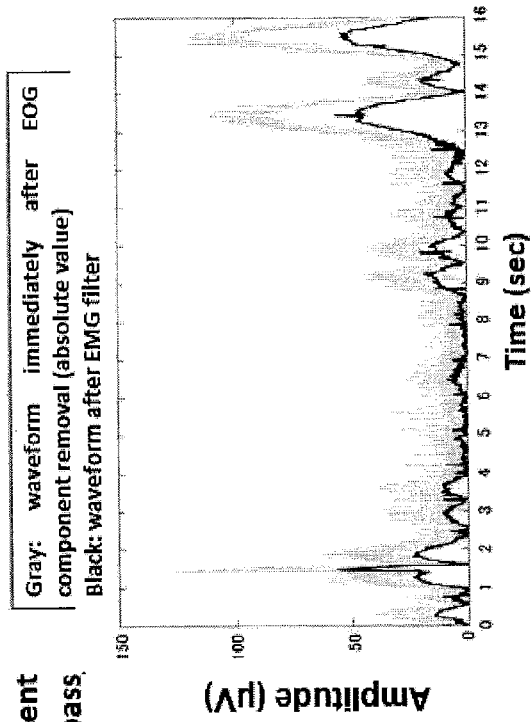
FIG. 27 shows feature extraction process (2): process for removal of EMG. Process 1: 3× length of stimulation section is set to a low cut frequency and 30 Hz high cut frequency in the waveform after removal of EOG to eliminate noise components from the wavelength. *3× stimulation section was used because brainwave activity continues after application of stimulation, so this was set to be weak. Since components of 30 Hz or greater are removed from the original data at this stage, "$\gamma$ band" was not used here as a feature.

After EOG correction, 30 Hz high pass filter was applied to an EEG waveform for 3-times the stimulation application segment of 15 second, i.e., 45 seconds (1/45s=0.022 Hz) to reduce the myogenic potential (procedure 1 in FIG. 27=EMG removing process). The EOG component that used the EOG removing process was reverse utilized as the "fifth data" (procedure in FIG. 28). This takes into consideration the fact that the blink reflex changes with pain. Data from 5 seconds after applying stimulation to 15 seconds after applying stimulation was sampled each second, for each electrode and each level of stimulation to obtain a total of 180 epochs for each electrode. After conversion to an absolute value for each epoch, the mean potential was calculated, and a z value was calculated using the standard deviation and mean potential for 30 seconds before starting the experiment.

(Extraction of Feature of Frequency Power)

For frequency analysis, 180 epochs of each electrode used for creating a feature of amplitude were subjected to Fourier transform and then the frequency power was calculated (data from log 10 conversion of real number portion). The mean value of frequency power in the δ (1 to 3 Hz), θ (4 to 7 Hz), α (8 to 13 Hz), and β (14 to 30 Hz) bands was calculated for each hot stimulation level. The z value was calculated for each electrode and each frequency band using the standard deviation and mean frequency power of 30 second rest.

(Pain Differentiation Analysis by Machine Learning)

Having pain (level 6) and no pain (level 1) from thermal stimulation on 170 participants were differentiated using machine learning of linear multiple regression models. 25 features (standardized among individuals) obtained by the extraction method described above were used. For each individual, the pain levels of 30 samples of having pain and 30 samples of no pain were differentiated and estimated by the following procedure. First, all 10200 samples were divided into learning data for 10140 samples of 169 subjects and test data for 60 samples of one subject. 10-fold cross validation was performed using the learning data, and a partial regression coefficient of 25 features in a linear differentiation model were determined. The coefficient was used to estimate the pain level of test data for 60 samples of one subject. This process was performed 170 times for the number of subjects. Subjects with differentiation accuracy of less than 70% were identified and excluded from the data. The accuracy of the differentiation model was increase by continuing this process until there was no subject with differentiation accuracy of less than 70% to create the final version of the pain differentiation model. Data for all 170 subjects were retested using the final differentiation model and feature data created during 10 seconds from 5 to 15 seconds after applying stimulation which is associated with sharper pain with less effect of noise.

The final differentiation model was used to differentiate and estimate test data obtained in a different test on subjects who did not participate in this test (40° C., 44° C., and 48° C. were randomly applied) in accordance with temporal changes. The test data was from an EOG channel obtained by main component analysis and four electrodes at frontal portions in the same manner as the data for creating the final differentiation model. 25 features of the absolute mean amplitude and frequency power ($\delta$, $\theta$, $\alpha$, $\beta$) during 15 seconds were obtained by moving processing for creating while shifting by one point at a time. The features were inputted into the final differentiation model to calculate the pain estimation values to estimate the temporal change in pain.

To quantify the degree of certainty of pain generation, "pain occupancy (PO)" was calculated using the pain estimation value obtained upon creation of the final differentiation model. Pain occupancy is a new "pain differentiation support indicator" calculated based on the number of estimation values for samples of no pain and the number of estimation values for samples of having pain obtained upon creation of the final differentiation model. The minimum value and maximum value are found from all pain estimation values, and the range thereof is divided, for example, in a unit of 0.1. This unit is determined by the breadth of the range and the density of estimation values, but it is desirable that occupancy can be continuously shown in accordance with the change in the estimation value as much as possible if there are both or one of the estimation values for having pain/no pain in each unit. Occupancy (%) is calculated by the following equation.

$Po_i$=number $_i$ of estimation values for sample having pain/(number $_i$ of estimation values for sample for having pain+number $_i$ of estimation values for samples with no pain)×100 i: number of divisions in the range of pain estimation values

For example, if the pain estimation value is in the range of "−1 to 2", the range is divided into a unit of "0.1". The number of estimation values for having pain at an estimation value of "1" is set to "30" and the number of estimation values for no pain is set to "10". In such a case, the likelihood of having pain is "30/(30+10)×100=75%" for unknown pain sample data. Investigators monitoring pain can objectively differentiate pain by using this indicator.

(Results and Discussion)

Figure 29:
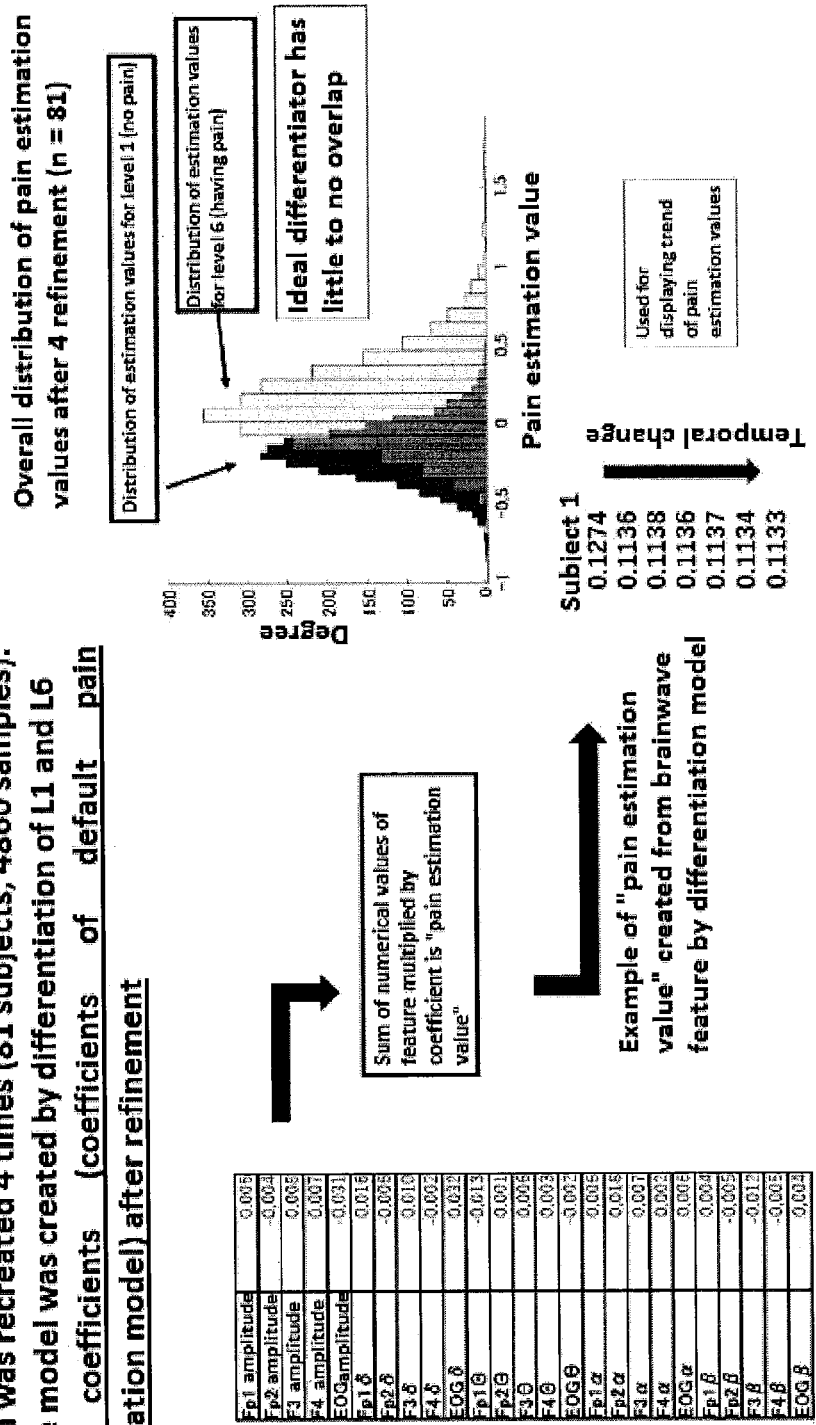
FIG. 29 shows a differentiation model (standardized in rest section, with EOG feature). Subjects at or below the chance level were removed, and the model was recreated 4 times (81 subjects, 4860 samples). The base model was created by differentiation of L1 (40° C.) and L6 (50° C.). The left side shows feature coefficients (coefficients of default pain differentiation model) after refinement. The right graph shows the overall distribution of pain estimation values after four refinements.

FIG. 29 shows a feature coefficient of the final differentiation model and a histogram of pain estimation values for the remaining 81 subjects after refinement of the model. Subjects with differentiation accuracy of less than 70% were repeatedly removed. The model was refined to increase the differentiation accuracy for a total of "4 times". Subjects contained in the final differentiation model was "81" thereby. As shown in FIG. 29, estimation values for samples with no pain (n=2430) and estimation values for samples having pain (n=2430) exhibit a double peak distribution with non-overlapping areas while including area where they both overlap. In other words, the overlapping area is an area where incorrect judgment of having pain is likely to occur. FIG. 30 summarizes the differentiation accuracy information for the final model. For differentiation accuracy of the final model, 5 to 15 seconds after applying stimulation was used in order to reduce noise and extract features that are more strongly related to pain. When pain was differentiated and estimated by preparing such feature data for 170 subjects, the mean differentiation accuracy was "79.4±26.4%". Subjects with differentiation accuracy of 70% or greater reached 93 (54.7%), and subjects with differentiation accuracy at or above the chance level reached 147 (86.5%).

FIG. 31 is a model constructed for pain occupancy, i.e., certainly indicator for occurrence of pain, based on the distribution characteristic of pain estimation values in FIG. 29. The minimum value of all pain estimation values (n=4860) was "−1", and the maximum value was "2". In this regard, the range of estimation values from −1 to 2 was divided in a unit of "0.1", and pain occupancy was calculated at each unit in the scale. For the actual estimation values indicated by a black marker (●), the possibility of pain occurring is 0% at "−0.9", and nearly 100% at "0.6". However, actual measurement values are sparse data with missing values, so that the occupancy of lower ranking estimation values from −1 to −2 was interpolated to "0" and fitted to a sigmoid function to create the following "pain occupancy function". Pain occupancy function:

$$y=0.20+102.71/(1+10^{(19.32-x)\times 0.16})$$

The objective judgment on pain can be more refined by using occupancy calculated by this function or a secondary indicator obtained by combining the occupancy.

Finally, FIG. 32 shows a pain differentiation model and an example of application of pain occupancy assuming actual online monitoring. The results are chronological data for about 4 minutes in the early stages when one subject was randomly applied with 40° C., 44° C., or 48° C. thermal pain stimulation multiple times. 25 features were created by a 15 second moving processing method from recorded data and inputted into the differentiation model with the feature coefficients in FIG. 29. The top row of graphs is the temporal change in pain estimation values calculated by the final differentiation model. A pattern increasing in response to an increase in the subjective evaluation of the degree of unpleasantness of pain is especially notable when 48° C. stimulation was applied. The correlation coefficient is r=0.45 (p? 0.0), thus showing significant association. Pain occupancy is shown in the second row from the top. Specifically, an increase in the pain estimation value at 48° C. indicates that a subject feels the pain as unpleasant at a probability of about 70%. In actual clinical settings, this quantitatively indicates that a physician or investigator should clinically intervene at this point.

Example 8: Comparison of Machine Learning with a Process of Contracting Features (Method)
(Participants)

40 healthy adult subjects in their 20s to 70s participated in the high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

FIG. 33 shows the summary of the high temperature stimulation paradigm used in the test. A temperature stimulation system (Pathway; Medoc Co., Ltd., Ramat Yishai, Israel) was used to apply high temperature stimulation to the right forearm of the participants. High temperature stimulation included six levels of temperature intensities (increased by 2° C. from 40° C. to 50° C.). Each temperature level consisted of three stimulations with about a 5 second inter-stimulus interval (ISI). Each stimulation had a plateau lasting 5 seconds, and a waiting period for increase and decrease from the standard temperature (35° C.) was about 10 seconds. After three stimulations at each level, the intervals between blocks lasted 100 seconds. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Analysis)
(Extraction of Feature of Amplitude)

The following regression filter was applied to continuous EEG data under high temperature stimulation conditions to reduce eye movement noise (EOG):

$$\text{Raw EEG} = \beta \times \text{EOG} + C$$

$$\text{EEG estimate} = \text{raw EEG} - \beta \times \text{EOG} \qquad \text{[Numeral 101]}$$

β: regression coefficient
C: intercept
EEG estimate: estimated EEG

Fp1 was the closest to the left eye and heavily affected by the eye movement, so that Fp1 data was used as EOG data. EOG data can be extracted from all electrode data using main component analysis, independent component analysis, or the like. After EOG correction, epoch waveforms from 5 seconds before applying stimulation to 15 seconds after applying stimulation were sampled for each stimulation level. After baseline correction using the mean potential before applying stimulation, artifacts were removed at ±100 μV. The potential was converted to absolute values, and then standardized with the maximum amplitude, and mean amplitude for 15 seconds after applying stimulation was found for each level as the brainwave amplitude feature.

(Extraction of Feature of Frequency Power)

For frequency analysis, brainwave data was sampled from the start of stimulation to 15 seconds after applying stimulation for each stimulation level without EOG correction. After Fourier transform was applied, the frequency power was calculated (data for log 10 conversion of real number portion). The mean value of power was calculated for each level for each of δ (1 to 3 Hz), θ (4 to 7 Hz), α (8 to 13 Hz), β (14 to 30 Hz), and γ (31 to 100 Hz) and standardized with the maximum value for each individual using data for all levels as the frequency feature (4 electrodes×5 bands=20 features).

(Differentiation Analysis with Contracting of Number of Features)

High temperature stimulation on 40 participants was differentiated using Support Vector Machine Recursive Feature Elimination (SVM-RFE) (Guyon I, Weston J, Barnhill S, & Vapnik V. Gene selection for cancer classification using Support Vector Machine. Machine Learning 46, 389-422, 2002) (FIG. 34). As shown in FIG. 34, "24" features (standardized among individuals) was used. The pain level was set to "two levels (painful/not painful)". 24 brainwave features were ranked as the ranking of features. The differentiation algorithm was determined by finding a combination of features with the highest differentiation accuracy with "leave-one-out cross validation" of data using support vector machine (SVM). Randomizing tests (1000 times) were conducted by randomizing the unpleasantness label and calculating differentiation accuracy of the chance levels using the number of features with the highest differentiation accuracy (deemed significant differentiation accuracy if accounting for the top 95% or greater). Statistical software package R and R-code of SVM-RFE (http://github.com/johncolby/SVM-RFE) were used for data analysis. The detailed flow is shown in FIG. 34, which is specifically as follows.

Features were arranged in the order of no pain to having pain, and an approximating sigmoid function or a step function is generated. A sigmoid function (Numeral 102) and a step function (Numeral 103) are expressed as follows.

$$Y = 1/e^{-ax} \qquad \text{[Numerical 102]}$$

a: gain $$Y = 0 \text{ if } x < a$$

$$Y = 1 \text{ if } x > a \qquad \text{[Numeral 103]}$$

All 24 features were approximated with an approximation function (simple linear regression or correlation analysis), and 24 approximation indices ($R^2$ values or correlation coefficients) are calculated (S10010). Next, the features are ranked based on the magnitude of the approximation indices (absolute value). Greater approximation index indicates higher ranking and feature having a better fit according to a binomial classification property of having pain or no pain (S10020). Top ranking features are inputted into an SVM model one at a time in order. The differentiation accuracy of each model was calculated by leave-one-out cross validation on 240 samples. A radial basis (Gaussian) function was used as the kernel (Numerical 104). Cost=10 and Gamma=1/number of dimensions were used as the model parameters (S10030).

Radial basis function:

$$G(x1, x2) = \exp(-|x1 - x2|^2) \qquad \text{[Numeral 104]}$$

G: radial basis (Gaussian) function
x: data point
exp: exponential function.

The model with the highest differentiation accuracy and fewest features among all 24 models was defined as the "economical differentiation model" (S10040).

(Results and Discussion)

FIG. 35 shows a ranking list for 24 features and top ranking features in descending order. It was found that compared to a differentiation model using all 24 features, an economical pain differentiation/estimation model exhibits a "71.3%" two level pain differentiation accuracy by using only two top ranking features with high sigmoid approximation.

For the existing SVM-RFE model (economical pain differentiation/estimation model, 1) the same top 4 types of features were included in the existing SVM with contracting of features as a model for sigmoid contracting 2) used as the comparative example. 2) While the same "71.3%" differentiation accuracy is materialized with one feature, the difference was only one feature. 3) Calculation cost is high because leave-one-out cross validation is performed 240 times for single SVM model construction, and this process is performed 24 times for ranking 24 features.

FIG. 37 shows a difference in calculation cost for sigmoid contracting and contracting in SVM-RFE. The differentiation model with contracting of the invention can be generated by 1) creating a differentiation function, 2) fitting this to each feature to calculate a model approximation coefficient, and 3) ranking features based on the coefficient, while model generation is conducted under the following conditions for SVM-RFE.

Abbreviations

Training data

Sample=$[x_1, x_2, \ldots, x_k, \ldots, x]$

Classification label

Class=$[1,0,1,0, \ldots, y_k, \ldots, y]$

Set of features remaining after RFE

Sfeature=$[1, 2, \ldots, n]$

Feature ranking

Rank=[ ]

For SVM-RFE, the following process is repeated the same number of times as the number of features to obtain a ranking of features.

1. Limit Training Data to Remaining Features

X=Sample(:,Sfeature)

2. Train a Differentiator (SVM)

Classifier=SVM(X,Class)

3. Calculate Weighting Coefficients of Feature

Weight=$\Sigma a_k y_k x_k$

4. Calculate Ranking Criterion for all Features

Criterion=(Weight)$^2$, for all $_i$

5. Find the Feature with the Lowest Ranking Criterion

F=argmin(Criterion)

6. Update Ranking List of Remaining Features

Rank=[Sfeature(F),Rank]

7. Exclude Feature with the Lowest Ranking Criterion

Sfeature=Sfeature(1:f−1,f+1:length(Sfeature))

8. Output Feature Ranking List:
Feature ranked list r,
Since these steps are repeated the same number of times as the number of features, cross validation for 240 samples would be repeated 24 times, such that the cross validation cost performed before identifying an actual economical differentiation model was 5760 times. Meanwhile, the present invention does not perform differentiation analysis for ranking features, so the calculation cost is much lower than that described above.

Even after re-ranking using a value of difference (Diff) in differentiation accuracy of adjacent models that are n−1 feature and n feature models (S10020), differentiation analysis (S10030), and model determination (S10040) as shown in FIG. 34 (also see Example 11 described below), the value of difference (gain) in differentiation accuracy between No. 1 and No. 2 features is the greatest (6.1%) as shown in FIG. 35, so that a model using the No. 1 and No. 2 features would be the model with the highest differentiation accuracy (71.3%).

(Discussion)

The Examples in the present invention are 1) advantageous over conventional SVM that uses all features. For example, SVM using all features differentiates and estimates by using all features obtained without selecting features, SVM had problems of using features with low contribution, and not necessarily resulting in the best differentiation accuracy. The Examples in the present invention are also 2) advantageous over the comparative example SVM-RFE. SVM-RFE shown in 1 to 8 described above contracts features by repeating differentiation/estimation over and over. However, this has a problem of high calculation cost and correlation bias of features. In other words, the problem is that a high number of features with strong correlation can result in an error of evaluating the features lower than reality such that the features are eliminated from the model. It was also problematic that features that remain until the end are not necessarily feature with the highest classification ability. In comparison, contracting of the invention is a process of using a sigmoid or step function changing between two values of "0, 1" as shown in the example of binomial classification to select a feature that fits the function as much as possible. This is based on a simple idea that it is desirable to find a feature corresponding to "0, 1" because the objective is to separate into "0, 1". This is significant in that use of a model by selecting features from top of the ranking is able to produce the best result with minimum effort. Although not included in the Examples, the present invention can include, as a secondary process, a model tuning technology for further improving the differentiation accuracy of a model by sequentially including excluded features to the optimal model created from the top ranking features.

Example 9: Validation of Economical Differentiation Model

This Example validated a model using top ranking features used in the economical differentiation model identified in Example 8.

(Method)

Participants, experimental method, EEG data collection method, and analysis method are in accordance with Example 8. An economical differentiation model was validated as follows. First, all 240 samples were divided into 10 without randomization among subjects, and 10 data sets were created for each 4 subjects. 90% (for 36 subjects) was used as data for creating a machine learning (SVM) model, and the pain level of the remaining 10% (4 subjects) was differentiated/estimated. In other words, a method of differentiating among subjects was employed. The features used were the top two ranking features (Fz or Fpz) identified in Example 8. Cost=10 and Gamma=½ (number of dimensions) were used as the model parameters (Results)

Results of 10 cross validations are shown in the table of FIG. 38. The range of differentiation accuracy was "62 to 83%" and the mean differentiation accuracy was "71.5%". The economical differentiation/estimation model has differentiation accuracy exceeding 70% for differentiation/estimation among subjects using test data of different objects. Thus, it was found that a feature of Fz or Fpz, or the vicinity thereof can be generally useful for differentiating pain.

Example 10: Differentiation/Estimation Model with Process of Double Contracting

Examples 8 and 9 validated a model creation process for contracting features by fitting an approximation function to the features. This Example studies a model creation process with a process of contracting in a larger scale differentiation/estimation process using about 30000 samples and double the number of features, i.e., about 50.

(Method)

(Participants)

132 healthy adult subjects in their 20s to 70s participated in high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

Figure 39:
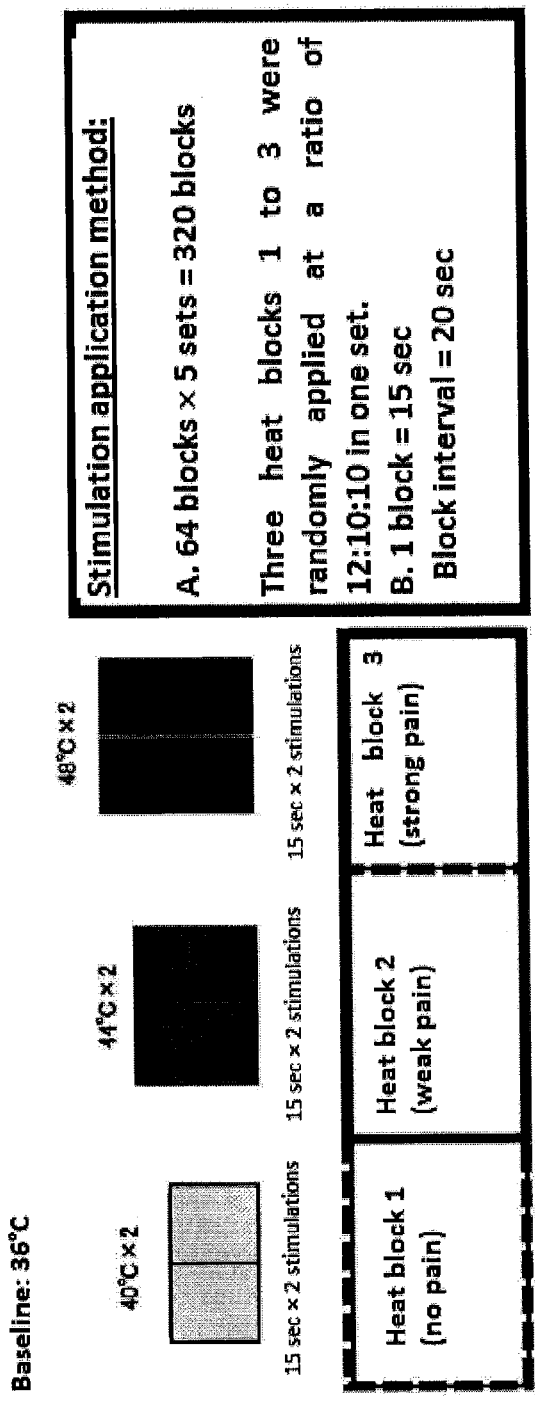
FIG. 39 shows a high temperature stimulation block paradigm used in an experiment for creating a model for differentiating 32160 samples. The paradigm includes three blocks for no pain, weak pain, and strong pain. Each stimulation was applied for 15 seconds. The time interval between blocks was 20 seconds. There were a total of 5 sets, and each set included 64 blocks.

FIG. 39 shows the summary of the high temperature stimulation block random paradigm used in the test. A temperature stimulation system (Pathway; Medoc Co., Ltd., Ramat Yishai, Israel) was used to apply high temperature stimulation to the right forearm of the participants. High temperature stimulation included three levels of temperature intensities (40° C., 44° C., and 48° C.), with 36° C. as the baseline temperature. Each temperature block consisted of two stimulations with each stimulation lasting 15 seconds and block interval of 20 seconds. A set included 64 heat blocks of the three types described above at a ratio of "12:10:10". The entire test included 5 sets for a total of 320 blocks. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Analysis: Feature Extraction Process)

Figure 40:
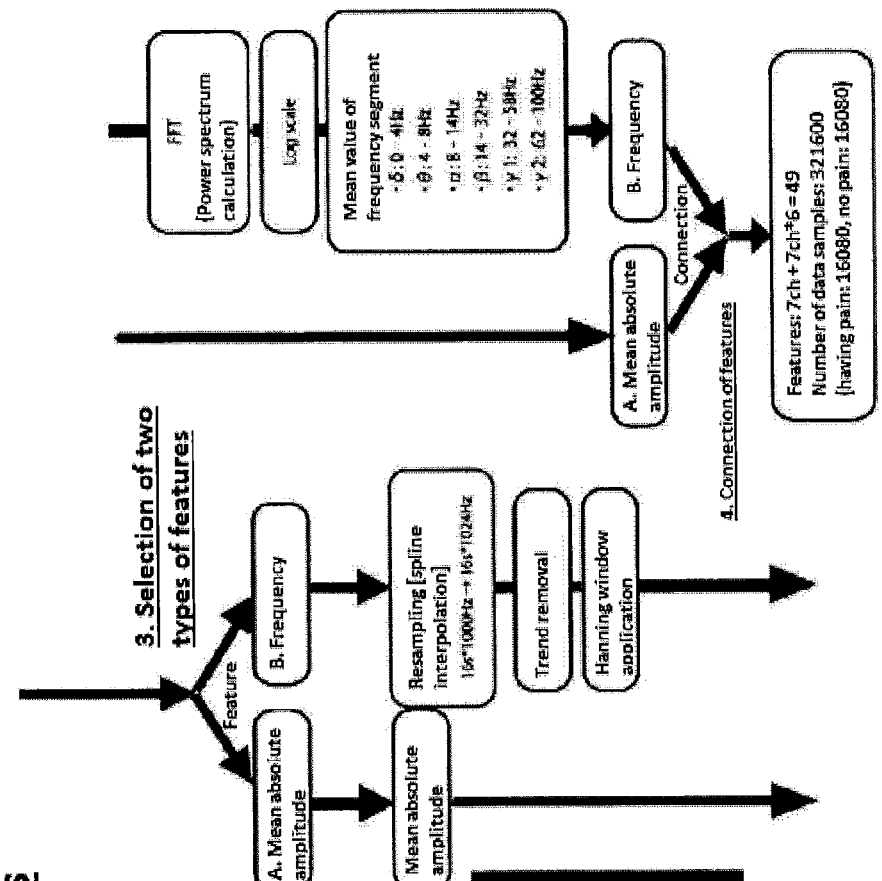
FIG. 40 shows a process of extracting a feature used in a differentiation model. The process includes 1) EEG data collection, 2) data sampling, 3) selection of two types of features, and 4) connection of features. A total of 49 features were obtained through these processes.

FIG. 40 shows the process of extracting features used in differentiation/estimation. 1) "EEG data collection" was performed using a commercially available electroencephalograph from Ag/AgC17 electrodes on the scalp (Fp1, Fp2, F3, F4, C3, C4, and Pz). The lead electrode was the earlobe. Each of the left and right electrodes was connected to the earlobe electrode on the same side. The frequency band was 0.3 to 120 Hz, and the sampling frequency was 1000 Hz. The impedance was maintained at 15 kΩ or less. 2) For "data sampling", 16080 samples for no pain and 16080 samples for having pain for a total of 32160 samples were extracted for 16 seconds after applying each stimulation from a total of 130 subjects while limited to 40° C. no pain condition and 48° C. having pain condition. 3) For the "selection of two types of features", frequency power and mean absolute amplitude of the sampled brainwave epochs were used. The data sampling frequency was resampled from 1000 Hz to 1024 Hz (to increase the speed of discrete Fourier transform), the waveform trend was removed, and Hanning window function was applied, and then FFT (Fast Fourier Transform) was performed. Log conversion was applied to the real number portion to calculate the frequency power, and the mean value of frequency power for all 6 bands (δ, θ, α, β, γ1, and γ2) was found. 4) All 49 features were obtained in each subject by "connection of features".

(Differentiation/Estimation)

Figure 41:
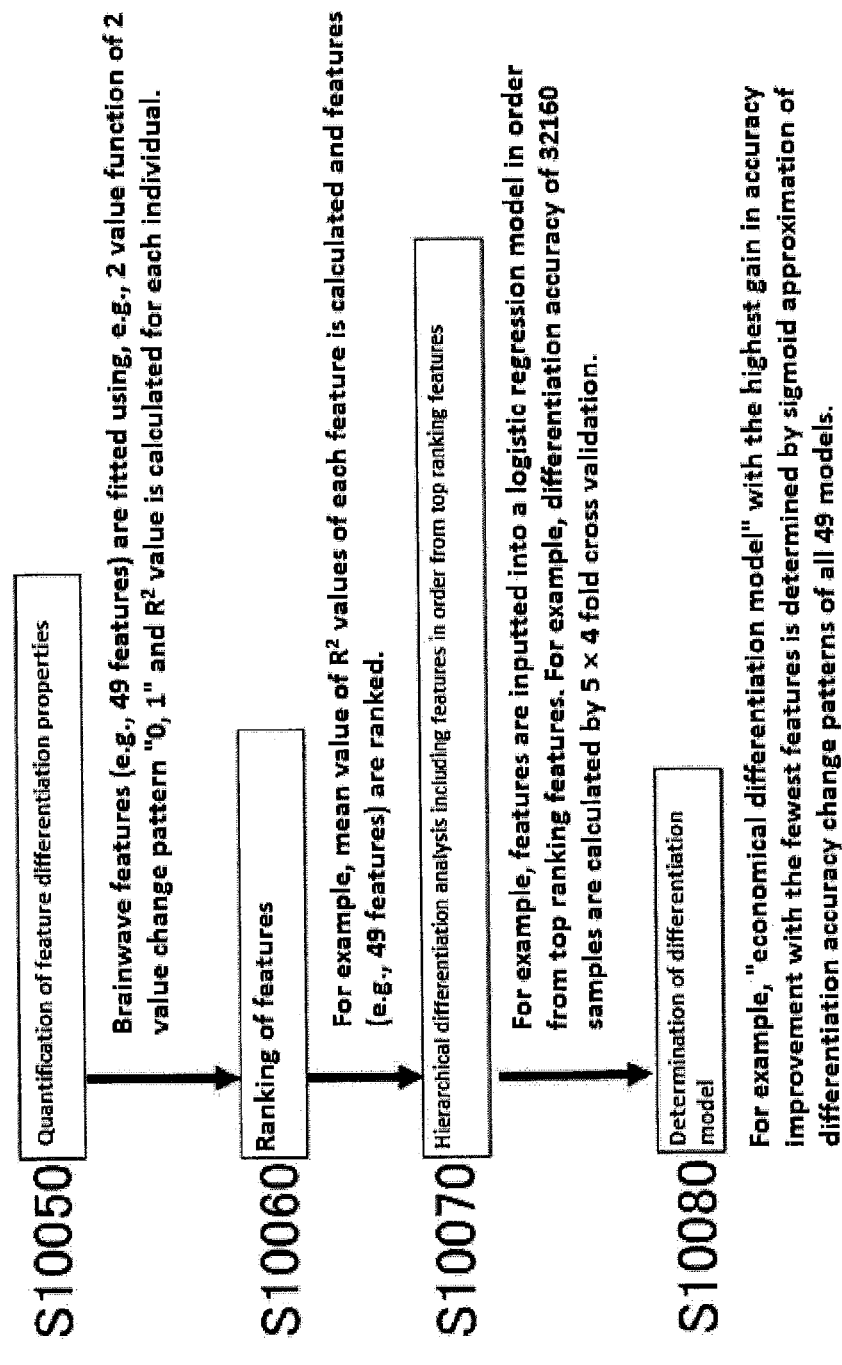
FIG. 41 shows a differentiation model determination process using double contracting process upon selecting a differentiation model and features. The process includes the same processes as the differentiation model determination process in FIG. 34 up to 1) quantification of feature differentiation properties, 2) ranking of features, and 3) hierarchical differentiation analysis that inputs features into a model in order from higher ranking features. Meanwhile, approximation of a change in differentiation accuracy using a sigmoid function or the like to select an economical differentiation model is newly included as of the final differentiation model selection. All numerical values in the figure are exemplary.

Before differentiation/estimation, 49 features were ranked in accordance with the process of FIG. 41 in the same manner as Examples 8 and 9. Specifically, samples were arranged in order or no pain and having pain for each individual, and 49 features were approximated with a sigmoid function to calculate the $R^2$ values as a fitting indicator (S10050). The mean value of $R^2$ values of 49 features of all subjects was calculated, and the features were ranked (S10060). The features were inputted into a logistic regression model in order from top ranking features to calculate differentiation accuracy of 32160 samples by 5×4 fold cross validation (S10070). This Examples using about 30000 samples differs from Examples 8 and 9 in the determination process of a differentiation model (S10080). In selecting a differentiation model in this Example, sigmoid function approximation was performed on a pattern of change in differentiation accuracy for all differentiation models. (i.e., 49 models using one feature to all 49 features), and the model with the highest gain in differentiation accuracy improvement and fewest features was determined as another embodiment of the "economical differentiation model". Of course, selection of a model when there is a model materializing the highest differentiation accuracy using the maximum number of features is not excluded.

(Results)

FIGS. 42A and B show a pattern of change in differentiation accuracy of all 49 models. FIG. 42A shows the change in mean differentiation accuracy of 5×4-fold cross validation as of model creation, and FIG. 42B shows a change in differentiation accuracy of final test data. Both patterns of change reach the first inflection point in the range of 10 to 20 features and the second inflection point in the range of 30 to 40 features. The variation range of the first inflection area is relatively greater in both data. Thus, as shown in FIG. 42C, the point where the maximum value "63.7%" in the approximation function is exceeded upon sigmoid function approximation of a change up to immediately before the second inflection area (1 to 33 feature model) using the final test data was a differentiation model using 23 features, exhibiting differentiation accuracy of "63.8%". It was found from calculating the gain in differentiation accuracy improvement by such inflection by numerical equation 5 that a gain of "54%", i.e., improvement of 54% in the overall differentiation accuracy change occurred in the area with this number of features.

Gain (%)=(approximated accuracy maximum value−approximated accuracy minimum value)/(observed accuracy maximum value−observed accuracy minimum value)×100    [Numeral 105]

FIG. 43 shows 23 features inputted into this model. While the mean amplitude includes only electrodes at the frontmost portion of the prefrontal portion of Fp1 and Fp2, nine Fp1 and Fp2 were included for frequency power, so that these two poles accounted for 40% of the whole (9/23). As shown in FIGS. 42A and B, differentiation accuracy can gradually increase by increasing features when the number of samples is high, but this Example shows that function approximation as of the selection of features and selection of a differentiation model is effective when differentiating and estimating using an economical model.

Although not wishing to be bound by any theory, the reason a differentiation model exhibited the maximum gain at 23 features in FIG. 43, i.e., the reason 23 is more "economical" than 49, is the premise of the model efficiency problem of "how to attain maximum gain with fewest number of features". It can be understood that a factor associated with a dramatic improvement in differentiation accuracy is more likely to be present in the vicinity of the inflection point for a greater gain.

Example 11: Differentiation/Estimation Model 2 with a Process of Double Contracting for Accelerating the Arrival to Maximum Gain Example 10 showed a method of using an economical differentiation model using the number of features exhibiting the maximum gain in differentiation accuracy. Meanwhile, there is also a point exhibiting an inflection of the second sigmoid function approximation at the latter half of differentiation model accuracy, showing that there is room for further improvement in the differentiation model selection method. In this regard, Example 11 developed a methodology of efficiently combining a "main feature" that shows a sigmoid function pattern more strongly and a "supporter feature" that does not strongly show a sigmoid function pattern, but strongly contributes to the differentiation accuracy of a model by re-ranking features and inputting features with high gain in differentiation accuracy improvement at an early stage. With this methodology, maximum differentiation accuracy can be nearly materialized with the same number of features as Example 10.

(Method)

The following process was performed in accordance with Example 10 up to immediately before differentiation/estimation analysis.

(Participants)

132 healthy adult subjects in their 20s to 70s participated in high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

FIG. 39 shows the summary of the high temperature stimulation block random paradigm used in the test. A temperature stimulation system (Pathway; Medoc Co., Ltd., Ramat Yishai, Israel) was used to apply high temperature stimulation to the right forearm of the participants. High temperature stimulation included three levels of temperature intensities (40° C., 44° C., and 48° C.), with 36° C. as the baseline temperature. Each temperature block consisted of two stimulations, with each stimulation lasting 15 seconds, and block interval of 20 seconds. A set included 64 heat blocks of the three types described above at a ratio of "12:10:10". The entire test included 5 sets for a total of 320 blocks. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Analysis: Feature Extraction Process)

FIG. 40 shows the process of extracting features used in differentiation/estimation. 1) "EEG data collection" was performed using a commercially available electroencephalograph from Ag/AgC17 electrodes on the scalp (Fp1, Fp2, F3, F4, C3, C4, and Pz). The lead electrode was the earlobe. Each of the left and right electrodes was connected to the earlobe electrode on the same side. The frequency band was 0.3 to 120 Hz, and the sampling frequency was 1000 Hz. The impedance was maintained at 15 kΩ or less. 2) For "data sampling", 16080 samples for no pain and 16080 samples for having pain for a total of 32160 samples were extracted for 16 seconds after applying each stimulation from a total of 132 subjects while limited to 40° C. no pain condition and 48° C. having pain condition. 3) For the "selection of two types of features", frequency power and mean absolute amplitude of the sampled brainwave epochs were used. The data sampling frequency was resampled from 1000 Hz to 1024 Hz (to increase the speed of discrete Fourier transform), the waveform trend was removed, and Hanning window function was applied, and then FFT (Fast Fourier Transform) was performed. Log conversion was applied to the real number portion to calculate the frequency power, and the mean value of frequency power for all 6 bands ($\delta$, $\theta$, $\alpha$, $\beta$, $\gamma 1$, and $\gamma 2$) was found. 4) All 49 features were obtained in each subject by "connection of features".

(Differentiation/Estimation)

First ranking and differentiation/estimation were performed on 49 features in accordance with processes S10050 and S10070 in FIG. 44 in the same manner as Example 10. Samples were arranged in order of no pain and having pain for each individual, and 49 features were approximated with a sigmoid function to calculate the $R^2$ values as a fitting indicator (S10050). The means value of $R^2$ values of 49 features of all subjects was calculated, and the features were ranked (S10060). The features were inputted into a logistic regression model in order from top ranking features to calculate differentiation accuracy of 32160 samples by 5×4 fold cross validation (S10070). Examples 11 then calculated a value of difference (Diff) in differentiation accuracy of adjacent models that are n−1 feature model and n feature model, and re-ranked the features other than the highest ranking feature (single main feature) or single main feature and group of main features exhibiting significant correlation (S10070-1). Differentiation/estimation is then performed while increasing features one at a time (S10070-2) to determine a differentiation model (S10080).

(Results)

FIG. 45 shows the difference in differentiation accuracy after re-ranking. There is a ceiling effect in differentiation accuracy at about the same number of features, i.e., 10 to 15, compared to the first ranking by $R^2$ values in the accuracy as of the differentiation model creation (as of cross validation; FIG. 45A) and in the accuracy as of validation by test data (FIG. 45B). When re-ranked 1 to 3 times by the value of difference, the ceiling was nearly reached with the number of features at 10 to 15 upon the second ranking.

The results described above suggest that features with low approximation to a binomial function, i.e., supporter features, were incorporated into the feature ranking by re-ranking by the value of difference in differentiation accuracy of the n−1 feature model and n feature model, and combined with a main feature with high approximation to the binomial function at an early stage. In this manner, the feature contracting process is strengthened by re-ranking of features so that an economical differentiation model with high gain in differentiation accuracy can be created even with few features.

Example 12: Contracting Process Using Hyperparameter

Figure 49:
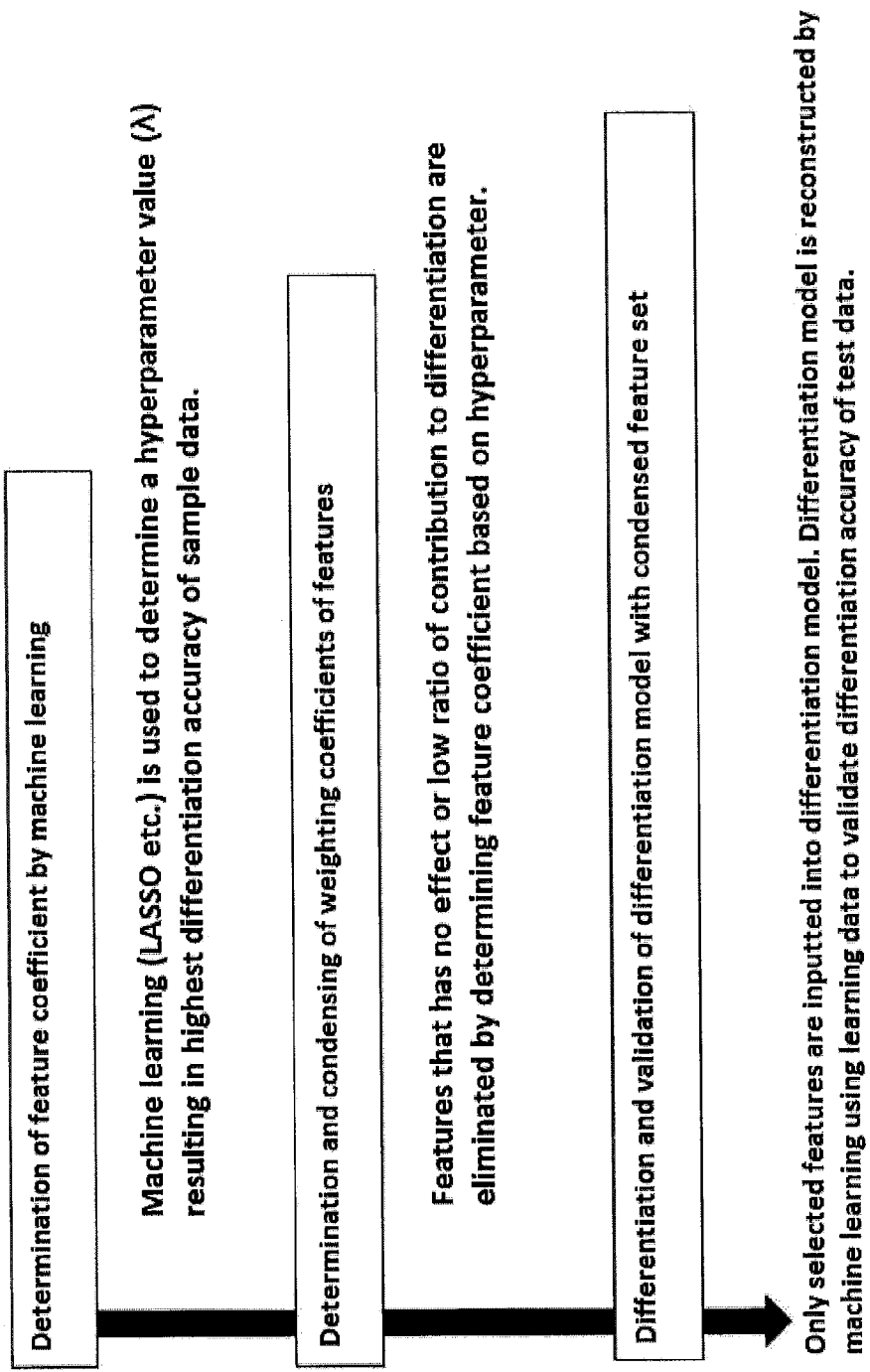
FIG. 49 shows a schematic diagram of a contracting process based on a hyperparameter. All numerical values in the figure are exemplary.

In this Example, a contracting process based on a hyperparameter is performed (see FIG. 49).

(Materials and Procedure)

The materials and procedure are roughly as described in FIG. 49.
1) Determination of feature coefficient by machine learning: determine a hyperparameter value (λ or the like) at which the differentiation accuracy of sample data would be the highest by using machine learning (LASSO or the like).
2) Determination of weighting coefficient and contracting of features: exclude features that have no effect or low contribution to differentiation by determining a feature coefficient based on the hyperparameter.
3) Determination and validation of differentiation model by contracted set of features: input only selected features into a differentiation model, and reconstruct the differentiation model with machine learning using learned data to validate differentiation accuracy of test data.

(Detailed Description)

The procedure described above is explained in detail hereinafter.

Based on FIG. 49, data for 164 subjects is divided into learning data for 163 subjects and test data for one subject as shown for example in Example 13. Next, the learning data is divided into 10. 90% of data is used to repeat cross validation. Λ is determined based on the mean square error at which LASSO approximation of 10% of samples is minimized, and the features and coefficient used in a model are determined.

Example 13: Backward Elimination Sampling

This Example performed backward elimination sampling, i.e., a method of gradually eliminating samples (subjects) with low percentage of correct answer from the entire sample.

(Objective)

This Example demonstrated a refining method for increasing differentiation accuracy by gradually reducing samples by a method known as backward elimination sampling. This methodology is a method used as one type of differentiation accuracy improvement methods. While conventional contracting methods were differentiation model creation methods with contracting of the feature base for selecting only features that are effective for improving differentiation accuracy, this method is a method of creating a prototype of a differentiation model by selecting features and gradually eliminating samples that are not involved in the improvement of differentiation accuracy from a model. Creation of a prototype of a differentiation model used in an initial pain differentiation apparatus is creation of an "exemplary model" based on objects in which a change in brainwave feature is observed when pain is sensed. In this regard, pain experiment associated with differentiation of two levels ("painful, not painful") of acute neurological pain (electrical pain) was performed.

(Procedure)
(Participants)

164 healthy adult subjects (in their 20s to 70s) participated in the electrical stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

An electrical stimulation application apparatus (Painvision, Nipro) was used to apply electrical stimulation to the inside part of the right forearm. Threshold values were identified for low (not painful), moderate (painful), and high levels (very painful) of electrical stimulation for each individual. Stimulation was applied three times, continuously for 15 seconds. The time interval between levels was 100 seconds. Subjects continuously evaluated unpleasantness of pain (range of evaluation: 0 to 100) during the experiment. Brainwave data was recorded from seven electrodes at the frontal portions (Fp1, Fp2, F3, and F4), central portions (C3, and C4), and parietal portion (Pz). Reference electrodes were placed on both left and right earlobes, and an earth electrode was placed on the forehead. The sampling frequency was 1000 Hz. The recorded frequency band was from 0.5 to 120 Hz. The electrical impedance was 15 kΩ.

(Brainwave Feature Extraction Process)

A change in eye movement (EOG) was identified in main component analysis with seven electrodes using brainwave data for all time frames (first component), a filter was applied at 1 to 30 Hz to remove low and high frequencies for cleaning, and then the original brainwave data was subjected to regression analysis using the EOG component to diminish the EOG component. A 30 Hz low pass filter was applied to the waveform thereof to reduce myogenic potential noise. For example, the brainwave potential power upon recording was reduced to about 40% by this process for a certain subject. Three types of brainwave features (absolute mean amplitude, potential correction, and entropy) for 15 seconds after applying electrical stimulation of each level were extracted. For extraction of the feature of frequency power, features in the five frequency bands, i.e., δ (1 to 3 Hz), θ (4 to 7 Hz), α (8 to 13 Hz), β (14 to 30 Hz), and γ (31 to 100 Hz), were extracted at each electrode using data without applying a 30 Hz low pass filter. This resulted in 53 features in total. All subject samples were converted into z values within each feature for data for each paradigm.

(Refinement of Differentiation Model by Backward Elimination)

Figure 46:
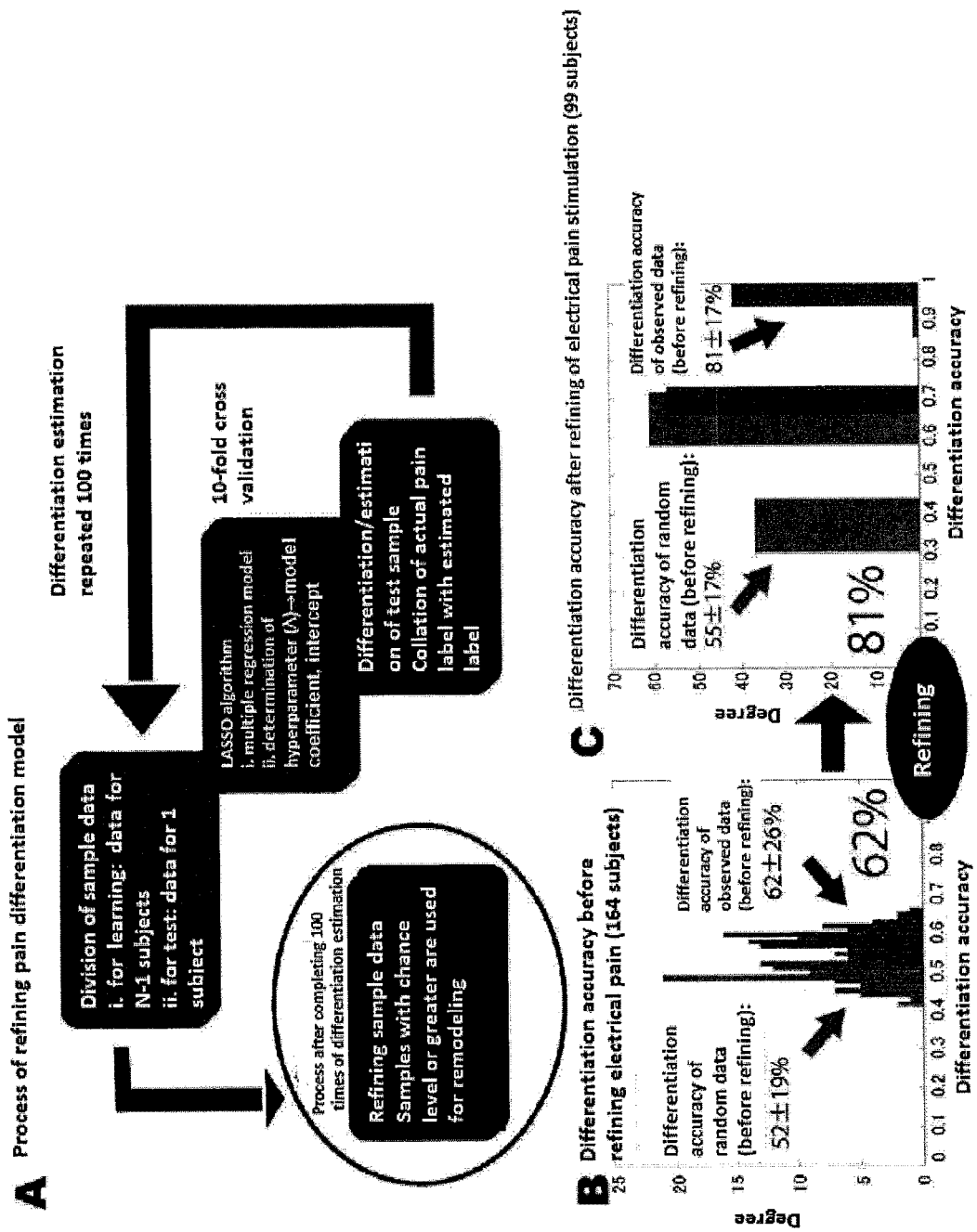
FIG. 46 shows a flow chart for a differentiation model refining/improving method (A), and the actual improvement in differentiation accuracy from before refining (B) to after refining (C) in an Example using electrical stimulation (Example 13).

Differentiation and estimation were classified into two classifications "having unpleasant pain (level 3)/no pain (level 1)". As shown in FIG. 46, a multiple regression model was used for differentiation. This identified a λ value for outputting a value of least mean squares of model approximation and 10-fold cross validation of a coefficient of a feature from learning data (n−1 subject data) by the LASSO algorithm to determine the feature coefficient and intercept of a differentiation model. After creating a differentiation model, differentiation/estimation of test data (data for one subject) was repeated for the number of subjects, i.e., 164 times. Then, only subjects with differentiation accuracy at or above the chance level (>50%) were kept. The process was repeated to refine the differentiation model in a stepwise manner. In the final model and model before refinement, the differentiation accuracy of samples with randomized test data label was calculated and compared to the differentiation accuracy of actual measurement data.

(Results)

The mean differentiation accuracy of all 164 subjects at the first stage was "62±26%", which was about 10% higher compared to "52±19% for when pain labels were randomized. In this regard, when the procedure for improving differentiation accuracy was repeated to refine the differentiation accuracy, accuracy improved to the second stage (n=112, differentiation accuracy: 76±20%), third stage (n=103, differentiation accuracy: 80±18%), fourth stage (n=100, differentiation accuracy: 80±17%), and fifth stage (n=99, differentiation accuracy: 81±17%). For the final model, differentiation accuracy was 26% higher than "55±17%" of randomized samples (paired t-test: t=17.86, df=98, p<0.0001). The above results demonstrated that differentiation accuracy can be improved to 80% by refining a model in relation to two classifications of pain from electrical stimulation with relatively low unpleasantness.

Example 14: Implementation Example of Medical Equipment: Cloud=Saas

Figure 52:
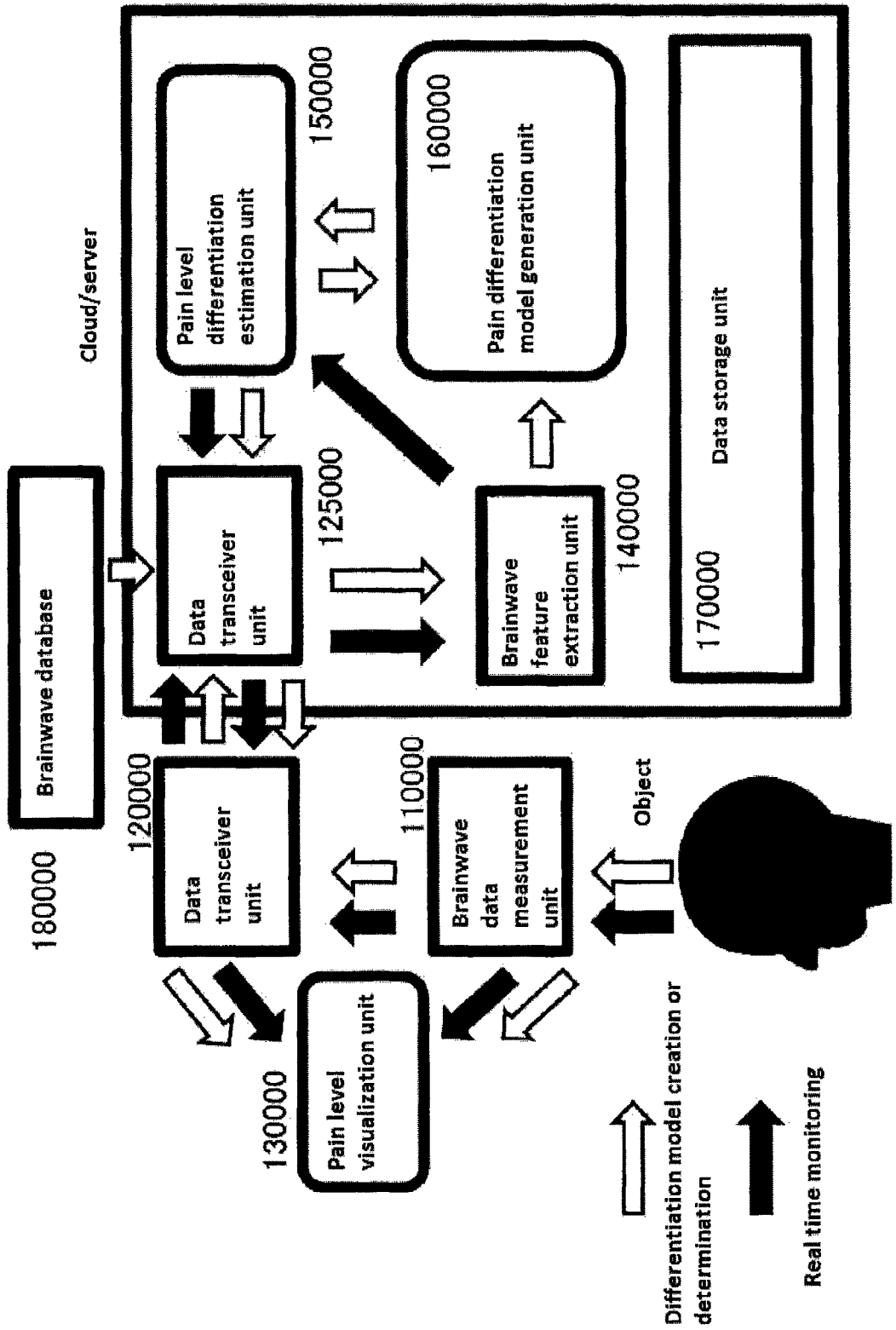
FIG. 52 is a schematic diagram of the device of the invention, showing an embodiment of the device portion (left side) having only a function for obtaining brainwaves, transmitting/receiving data, and making them visible. This is an embodiment presuming that analysis and determination/differentiation model generation and the like are performed on the cloud or a server. A brainwave feature (analysis data) is extracted on the server side in this model.

An implementation example of using SaaS type service as a medical equipment is described (FIG. 52) First, the terminal side is as follows.
1. Incorporation of Brainwave Data: Standard Equipment for Both C1 and D1
   Provided from the cloud or server as SaaS is as described below (features can be extracted on the cloud side as shown in FIG. 52).
2. Extraction of Features:
   Standard (potential, frequency, potential correction, entropy)
   Option (others, features that increase differentiation accuracy)
3. Pain Differentiation Model:
   Standard (general differentiation model installed by default)
   Option 1 (tailor-made differentiation model, where price changes depending on model creation)
   Option 2 (creation of facility dedicated differentiation model)
   Option 3 (client requested setting)
   Option 4 (model creatable by the client themselves)
   Option 5 (increase in the number of created differentiation models)
4. Improvement of Differentiation Model
   Option 1 (period of 1 year, 1 to 2 times a year)
   Option 2 (period of 1 year, once every 1 or 2 months)
   Option 3 (extended period, once or twice a year)
   Option 4 (extended period, once every 1 or 2 months).
5. Data Storage
   Standard (up to 10 Gb on the cloud),
   Option 1 (additional 1 Tb on the cloud),
   Option 2 (parameter is set for divided storage on the cloud)
   Option 3 (stored by differentiation model on the cloud)
   Data is stored, and data is imported from all sold apparatuses to create big data, and a differentiation model is continuously updated or a new model is constructed so that a new application such as "burn pain differentiation model" can be provided.
6. Data Analysis Option: Classification of Patient Pattern (Search for Patient Cluster Based on Change in the Pattern of Features or Differentiation Accuracy)
   The envisioned embodiment of the services described above are the following.
   Before starting pain monitoring, reference pain stimulation is applied to an object a plurality of times, and brainwave data is recorded at the brainwave data measurement unit 110000. The recorded data is transmitted from the data transceiver unit 120000 to 125000. The standard feature (potential, frequency, potential correlation, and entropy) or optional features are extracted at the brainwave feature extraction unit 140000, and pain is labeled (painful, not painful, or the like). The extracted features are transmitted to the pain differentiation model generation unit 160000. A differentiation model prototype is created using a standard general differentiation algorithm. At this time, the contracting process described in the Examples is used to determine a model with the highest differentiation accuracy (differentiation MAX model). This model is stored in the pain level differentiation estimation unit 150000, and the differentiation accuracy is displayed at the pain level visualization unit 130000 as the preliminary stages of real-time monitoring. For example, if tailor-made differentiation model creation is implemented on an apparatus as an option upon model creation, brainwave data of similar subjects is selected based on information of objects of monitoring from the brainwave database 180000, and transmitted to the brainwave feature extraction unit 140000 via the data transceiver unit 125000, and a feature of pain levels is extracted to create a differentiation model before refining at the pain differentiation model generation unit 160000. Based on a process of progressive sampling, a model sample set resulting in the highest differentiation accuracy is obtained with test data as the sample data of object being monitored, and a prototype of a differentiation model is created and stored in the pain level differentiation estimation unit 150000.

Example 15: For Segregated Facility in a Hospital

An example of a segregated facility in a hospital is described in accordance with Example 14.

A segregated facility in a hospital requires a special scheme as shown in FIG. 53.

Example 15 describes a case where SaaS is limited such that cloud service is not available upon diagnosis. Aside from creation of a differentiation MAX model using a standard general algorithm, pain monitoring with the highest accuracy implementing the brainwave database 180000 option and tailor-made differentiation model option are specifically described. Before starting pain monitoring, brainwave data of similar subjects is selected based on general clinical information of an object of monitoring from the brainwave database 180000 in the cloud environment, and transmitted to the brainwave feature extraction unit 140000 via the data transceiver unit 125000. Pain level features are extracted and stored in the data storage unit 170000. Brainwave data from applying a reference stimulation in advance to an object is recorded on the brainwave data measurement unit 110000, and transmitted to the brainwave feature extraction unit 145000 via the data transceiver units 120000 and 125000 to extract features, which are stored in the data storage unit 170000. Data for creating a model obtained from the database and testing sample data for a monitoring object is transmitted to the pain differentiation model generation unit 160000. A prototype of a differentiation model resulting in the highest differentiation accuracy of sample data of the object is created based on progressive sampling and stored in the pain level differentiation estimation unit 150000 via the transceiver units 125000 and 120000.

When monitoring pain of an object online, the brainwave data measurement unit 110000 records brainwave data from an object without reference to the cloud. Standard (potential, frequency, potential correlation, and entropy) or optional features are created at the brainwave feature extraction unit 140000 from the data and transmitted to the pain level differentiation estimation unit 150000. Differentiation/estimation results are transmitted to the pain level visualization unit 130000, where points for pain or chronological change (trend) of pain levels is displayed.

Example 16: Summary of "Tailor-Made Pain Differentiation Estimation Method 1"

In this Example, a tailor-made pain differentiation estimation method was performed. This estimation method is a method for creating a plurality of individual models and determining a "differentiation MAX model" (differentiation maximum model herein) with the highest differentiation accuracy for each individual. The differentiation MAX model is conceptualized as the "main model" in the improved tailor-made method described below. The procedures are shown below.

(Procedures)
(Objects)

132 healthy adult subjects in their 20s to 70s participated in the high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

Figure 54:
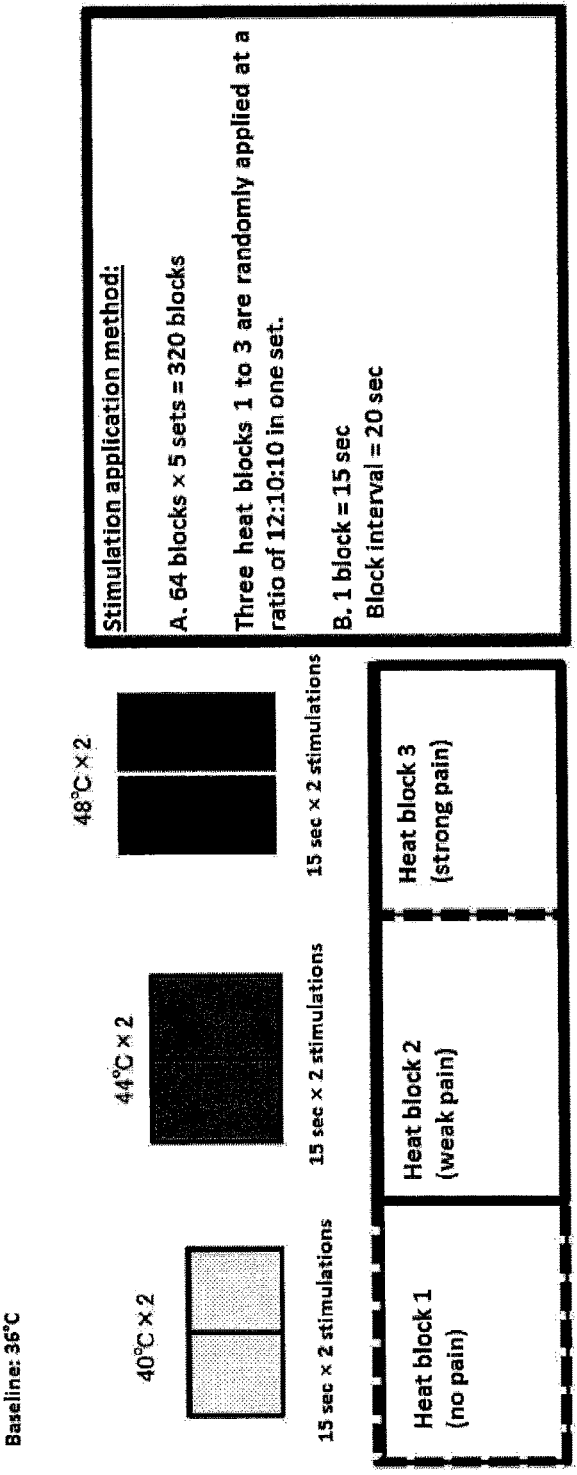
FIG. 54 shows a high temperature stimulation applying paradigm that is shared by Example 16 and the like. There were three types of high temperature blocks in total, consisting of no pain block (40° C.), weak pain block (44° C.), and strong pain block (48° C.). Each block contained 2 stimulations at 15 seconds each that continued for a total of 30 seconds. The time interval between blocks was 20 seconds. Subjects underwent all 64 blocks for a total of 5 sets.

FIG. 54 shows the summary of the high temperature stimulation block random paradigm used in the test. A temperature stimulation system (Pathway; Medoc Co., Ltd., Ramat Yishai, Israel) was used to apply high temperature stimulation to the right forearm of the participants. High temperature stimulation included three levels of temperature intensities (40° C., 44° C., and 48° C.), with 36° C. as the baseline temperature. Each temperature block consisted of two stimulations, with each stimulation lasting 15 seconds and block interval of 20 seconds. A set included 64 heat blocks of the three types described above at a ratio of "12:10:10". The entire test included 5 sets for a total of 320 blocks. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Analysis: Feature Extraction Process)

FIG. 55 shows the process of extracting features used in differentiation/estimation. 1) "EEG data collection" was performed using a commercially available electroencephalograph from Ag/AgC17 electrodes on the scalp (Fp1, Fp2, F3, F4, C3, C4, and Pz). The lead electrode was the earlobe. Each of the left and right electrodes was connected to the earlobe electrode on the same side. The frequency band was 0.3 to 120 Hz, and the sampling frequency was 1000 Hz. The impedance was maintained at 15 kΩ or less. 2) For "data sampling", 16080 samples for no pain and 16080 samples for having pain for a total of 32160 samples were extracted for 16 seconds after applying each stimulation from a total of 130 subjects while limited to 40° C. no pain condition and 48° C. having pain condition. 3) For the "selection of two types of features", frequency power and mean absolute amplitude of the sampled brainwave epochs were used. The data sampling frequency was resampled from 1000 Hz to 1024 Hz (to increase the speed of discrete Fourier transform), the waveform trend was removed, and Hanning window function was applied, and then FFT (Fast Fourier Transform) was performed. Log conversion was applied to the real number portion to calculate the frequency power, and the mean value of frequency power for all 6 bands (δ, θ, α, β, γ1, and γ2) was found. 4) All 49 features were obtained in each subject by "connection of features".

(Differentiation MAX Model Creation Methodology)

Figure 57:
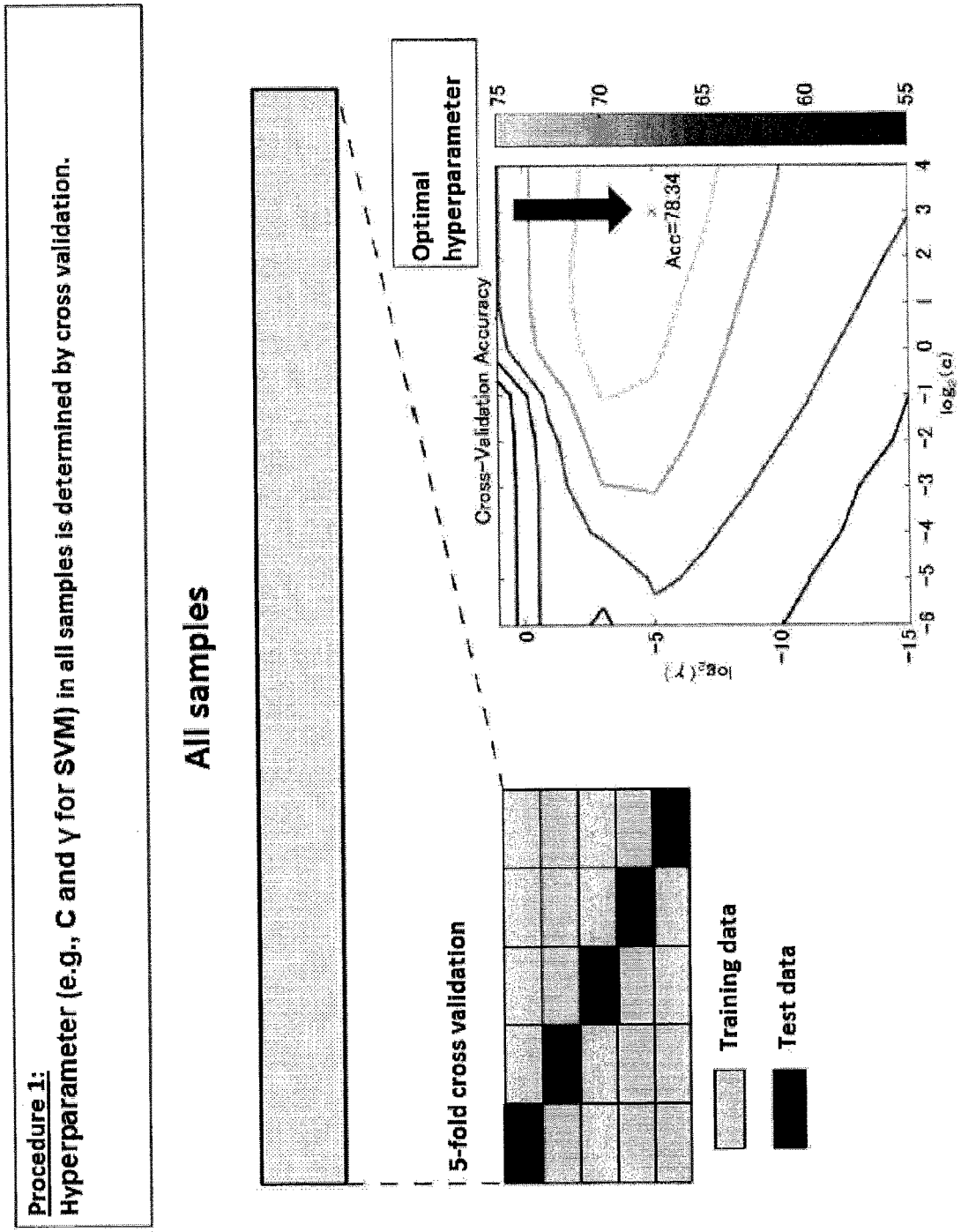
FIG. 57 is a schematic diagram summarizing procedure 1. In procedure 1, a hyperparameter (e.g., C and γ for SVM) is determined in all samples by cross validation. The optimal hyperparameter is determined thereby.

Procedure 1: By cross validation, a hyperparameter (C or γ for support vector machine) for the entire sample was determined (FIG. 57).

This is explained based on FIG. 57 as follows.

This Example has 16080 vectors for no pain and 16080 vectors for having pain. SVM finds a point vector (i.e., support vector) for both groups that would maximize the margin from a classifier (hyperplane) for separating the two groups by using a classification function (Gaussian function in this example) called the kernel. To solve the optimization problem, regularization including a penalty term (C) and γ parameter (inside the kernel) is performed using cross validation. In procedure 1, SVM was performed using all samples. In actuality, data was divided into 5, cross validation was performed, and hyperparameters C=2 and γ=0.125 were determined to create a single differentiation model.

Figure 58:
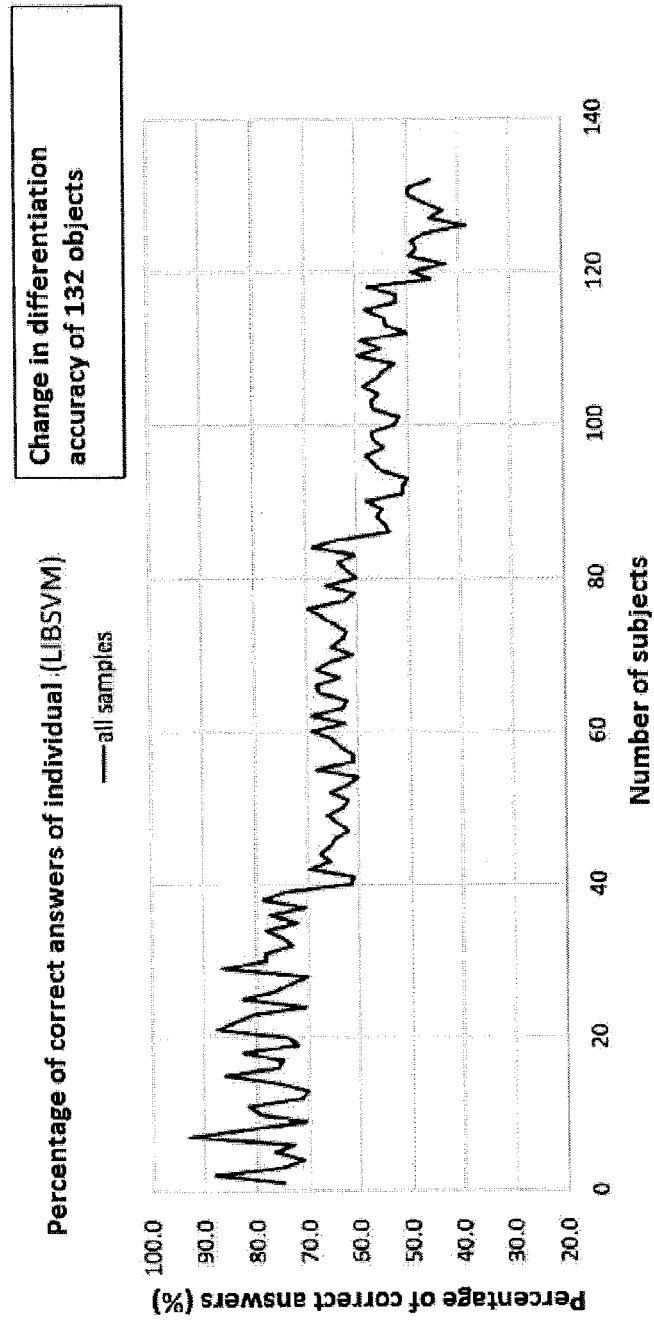
FIG. 58 is a schematic diagram summarizing procedure 2. In procedure 2, a model is created from all samples using the hyperparameter of procedure 1 to calculate differentiation accuracy at the individual level. The schematic diagram shows C=2, and γ=0.125 used in Example 16. A graph rearranging subjects in descending order from the highest differentiation accuracy is shown.

Procedure 2: A model was created from all samples using the hyperparameter of procedure 1 and the differentiation accuracy was calculated at the individual level (FIG. 58).

This is explained based on FIG. 58 as follows.

Since hyperparameters C=2 and γ=0.125 of a single model were determined by procedure 1, this model was used to differentiate/estimate a pain level for each individual. FIG. 58 plots the results.

Figure 59:
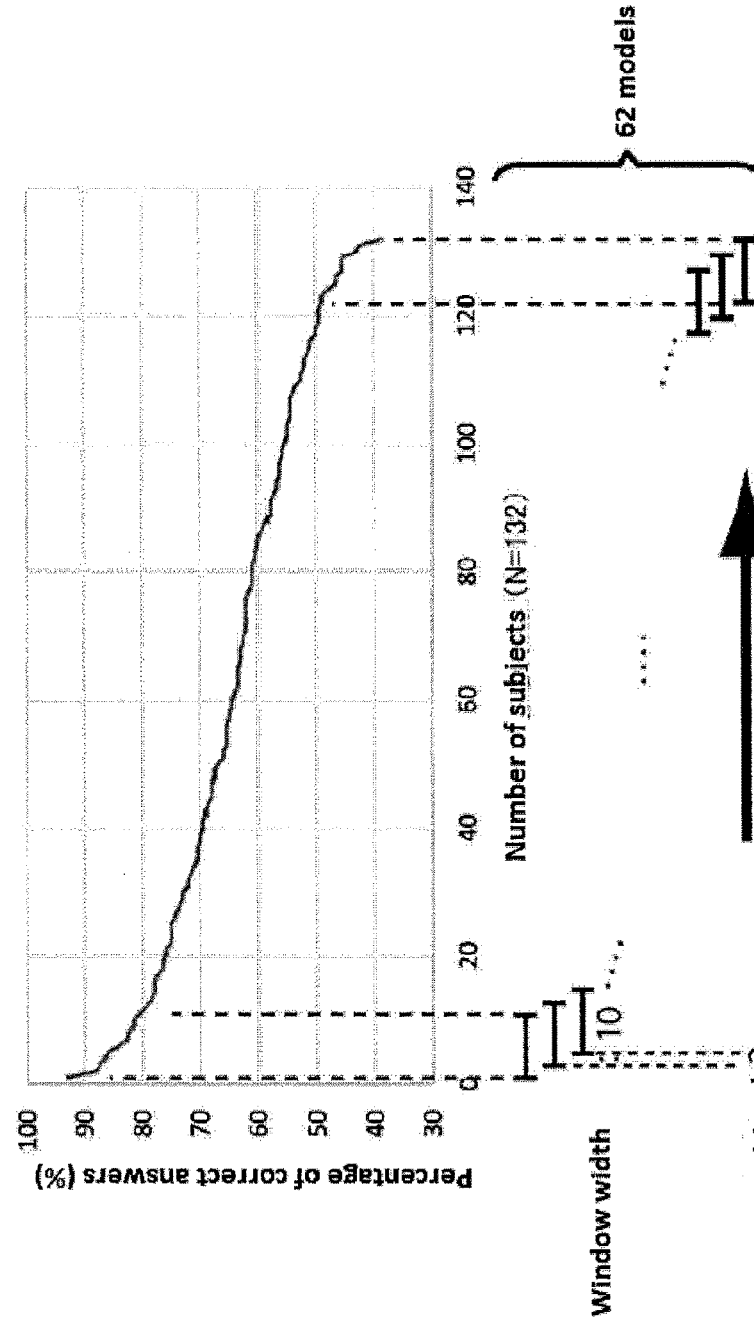
FIG. 59 is a schematic diagram summarizing procedure 3. In procedure 3, a group of subjects with close differentiation accuracy is created from the ranking of differentiation accuracy at the individual level.

Procedure 3: A group of subjects with close differentiation accuracy was created from ranking of differentiation accuracy at the individual level (FIG. 59).

This is explained based on FIG. 59 as follows.

Subjects were rearranged in descending order based on the differentiation accuracy of individuals obtained in procedure 2. A total of 62 groups (i.e., number of individual models to be created) were obtained with 10 subjects as a group while shifting the subjects by two subjects at a time.

Figure 60:
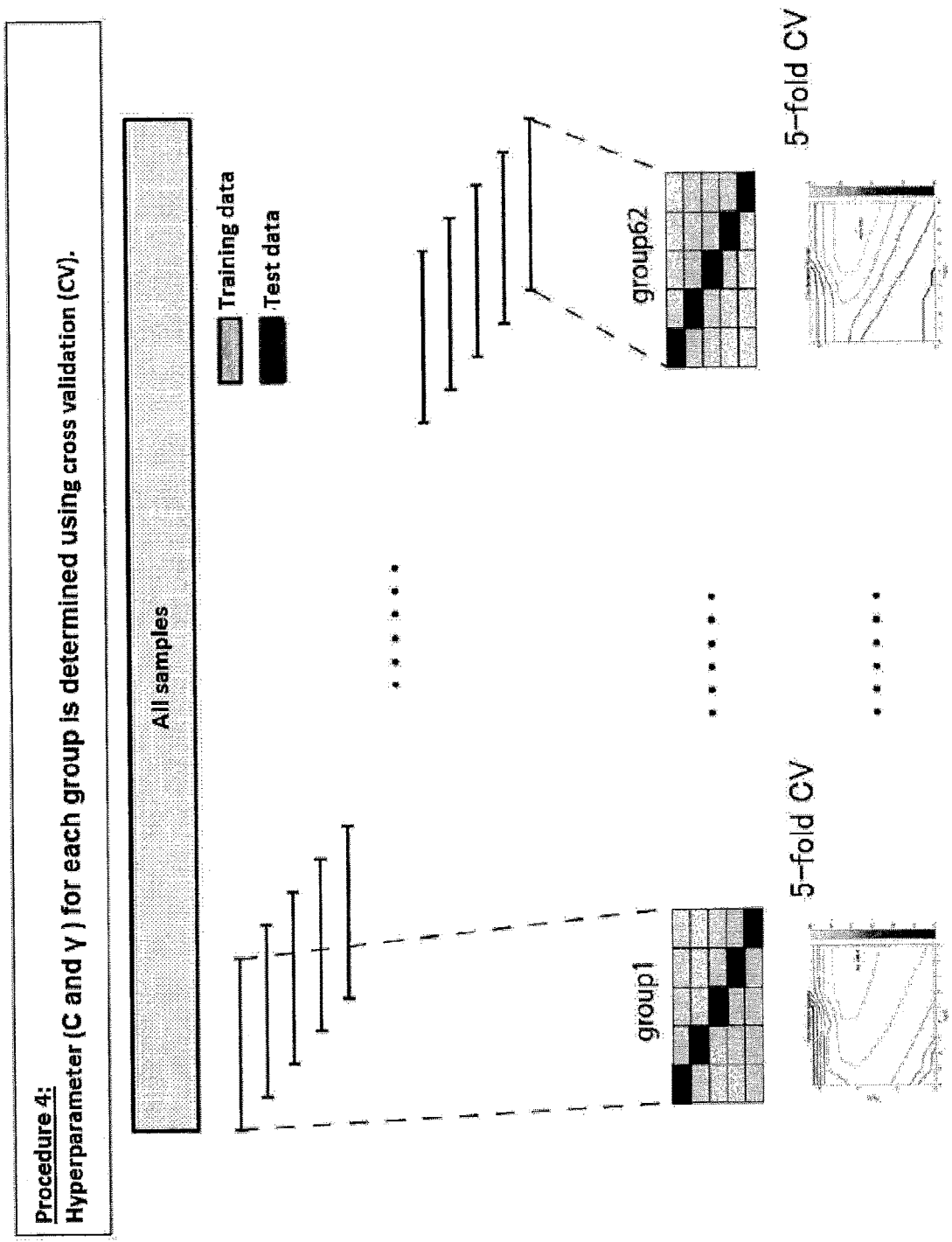
FIG. 60 is a schematic diagram summarizing procedure 4. In procedure 4, an optimal hyperparameter (e.g., C and γ for SVM) for each group is determined using the grouped samples.

Procedure 4: A hyperparameter was determined for each group by CV (FIG. 60).

This is explained based on FIG. 60 as follows.

SVM in procedure 1 was performed individually on the 62 groups obtained in procedure 3 to determine a hyperparameter of each group and create 62 individual differentiation models.

Figure 61:
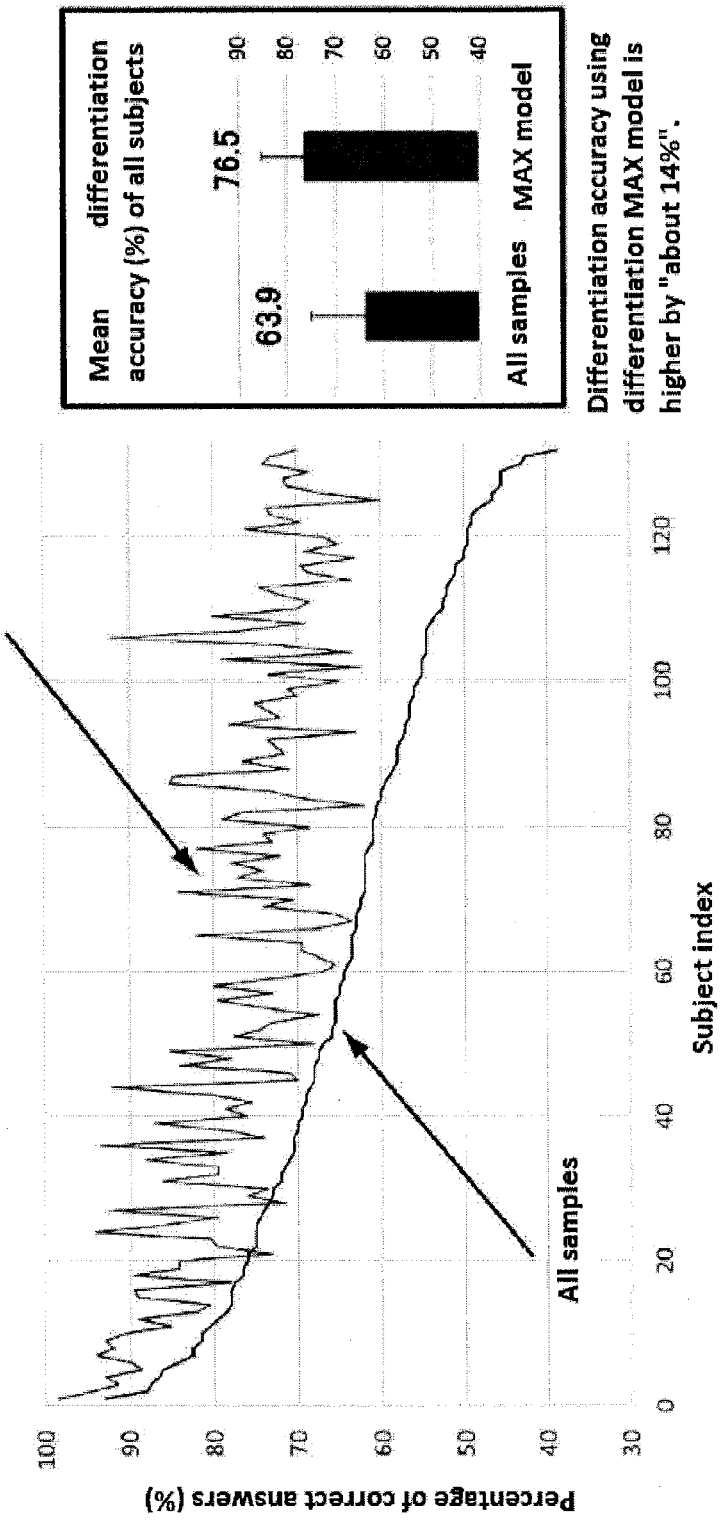
FIG. 61 is a schematic diagram summarizing procedure 5. In procedure 5, differentiation accuracy at the individual level is calculated the same number of times as the number of models using a differentiation model set obtained in procedure 4, and a differentiation maximum model ("differentiation MAX model") is identified for each individual from thereamong. The mean differentiation accuracy for all subjects improved about 14% from 64% to 77% by this method.

Procedure 5: The hyperparameter found in procedure 4 was used to create a model from a sample of each group. The differentiation accuracy at the individual level was calculated to identify the "differentiation MAX model" (FIG. 61).

This is explained based on FIG. 61 as follows.

The 62 models obtained in procedure 4 were used for differentiation and estimation of pain level samples of individuals, and a model with the highest differentiation accuracy ("differentiation MAX model") was determined for each individual.

(Results)

FIG. 61 shows the results. The accuracy function of single differentiation model from all samples continuously decreased from an object with 90% accuracy to an object with 40% accuracy, while a decrease in the differentiation accuracy of a differentiation MAX model fitted to individuals was suppressed, with the lowest accuracy at 60%. The differentiation accuracy for all 132 subjects was about 64% for single models, while the differentiation accuracy improved about 13% in MAX models, reaching 77%.

As shown in FIG. 62, subjects were separated by sex and age to study how a differentiation MAX model improves differentiation accuracy in each group. For a single model, differentiation accuracy did not reach 70% in any age group for males and was, at most, about 65% for males in their 40s. The differentiation accuracy was higher overall for females than males, where the lowest accuracy was 65% and reached 70% in females in their 20s. Meanwhile, a differentiation MAX model exhibited differentiation accuracy of 70% in all generations except the 60s for males, so that the accuracy improved overall nearly about 10%. For females, no generation fell below 70% at the lowest level. The accuracy reached 77% in females in their 20s.

The above results show that pain can be differentiated and estimated more accurately by determining an optimal differentiation model for individuals before differentiation and estimation. Since there is a difference in differentiation accuracy by sex and age, a model can be created by taking into consideration demographic factors when creating an individual model.

Example 17: Tailor-Made Pain Differentiation Estimation Method 2

This Example improved the differentiation accuracy by a differentiation model combination technology (ensemble method). This method is characterized by rearranging individual models by differentiation accuracy and determining a differentiation model set by a majority vote on differentiation results while continuously increasing differentiation models in accordance with the order.

(Procedure)
(Objects)

132 healthy adult subjects in their 20s to 70s participated in the high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

In the same manner as Example 16, a high temperature stimulation paradigm was used (FIG. 54). A temperature stimulation system (Pathway; Medoc Co., Ltd., Ramat Yishai, Israel) was used to apply high temperature stimulation to the right forearm of the participants. High temperature stimulation included three levels of temperature intensities (40° C., 44° C., and 48° C.), with 36° C. as the baseline temperature. Each temperature level consisted of two stimulations with each stimulation lasting 15 seconds and block interval of 20 seconds. A set included 64 heat blocks of the three types described above at a ratio of "12:10:10". The entire test included 5 sets for a total of 320 blocks. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Analysis: Feature Extraction Process)

FIG. 55 shows the process of extracting features used in differentiation/estimation. 1) "EEG data collection" was performed using a commercially available electroencephalograph from Ag/AgC17 electrodes on the scalp (Fp1, Fp2, F3, F4, C3, C4, and Pz). The lead electrode was the earlobe. Each of the left and right electrodes was connected to the earlobe electrode on the same side. The frequency band was 0.3 to 120 Hz, and the sampling frequency was 1000 Hz. The impedance was maintained at 15 kΩ or less. 2) For "data sampling", 16080 samples for no pain and 16080 samples for having pain for a total of 32160 samples were extracted for 16 seconds after applying each stimulation from a total of 130 subjects while limited to 40° C. no pain condition and 48° C. having pain condition. 3) For the "selection of two types of features", frequency power and mean absolute amplitude of the sampled brainwave epochs were used. The data sampling frequency was resampled from 1000 Hz to 1024 Hz (to increase the speed of discrete Fourier transform), the waveform trend was removed, and Hanning window function was applied, and then FFT (Fast Fourier Transform) was performed. Log conversion was applied to the real number portion to calculate the frequency power, and the mean value of frequency power for all 6 bands (δ, θ, α, β, γ1, and γ2) was found. 4) All 49 features were obtained in each subject by "connection of features".

(Ensemble Differentiation Model Creation Methodology 1)

See the above descriptions for procedures 1 to 5, since they are the same in Example 16 (FIG. 63). Procedure 6 and thereafter are described hereinafter.

Procedure 6: Models were rearranged in the descending order of differentiation accuracy using 62 models one at a time. Since differentiation/estimation results are calculated by 62 models for each individual, the models are rearranged in descending order by accuracy.

Procedure 7: Differentiation models were increased one at a time to calculate differentiation accuracy by the "ensemble method", and the number of differentiation models with the highest differentiation accuracy was employed ("ensemble pruning").

FIG. 64 shows the summary of the ensemble method. Learning data is divided into groups by specific criteria. For example, this Example created 62 groups based on differentiation accuracy of a single model for all samples. Machine learning is run for each group to create individual classification models ($C_i$: i=1, 2, . . . , N). Individual models independently differentiate and predict unknown test data and vote on a prediction result (differentiation label such as "1" and "−1"). The final differentiation result is determined by results of majority vote.

Figure 65:
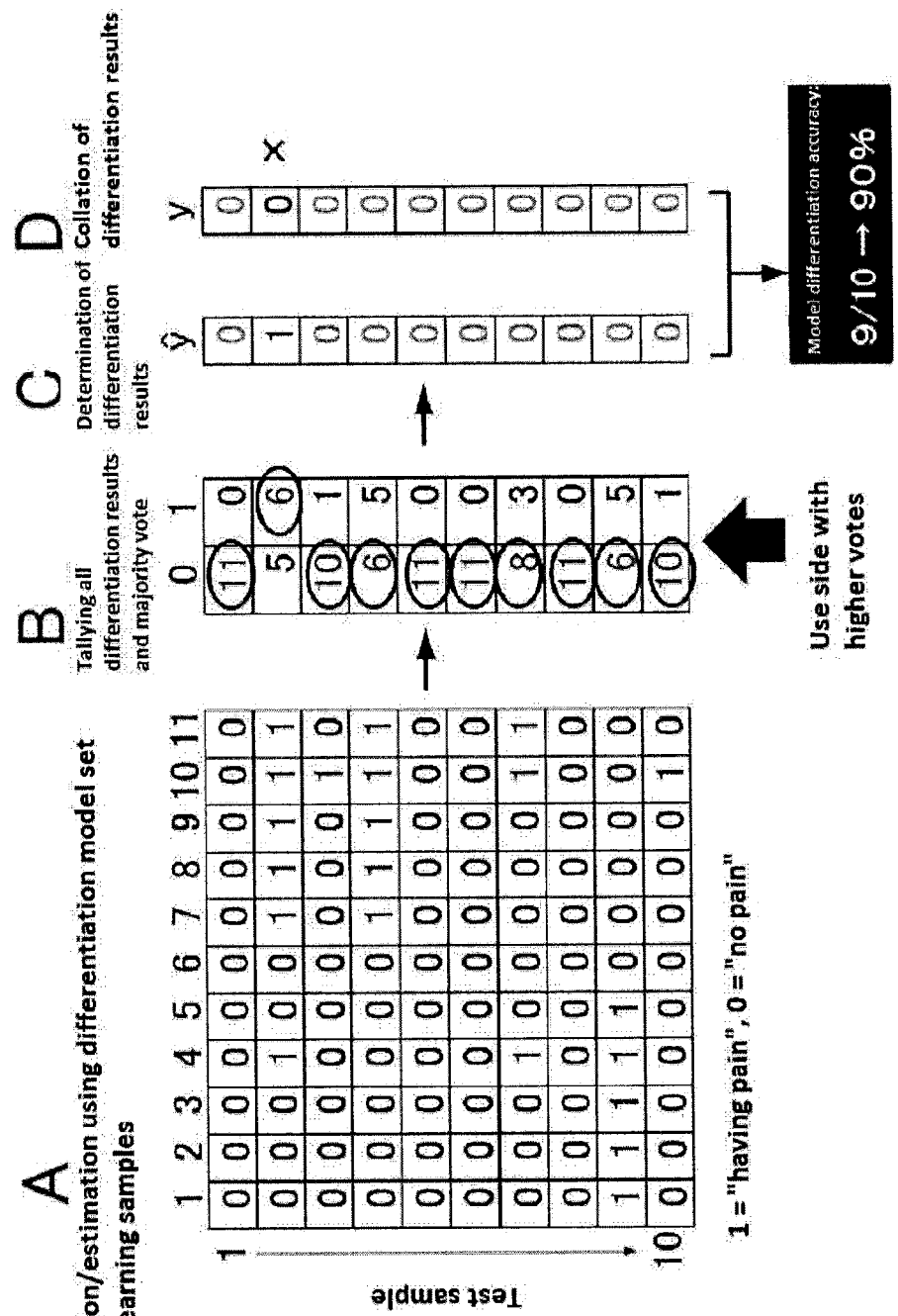
FIG. 65 shows another conceptual diagram 2 of the ensemble method. The flow of calculating differentiation accuracy is shown. In the example, having pain is labeled "1", and no pain is labeled "0". Test data (individual pain sample) is predicted with each differentiation model obtained by grouping of learning data (sample). Majority voting is held on the results. The final differentiation prediction is determined as "having pain" if there are more votes for label "1", and "no pain" if there are more votes for label "0". This is compared with the actual pain label to determine the differentiation accuracy of an ensemble differentiation model. This example is an example of bagging.

FIG. 65 is the flow of the ensemble method using dummy test data, where there are 11 individual models and 10 samples for test data to be differentiated or estimated. For example, having pain=1 and no pain=0, and individual models independently output estimation results (FIG. 65A). The differentiation results of individual models are tallied (FIG. 65B) and overall prediction of having pain or no pain is determined by majority vote (FIG. 65C). Actual pain label and estimation result are collated to calculate the differentiation accuracy of the ensemble model (FIG. 65D). In this example, the second sample from the top does not match, so that the model differentiation accuracy would be 90%.

(Results)
(Object 1)

Figure 66:
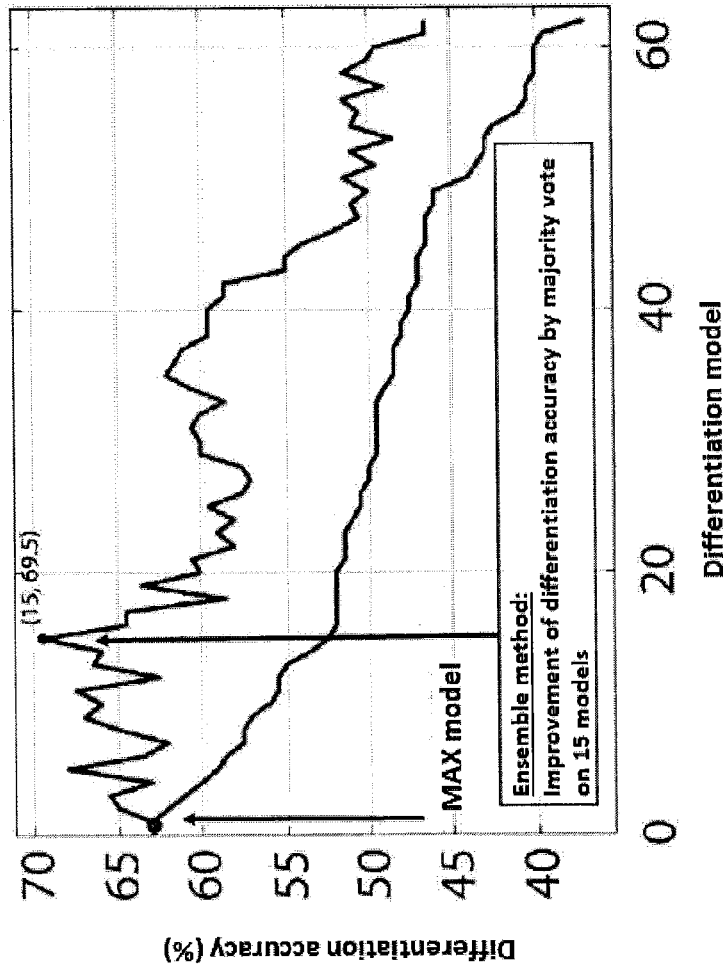
FIG. 66 shows example 1 for improved differentiation accuracy by ensemble pruning. This example shows results for object 1. A model for differentiation or estimation by majority voting of 15 differentiation models materialized improvement in accuracy with the ensemble method. The differentiation accuracy from the ensemble method performed in Example 17 improved about 7% compared to the differentiation maximum (MAX) method using a single model in Example 16.

FIG. 66 shows results of determining a differentiation model by the ensemble method for object 1. While the differentiation accuracy was 63% for single differentiation MAX, differentiation accuracy improved 7% by using 15 model sets by the ensemble method to materialize nearly 70% differentiation accuracy.

(Object 2)

Figure 67:
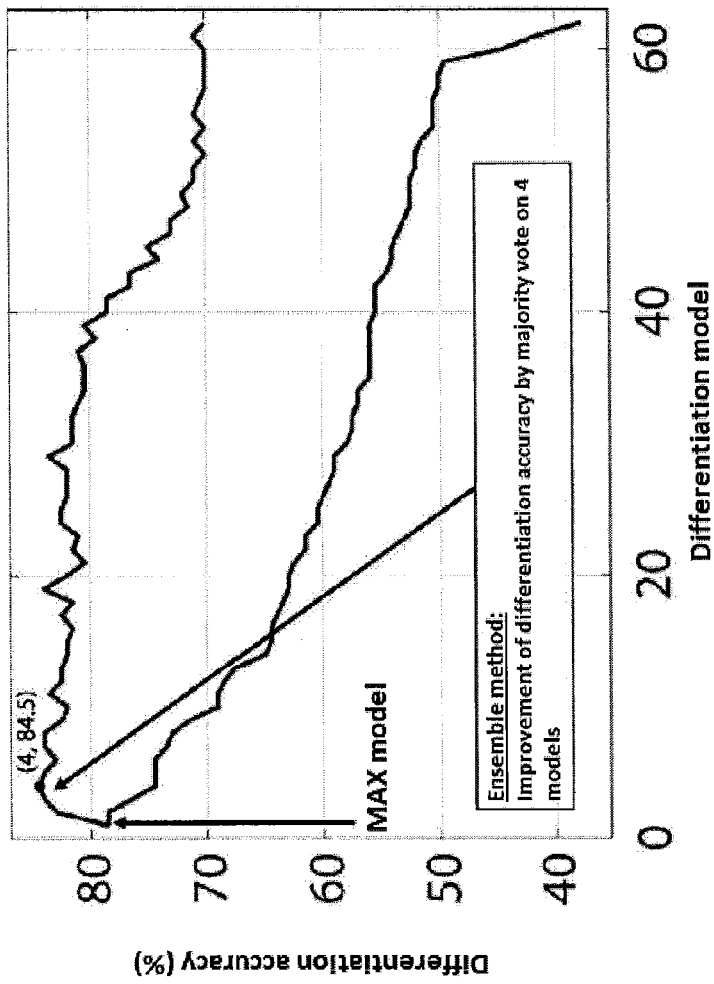
FIG. 67 shows example 2 for improved differentiation accuracy by ensemble pruning. This example shows results for object 2. A differentiation accuracy from majority voting of 4 differentiation models materialized improvement in accuracy with the ensemble method. The differentiation accuracy from the ensemble method performed in another example of Example 17 similarly improved about 7% compared to the differentiation maximum (MAX) method using a single model in Example 16.

FIG. 67 shows results of determining a differentiation model by the ensemble method for object 2. While the differentiation accuracy was 78% for single differentiation MAX, differentiation accuracy improved 7% by using 4 model sets by the ensemble method to materialize 85% differentiation accuracy.

(All 132 Subjects)

FIG. 68 shows an outline of the differentiation estimation results by the ensemble method on all objects. Compared to 64% for a single model using all samples, the differentiation MAX model in Example 16 improved accuracy by about 13%, but this ensemble method improved accuracy by an addition 3%.

Example 18: Tailor-Made Pain Differentiation Estimation Method 3

This Example improved differentiation accuracy by a differentiation model combination technology (ensemble method). This method is characterized by rearranging individual models by differentiation accuracy, conceptually distinguish a model with the maximum differentiation accuracy as the "main model" and the rest as "supporter models" for fine tuning differentiation, and comprehensively inputting supporter models one at a time while fixing the main model to improve differentiation accuracy.

(Procedure)
(Objects)

132 healthy adult subjects in their 20s to 70s participated in the high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

In the same manner as Example 16, a high temperature stimulation block random paradigm was used (FIG. 54). A temperature stimulation system (Pathway; Medoc Co., Ltd., Ramat Yishai, Israel) was used to apply high temperature stimulation to the right forearm of the participants. High temperature stimulation included three levels of temperature intensities (40° C., 44° C., and 48° C.), with 36° C. as the baseline temperature. Each temperature block consisted of two stimulations with each stimulation lasting 15 seconds and block interval of 20 seconds. A set included 64 heat blocks of the three types described above at a ratio of "12:10:10". The entire test included 5 sets for a total of 320 blocks. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Analysis: Feature Extraction Process)

FIG. 55 shows the process of extracting features used in differentiation and estimation. 1) "EEG data collection" was performed using a commercially available electroencephalograph from Ag/AgC17 electrodes on the scalp (Fp1, Fp2, F3, F4, C3, C4, and Pz). The lead electrode was the earlobe. Each of the left and right electrodes was connected to the earlobe electrode on the same side. The frequency band was 0.3 to 120 Hz, and the sampling frequency was 1000 Hz. The impedance was maintained at 15 kΩ or less. 2) For "data sampling", 16080 samples for no pain and 16080 samples for having pain for a total of 32160 samples were extracted for 16 seconds after applying each stimulation from a total of 130 subjects while limited to 40° C. no pain condition and 48° C. having pain condition. 3) For the "selection of two types of features", frequency power and mean absolute amplitude of the sampled brainwave epochs were used. The data sampling frequency was resampled from 1000 Hz to 1024 Hz (to increase the speed of discrete Fourier transform), the waveform trend was removed, and Hanning window function was applied, and then FFT (Fast Fourier Transform) was performed. Log conversion was applied to the real number portion to calculate the frequency power, and the mean value of frequency power for all 6 bands ($\delta$, $\theta$, $\alpha$, $\beta$, $\gamma1$, and $\gamma2$) was found. 4) All 49 features were obtained in each subject by "connection of features".

(Ensemble Differentiation Model Creation Methodology 3)

See the above descriptions for procedures 1 to 5, since they are the same in Example 16 (FIG. 63). Procedure 6 and thereafter are described hereinafter. (FIG. 69) Procedure 6A: Models were rearranged in the descending order of differentiation accuracy using 62 models one at a time. This procedure is the same as Example 17. For each individual, the differentiation accuracy of models gradually decreases, with the differentiation MAX model at the top.

Procedure 7A: The differentiation accuracy was improved stepwise by selecting the differentiation MAX model as the "main model" and comprehensively adding the remaining "supporter models" one at a time.

The differentiation accuracy is tested by fixing device the differentiation MAX model as the main model (procedure 1 in FIG. 70) and comprehensively adding the remaining "supporter models" one at a time (procedures 2 and 3 in FIG. 70). For example, for 62 individual differentiation models, there is one main model and 61 supporter models. Therefore, 61 differentiation accuracy results are obtained in the first stage of adding one supporter model. The supporter model set is updated while keeping the ensemble model with the highest differentiation accuracy thereamong (procedure 4 in FIG. 70). The process described above is repeated. The process ends at the stage where the supporter model set is a null set, and the best ensemble differentiation model is determined (procedure 5 in FIG. 70).

(Results)
(Object 1)

Figure 71:
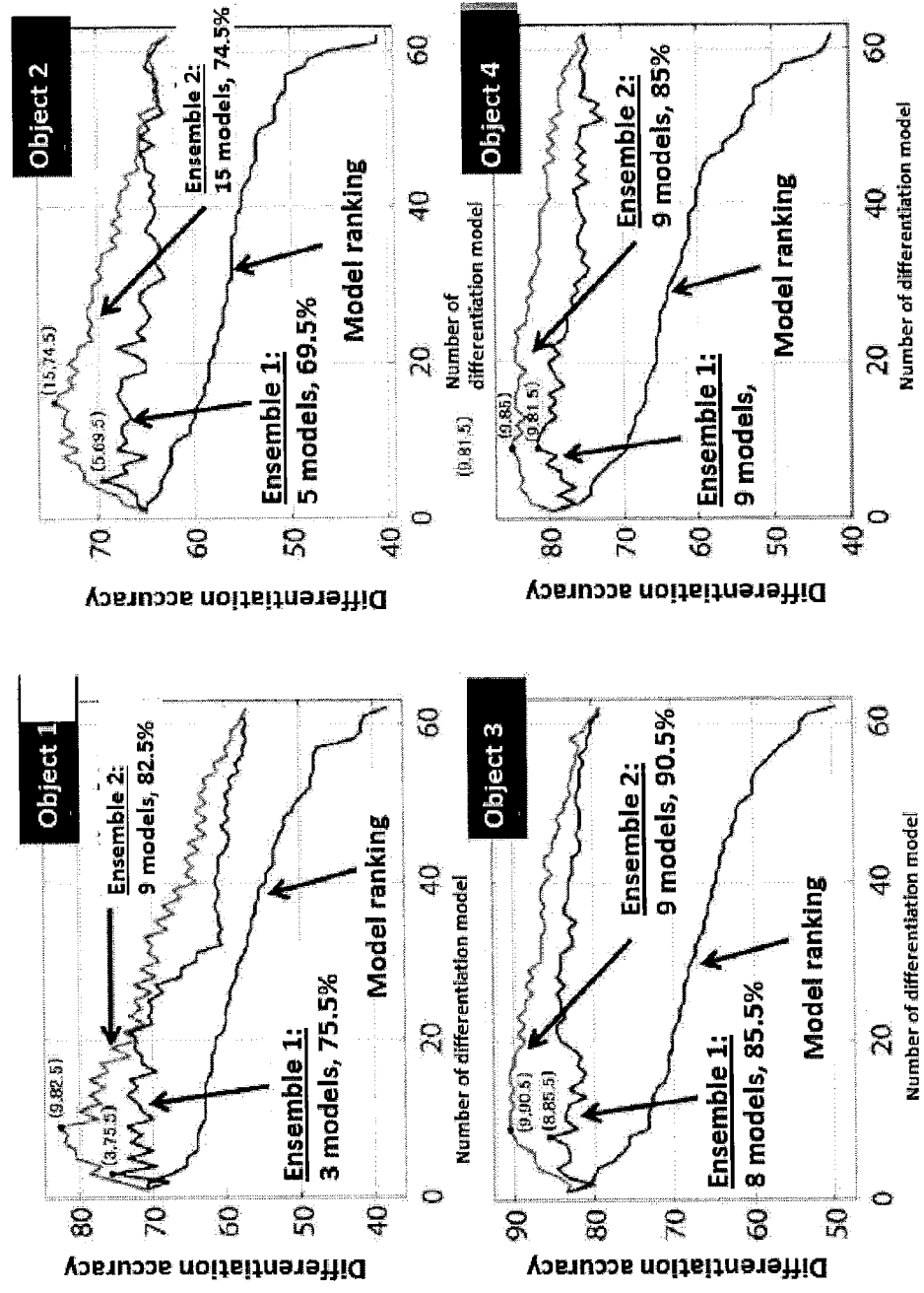
FIG. 71 shows an example of improved differentiation accuracy by improved ensemble pruning method. Objects 1 to 4 used in Example 18 are shown. Differentiation accuracy improved 5 to 10% early stages of repeating for all objects.

This is explained based on FIG. 71 as follows.

For object 1, differentiation accuracy was 76% when using 3 models in the ensemble method 1 of Example 17, but accuracy improved to 83% with 9 models in ensemble method 2 of this Example.

(Object 2)

For object 2, differentiation accuracy was 70% when using 5 models in ensemble method 1, but accuracy improved to 75% with 15 models in ensemble method 2.

(Object 3)

For object 3, differentiation accuracy was 86% when using 8 models in ensemble method 1, but accuracy improved to 91% with 9 models in ensemble method 2 of this Example.

(Object 4)

For object 4, differentiation accuracy was 82% when using 9 models in ensemble method 1, but accuracy improved to 85% with 9 models in ensemble method 2.

(All 132 Subjects)

Figure 72:
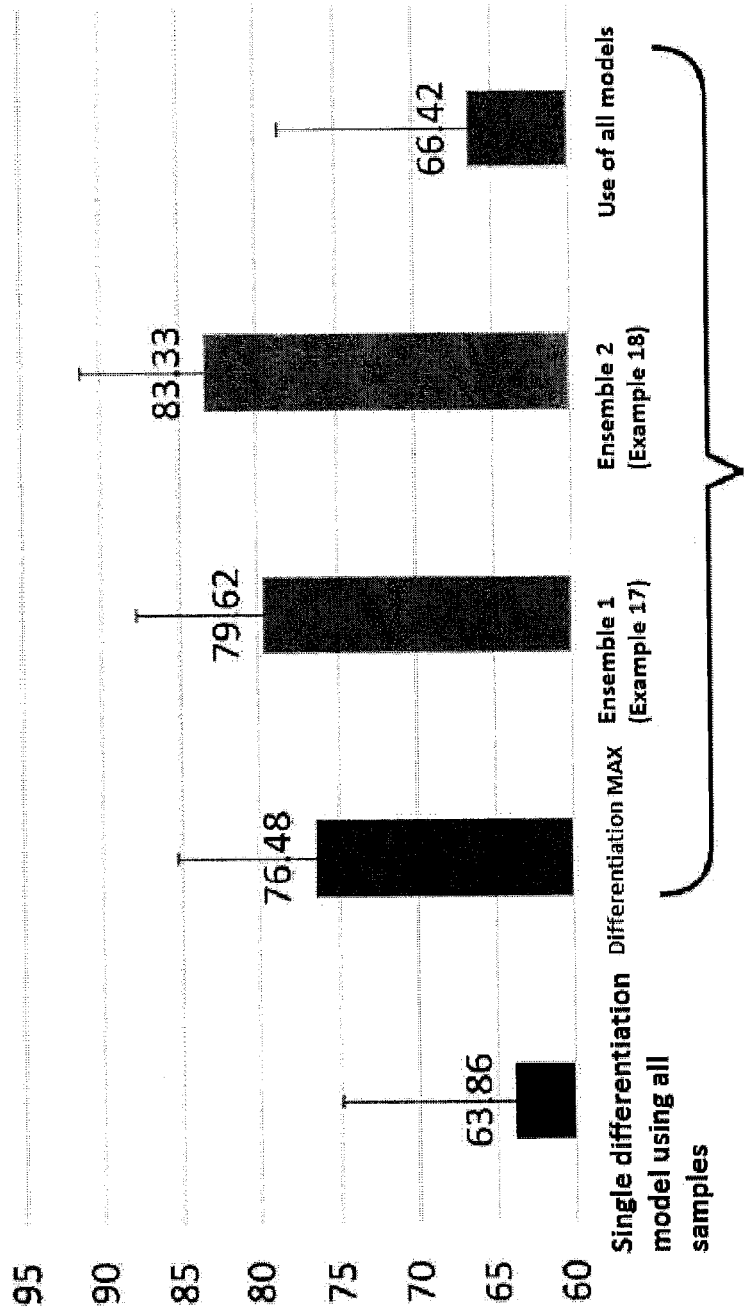
FIG. 72 shows a summary of improvement in differentiation accuracy by ensemble method 2 (improved method). Comparison of five differentiation methodologies for all objects is shown. Ensemble method 2 (improved method) further improves differentiation accuracy by about 4% compared to improved ensemble method 1 in Example 17, not to mention the single differentiation model using all samples and ensemble method using all models, to materialize differentiation accuracy of about 83%.

As shown in FIG. 72, ensemble method 2 in this Example improved differentiation accuracy further by about 3% compared to ensemble method 1 (80%) in Example 17 to reach differentiation accuracy of "about 83%". While ensemble method 2 in this Example further improved accuracy among ensemble methods, accuracy improved 7% compared to a single differentiation MAX model (76%), 17% compared to the ensemble method using all 62 models (66%), and 19% compared to a single differentiation model of all samples (64%).

The above results show that a finer tailor-made differentiation model matching the pain reaction of an individual can be created by attempting a plurality of ensemble methods based on a fundamental process for creating an individual model and identifying a differentiation MAX model.

Example 19: Tailor-Made Pain Differentiation Estimation Method 4 with Calibration This Example improved differentiation accuracy by a differentiation model combination technology (ensemble method). This method is characterized by separating sample data of individuals into dummy "reference sample" and "monitoring sample" and determining an ensemble differentiation model based on the reference sample and then testing how accurately monitoring samples can be differentiated while presuming online pain monitoring.

(Procedure)
(Objects)

132 healthy adult subjects in their 20s to 70s participated in the high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

A high temperature stimulation block random paradigm was used (FIG. 54). A temperature stimulation system (Pathway; Medoc Co., Ltd., Ramat Yishai, Israel) was used to apply high temperature stimulation to the right forearm of the participants. High temperature stimulation included three levels of temperature intensities (40° C., 44° C., and 48° C.), with 36° C. as the baseline temperature. Each temperature block consisted of two stimulations with each stimulation lasting 15 seconds and block interval of 20 seconds. A set included 64 heat blocks of the three types described above at a ratio of "12:10:10". The entire test included 5 sets for a total of 320 blocks. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Analysis: Feature Extraction Process)

FIG. 55 shows the process of extracting features used in differentiation/estimation. 1) "EEG data collection" was performed using a commercially available electroencephalograph from Ag/AgC17 electrodes on the scalp (Fp1, Fp2, F3, F4, C3, C4, and Pz). The lead electrode was the earlobe. Each of the left and right electrodes was connected to the earlobe electrode on the same side. The frequency band was 0.3 to 120 Hz, and the sampling frequency was 1000 Hz. The impedance was maintained at 15 kΩ or less. 2) For "data sampling", 16080 samples for no pain and 16080 samples for having pain for a total of 32160 samples were extracted for 16 seconds after applying each stimulation from a total of 130 subjects while limited to 40° C. no pain condition and 48° C. having pain condition. 3) For the "selection of two types of features", frequency power and mean absolute amplitude of the sampled brainwave epochs were used. The data sampling frequency was resampled from 1000 Hz to 1024 Hz (to increase the speed of discrete Fourier transform), the waveform trend was removed, and Hanning window function was applied, and then FFT (Fast Fourier Transform) was performed. Log conversion was applied to the real number portion to calculate the frequency power, and the mean value of frequency power for all 6 bands (δ, θ, α, β, γ1, and γ2) was found. 4) All 49 features were obtained in each subject by "connection of features".

(Tailor-Made Differentiation Estimation Method 4 with Calibration)

See the descriptions above (FIG. 63) for the procedure to create an individual differentiation model (one of estimation method 1, estimation method 2, or estimation method 3) before the additional procedures, because they are the same as procedures 1 to 4 in Example 16 (FIG. 73).

Additional Procedure 1:

All samples of individuals (n samples) were divided into reference samples (m samples) and test samples (n−m samples).

Specifically, the following monitoring situation was presumed. In an actual setting, the pain reaction properties of an object are not known when envisioning an object with some type of pain. Thus, before starting actual pain monitoring, it is necessary to determine what differentiation model is appropriate. This is at the core of a tailor-made differentiation method. If an actual monitoring situation is presumed, stimulation with pain or no pain is applied a plurality of times to an object in advance to record brainwave data. Since an individual differentiation model is determined by using such data, such pain stimulation is referred to as "reference stimulation". Since stimulation is applied at the earliest time before starting monitoring, the earliest segment of sample data of individuals was used as the pseudo "reference sample". In actual pain monitoring settings, this process is performed in the individual pain differentiation model creation unit 203000 of the pain differentiation/estimation model generation unit 203000 (FIG. 77).

Additional Procedure 2:

The optimal reference differentiation model was determined using m reference samples.

Specifically, reference samples are inputted into each individual differentiation model (62 models) created in procedures 1 to 4 for differentiation and estimation. In doing so, for comparison, only the differentiation maximum (MAX) model was used (estimation method 1), or estimation method 2 or 3 for combining remaining models with the differentiation MAX mode was performed to determine a differentiation model with the highest accuracy. In an actual pain monitoring setting, this process is performed in the pain differentiation model ranking unit 203300 and the ensemble pain differentiation model creation unit 203400 of the pain differentiation/estimation model generation unit 203000 (FIG. 77).

Additional Procedure 3:

The created reference differentiation model was used to validate the differentiation and estimation with n−m test samples.

Specifically, this is a process for differentiating unknown samples with an ensemble model that was created with reference samples by using existing experimental data. Features extracted from the unknown samples were inputted into the model for differentiation and estimation. In an actual pain monitoring setting, this process is performed in the pain differentiation model transmission unit 203500 of the pain differentiation/estimation model generation unit 203000 (FIG. 77) and the pain differentiation/estimation unit 204000. Specifically, the ensemble differentiation model created at the ensemble pain differentiation model creation unit 203400 is transmitted to the pain differentiation/estimation unit 204000 through the pain differentiation model transmission unit 203500. Test samples pseudo-express brainwave data recorded through the brainwave data measurement unit 205200 from the object 206000 at the time of online monitoring. This data is converted to a feature at the feature extraction unit 202000, transmitted to the pain differentiation/estimation unit 204000, and differentiated/estimated in the created ensemble differentiation model.

(Results)
(Individual Result of One Object)

Figure 74:
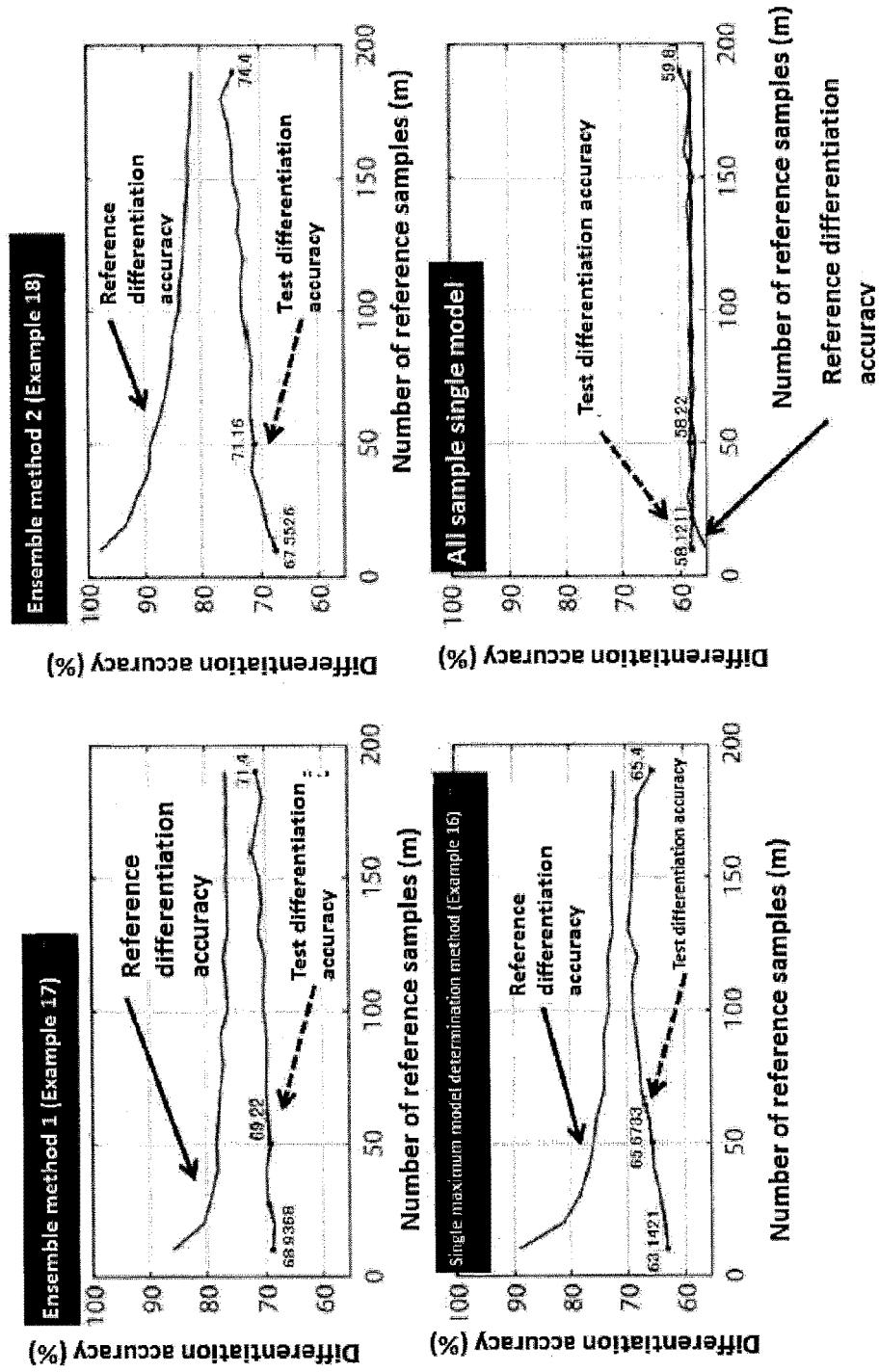
FIG. 74 is a comparison of differentiation accuracy results with calibration for one object. The percentage of correct answers of a reference differentiation model stabilizes by about 50 reference samples in the three models other than the single model of all samples (ensemble 1, ensemble 2, and differentiation maximum (MAX)). While a test differentiation accuracy using a reference differentiation model exhibits a slow increase, there is one significant change. Maximum reference stimulation application before actual pain monitoring can be understood to be, at most, about 50 times.

FIG. 74 shows results for one object. The horizontal axis of each graph indicates the number of reference samples used (m samples), and the vertical axis indicates the differentiation accuracy (%). A single model using all samples consistently has relatively low differentiation accuracy (about 60%), whereas the other three models exhibit different patterns of change in differentiation accuracy. The differentiation accuracy of reference samples rapidly decreases and settles by about 50 samples in all three models. In other words, the number used as reference stimulation is highly likely to be sufficient up to about "50 stimulations". Meanwhile, differentiation accuracy of test data using a differentiation model determined by reference samples exhibited a slow increase while a rapid change in accordance with the change in the number of samples was not observed. It was confirmed from the results that if reference stimulation is applied 50 times or less to create a differentiation model, this can be potentially used effectively in actual pain monitoring at individual levels.

(Overall Results for 132 Subjects)

FIG. 75 shows a pattern of change in mean differentiation accuracy for all 132 subjects. The horizontal axis of each graph indicates the number of reference samples (m samples) and the vertical axis indicates the differentiation accuracy (%). Similar patterns as the results for individuals in FIG. 74 are observed in mean data for all 132 subjects. Low differentiation accuracy of about 60% is consistently maintained in an all sample model. A difference is not observed between reference and test samples. Differentiation accuracy of reference samples rapidly decreases and then settles by about 50 samples for all other three samples. It is also highly likely that the number of reference stimulations used is sufficient with a maximum of 50 stimulations. Meanwhile, the test differentiation accuracy with a reference differentiation model exhibited an inversely proportional increase up to about 50 samples, other than ensemble method 1 (Example 17). In view of the results, the efficacy of applying reference stimulation up to 50 times to create a differentiation model was able to be confirmed from analysis of all 132 subjects. Examples of presumed lower limit include, but are not limited to, 20 for level 2 of no pain and about 30 for level 3.

(Comparison of Number of Reference Samples)

FIG. 76 summarizes the results of creating an ensemble model with 10 and 50 reference samples to differentiate and estimate test data. The test differentiation accuracy was similar even if the number of reference samples increased for a single model of all samples and ensemble method 1 (Example 17) (single model: 63.9->63.9%, ensemble 1: 73.8->73.0%). Meanwhile, accuracy improved about 5% for ensemble method 2 (Example 18) (70.2->74.9%), and about 4% for differentiation MAX (67.7->71.7%).

In view of the above results, setting of maximum of 50 times (25 with pain and 25 with no pain, or the like) as the number of reference stimulations applied before monitoring is appropriate when the total number is 132, as the initial setting of the apparatus 208000, although the number is dependent on which model is used as the differentiation model. Those skilled in the art can appropriately determine the number of reference samples in accordance with the given condition.

Example 20: Extraction of Dominant Features by Process of Contracting Features

In this Example, prioritized brainwave features and the correlation thereof were determined based on the processing shown in FIG. 79.

(Method)
(Participant)

40 healthy adult subjects in their 20s to 70s participated in the high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

Figure 81:
FIG. 81 shows an example of a high temperature stimulation paradigm used in Example 20. There were six levels of high temperature stimulation, and 3 stimulations were applied for each level. The time during which stimulation was applied was 15 seconds, and the time interval between level blocks was 100 seconds. The features were the mean frequency power ($\delta$, $\theta$, $\alpha$, $\beta$, and $\gamma$) and mean absolute amplitude of 3 stimulation at each level (15 seconds). The two levels to be differentiated is weak pain (levels 1 to 3) and strong pain (levels 4 to 6). The number of samples was strong/weak×3 levels×40 subjects=240.

FIG. 81 shows the summary of the high temperature stimulation paradigm used in the test. A temperature stimulation system (Pathway; Medoc Co., Ltd., Ramat Yishai, Israel) was used to apply high temperature stimulation to the right forearm of the participants. High temperature stimulation included six levels of temperature intensities (increased by 2° C. from 40° C. to 50° C.). Each temperature level consisted of three stimulations. Each stimulation had a plateau lasting 5 seconds (stimulation application time). Six levels of high temperature stimulation were used, and waiting period for increase and decrease from the standard temperature (35° C.) was about 10 seconds. After three stimulations at each level, the intervals between blocks lasted 100 seconds. The participants continuously evaluated pain intensities in the range of 0 to 100 (0="no pain"; 100="unbearable pain") on a computerized visual analog scale (COVAS). COVAS data was simultaneously recorded with changes in stimulation intensities. The following parameters were used.

Feature: Mean amplitude of three stimulations (for 15 seconds) for each level and
Mean frequency power ($\delta$, $\theta$, $\alpha$, $\beta$, $\gamma$)
Differentiation levels: weak pain (levels 1 to 3) and strong pain (levels 4 to 6)
Number of samples: weak/strong×three levels×40 subjects=240

(EEG Analysis)
(Extraction of Feature of Amplitude)

The following regression filter was applied to continuous EEG data under high temperature stimulation conditions to reduce eye movement noise (EOG):

Raw EEG=$\beta$×EOG+C

EEG estimate=raw EEG−$\beta$×EOG  [Numeral 301]

$\beta$: regression coefficient
C: intercept
EEG estimate: estimated EEG

Fp1 was the closest to the left eye and heavily affected by the eye movement, so that Fp1 data was used as EOG data. EOG data can be extracted from all electrode data using main component analysis, independent component analysis, or the like. After EOG correction, epoch waveforms from 5 seconds before applying stimulation to 15 seconds after applying stimulation were sampled for each stimulation level. After baseline correction using the mean potential before applying stimulation, artifacts were removed at ±100 µV. The potential was converted to absolute values, and then standardized with the maximum amplitude, and mean amplitude for 15 seconds after applying stimulation was found for each level as the brainwave amplitude feature.

(Extraction of Feature of Frequency Power)

For frequency analysis, brainwave data was sampled from the start of stimulation to 15 seconds after applying stimulation for each stimulation level without EOG correction. After Fourier transform was applied, the frequency power was calculated (data for log 10 conversion of real number portion). The mean value of power was calculated for each level for each of δ (1 to 3 Hz), θ (4 to 7 Hz), α (8 to 13 Hz), β (14 to 30 Hz), γ (31 to 100 Hz) and standardized with the maximum value for each individual using data for all levels as the frequency feature (4 electrodes×5 bands=20 features).

(Differentiation Analysis with Contracting of Number of Features)

High temperature stimulation on 40 participants was differentiated using Support Vector Machine (SVM) (Guyon I, Weston J, Barnhill S, & Vapnik V. Gene selection for cancer classification using Support Vector Machine. Machine Learning 46, 389-422, 2002) (FIG. 79). As shown in FIG. 79, "24" features (standardized among individuals) was used. The pain level was set to "two levels (painful/not painful)". 24 brainwave features were ranked as the ranking of features. The differentiation algorithm was determined by finding a combination of features with the highest differentiation accuracy with "leave-one-out cross validation" using Gaussian kernel. Randomizing tests (1000 times) were conducted by randomizing the unpleasantness label and calculating differentiation accuracy of even levels using the number of features with the highest differentiation accuracy (deemed significant differentiation accuracy if accounting for the top 95% or greater). Statistical software package R and R-code of SVM-RFE (http://github.com/johncolby/SVM-RFE) were used for data analysis. The detailed flow is shown in FIG. 79, which is specifically as follows.

Features were arranged in the order of no pain to having pain, and an approximating sigmoid function or a step function is generated. A sigmoid function (Numeral 302) and a step function (Numeral 303) are expressed as follows.

$$Y = 1/e^{-ax} \qquad \text{[Numerical 302]}$$

a: gain $$Y = 0 \text{ if } x < a$$

$$Y = 1 \text{ if } x > a \qquad \text{[Numerical 303]}$$

All 24 features were approximated with an approximation function (simple regression analysis or correlation analysis) and 24 approximation indices ($R^2$ values or correlation coefficients) are calculated (S30010). Next, the features are ranked based on the magnitude of the approximation indices (absolute value). Greater approximation index indicates higher ranking, and the feature having a better fit according to a binomial classification property of having pain or no pain (S30020). Top ranking features are inputted into an SVM model one at a time in order. The differentiation accuracy of each model was calculated by leave-one-out cross validation on 240 samples. A radial basis (Gaussian) function was used as the kernel (Numerical 304). Cost=10 and Gamma=1/number of dimensions were used as the model parameters (S30030).

Radial basis function:

$$G(x1, x2) = \exp(-|x1 - x2|^2) \qquad \text{[Numerical 304]}$$

G: radial basis (Gaussian) function
x: data point
exp: exponential function.

The model with the highest differentiation accuracy and fewest features among all 24 models was defined as the "economical differentiation model" (S30040).

(Results and Discussion)

FIG. 82 shows a ranking list for 24 features and top ranking features in descending order. It was found that compared to a differentiation model using all 24 features, an economical pain differentiation/estimation model exhibits a "71.3%" two level pain differentiation accuracy by using only two top ranking features with high sigmoid approximation.

(Discussion)

The contracting of the invention is a process of using a sigmoid or step function changing between two values of "0, 1" as shown in the example of binomial classification to select a feature that fits the function as much as possible. This is based on a simple idea that it is desirable to find a feature corresponding to "0, 1" because the objective is to separate into "0, 1". This is significant in that use of a model by selecting features from top of the ranking is able to product the best result with minimum effort. The two prioritized brainwave features are absolute mean amplitude (C4) and frequency power (θ power of Fz) of the frontal and central portions in Example 20. Differentiation accuracy of 70% was materialized with only two features.

Example 21: High Temperature Stimulation Block Random Application Paradigm

This Example determined a differentiation model by re-ranking of features and determined priority brainwave features.

(Experimental Stimulation and Procedure)

Figure 83:
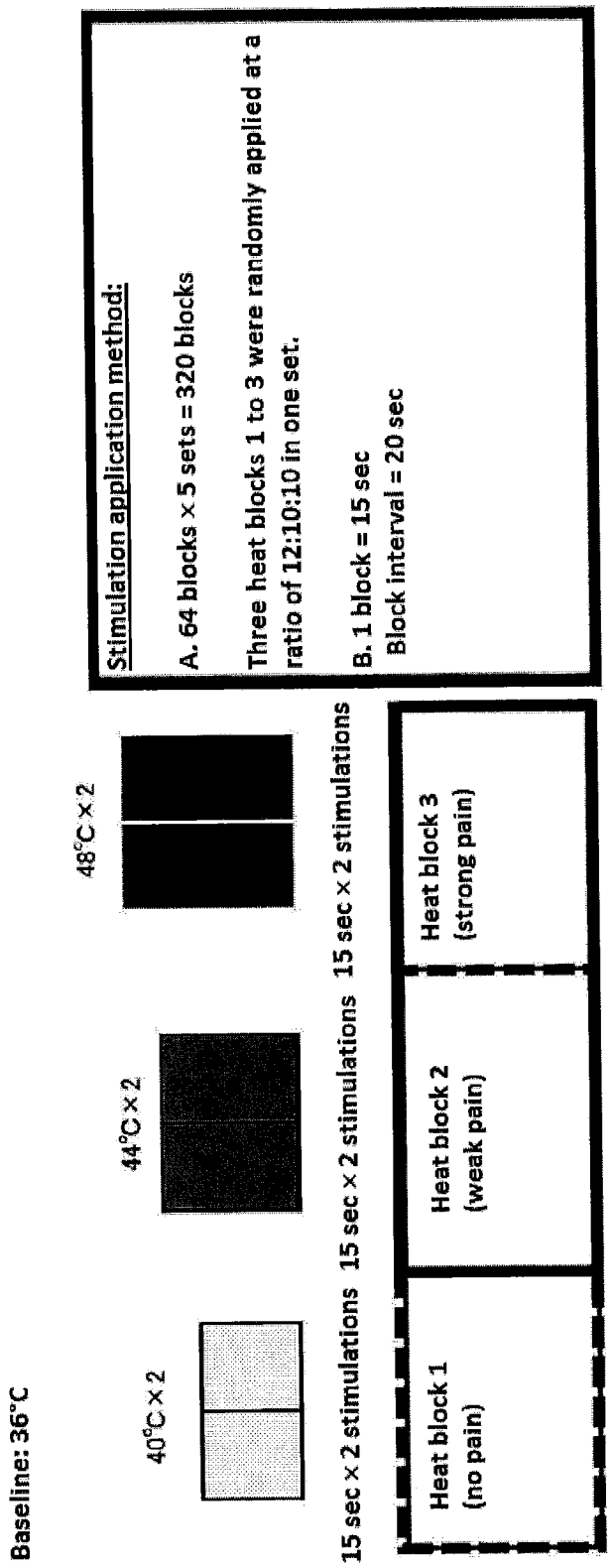
FIG. 83 shows a high temperature stimulation block paradigm used in an experiment for creating a model for differentiating 32160 samples in Example 21. The paradigm included 3 blocks, i.e., no pain, weak pain, and strong pain. Each stimulation was applied twice for 15 seconds. The time interval between blocks was 20 seconds. There were a total of 5 sets, and each set contained 64 blocks. Three heat blocks 1 to 3 were randomly applied at a ratio of 12:10:10 in one set.

FIG. 83 shows the summary of the high temperature stimulation block random paradigm used in the test. A temperature stimulation system (Pathway; Medoc Co., Ltd., Ramat Yishai, Israel) was used to apply high temperature stimulation to the right forearm of the participants. High temperature stimulation included three levels of temperature intensities (40° C., 44° C., and 48° C.), with 36° C. as the baseline temperature. Each temperature block consisted of two stimulations with each stimulation lasting 15 seconds and block interval of 20 seconds. A set included 64 heat blocks of the three types described above at a ratio of "12:10:10". The entire test included 5 sets for a total of 320 blocks. The participants continuously evaluated pain intensities in the range of 0 to 100 (0="no pain"; 100="unbearable pain") on a computerized visual analog scale (COVAS). COVAS data was simultaneously recorded with changes in stimulation intensities.

(EEG Analysis: Feature Extraction Process)

Figure 84:
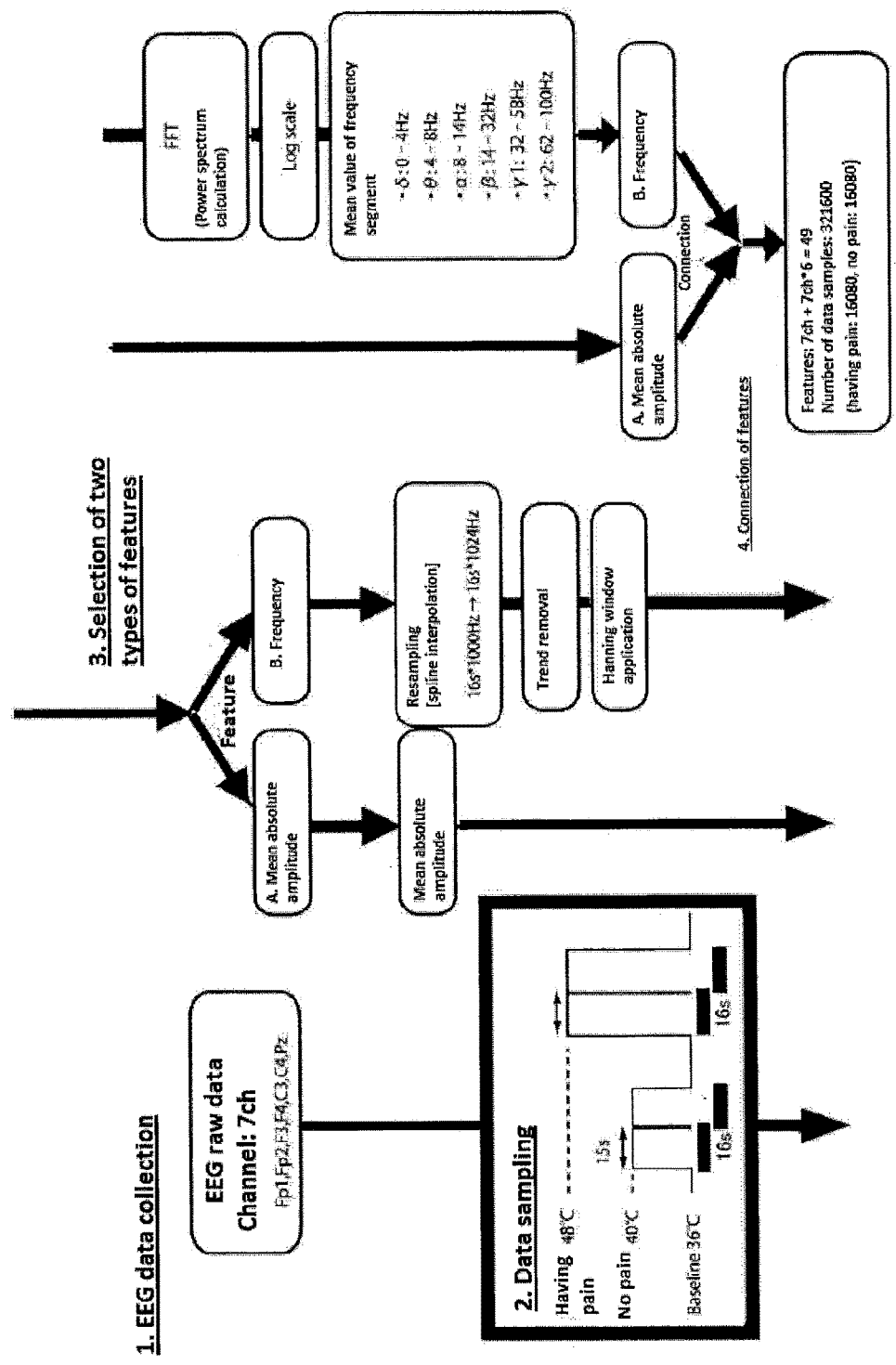
FIG. 84 shows a process of extracting a feature used in a differentiation model in Example 21. The process includes 1) EEG data collection, 2) data sampling, 3) selection of two types of features, and 4) connection of features. A total of 49 features were obtained through these processes.

FIG. 84 shows the process of extracting features used in differentiation/estimation. 1) "EEG data collection" was performed using a commercially available electroencephalograph from Ag/AgC17 electrodes on the scalp (Fp1, Fp2, F3, F4, C3, C4, and Pz). The lead electrode was the earlobe. Each of the left and right electrodes was connected to the earlobe electrode on the same side. The frequency band was 0.3 to 120 Hz, and the sampling frequency was 1000 Hz. The impedance was maintained at 15 kΩ or less. 2) For "data sampling", 16080 samples for no pain and 16080 samples for having pain for a total of 32160 samples were extracted for 16 seconds after applying each stimulation from a total of 130 subjects while limited to 40° C. no pain condition and 48° C. having pain condition. 3) For the "selection of two types of features", frequency power and mean absolute amplitude of the sampled brainwave epochs were used. The data sampling frequency was resampled from 1000 Hz to 1024 Hz (to increase the speed of discrete Fourier transform), the waveform trend was removed, and Hanning window function was applied, and then FFT (Fast Fourier Transform) was performed. Log conversion was applied to the real number portion to calculate the frequency power, and the mean value of frequency power for all 6 bands ($\delta$, $\theta$, $\alpha$, $\beta$, $\gamma1$, and $\gamma2$) was found. 4) All 49 features were obtained in each subject by "connection of features".

The above results elucidated that, as shown in FIG. 85, features with high degree of contribution tend to aggregate at the top of the ranking by repeating re-ranking of features by the value of difference (Diff) in adjacent differentiation accuracies, and differentiation accuracy nearly reached the ceiling with the earliest stage of 2nd re-ranking and fewest number of features of 12. In view of the difference in differentiation accuracy after re-ranking, there is a ceiling effect in differentiation accuracy at about the same number of features, i.e., 10 to 15, compared to the first ranking by $R^2$ values in the accuracy as of the differentiation model creation (as of cross validation; FIG. 85) and in the accuracy as of validation by test data. When re-ranked 1 to 3 times by the value of difference, it was revealed that the ceiling was nearly reached with the number of features at 10 to 15 upon the second ranking. The standard deviation of differentiation accuracy up to ranks 1 to 12 was "1.4", exhibiting a property of improvement of "about 10-fold" of "0.11" of ranking 13 and thereafter (FIG. 85). In other words, it is noteworthy that if features are rearranged in descending order by the Diff value and features with high score (%) of improving differentiation accuracy (SD of accuracy also relatively increases) are inputted at an early stage of model creation, a differentiation model can be improved early, and this can be materialized using seven electrodes, which is less than half of common 10 to 20 electrode position placements.

Example 22 Extraction of Priority Feature Using Feature Coefficient Information

This Example investigated the features that are effective in differentiation and feature correlation by using coefficient information on features used in a differentiation model. As shown in FIG. 87, priority features were narrowed down using a high temperature stimulation paradigm. The samples used had distributions of age and sex as shown in FIG. 86.
(Methods and Materials)
(Methods/Conditions)
(Participants)
159 healthy adult subjects in their 20s to 70s (see FIG. 86) performed the high temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.
(Experimental Stimulation and Procedure)
FIG. 87 shows the summary of the high temperature stimulation paradigm used in the test. A temperature stimulation system (Pathway; Medoc Co., Ltd., Ramat Yishai, Israel) was used to apply high temperature stimulation to the right forearm of the participants in the same manner as Example 20 (see FIG. 81). High temperature stimulation included six levels of temperature intensities (increased by 2° C. from 40° C. to 50° C.). Each temperature level consisted of three stimulations. Each stimulation had a plateau (stimulation application time) lasting 5 seconds. Six levels of high temperature stimulation was used, and waiting period for increase and decrease from the standard temperature (35° C.) was about 10 seconds. After three stimulations at each level, the intervals between blocks lasted 100 seconds. Brainwave data was continuously recorded during the experiment. The sampling frequency was 1000 Hz and the frequency band was 0.3 to 120 Hz. The impedance was equal to or less than 15 k$\Omega$. Electrodes used for recording were Fp1, Fp2, F3, F4, C3, C4, and Pz. Reference electrode were the left and right earlobes, and an earth electrode was placed on the forehead. The participants continuously evaluated pain intensities in the range of 0 to 100 (0="no pain"; 100="unbearable pain") on a computerized visual analog scale (COVAS). COVAS data was simultaneously recorded with changes in stimulation intensities. Further, the following parameters were used. Two levels were used for differentiating pain. The number of samples was 2 levels×3 runs×158 subjects=948 samples.
(Signal Processing Before Extraction of Features)
In order to diminish eye movement noise (EOG), main component analysis was performed on EEG data using data from seven electrodes to extract an EOG component (first component). Low/high frequency components (1 to 30 Hz band frequency filter) were removed, and EOG components were removed from each electrode data using the regression equation of Numeral 311.

Raw EEG=$\beta$×EOG+$C$

EEG estimate=raw EEG−$\beta$×EOG    [Numeral 311]

$\beta$: regression coefficient
$C$: intercept
EEG estimate: estimated EEG
After correction of EOG, a 30 Hz low pass filter was further applied to reduce myogenic potential noise. After converting amplitudes to absolute values, the epoch waveform of 15 seconds after applying stimulation was sampled to calculate features of absolute mean amplitude, frontal-parietal potential correlation (Fp1, Fp2, P3, F4, and Pz), and multiscale entropy (MSE). For frequency power, waveforms after EOG correction were subjected to Fourier transform without applying a 30 Hz low pass filter to calculate the band power for each of $\delta$ (1 to 3 Hz), $\theta$ (4 to 7 Hz), $\alpha$ (8 to 13 Hz), $\beta$ (14 to 30 Hz), and $\gamma$ (31 to 100 Hz). As shown in FIG. 88, 53 parameters (features, feature coefficients) were obtained with 7 electrodes by the above process. Each parameter was standardized with the maximum value for each individual using data for all levels. Parameters are summarized below.
1. Mean Amplitude (7 Mean Amplitudes):
A mean value of absolute values of amplitudes during 15 seconds after applying stimulation at 7 electrodes (Fp1, Fp2, F3, F4, C3, C4, and Pz) was used. This was standardized among individuals.
2. Frontal-Parietal Potential Correlation (4 Correlations)
The potential correlation of four frontal electrodes (Fp1, Fp2, F3, and F4) and parietal Pz was used.
3. Frequency Power (35 Frequency Powers)
Five bands of "$\delta$, $\theta$, $\alpha$, $\beta$, and $\gamma$" at seven electrodes (Fp1, Fp2, F3, F4, C3, C4, and Pz) were used.
4. Complexity Index (Multiscale Entropy: 7 Indices)
Multiscale entropy (MSE) at seven electrodes (Fp1, Fp2, F3, F4, C3, C4, and Pz) was calculated as follows in accordance with the calculation shown in FIG. 89. First, chronological data is divided and coarse grained by time scale (τ: number of division of data). MSE is found by calculating the percentage of a distant data pair separated by m points being within r % of the standard deviation of data in the time frame of m and m+1 for each divided data, and calculating the negative natural logarithm of the ratio thereof (percentage of m+1 time frame/percentage of m time frame). Since there are the same number of $S_E$ as the number of division of time scale, the sum is found as the complexity index (C). This Example used the following setting for calculating MSE.

1. Length of time of time scale: 20 to 50 ms
2. Distance between comparison points (m): 2 points
3. Threshold value for similarity (r: threshold for similarity): within 15% of SD for all data (Results)

Figure 90:
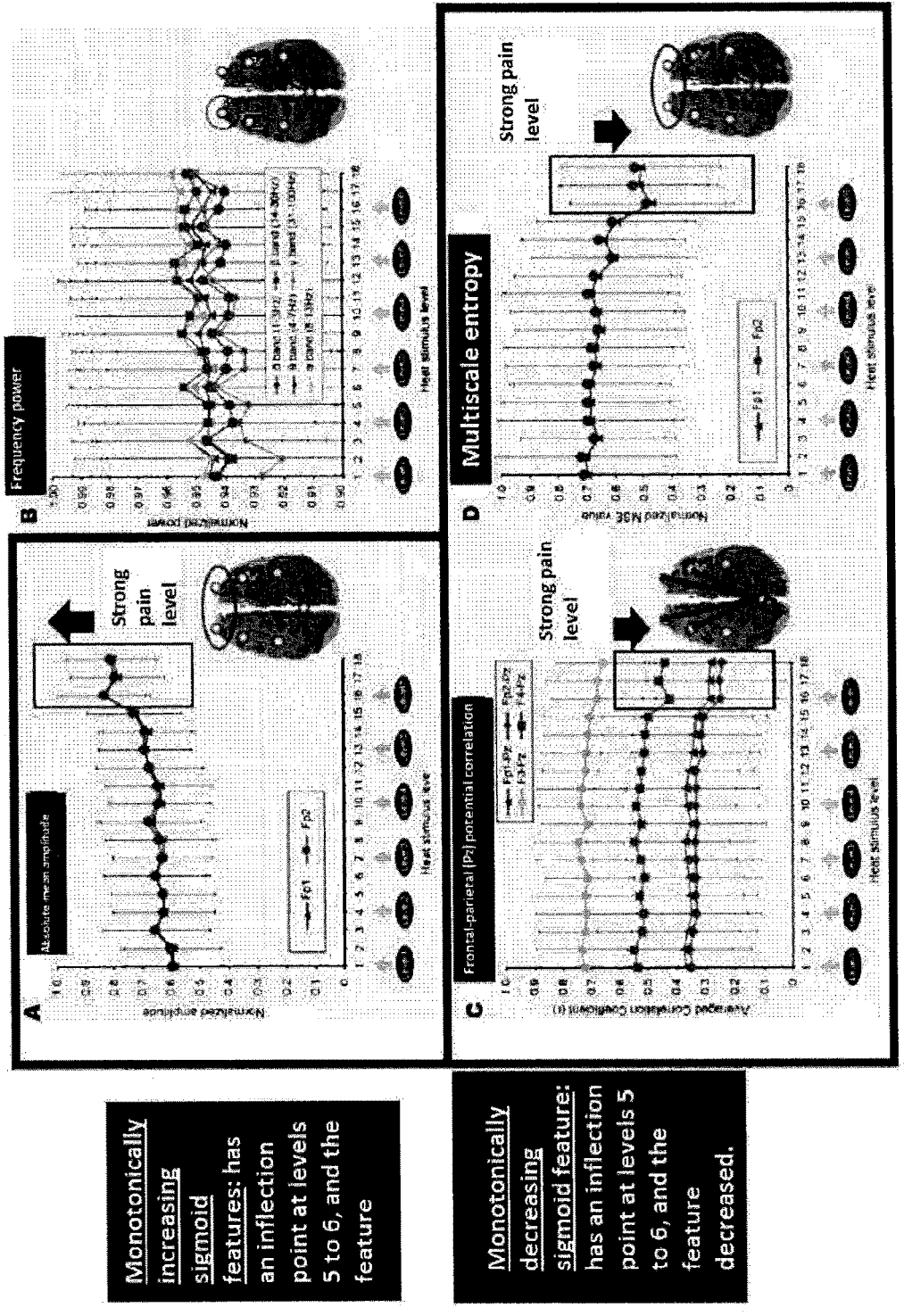
FIG. 90 shows a change in monotonically increasing sigmoid and monotonically decreasing sigmoid features. A shows the absolute mean amplitude, and B shows the frequency power. C shows frontal-parietal amplitude correlation (also known as potential correction), and D shows multiscale entropy (MSE). Monotonically increasing sigmoid: has an inflection point at monotonically increasing sigmoid feature: levels 5 to 6 in A, and the feature increased. Monotonically decreasing sigmoid: has an inflection point at monotonically decreasing sigmoid feature: levels 5 to 6 in C and D, and the feature decreased.

FIG. 90 shows the results. A shows the absolute mean amplitude, and B shows the frequency power. C shows frontal-parietal potential (absolute mean amplitude) correlation. D shows multiscale entropy (MSE). A exhibits a monotonically increasing sigmoid pattern. An inflection point is observed at levels 5 to 6, and features increased. C and D exhibit a monotonically decreasing sigmoid pattern having an inflection point at levels 5 to 6, where features decreased. For potential correlation in particular, a change in activity at the frontal and parietal portions is observed if the pain intensity increases in view of prior art, so that an increase in correlation between the two electrodes was initially expected, but the opposite pattern was surprisingly exhibited. Frequency power (FIG. 90B) exhibited an increasing trend overall with an increase in pain levels.

As shown in FIG. 91, a sigmoidal feature is a form of feature exhibiting "discrete feature", i.e., feature exhibiting a binomial distribution property. In actual pain monitoring, a plurality of pain test stimulations can be applied to an object to find the distribution property of features for no pain and having pain. FIG. 91 shows a schematic diagram from function or curve fitting to plotting of a histogram of features. The numerical value where distributions of samples for no pain and having pain intersect is used as the "differentiation threshold value". Samples less than the threshold value are converted to a category scale of "−1" and samples that are greater than the threshold value are converted to a category scale of "1" for each feature by using this threshold value. Poincare distribution or the like can also be used as the distribution for determining such a threshold value.

Machine learning was performed using a multiple regression model for differentiation analysis of adjacent levels, i.e., levels 1 and 2, 2 and 3, 3 and 4, 4 and 5, and 5 and 6, and the most distant level 1 and level 6 using the 53 parameters described above. Data was divided as 80% learning data and 20% test data. A model was created by cross validation using the learning data for differentiation/ estimation of test data.

(Results of Extraction of Dominant Features (Two Classifications))

Since differentiation accuracy at or above the chance level (50%) was obtained between levels 4 and 5, levels 5 and 6, and levels 1 and 6, a mean coefficient in three differentiation models was calculated to rank 53 parameters (FIG. 92). Next, when features including 30% or more zero coefficient were eliminated in differentiation/estimation performed 100 times, six features were extracted.

Figure 93:
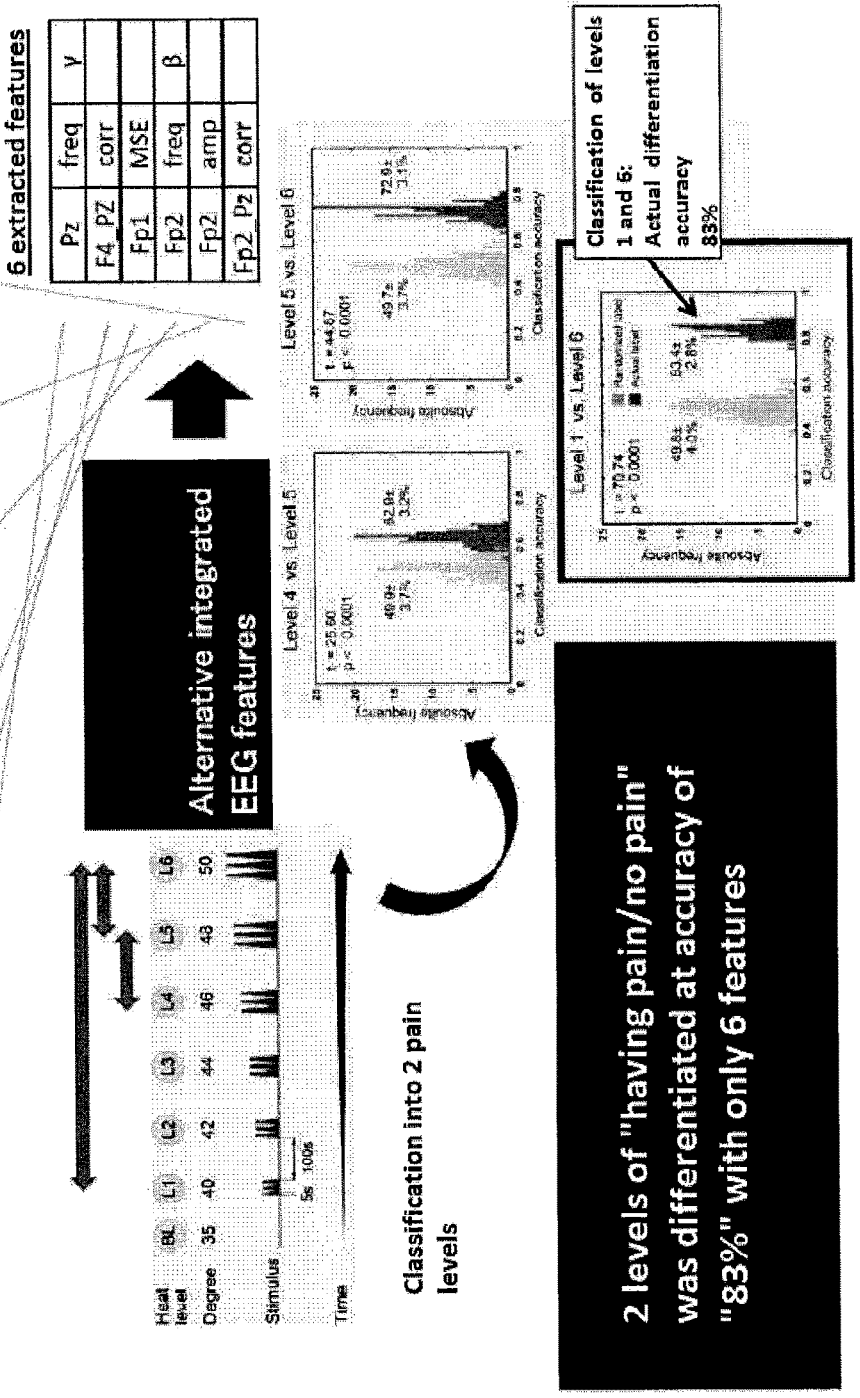
FIG. 93 shows differentiation and estimation results (linear model) using dominant features. It was found that two levels of "having pain and no pain" can be differentiated at an accuracy of "83%" using six features (parameters) calculated in FIG. 91.

FIG. 92 shows the specific dominant features. The results revealed that significant accuracy can be attained by using frequency power of electrode Pz, potential correlation of F4 to Pz, MSE of electrode Fp1, frequency power of electrode Fp2, mean amplitude of Fp2, and potential correlation of Fp2 to Pz as dominant features. This feature set can be referred to as "alternative integrated EEG features", which is extracted by various signal processing methods from limited electrodes and adaptively alternated depending on the monitoring environment or individual difference by the contracting process and integrally contributes to a pain differentiation model via a linear multiple regression model in this Example. When only six of the parameters were used to run machine learning on all samples again, levels 1 and 6, i.e., two farthest levels of "having strong pain/no pain" was able to be differentiated at an accuracy of "83%" as shown in FIG. 93.

The above results demonstrated that primary feature (mean potential, frequency power, and MSE) and secondary feature correlation parameters are effective in differentiating pain of samples exceeding 150.

Example 23: Example of Creating a Differentiation Model Generalized for Hot and Cold Including Phase Synchronization Parameter A generalized differentiation model for two classifications of having pain and no pain for data exceeding a total of 300 samples in total of high temperature and low temperature stimulation including a new parameter of phase synchronization between electrodes was created to find dominant features.

(Participants)

Total of 292 healthy adult subjects in their 20s to 70s participated in the high and low temperature stimulation paradigm experiments. Informed consent was obtained from the participants prior to the experiment. All participants self-reported as having no history of a neurological and/or psychiatric illness, or acute and/or chronic pain under clinical drug therapy conditions. This Example was in compliance with the Declaration of Helsinki and conducted under approval of the Osaka University Hospital ethics committee.

(Experimental Stimulation and Procedure)

A temperature stimulation system (Pathway; Medoc Co., Ltd., Ramat Yishai, Israel) was used to apply high temperature stimulation to the right forearm of the participants. High temperature stimulation included six levels of temperature intensities (increased by 2° C. from 40° C. to 50° C.). Meanwhile, there was difficulty in applying the lowest temperature of −10° C., so that low temperature stimulation included five levels of temperature intensities (decreased by 5° C. from 15° C. to −5° C.). Each temperature level consisted of three stimulations (15 seconds each). Each stimulation had a plateau (stimulation application time) lasting 5 seconds. The waiting period for increase and decrease from the standard temperature was about 10 seconds. After three stimulations at each level, the intervals between blocks lasted 100 seconds. Brainwave data was continuously recorded during the experiment. The sampling frequency was 1000 Hz and the frequency band was 0.3 to 120 Hz. The impedance was equal to or less than 15 kΩ. Electrodes that recorded were Fp1, Fp2, F3, F4, C3, C4, and Pz. Reference electrode were the left and right earlobes, and an earth electrode was placed on the forehead. The participants continuously evaluated pain intensities in the range of 0 to 100 (0="no pain"; 100="unbearable pain") on a computerized visual analog scale (COVAS). COVAS data was simultaneously recorded with changes in stimulation intensities. Further, the following parameters were used. Two levels were used for differentiating pain. The number of samples was 2 levels×3 runs×309 subjects=1854 samples.

(Signal Processing Before Extraction of Features)

In order to diminish eye movement noise (EOG), main component analysis was performed on EEG data using data from 7 electrodes to extract an EOG component (first component). Low/high frequency components (1 to 30 Hz band frequency filter) were removed, and EOG components were removed from each electrode data using the regression equation of Numeral 312.

Raw EEG=β×EOG+C

EEG estimate=raw EEG−β×EOG       [Numeral 312]

β: regression coefficient
C: intercept
EEG estimate: estimated EEG

After correction of EOG, a 30 Hz low pass filter was further applied to reduce myogenic potential noise. After converting amplitudes to absolute values, the epoch waveform of 15 seconds after applying stimulation was sampled to calculate features of absolute mean amplitude, frontal-parietal potential correlation (Fp1, Fp2, F3, F4, and Pz), and multiscale entropy (MSE). For frequency power, waveforms after EOG correction were subjected to Fourier transform without applying a 30 Hz low pass filter to calculate the band power for $\delta$ (1 to 3 Hz), $\theta$ (4 to 7 Hz), $\alpha$ (8 to 13 Hz), $\beta$ (14 to 30 Hz), and $\gamma$ (31 to 100 Hz). The phase synchronization feature in each band between each electrode was also calculated. 159 parameters (features, feature coefficients) were obtained with 7 electrodes by the above process. Each parameter was standardized with the maximum value for each individual using data for all levels. Parameters are summarized below.

1. Mean Amplitude (7 Mean Amplitudes):
A mean value of absolute values of amplitudes during 15 seconds after applying stimulation at 7 electrodes (Fp1, Fp2, F3, F4, C3, C4, and Pz) was used. This was standardized among individuals.

2. Frontal-Parietal Potential Correlation (4 Correlations)
The potential correlation of four frontal electrodes (Fp1, Fp2, F3, and F4) and parietal Pz was used. Although not wishing to be bound by any theory, this is because the region associated with stimulation intensity and pain is understood to include the frontal and parietal portions.

3. Frequency Power (35 Frequency Powers)
Five bands of "$\delta, \theta, \alpha, \beta,$ and $\gamma$" at seven electrodes (Fp1, Fp2, F3, F4, C3, C4, and Pz) were used.

4. Complexity Index (Multiscale Entropy: 7 Indices)

5. Phase Synchronization (Phase Locking Value: 106 Phase Locking Values)
The phase synchronization properties between electrodes were calculated in each frequency band.

Machine learning was performed using a multiple regression model for differentiation analysis of the most distant level 1 and level 6 using the 159 features and feature correlation parameters described above. Data was divided into n−1 samples of learning data and one sample of test data (2 levels×3 runs), a model was created by cross validation using the learning data, differentiation and estimation of the test data was performed the same number of times as the number of samples to investigate the differentiation accuracy.

The electrodes were limited to those at the frontal and central portions, which are expected to be used in a pain apparatus. The electrode was used one at a time to investigate the pain accuracy of each electrode.

(Results)

As shown in FIG. 94, differentiation accuracy of actual pain level was "74.3±32.5%", which was significantly higher compared to the differentiation accuracy of "56.1±17.1%" for randomized samples (t=12.70, p<0.0001). When samples with differentiation accuracy at or below the chance level were eliminated in stages to create a differentiation model prototype by refining, 213 subjects (1278 samples) were included in the model. The differentiation accuracy indeed reached "94.6±12.7%", which was significantly higher than the differentiation accuracy of "35.4±11.3%" for the randomized samples (t=49.20, p<0.00001).

Figure 95:
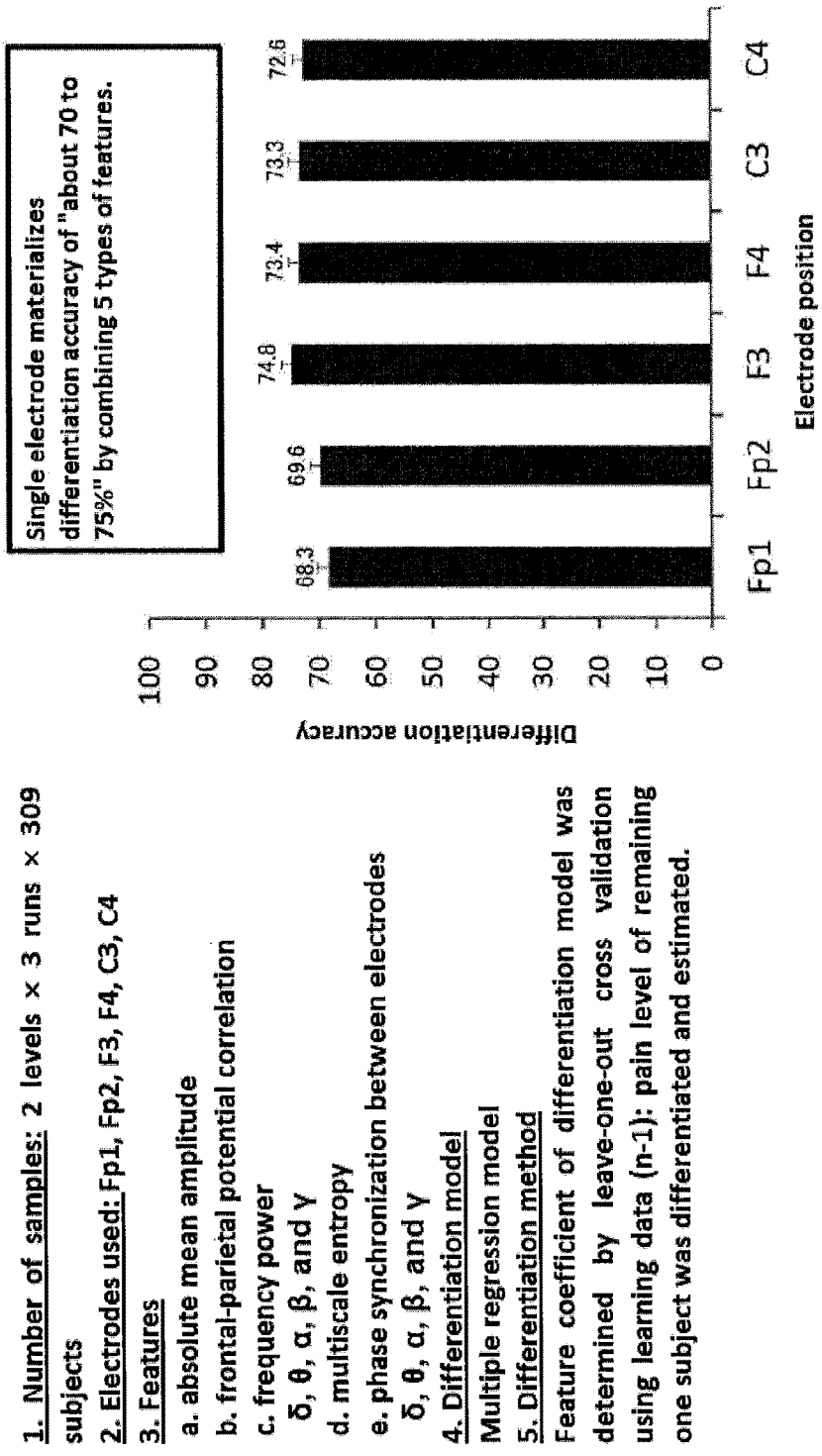
FIG. 95 shows an example of studying differentiation accuracy of each electrode by a generalized differentiation model comprising both high temperature and low temperature pain stimulation samples. A process of creating a differentiation model using n−1 samples, and estimating the pain level (2 levels×3 runs) for the remaining one sample was repeated for the same number of times as the number of subjects. The differentiation accuracy of each of the 6 electrodes at the frontal and center portions reached "about 70 to 75%". This indicates that a universal pain differentiation model can be created even with a limited number of electrodes, even at a minimum of one, by using a combination of parameters and electrodes at at least the frontal and middle portions.

As shown in FIG. 95, differentiation accuracy using one electrode at the frontal and central portions (total of 309 subjects: 1854 samples) exhibited about 70 to 75% differentiation accuracy. These results indicate that if parameters of primary features (sampled raw data, potential, frequency power, MSE, and the like) and derivative features (feature correlation) mainly involving electrodes at the frontal and central portions including Fp1, Fp2, F3, F4, C3, C4, and Pz used in this Example are combined, differentiation of two levels of having strong pain and no pain can be materialized indeed at 70% or greater or 90% accuracy with further model refinement even with few electrodes such as one electrode. If another long existing phase synchronization feature is inputted into a model, a further increase in the percentage of correct answers of 2 levels, 3 levels, or more levels is expected.

(Note)

As disclosed above, the present invention has been exemplified by the use of its preferred embodiments. However, it is understood that the scope of the present invention should be interpreted based solely on the Claims. It is also understood that any patent, patent application, and references cited herein should be incorporated herein by reference in the same manner as the contents are specifically described herein. The present application claims priority to Japanese Patent Application No. 2017-133422 (filed on Jul. 7, 2017), Japanese Patent Application No. 2017-199374 (filed on Oct. 13, 2017), Japanese Patent Application No. 2017-254565 (filed on Dec. 28, 2017), Japanese Patent Application No. 2017-254560 (filed on Dec. 28, 2017), and Japanese Patent Application No. 2018-2777 (filed on Jan. 11, 2018) with the Japan Patent Office. The entire content thereof is incorporated herein by reference in the same manner as the contents are specifically described herein.

INDUSTRIAL APPLICABILITY

The present invention is capable of differentiating pain accurately and over time, and enables diagnosis or therapy of pain in more detail.

The present invention can provide a method that can differentiate pain with a differentiation model using fewer features or a model with high rate of improvement in differentiation accuracy, and can diagnose or treat pain more finely.

REFERENCE SIGNS LIST

1000: object
1100: system comprising a pain level differentiation/estimation apparatus
1110: pain level differentiation/estimation apparatus
1111: measurement unit
1112: feature extraction unit 1113: pain index generation unit
1114: standard determination unit
1115: pain level monitoring unit
1120: electroencephalograph
101000: feature contracting unit
102000: feature extraction unit
103000: pain differentiation/estimation model generation unit
104000: pain differentiation/estimation unit
105000: reference stimulation application unit
105200: brainwave data measurement unit
106000: object
107000: pain level visualization unit
108000: apparatus
110000: brainwave data measurement unit
120000: data transceiver unit
125000: data transceiver unit
130000: pain level visualization unit
135000: pain level visualization unit
140000: brainwave feature extraction unit
145000: brainwave feature extraction unit
150000: pain level differentiation estimation unit
160000: pain differentiation model generation unit
170000: data storage unit
180000: brainwave database
201000: feature contracting unit
202000: feature extraction unit
203000: pain differentiation/estimation model generation unit
203100: pain brainwave database
203200: individual pain differentiation model creation unit
203300: pain differentiation model ranking unit
203400: ensemble pain differentiation model creation unit
203500: pain differentiation model transmission unit
204000: pain differentiation/estimation unit
205000: reference stimulation application unit
205200: brainwave data measurement unit
206000: object
207000: pain level visualization unit
208000: apparatus
301000: feature contracting unit
302000: feature extraction unit
303000: pain differentiation/estimation model generation unit
304000: pain differentiation/estimation unit
305000: reference stimulation application unit
305200: brainwave data measurement unit
306000: object
307000: pain level visualization unit
307500: data storage unit
308000: apparatus

The invention claimed is:

1. A computer implemented method for causing a computer to execute processing to obtain an improved differentiation model based on an accuracy of a single differentiation model to be derived by machine learning, the computer including a processor, a memory for storing the program and an interface configured to communicate with a database storing brainwave data samples of subjects respectively associated with pain labels, comprising:
   a. dividing, by the processor, the brainwave data samples of the subjects into a first predetermined number of first groups;
   b. determining, by the processor, a hyperparameter of a penalty term of the single differentiation model by executing k-fold cross-validation of supervised machine learning on the brainwave data samples of the first groups according to the pain labels, where k equals to the first predetermined number;
   c. generating, by the processor, the single differentiation model by using the determined hyperparameter and all the brainwave data samples of the subjects to calculate first differentiation accuracy for each of the subjects;
   d. ranking, by the processor, the subjects based on the first differentiation accuracy to group the subjects into a second predetermined number of second groups according to ranking order;
   e. determining, by the processor, an individual hyperparameter of the penalty term of an individual differentiation model for each of the second groups by executing l-fold cross-validation of supervised machine learning on the brainwave data samples of each of the second groups, where l is a predetermined number common to the second groups;
   f. generating, by the processor, the individual differentiation model for each of the second groups using the determined individual hyperparameter; and
   g. identifying a differentiation maximum (MAX) model for each of the subjects among the individual differentiation models by searching for the individual differentiation model with the highest second differentiation accuracy for each of the subject.

2. The method of claim 1, further comprising:
   i) ranking, by the processor, the individual differentiation models in descending order based on the second differentiation accuracy for each of the subjects;
   ii) calculating, by the processor, values of third differentiation accuracy by an ensemble method, wherein the ensemble method includes,
      preparing serially ensembles of the individual differentiation models by incorporating into an initial one of the ensembles the individual differentiation model one by one according to the descending order, wherein the initial one includes the differentiation maximum (MAX) model, and
      calculating each of the values of the third differentiation accuracy based on voting of the individual differentiation models included in the ensemble; and
   iii) determining, by the processor, the ensemble with the highest value of the third differentiation accuracy to generate an improved differentiation model for each of the subjects.

3. The method of claim 1, wherein the individual differentiation models include the differentiation maximum (MAX) model for each of the subjects as a main model and the rest of the individual differentiation models as a supporter model set, further comprising,
   i) calculating, by the processor, values of third differentiation accuracy by an ensemble method, wherein the ensemble method includes,
      preparing ensembles each including the main model and one of the individual differentiation models included in the supporter model set by combining the main model with respective ones in the supporter model set to generate the ensembles, and
      calculating each of the values of the third differentiation accuracy based on voting of the individual differentiation models included in the ensemble, and
   ii) selecting, by the processor, the individual differentiation model included in the ensemble with the highest value of the third differentiation accuracy, and
   iii) updating the main model by setting the main model as a set of the main model and the selected individual differentiation model and updating the supporter model set by eliminating the selected individual differentiation model from the supporter model set, and iv) repeating the steps i) to iii) until updating of the supporter model set by elimination of the selected individual differentiation model from the supporter model set terminates to determine an improved differentiation model for each of the subjects as the ensemble with the highest value of the third differentiation accuracy.

4. A non-transitory recording medium storing a program for causing a computer to execute processing to obtain an improved differentiation model based on an accuracy of a single differentiation model to be derived by machine learning, the computer including a processor, a memory for storing the program and an interface configured to communicate with a database storing brainwave data samples of subjects respectively associated with pain labels, the processing comprising:

a. dividing, by the processor, the brainwave data samples of the subjects into a first predetermined number of first groups;

b. determining, by the processor, a hyperparameter of a penalty term of the single differentiation model by executing k-fold cross-validation of supervised machine learning based on the brainwave data samples of the first groups according to the pain labels, where k equals to the first predetermined number;

c. generating, by the processor, the single differentiation model by using the determined hyperparameter and all the brainwave data samples of the subjects to calculate first differentiation accuracy for each of the subjects;

d. ranking, by the processor, the subjects based on the first differentiation accuracy to group the subjects into a second predetermined number of second groups according to ranking order;

e. determining, by the processor, an individual hyperparameter of the penalty term of an individual differentiation model for each of the second groups by executing l-fold cross-validation of supervised machine learning on the brainwave data samples of each of the second groups, where l is a predetermined number common to the second groups;

f. generating, by the processor, the individual differentiation model for each of the second groups using the determined individual hyperparameter; and g. identifying a differentiation maximum (MAX) model for each of the subjects among the individual differentiation models by searching for the individual differentiation model with the highest second differentiation accuracy for each of the subjects.

5. A system for executing a computer-implemented method to obtain an improved differentiation model based on an accuracy of a single differentiation model to be derived by machine learning, the system comprising:

a processor;

a memory for storing a machine learning program; and an interface configured to communicate with a database storing brainwave data samples of subjects respectively associated with pain labels;

wherein the processor configured to:

divide the brainwave data samples into a predetermined number of first groups;

determine a hyperparameter of a penalty term of the single differentiation model by executing k-fold cross-validation of supervised machine learning on the brainwave data samples of the first groups according to the pain labels, where k equals to the first predetermined number;

generate the single differentiation model by using the determined hyperparameter and all the brainwave data samples of the subjects to calculate first differentiation accuracy for each of the subjects;

rank the subjects based on the first differentiation accuracy to group the subjects into a second predetermined number of second groups according to ranking order;

determine an individual hyperparameter of the penalty term of an individual differentiation model for each of the second groups by executing l-fold cross-validation of supervised machine learning on the brainwave data samples of each of the second groups, where l is a predetermined number common to the second groups;

generate the individual differentiation model for each of the second groups using the determined individual hyperparameter; and identify a differentiation maximum (MAX) model for each of the subjects among the individual differentiation models by searching for the individual differentiation model with the highest second differentiation accuracy for each of the subjects.

\* \* \* \* \*